(12) United States Patent
Haack et al.

(10) Patent No.: US 10,758,592 B2
(45) Date of Patent: *Sep. 1, 2020

(54) EXENDIN-4 DERIVATIVES AS DUAL GLP1/GLUCAGON AGONISTS

(71) Applicant: SANOFI, Paris (FR)

(72) Inventors: Torsten Haack, Frankfurt am Main (DE); Michael Wagner, Frankfurt am Main (DE); Bernd Henkel, Frankfurt am Main (DE); Siegfried Stengelin, Frankfurt am Main (DE); Andreas Evers, Frankfurt am Main (DE); Martin Bossart, Frankfurt am Main (DE)

(73) Assignee: SANOFI, Paris (FR)

(*) Notice: Subject to any disclaimer, the term of this patent is extended or adjusted under 35 U.S.C. 154(b) by 0 days.

This patent is subject to a terminal disclaimer.

(21) Appl. No.: 15/837,958

(22) Filed: Dec. 11, 2017

(65) Prior Publication Data

US 2018/0185450 A1 Jul. 5, 2018

Related U.S. Application Data

(60) Continuation of application No. 15/130,647, filed on Apr. 15, 2016, now abandoned, which is a division of application No. 14/049,597, filed on Oct. 9, 2013, now Pat. No. 9,365,632.

(30) Foreign Application Priority Data

Oct. 9, 2012 (EP) .................................... 12306232
Feb. 27, 2013 (EP) .................................... 13305222

(51) Int. Cl.
*A61K 38/26* (2006.01)
*C07K 14/575* (2006.01)
*C07K 14/605* (2006.01)
*A61K 38/28* (2006.01)
*A61K 45/06* (2006.01)
*A61K 38/22* (2006.01)
*A61K 38/00* (2006.01)

(52) U.S. Cl.
CPC .......... *A61K 38/26* (2013.01); *A61K 38/2264* (2013.01); *A61K 38/28* (2013.01); *A61K 45/06* (2013.01); *C07K 14/605* (2013.01); *A61K 38/00* (2013.01); *Y02A 50/401* (2018.01)

(58) Field of Classification Search
None
See application file for complete search history.

(56) References Cited

U.S. PATENT DOCUMENTS

| | | |
|---|---|---|
| 5,424,286 A | 6/1995 | Eng |
| 5,641,757 A | 6/1997 | Bornstein et al. |
| 6,284,727 B1 | 9/2001 | Kim et al. |
| 6,329,336 B1 | 12/2001 | Bridon et al. |
| 6,344,180 B1 | 2/2002 | Holst et al. |
| 6,410,511 B2 | 6/2002 | L'Italien et al. |
| 6,429,197 B1 | 8/2002 | Coolidge et al. |
| 6,451,974 B1 | 9/2002 | Hansen |
| 6,458,924 B2 | 10/2002 | Knudsen et al. |
| 6,482,799 B1 | 11/2002 | Tusé et al. |
| 6,506,724 B1 | 1/2003 | Hiles et al. |
| 6,514,500 B1 | 2/2003 | Bridon et al. |
| 6,528,486 B1 | 3/2003 | Larsen et al. |
| 6,579,851 B2 | 6/2003 | Goeke et al. |
| 6,593,295 B2 | 7/2003 | Bridon et al. |
| 6,703,359 B1 | 3/2004 | Young et al. |
| 6,706,689 B2 | 3/2004 | Coolidge et al. |
| 6,723,530 B1 | 4/2004 | Drucker |
| 6,821,949 B2 | 11/2004 | Bridon et al. |
| 6,828,303 B2 | 12/2004 | Kim et al. |
| 6,849,714 B1 | 2/2005 | Bridon et al. |
| 6,858,576 B1 | 2/2005 | Young et al. |
| 6,861,236 B2 | 3/2005 | Moll et al. |
| 6,872,700 B1 | 3/2005 | Young et al. |
| 6,884,579 B2 | 4/2005 | Holst et al. |
| 6,887,470 B1 | 5/2005 | Bridon et al. |
| 6,887,849 B2 | 5/2005 | Bridon et al. |
| 6,894,024 B2 | 5/2005 | Coolidge et al. |
| 6,902,744 B1 | 6/2005 | Kolterman et al. |
| 6,924,264 B1 | 8/2005 | Prickett et al. |
| 6,956,026 B2 | 10/2005 | Beeley et al. |
| 6,969,702 B2 | 11/2005 | Bertilsson et al. |
| 6,972,319 B1 | 12/2005 | Pan et al. |
| 6,982,248 B2 | 1/2006 | Coolidge et al. |
| 6,989,366 B2 | 1/2006 | Beeley et al. |
| 6,998,387 B1 | 2/2006 | Goke et al. |
| 7,056,734 B1 | 6/2006 | Egan et al. |
| 7,056,887 B2 | 6/2006 | Coolidge et al. |
| 7,105,489 B2 | 9/2006 | Hathaway et al. |
| 7,105,490 B2 | 9/2006 | Beeley et al. |
| 7,115,569 B2 | 10/2006 | Beeley et al. |
| 7,138,375 B2 | 11/2006 | Beeley et al. |
| 7,138,546 B2 | 11/2006 | Tang |
| 7,141,240 B2 | 11/2006 | Perfetti et al. |
| 7,141,547 B2 | 11/2006 | Rosen et al. |
| 7,144,863 B2 | 12/2006 | Defelippis et al. |
| 7,153,825 B2 | 12/2006 | Young et al. |

(Continued)

FOREIGN PATENT DOCUMENTS

| | | |
|---|---|---|
| CN | 1938334 A | 3/2007 |
| CN | 101538323 A | 9/2009 |

(Continued)

OTHER PUBLICATIONS

US 8,729,011 B2, 05/2014, Dimarchi et al. (withdrawn)

(Continued)

*Primary Examiner* — Julie Ha
*Assistant Examiner* — Kristina M Hellman
(74) *Attorney, Agent, or Firm* — Lathrop GPM LLP; James H. Velema, Esq.

(57) ABSTRACT

The present invention relates to exendin-4 derivatives and their medical use, for example in the treatment of disorders of the metabolic syndrome, including diabetes and obesity, as well as reduction of excess food intake.

23 Claims, 13 Drawing Sheets

Figure 2:
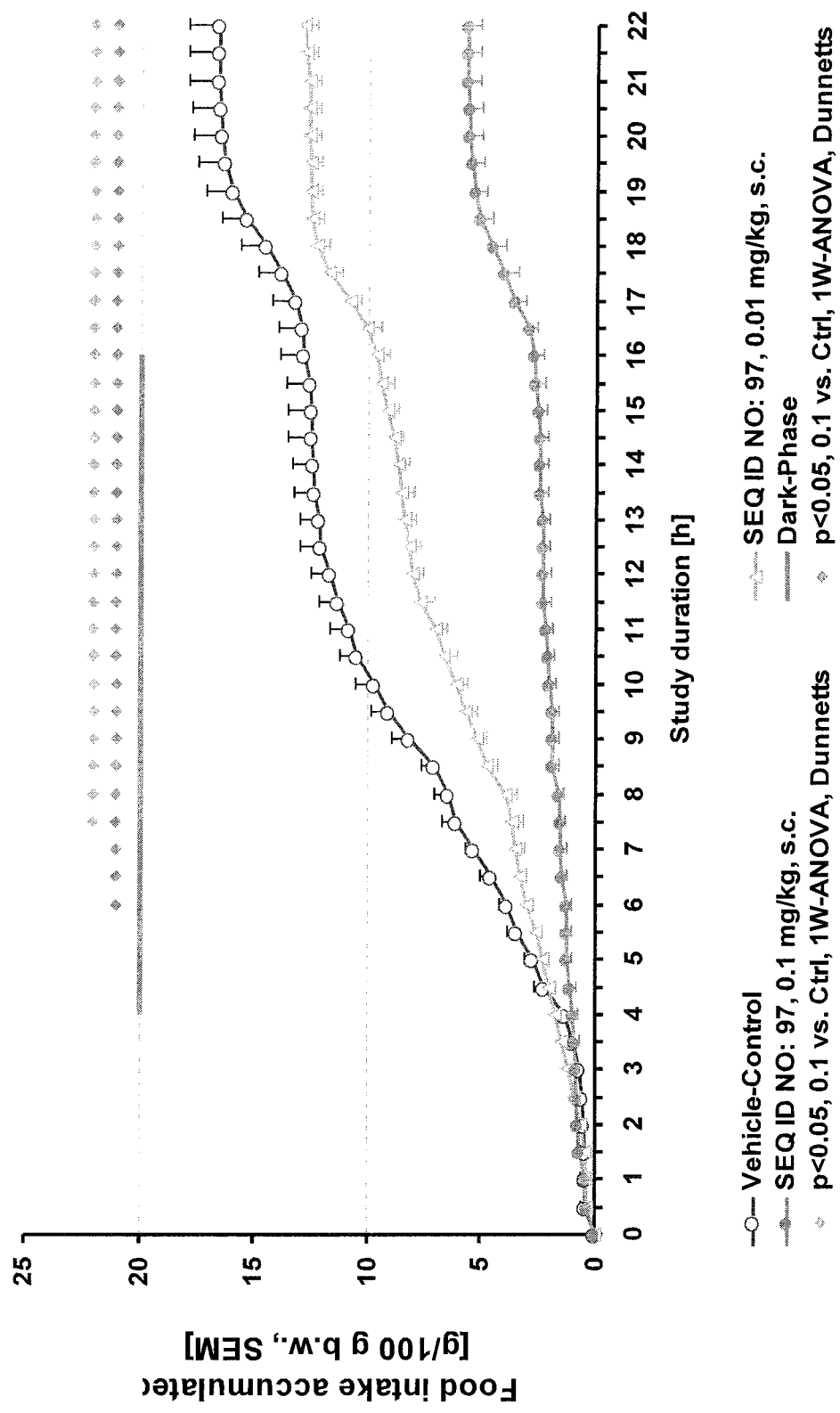

Specification includes a Sequence Listing.

(56) References Cited

U.S. PATENT DOCUMENTS

| | | |
|---|---|---|
| 7,157,555 B1 | 1/2007 | Beeley et al. |
| 7,179,788 B2 | 2/2007 | Defelippis et al. |
| 7,189,690 B2 | 3/2007 | Rosen et al. |
| 7,220,721 B1 | 5/2007 | Beeley et al. |
| 7,223,725 B1 | 5/2007 | Beeley et al. |
| 7,256,253 B2 | 8/2007 | Bridon et al. |
| 7,259,136 B2 | 8/2007 | Hathaway et al. |
| 7,259,233 B2 | 8/2007 | Dodd et al. |
| 7,259,234 B2 | 8/2007 | Bachovchin et al. |
| 7,265,087 B1 | 9/2007 | Göke et al. |
| 7,271,149 B2 | 9/2007 | Glaesner et al. |
| 7,297,761 B2 | 11/2007 | Beeley et al. |
| 7,312,196 B2 | 12/2007 | L'Italien et al. |
| 7,329,646 B2 | 2/2008 | Sun et al. |
| 7,399,489 B2 | 7/2008 | Kolterman et al. |
| 7,399,744 B2 | 7/2008 | Mack et al. |
| 7,407,932 B2 | 8/2008 | Young et al. |
| 7,407,955 B2 | 8/2008 | Himmelsbach et al. |
| 7,414,107 B2 | 8/2008 | Larsen |
| 7,419,952 B2 | 9/2008 | Beeley et al. |
| 7,442,680 B2 | 10/2008 | Young et al. |
| 7,442,682 B2 | 10/2008 | Kitaura et al. |
| 7,452,858 B2 | 11/2008 | Hiles et al. |
| 7,456,254 B2 | 11/2008 | Wright et al. |
| 7,476,652 B2 | 1/2009 | Brunner-Schwarz et al. |
| 7,507,714 B2 | 3/2009 | Pan et al. |
| 7,521,423 B2 | 4/2009 | Young et al. |
| 7,544,657 B2 | 6/2009 | Ebbehøj et al. |
| 7,563,871 B2 | 7/2009 | Wright et al. |
| 7,576,050 B2 | 8/2009 | Greig et al. |
| 7,585,837 B2 | 9/2009 | Shechter et al. |
| 7,592,010 B2 | 9/2009 | Rosen et al. |
| 7,595,293 B2 | 9/2009 | Engelund et al. |
| 7,595,294 B2 | 9/2009 | Nestor |
| 7,608,692 B2 | 10/2009 | Prickett et al. |
| 7,612,176 B2 | 11/2009 | Wright et al. |
| 7,632,806 B2 | 12/2009 | Juul-Mortensen et al. |
| 7,638,299 B2 | 12/2009 | Cho et al. |
| 7,682,356 B2 | 3/2010 | Alessi et al. |
| 7,683,030 B2 | 3/2010 | Prickett et al. |
| 7,691,963 B2 | 4/2010 | Prickett et al. |
| 7,696,161 B2 | 4/2010 | Beeley et al. |
| 7,700,549 B2 | 4/2010 | Beeley et al. |
| 7,704,953 B2 | 4/2010 | Herman et al. |
| 7,713,930 B2 | 5/2010 | Brunner-Schwarz et al. |
| 7,723,471 B2 | 5/2010 | Levy et al. |
| 7,741,269 B2 | 6/2010 | Young et al. |
| 7,749,955 B2 | 7/2010 | Hansen et al. |
| 7,772,189 B2 | 8/2010 | Herman et al. |
| 7,790,681 B2 | 9/2010 | Hathaway et al. |
| 7,799,344 B2 | 9/2010 | Oberg |
| 7,799,759 B2 | 9/2010 | Rosen et al. |
| 7,803,404 B2 | 9/2010 | Hokenson et al. |
| 7,829,664 B2 | 11/2010 | Tatake et al. |
| 7,847,079 B2 | 12/2010 | Rosen et al. |
| 7,858,740 B2 | 12/2010 | Beeley et al. |
| 7,867,972 B2 | 1/2011 | Ballance et al. |
| 7,879,028 B2 | 2/2011 | Alessi et al. |
| 7,888,314 B2 | 2/2011 | Hathaway et al. |
| 7,897,560 B2 | 3/2011 | Dorwald et al. |
| 7,906,146 B2 | 3/2011 | Kolterman et al. |
| 7,928,065 B2 | 4/2011 | Young et al. |
| 7,928,186 B2 | 4/2011 | Chang |
| 7,935,786 B2 | 5/2011 | Larsen |
| 7,939,494 B2 | 5/2011 | Khan et al. |
| 7,960,341 B2 | 6/2011 | Hathaway et al. |
| 7,977,306 B2 | 7/2011 | Rosen et al. |
| 7,981,861 B2 | 7/2011 | Coolidge et al. |
| 7,989,585 B2 | 8/2011 | Dodd et al. |
| 7,994,121 B2 | 8/2011 | Bachovchin et al. |
| 7,994,122 B2 | 8/2011 | Riber et al. |
| 8,008,255 B2 | 8/2011 | Ong et al. |
| 8,012,464 B2 | 9/2011 | Rosen et al. |
| 8,026,210 B2 | 9/2011 | Young et al. |
| 8,030,273 B2 | 10/2011 | Lau et al. |
| 8,039,432 B2 | 10/2011 | Bridon et al. |
| 8,057,822 B2 | 11/2011 | Prickett et al. |
| 8,071,539 B2 | 12/2011 | Rosen et al. |
| 8,076,288 B2 | 12/2011 | Levy et al. |
| 8,080,516 B2 | 12/2011 | Bridon et al. |
| 8,084,414 B2 | 12/2011 | Bridon et al. |
| 8,093,206 B2 | 1/2012 | Bridon et al. |
| 8,097,239 B2 | 1/2012 | Johnsson et al. |
| 8,097,586 B2 | 1/2012 | Lv et al. |
| 8,114,632 B2 | 2/2012 | Melarkode et al. |
| 8,114,833 B2 | 2/2012 | Pedersen et al. |
| 8,114,958 B2 | 2/2012 | Soares et al. |
| 8,114,959 B2 | 2/2012 | Juul-Mortensen |
| 8,119,648 B2 | 2/2012 | Himmelsbach et al. |
| 8,143,217 B2 | 3/2012 | Balkan et al. |
| 8,158,579 B2 | 4/2012 | Ballance et al. |
| 8,158,583 B2 | 4/2012 | Knudsen et al. |
| 8,178,495 B2 | 5/2012 | Chilkoti |
| 8,178,541 B2 | 5/2012 | Himmelsbach et al. |
| 8,197,450 B2 | 6/2012 | Glejbol et al. |
| 8,211,439 B2 | 7/2012 | Rosen et al. |
| 8,232,281 B2 | 7/2012 | Dugi et al. |
| 8,236,760 B2 | 8/2012 | Pimentel et al. |
| 8,252,739 B2 | 8/2012 | Rosen et al. |
| 8,263,545 B2 | 9/2012 | Levy et al. |
| 8,263,550 B2 | 9/2012 | Beeley et al. |
| 8,263,554 B2 | 9/2012 | Tatarkiewicz et al. |
| 8,268,781 B2 | 9/2012 | Gotthardt et al. |
| 8,278,272 B2 | 10/2012 | Greig et al. |
| 8,278,420 B2 | 10/2012 | Wang et al. |
| 8,288,338 B2 | 10/2012 | Young et al. |
| 8,293,726 B2 | 10/2012 | Habib |
| 8,293,869 B2 | 10/2012 | Bossard et al. |
| 8,293,871 B2 | 10/2012 | Wright et al. |
| 8,299,024 B2 | 10/2012 | Rabinovitch et al. |
| 8,299,025 B2 | 10/2012 | Alessi et al. |
| 8,329,419 B2 | 12/2012 | Nicolaou et al. |
| 8,329,648 B2 | 12/2012 | Fineman et al. |
| 8,338,368 B2 | 12/2012 | Dimarchi et al. |
| 8,343,910 B2 | 1/2013 | Shechter et al. |
| 8,372,804 B2 | 2/2013 | Richardson et al. |
| 8,377,869 B2 | 2/2013 | Richardson et al. |
| 8,389,473 B2 | 3/2013 | Hathaway et al. |
| 8,404,637 B2 | 3/2013 | Levy et al. |
| 8,410,047 B2 | 4/2013 | Bock et al. |
| 8,420,604 B2 | 4/2013 | Hokenson et al. |
| 8,424,518 B2 | 4/2013 | Smutney et al. |
| 8,426,361 B2 | 4/2013 | Levy et al. |
| 8,431,685 B2 | 4/2013 | Wright et al. |
| 8,445,647 B2 | 5/2013 | Prickett et al. |
| 8,450,270 B2 | 5/2013 | Dimarchi et al. |
| 8,454,971 B2 | 6/2013 | Day et al. |
| 8,461,105 B2 | 6/2013 | Wright et al. |
| 8,481,490 B2 | 7/2013 | Tatarkiewicz et al. |
| 8,485,180 B2 | 7/2013 | Smutney et al. |
| 8,497,240 B2 | 7/2013 | Levy et al. |
| 8,499,757 B2 | 8/2013 | Smutney et al. |
| 8,546,327 B2 | 10/2013 | Dimarchi et al. |
| 8,551,946 B2 | 10/2013 | Dimarchi et al. |
| 8,551,947 B2 | 10/2013 | Coolidge et al. |
| 8,557,769 B2 | 10/2013 | Coskun et al. |
| 8,557,771 B2 | 10/2013 | Fan et al. |
| 8,569,481 B2 | 10/2013 | Köster et al. |
| 8,575,097 B2 | 11/2013 | Xu et al. |
| 8,580,919 B2 | 11/2013 | Bossard et al. |
| 8,598,120 B2 | 12/2013 | Soares et al. |
| 8,603,761 B2 | 12/2013 | Nicolaou et al. |
| 8,603,969 B2 | 12/2013 | Levy et al. |
| 8,614,181 B2 | 12/2013 | Juul-Mortensen et al. |
| 8,617,613 B2 | 12/2013 | Wright et al. |
| 8,636,001 B2 | 1/2014 | Smutney et al. |
| 8,641,683 B2 | 2/2014 | Glejbol et al. |
| 8,642,544 B2 | 2/2014 | Alfaro-Lopez et al. |
| 8,664,232 B2 | 3/2014 | Himmelsbach et al. |
| 8,669,228 B2 | 3/2014 | Dimarchi et al. |
| 8,673,927 B2 | 3/2014 | Dugi et al. |
| 8,697,647 B2 | 4/2014 | Levy et al. |
| 8,697,838 B2 | 4/2014 | Dimarchi et al. |
| 8,710,002 B2 | 4/2014 | Rothkopf |

(56) References Cited

U.S. PATENT DOCUMENTS

| | | |
|---|---|---|
| 8,710,181 B2 | 4/2014 | Christiansen et al. |
| 8,716,221 B2 | 5/2014 | Lv et al. |
| 8,729,018 B2 | 5/2014 | Chilkoti |
| 8,729,019 B2 | 5/2014 | Oberg et al. |
| 8,735,350 B2 | 5/2014 | Shechter et al. |
| 8,748,376 B2 | 6/2014 | Ludvigsen et al. |
| 8,759,290 B2 | 6/2014 | James |
| 8,759,295 B2 | 6/2014 | Ghosh et al. |
| 8,772,232 B2 | 7/2014 | Lau et al. |
| 8,778,872 B2 | 7/2014 | Dimarchi et al. |
| 8,785,396 B2 | 7/2014 | Leone-Bay et al. |
| 8,801,700 B2 | 8/2014 | Alessi et al. |
| 8,809,499 B2 | 8/2014 | Fan et al. |
| 8,816,047 B2 | 8/2014 | Levetan et al. |
| 8,841,255 B2 | 9/2014 | Chilkoti |
| 8,853,157 B2 | 10/2014 | Knudsen et al. |
| 8,853,160 B2 | 10/2014 | Greig et al. |
| 8,877,252 B2 | 11/2014 | Wright et al. |
| 8,877,709 B2 | 11/2014 | Shechter et al. |
| 8,883,449 B2 | 11/2014 | Kjeldsen et al. |
| 8,889,619 B2 | 11/2014 | Bai et al. |
| 8,900,593 B2 | 12/2014 | Day et al. |
| 8,969,288 B2 | 3/2015 | Dimarchi et al. |
| 8,969,294 B2 | 3/2015 | Bianchi et al. |
| 8,980,830 B2 | 3/2015 | Dimarchi et al. |
| 8,981,047 B2 | 3/2015 | Dimarchi et al. |
| 9,018,164 B2 | 4/2015 | Dimarchi et al. |
| 9,181,305 B2 | 11/2015 | Haack et al. |
| 9,365,632 B2 | 6/2016 | Haack et al. |
| 9,670,261 B2 | 6/2017 | Haack et al. |
| 9,694,053 B2 | 7/2017 | Haack et al. |
| 9,745,360 B2 | 8/2017 | Haack et al. |
| 9,750,788 B2 | 9/2017 | Kadereit et al. |
| 9,751,926 B2 | 9/2017 | Kadereit et al. |
| 9,758,561 B2 | 9/2017 | Bossart et al. |
| 9,771,406 B2 | 9/2017 | Bossart et al. |
| 9,775,904 B2 | 10/2017 | Bossart et al. |
| 9,789,165 B2 | 10/2017 | Kadereit et al. |
| 2001/0011071 A1 | 8/2001 | Knudsen et al. |
| 2001/0027180 A1 | 10/2001 | Isaacs |
| 2001/0043934 A1 | 11/2001 | L'Italien et al. |
| 2002/0061838 A1 | 5/2002 | Holmquist et al. |
| 2002/0137666 A1 | 9/2002 | Beeley et al. |
| 2002/0146405 A1 | 10/2002 | Coolidge et al. |
| 2003/0036504 A1 | 2/2003 | Kolterman et al. |
| 2003/0050237 A1 | 3/2003 | Kim et al. |
| 2003/0069182 A1 | 4/2003 | Rinella et al. |
| 2003/0087820 A1 | 5/2003 | Young et al. |
| 2003/0087821 A1 | 5/2003 | Beeley et al. |
| 2003/0092606 A1 | 5/2003 | L'Italien et al. |
| 2003/0119021 A1 | 6/2003 | Koster et al. |
| 2003/0119734 A1 | 6/2003 | Flink et al. |
| 2003/0180287 A1 | 9/2003 | Gombotz et al. |
| 2003/0216287 A1 | 11/2003 | Tang |
| 2003/0220255 A1 | 11/2003 | Knudsen et al. |
| 2004/0023871 A1 | 2/2004 | Hiles et al. |
| 2004/0029784 A1 | 2/2004 | Hathaway |
| 2004/0037826 A1 | 2/2004 | Michelsen et al. |
| 2004/0038865 A1 | 2/2004 | Gelber et al. |
| 2004/0048783 A1 | 3/2004 | Brunner-Schwarz et al. |
| 2004/0097510 A1 | 5/2004 | Himmelsbach et al. |
| 2004/0209255 A1 | 10/2004 | Koster et al. |
| 2004/0209803 A1 | 10/2004 | Baron et al. |
| 2004/0242853 A1 | 12/2004 | Greig et al. |
| 2004/0266670 A9 | 12/2004 | Hiles et al. |
| 2004/0266678 A1 | 12/2004 | Beeley et al. |
| 2004/0266683 A1 | 12/2004 | Hathaway et al. |
| 2004/0266692 A1 | 12/2004 | Young et al. |
| 2005/0009742 A1 | 1/2005 | Bertilsson et al. |
| 2005/0009847 A1 | 1/2005 | Bertilsson et al. |
| 2005/0009988 A1 | 1/2005 | Harris et al. |
| 2005/0043238 A1 | 2/2005 | Young et al. |
| 2005/0059601 A1 | 3/2005 | Beeley et al. |
| 2005/0096276 A1 | 5/2005 | Coolidge et al. |
| 2005/0101537 A1 | 5/2005 | Beeley et al. |
| 2005/0106214 A1 | 5/2005 | Chen |
| 2005/0143303 A1 | 6/2005 | Quay et al. |
| 2005/0171019 A1 | 8/2005 | Young et al. |
| 2005/0186174 A1 | 8/2005 | Bossard |
| 2005/0197287 A1 | 9/2005 | Mack et al. |
| 2005/0209142 A1 | 9/2005 | Bertilsson et al. |
| 2005/0215469 A1 | 9/2005 | Beeley et al. |
| 2005/0215475 A1 | 9/2005 | Ong et al. |
| 2005/0267034 A1 | 12/2005 | Prickett et al. |
| 2005/0271702 A1 | 12/2005 | Wright et al. |
| 2005/0281879 A1 | 12/2005 | Chen et al. |
| 2006/0003918 A1 | 1/2006 | Kim et al. |
| 2006/0057137 A1 | 3/2006 | Steiness |
| 2006/0069029 A1 | 3/2006 | Kolterman et al. |
| 2006/0073182 A1 | 4/2006 | Wong et al. |
| 2006/0074012 A1 | 4/2006 | Hiles et al. |
| 2006/0079448 A1 | 4/2006 | Bertilsson et al. |
| 2006/0084605 A1 | 4/2006 | Engelund et al. |
| 2006/0094652 A1 | 5/2006 | Levy et al. |
| 2006/0094653 A1 | 5/2006 | Levy et al. |
| 2006/0110423 A1 | 5/2006 | Wright et al. |
| 2006/0135586 A1 | 6/2006 | Kozlowski et al. |
| 2006/0135747 A1 | 6/2006 | Levy et al. |
| 2006/0148713 A1 | 7/2006 | Beeley et al. |
| 2006/0165733 A1 | 7/2006 | Betz et al. |
| 2006/0171920 A1 | 8/2006 | Shechter et al. |
| 2006/0172001 A1 | 8/2006 | Ong et al. |
| 2006/0178304 A1 | 8/2006 | Juul-Mortensen et al. |
| 2006/0183677 A1 | 8/2006 | Young et al. |
| 2006/0183682 A1 | 8/2006 | Juul-Mortensen |
| 2006/0210614 A1 | 9/2006 | Quay et al. |
| 2006/0247167 A1 | 11/2006 | Schlein et al. |
| 2006/0275252 A1 | 12/2006 | Harris et al. |
| 2006/0287221 A1 | 12/2006 | Knudsen et al. |
| 2006/0293232 A1 | 12/2006 | Levy et al. |
| 2006/0293499 A1 | 12/2006 | Bentley et al. |
| 2007/0010424 A1 | 1/2007 | Pedersen et al. |
| 2007/0010656 A1 | 1/2007 | Beeley et al. |
| 2007/0014818 A1 | 1/2007 | Betz et al. |
| 2007/0021336 A1 | 1/2007 | Anderson et al. |
| 2007/0037750 A1 | 2/2007 | Young et al. |
| 2007/0049531 A1 | 3/2007 | Knudsen et al. |
| 2007/0059373 A1 | 3/2007 | Oberg |
| 2007/0059374 A1 | 3/2007 | Hokenson et al. |
| 2007/0065469 A1 | 3/2007 | Betz et al. |
| 2007/0066528 A1 | 3/2007 | Beeley et al. |
| 2007/0092482 A1 | 4/2007 | Bossard et al. |
| 2007/0129284 A1 | 6/2007 | Kjeldsen et al. |
| 2007/0166352 A1 | 7/2007 | Wright et al. |
| 2007/0196416 A1 | 8/2007 | Li et al. |
| 2007/0281940 A1 | 12/2007 | Dugi et al. |
| 2008/0071063 A1 | 3/2008 | Allan et al. |
| 2008/0091176 A1 | 4/2008 | Alessi et al. |
| 2008/0119393 A1 | 5/2008 | Beeley et al. |
| 2008/0119569 A1 | 5/2008 | Wright et al. |
| 2008/0125348 A1 | 5/2008 | Wright et al. |
| 2008/0125349 A1 | 5/2008 | Wright et al. |
| 2008/0125351 A1 | 5/2008 | Wright et al. |
| 2008/0125353 A1 | 5/2008 | Hiles et al. |
| 2008/0125361 A1 | 5/2008 | Ludvigsen et al. |
| 2008/0171848 A1 | 7/2008 | Christiansen et al. |
| 2008/0176802 A1 | 7/2008 | Prickett et al. |
| 2008/0176804 A1 | 7/2008 | Mack et al. |
| 2008/0200390 A1 | 8/2008 | Prickett et al. |
| 2008/0213288 A1 | 9/2008 | Michelsen et al. |
| 2008/0214467 A1 | 9/2008 | Prickett et al. |
| 2008/0233053 A1 | 9/2008 | Gross et al. |
| 2008/0249007 A1 | 10/2008 | Lau et al. |
| 2008/0249018 A1 | 10/2008 | Kolterman et al. |
| 2008/0249089 A1 | 10/2008 | Himmelsbach et al. |
| 2008/0255159 A1 | 10/2008 | Himmelsbach et al. |
| 2008/0260838 A1 | 10/2008 | Hokenson et al. |
| 2008/0260847 A1 | 10/2008 | Wright et al. |
| 2008/0274952 A1 | 11/2008 | Soares et al. |
| 2008/0280814 A1 | 11/2008 | Ludvigsen et al. |
| 2008/0300171 A1 | 12/2008 | Balkan et al. |
| 2008/0312157 A1 | 12/2008 | Levy et al. |
| 2008/0318865 A1 | 12/2008 | Juul-Mortensen |
| 2009/0011976 A1 | 1/2009 | Ludvigsen et al. |

(56) References Cited

U.S. PATENT DOCUMENTS

| | | |
|---|---|---|
| 2009/0018053 A1 | 1/2009 | L'Italien et al. |
| 2009/0029913 A1 | 1/2009 | Beeley et al. |
| 2009/0035253 A1 | 2/2009 | Wright et al. |
| 2009/0036364 A1 | 2/2009 | Levy et al. |
| 2009/0043264 A1 | 2/2009 | Glejbol et al. |
| 2009/0054315 A1 | 2/2009 | Bock et al. |
| 2009/0069226 A1 | 3/2009 | Ong et al. |
| 2009/0082255 A1 | 3/2009 | Brunner-Schwarz et al. |
| 2009/0088369 A1 | 4/2009 | Steiness |
| 2009/0098130 A1 | 4/2009 | Bradshaw et al. |
| 2009/0110647 A1 | 4/2009 | Richardson et al. |
| 2009/0111749 A1 | 4/2009 | Richardson et al. |
| 2009/0137456 A1 | 5/2009 | Dimarchi et al. |
| 2009/0137466 A1 | 5/2009 | Anderson et al. |
| 2009/0163423 A1 | 6/2009 | Young et al. |
| 2009/0170750 A1 | 7/2009 | Kjeldsen et al. |
| 2009/0176704 A1 | 7/2009 | Beeley et al. |
| 2009/0180953 A1 | 7/2009 | Gotthardt et al. |
| 2009/0186817 A1 | 7/2009 | Ghosh et al. |
| 2009/0186819 A1 | 7/2009 | Carrier et al. |
| 2009/0203597 A1 | 8/2009 | Rabinovitch et al. |
| 2009/0203603 A1 | 8/2009 | Baron et al. |
| 2009/0215688 A1 | 8/2009 | Knudsen et al. |
| 2009/0215694 A1 | 8/2009 | Kolterman et al. |
| 2009/0221485 A1 | 9/2009 | James |
| 2009/0226431 A1 | 9/2009 | Habib |
| 2009/0232775 A1 | 9/2009 | Bertilsson et al. |
| 2009/0232807 A1 | 9/2009 | Glaesner et al. |
| 2009/0232891 A1 | 9/2009 | Gelber et al. |
| 2009/0239796 A1 | 9/2009 | Fineman et al. |
| 2009/0247463 A1 | 10/2009 | Wright et al. |
| 2009/0253625 A1 | 10/2009 | Greig et al. |
| 2009/0258818 A1 | 10/2009 | Surolia et al. |
| 2009/0264352 A1 | 10/2009 | Anderson et al. |
| 2009/0280169 A1 | 11/2009 | Leonard |
| 2009/0280170 A1 | 11/2009 | Lee et al. |
| 2009/0286716 A1 | 11/2009 | Knudsen et al. |
| 2009/0286723 A1 | 11/2009 | Levy et al. |
| 2009/0291886 A1 | 11/2009 | Ong et al. |
| 2009/0298757 A1 | 12/2009 | Bloom et al. |
| 2009/0308390 A1 | 12/2009 | Smutney et al. |
| 2009/0308391 A1 | 12/2009 | Smutney et al. |
| 2009/0308392 A1 | 12/2009 | Smutney et al. |
| 2009/0325860 A1 | 12/2009 | Constantino et al. |
| 2010/0009904 A1 | 1/2010 | Lv et al. |
| 2010/0016806 A1 | 1/2010 | Glejbol et al. |
| 2010/0022455 A1 | 1/2010 | Chilkoti |
| 2010/0029554 A1 | 2/2010 | Ghosh et al. |
| 2010/0041867 A1 | 2/2010 | Shechter et al. |
| 2010/0056451 A1 | 3/2010 | Juul-Mortensen et al. |
| 2010/0087365 A1 | 4/2010 | Cherif-Cheikh et al. |
| 2010/0099619 A1 | 4/2010 | Levy et al. |
| 2010/0137558 A1 | 6/2010 | Lee et al. |
| 2010/0152097 A1 | 6/2010 | Wright et al. |
| 2010/0152111 A1 | 6/2010 | Wright et al. |
| 2010/0168011 A1 | 7/2010 | Jennings, Jr. et al. |
| 2010/0173844 A1 | 7/2010 | Ludvigsen et al. |
| 2010/0185184 A1 | 7/2010 | Alessi et al. |
| 2010/0190699 A1 | 7/2010 | Dimarchi et al. |
| 2010/0190701 A1 | 7/2010 | Day et al. |
| 2010/0190715 A1 | 7/2010 | Schlein et al. |
| 2010/0196405 A1 | 8/2010 | Ng et al. |
| 2010/0197565 A1 | 8/2010 | Smutney et al. |
| 2010/0210505 A1 | 8/2010 | Bossard et al. |
| 2010/0216692 A1 | 8/2010 | Brunner-Schwarz et al. |
| 2010/0240586 A1 | 9/2010 | Bao et al. |
| 2010/0247661 A1 | 9/2010 | Hokenson et al. |
| 2010/0261637 A1 | 10/2010 | Spetzler et al. |
| 2010/0278924 A1 | 11/2010 | Oberg et al. |
| 2010/0292172 A1 | 11/2010 | Ghosh et al. |
| 2010/0317056 A1 | 12/2010 | Tiwari et al. |
| 2010/0317576 A1 | 12/2010 | Rothkopf |
| 2010/0331246 A1 | 12/2010 | Dimarchi et al. |
| 2011/0003004 A1 | 1/2011 | Hokenson et al. |
| 2011/0034373 A1 | 2/2011 | Coskun et al. |
| 2011/0034377 A1 | 2/2011 | Young et al. |
| 2011/0059181 A1 | 3/2011 | Hu et al. |
| 2011/0065633 A1 | 3/2011 | Dimarchi et al. |
| 2011/0065731 A1 | 3/2011 | Dugi et al. |
| 2011/0071076 A1 | 3/2011 | Beeley et al. |
| 2011/0091420 A1 | 4/2011 | Liu et al. |
| 2011/0097386 A1 | 4/2011 | Steiner et al. |
| 2011/0097751 A1 | 4/2011 | Nicolaou et al. |
| 2011/0098217 A1 | 4/2011 | Dimarchi et al. |
| 2011/0112277 A1 | 5/2011 | Kozlowski et al. |
| 2011/0118136 A1 | 5/2011 | Köster et al. |
| 2011/0123487 A1 | 5/2011 | Chilkoti |
| 2011/0129522 A1 | 6/2011 | Mevorat-Kaplan et al. |
| 2011/0136737 A1 | 6/2011 | Levy et al. |
| 2011/0152181 A1 | 6/2011 | Alsina-Fernandez et al. |
| 2011/0152182 A1 | 6/2011 | Alsina-Fernandez et al. |
| 2011/0152185 A1 | 6/2011 | Plum et al. |
| 2011/0166062 A1 | 7/2011 | Dimarchi et al. |
| 2011/0166554 A1 | 7/2011 | Alessi et al. |
| 2011/0171178 A1 | 7/2011 | Levetan et al. |
| 2011/0178014 A1 | 7/2011 | Hathaway et al. |
| 2011/0178242 A1 | 7/2011 | Harris et al. |
| 2011/0190200 A1 | 8/2011 | Dimarchi et al. |
| 2011/0195897 A1 | 8/2011 | Kajihara et al. |
| 2011/0230409 A1 | 9/2011 | Knudsen et al. |
| 2011/0237503 A1 | 9/2011 | Alsina-Fernandez et al. |
| 2011/0237510 A1 | 9/2011 | Steiner et al. |
| 2011/0245162 A1 | 10/2011 | Fineman et al. |
| 2011/0257092 A1 | 10/2011 | Dimarchi et al. |
| 2011/0263496 A1 | 10/2011 | Fineman et al. |
| 2011/0281798 A1 | 11/2011 | Kolterman et al. |
| 2011/0288003 A1 | 11/2011 | Dimarchi et al. |
| 2011/0301080 A1 | 12/2011 | Bush et al. |
| 2011/0301081 A1 | 12/2011 | Becker et al. |
| 2011/0301084 A1 | 12/2011 | Lau et al. |
| 2011/0306549 A1 | 12/2011 | Tatarkiewicz et al. |
| 2012/0004168 A1 | 1/2012 | Young et al. |
| 2012/0021978 A1 | 1/2012 | Werner et al. |
| 2012/0040899 A1 | 2/2012 | Costello et al. |
| 2012/0046222 A1 | 2/2012 | Alfaro-Lopez et al. |
| 2012/0071510 A1 | 3/2012 | Leone-Bay et al. |
| 2012/0071817 A1 | 3/2012 | Ward et al. |
| 2012/0094356 A1 | 4/2012 | Chung et al. |
| 2012/0100070 A1 | 4/2012 | Ahn et al. |
| 2012/0122783 A1 | 5/2012 | Dimarchi et al. |
| 2012/0135922 A1 | 5/2012 | Prickett et al. |
| 2012/0136318 A1 | 5/2012 | Lanin et al. |
| 2012/0148586 A1 | 6/2012 | Chou et al. |
| 2012/0149639 A1 | 6/2012 | Balkan et al. |
| 2012/0157932 A1 | 6/2012 | Glejbol et al. |
| 2012/0172295 A1 | 7/2012 | Dimarchi et al. |
| 2012/0177697 A1 | 7/2012 | Chen |
| 2012/0196795 A1 | 8/2012 | Ku et al. |
| 2012/0196796 A1 | 8/2012 | Soares et al. |
| 2012/0196802 A1 | 8/2012 | Lv et al. |
| 2012/0196804 A1 | 8/2012 | Dimarchi et al. |
| 2012/0208755 A1 | 8/2012 | Leung et al. |
| 2012/0208831 A1 | 8/2012 | Himmelsbach et al. |
| 2012/0209213 A1 | 8/2012 | Theucher |
| 2012/0225810 A1 | 9/2012 | Pedersen et al. |
| 2012/0231022 A1 | 9/2012 | Bass et al. |
| 2012/0238493 A1 | 9/2012 | Dimarchi et al. |
| 2012/0238496 A1 | 9/2012 | Fan et al. |
| 2012/0253023 A1 | 10/2012 | Levy et al. |
| 2012/0258912 A1 | 10/2012 | Bentley et al. |
| 2012/0258985 A1 | 10/2012 | Kozlowski et al. |
| 2012/0264683 A1 | 10/2012 | Coskun et al. |
| 2012/0264684 A1 | 10/2012 | Kajihara et al. |
| 2012/0276098 A1 | 11/2012 | Hamilton et al. |
| 2012/0277154 A1 | 11/2012 | Fan et al. |
| 2012/0283179 A1 | 11/2012 | Brunner-Schwarz et al. |
| 2012/0294855 A1 | 11/2012 | Van Cauter et al. |
| 2012/0295836 A1 | 11/2012 | Knudsen et al. |
| 2012/0295846 A1 | 11/2012 | Hagendorf et al. |
| 2012/0295850 A1 | 11/2012 | Tatarkiewicz et al. |
| 2012/0302501 A1 | 11/2012 | Coolidge et al. |
| 2012/0309975 A1 | 12/2012 | Colca et al. |
| 2012/0316108 A1 | 12/2012 | Chen et al. |
| 2012/0316138 A1 | 12/2012 | Colca et al. |

(56) References Cited

U.S. PATENT DOCUMENTS

| | | |
|---|---|---|
| 2012/0322725 A1 | 12/2012 | Dimarchi et al. |
| 2012/0322728 A1 | 12/2012 | Colca et al. |
| 2012/0329715 A1 | 12/2012 | Greig et al. |
| 2013/0005664 A1 | 1/2013 | Chilkoti |
| 2013/0023470 A1 | 1/2013 | Young et al. |
| 2013/0023471 A1 | 1/2013 | Rabinovitch et al. |
| 2013/0046245 A1 | 2/2013 | Raab et al. |
| 2013/0053350 A1 | 2/2013 | Colca et al. |
| 2013/0065826 A1 | 3/2013 | Soula et al. |
| 2013/0079277 A1 | 3/2013 | Chilkoti |
| 2013/0079278 A1 | 3/2013 | Lau et al. |
| 2013/0084277 A1 | 4/2013 | Arnold et al. |
| 2013/0085099 A1 | 4/2013 | Chilkoti |
| 2013/0085104 A1 | 4/2013 | Chilkoti |
| 2013/0089878 A1 | 4/2013 | Nicolaou et al. |
| 2013/0090286 A1 | 4/2013 | Dimarchi et al. |
| 2013/0095037 A1 | 4/2013 | Gotthardt et al. |
| 2013/0096258 A1 | 4/2013 | Bossard et al. |
| 2013/0104887 A1 | 5/2013 | Smutney et al. |
| 2013/0116172 A1 | 5/2013 | Dimarchi et al. |
| 2013/0116175 A1 | 5/2013 | Shechter et al. |
| 2013/0118491 A1 | 5/2013 | Richardson et al. |
| 2013/0123178 A1 | 5/2013 | Dimarchi et al. |
| 2013/0123462 A1 | 5/2013 | Dimarchi et al. |
| 2013/0125886 A1 | 5/2013 | Richardson et al. |
| 2013/0130977 A1 | 5/2013 | Wright et al. |
| 2013/0137631 A1 | 5/2013 | Levy et al. |
| 2013/0137645 A1 | 5/2013 | Rosendahl |
| 2013/0142795 A1 | 6/2013 | Bai et al. |
| 2013/0156849 A1 | 6/2013 | De Fougerolles et al. |
| 2013/0157934 A1 | 6/2013 | Dimarchi et al. |
| 2013/0157953 A1 | 6/2013 | Petersen et al. |
| 2013/0164310 A1 | 6/2013 | Annathur et al. |
| 2013/0165370 A1 | 6/2013 | Bock et al. |
| 2013/0165379 A1 | 6/2013 | Kolterman et al. |
| 2013/0172274 A1 | 7/2013 | Chilkoti |
| 2013/0178411 A1 | 7/2013 | Chilkoti |
| 2013/0178415 A1 | 7/2013 | Soula et al. |
| 2013/0184203 A1 | 7/2013 | Alfaro-Lopez et al. |
| 2013/0184443 A1 | 7/2013 | Bentley et al. |
| 2013/0189365 A1 | 7/2013 | Hokenson et al. |
| 2013/0199527 A1 | 8/2013 | Smutney et al. |
| 2013/0203660 A1 | 8/2013 | Day et al. |
| 2013/0209586 A1 | 8/2013 | Hathaway et al. |
| 2013/0217622 A1 | 8/2013 | Lee et al. |
| 2013/0236974 A1 | 9/2013 | De Fougerolles |
| 2013/0237592 A1 | 9/2013 | De Fougerolles et al. |
| 2013/0237593 A1 | 9/2013 | De Fougerolles et al. |
| 2013/0237594 A1 | 9/2013 | De Fougerolles et al. |
| 2013/0244278 A1 | 9/2013 | De Fougerolles et al. |
| 2013/0244279 A1 | 9/2013 | De Fougerolles et al. |
| 2013/0245104 A1 | 9/2013 | De Fougerolles et al. |
| 2013/0245105 A1 | 9/2013 | De Fougerolles et al. |
| 2013/0245106 A1 | 9/2013 | De Fougerolles et al. |
| 2013/0245107 A1 | 9/2013 | De Fougerolles et al. |
| 2013/0252281 A1 | 9/2013 | De Fougerolles et al. |
| 2013/0253043 A1 | 9/2013 | De Fougerolles et al. |
| 2013/0259923 A1 | 10/2013 | Bancel et al. |
| 2013/0259924 A1 | 10/2013 | Bancel et al. |
| 2013/0266640 A1 | 10/2013 | De Fougerolles et al. |
| 2013/0280206 A1 | 10/2013 | Kozlowski et al. |
| 2013/0281368 A1 | 10/2013 | Bilsky et al. |
| 2013/0281374 A1 | 10/2013 | Levy et al. |
| 2013/0284912 A1 | 10/2013 | Vogel et al. |
| 2013/0288958 A1 | 10/2013 | Lau et al. |
| 2013/0289241 A1 | 10/2013 | Bai et al. |
| 2013/0291866 A1 | 11/2013 | Smutney et al. |
| 2013/0291867 A1 | 11/2013 | Smutney et al. |
| 2013/0296236 A1 | 11/2013 | Silvestre et al. |
| 2013/0303442 A1 | 11/2013 | Levy et al. |
| 2013/0310310 A1 | 11/2013 | Liu et al. |
| 2013/0310538 A1 | 11/2013 | Chilkoti |
| 2013/0331322 A1 | 12/2013 | Young et al. |
| 2013/0336893 A1 | 12/2013 | Haack et al. |
| 2013/0338065 A1 | 12/2013 | Smutney et al. |
| 2013/0338071 A1 | 12/2013 | Knudsen et al. |
| 2013/0345134 A1 | 12/2013 | Sauerberg et al. |
| 2014/0007873 A1 | 1/2014 | Smutney et al. |
| 2014/0011732 A1 | 1/2014 | Spetzler et al. |
| 2014/0014106 A1 | 1/2014 | Smutney et al. |
| 2014/0017208 A1 | 1/2014 | Osei |
| 2014/0031281 A1 | 1/2014 | Wright et al. |
| 2014/0038891 A1 | 2/2014 | Prickett et al. |
| 2014/0056924 A1 | 2/2014 | Van Cauter |
| 2014/0066368 A1 | 3/2014 | Mack et al. |
| 2014/0083421 A1 | 3/2014 | Smutney et al. |
| 2014/0088003 A1 | 3/2014 | Wright et al. |
| 2014/0100156 A1 | 4/2014 | Haack et al. |
| 2014/0107019 A1 | 4/2014 | Erickson et al. |
| 2014/0107021 A1 | 4/2014 | Dimarchi et al. |
| 2014/0120120 A1 | 5/2014 | Woo et al. |
| 2014/0121352 A1 | 5/2014 | Shechter et al. |
| 2014/0128318 A1 | 5/2014 | Jung et al. |
| 2014/0128604 A1 | 5/2014 | Himmelsbach et al. |
| 2014/0135348 A1 | 5/2014 | Dugi et al. |
| 2014/0141467 A1 | 5/2014 | Tiwari et al. |
| 2014/0142037 A1 | 5/2014 | Yue |
| 2014/0162943 A1 | 6/2014 | Alfaro-Lopez et al. |
| 2014/0187483 A1 | 7/2014 | Steiness |
| 2014/0200183 A1 | 7/2014 | Hathaway et al. |
| 2014/0206608 A1 | 7/2014 | Haack et al. |
| 2014/0206609 A1 | 7/2014 | Haack et al. |
| 2014/0206613 A1 | 7/2014 | Rabinovitch et al. |
| 2014/0206615 A1 | 7/2014 | Knudsen et al. |
| 2014/0212419 A1 | 7/2014 | Dimarchi et al. |
| 2014/0212440 A1 | 7/2014 | Jung et al. |
| 2014/0213513 A1 | 7/2014 | Haack et al. |
| 2014/0213516 A1 | 7/2014 | Chilkoti |
| 2014/0220029 A1 | 8/2014 | Michelsen et al. |
| 2014/0220134 A1 | 8/2014 | Zierhut et al. |
| 2014/0221280 A1 | 8/2014 | Bloom |
| 2014/0221281 A1 | 8/2014 | Haack et al. |
| 2014/0221282 A1 | 8/2014 | Sun et al. |
| 2014/0227264 A1 | 8/2014 | Hamilton et al. |
| 2014/0235535 A1 | 8/2014 | Erickson et al. |
| 2014/0243263 A1 | 8/2014 | Rothkopf |
| 2014/0249299 A1 | 9/2014 | Levy et al. |
| 2014/0308358 A1 | 10/2014 | Oberg et al. |
| 2014/0309168 A1 | 10/2014 | Rosendahl |
| 2014/0315953 A1 | 10/2014 | Leone-Bay et al. |
| 2015/0011467 A1 | 1/2015 | Bloom et al. |
| 2015/0126440 A1 | 5/2015 | Day et al. |
| 2015/0164995 A1 | 6/2015 | Kadereit et al. |
| 2015/0164996 A1 | 6/2015 | Kadereit et al. |
| 2015/0164997 A1 | 6/2015 | Haack et al. |
| 2015/0166625 A1 | 6/2015 | Haack et al. |
| 2015/0166627 A1 | 6/2015 | Kadereit et al. |
| 2015/0216941 A1 | 8/2015 | Bley et al. |
| 2015/0232527 A1 | 8/2015 | Gong et al. |
| 2015/0315260 A1 | 11/2015 | Bossart et al. |
| 2015/0322128 A1 | 11/2015 | Bossart et al. |
| 2015/0322129 A1 | 11/2015 | Bossart et al. |
| 2015/0368311 A1 | 12/2015 | Haack et al. |
| 2016/0168225 A1 | 6/2016 | Haack et al. |
| 2016/0220643 A1 | 8/2016 | Haack et al. |
| 2016/0235855 A1 | 8/2016 | Xiong et al. |
| 2017/0216406 A1 | 8/2017 | Haack et al. |

FOREIGN PATENT DOCUMENTS

| | | |
|---|---|---|
| CN | 101559041 A | 10/2009 |
| CN | 101663317 A | 3/2010 |
| CN | 101798588 A | 8/2010 |
| CN | 101870728 A | 10/2010 |
| CN | 101601646 B | 3/2011 |
| CN | 102100906 A | 6/2011 |
| CN | 102363633 A | 2/2012 |
| CN | 102421796 A | 4/2012 |
| CN | 101444618 B | 6/2012 |
| CN | 102532301 A | 7/2012 |
| CN | 102649947 A | 8/2012 |
| CN | 102816244 A | 12/2012 |
| CN | 102827270 A | 12/2012 |
| CN | 101670096 B | 1/2013 |

(56) References Cited

FOREIGN PATENT DOCUMENTS

| | | |
|---|---|---|
| CN | 103304660 A | 9/2013 |
| CN | 103421094 A | 12/2013 |
| CN | 102552883 B | 2/2014 |
| CN | 103665148 A | 3/2014 |
| CN | 103833841 A | 6/2014 |
| CN | 103908657 A | 7/2014 |
| CN | 102766204 B | 10/2014 |
| CN | 104926934 A | 9/2015 |
| EP | 1 140 145 B1 | 7/2005 |
| EP | 0 619 322 B1 | 12/2005 |
| EP | 1 609 478 A1 | 12/2005 |
| EP | 1 143 989 B1 | 12/2006 |
| EP | 1 658 856 B1 | 3/2010 |
| EP | 1 684 793 B1 | 9/2011 |
| EP | 1 633 391 B1 | 10/2011 |
| EP | 2 387 989 A2 | 11/2011 |
| EP | 1 633 390 B1 | 1/2012 |
| EP | 2 494 983 A1 | 9/2012 |
| EP | 2 626 368 A2 | 8/2013 |
| EP | 2 664 374 A1 | 11/2013 |
| EP | 1 817 048 B1 | 2/2014 |
| EP | 2 769 990 A2 | 8/2014 |
| JP | 2014-227368 A | 12/2014 |
| KR | 10-2012-0137271 A | 12/2012 |
| KR | 10-2012-0139579 A | 12/2012 |
| KR | 10-2014-0018462 A | 2/2014 |
| KR | 10-2014-0058104 A | 5/2014 |
| KR | 10-2014-0058387 A | 5/2014 |
| KR | 10-2014-0130659 A | 11/2014 |
| KR | 10-2014-0133493 A | 11/2014 |
| RU | 2009121626 A | 2/2011 |
| WO | 1996/019229 A1 | 6/1996 |
| WO | 1998/005351 A1 | 2/1998 |
| WO | 1998/008871 A1 | 3/1998 |
| WO | 1998/030231 A1 | 7/1998 |
| WO | 1999/007404 A1 | 2/1999 |
| WO | 1999/025727 A2 | 5/1999 |
| WO | 1999/025728 A1 | 5/1999 |
| WO | 1999/034822 A1 | 7/1999 |
| WO | 1999/043708 A1 | 9/1999 |
| WO | 1999/047160 A1 | 9/1999 |
| WO | 1999/064061 A1 | 12/1999 |
| WO | 2000/015224 A1 | 3/2000 |
| WO | 2000/037098 A1 | 6/2000 |
| WO | 2000/041546 A2 | 7/2000 |
| WO | 2000/041548 A2 | 7/2000 |
| WO | 2000/055119 A1 | 9/2000 |
| WO | 2000/066629 A1 | 11/2000 |
| WO | 2000/071175 A1 | 11/2000 |
| WO | 2000/073331 A2 | 12/2000 |
| WO | 2001/051078 A1 | 7/2001 |
| WO | 2002/016309 A1 | 2/2002 |
| WO | 2002/034285 A2 | 5/2002 |
| WO | 2002/067989 A1 | 9/2002 |
| WO | 2003/011892 A2 | 2/2003 |
| WO | 2003/020201 A2 | 3/2003 |
| WO | 2003/061362 A2 | 7/2003 |
| WO | 2003/077851 A2 | 9/2003 |
| WO | 2003/084563 A1 | 10/2003 |
| WO | WO 2003087139 A2 | 10/2003 |
| WO | 2003/092581 A2 | 11/2003 |
| WO | 2003/099314 A1 | 12/2003 |
| WO | 2003/101395 A2 | 12/2003 |
| WO | 2003/105888 A1 | 12/2003 |
| WO | 2003/105897 A1 | 12/2003 |
| WO | 2004/004779 A1 | 1/2004 |
| WO | 2004/004780 A1 | 1/2004 |
| WO | 2004/004781 A1 | 1/2004 |
| WO | 2004/005342 A1 | 1/2004 |
| WO | 2004/012672 A2 | 2/2004 |
| WO | 2004/018468 A2 | 3/2004 |
| WO | 2004/035623 A2 | 4/2004 |
| WO | 2004/045592 A2 | 6/2004 |
| WO | 2004/056313 A2 | 7/2004 |
| WO | 2004/056317 A2 | 7/2004 |
| WO | 2004/062685 A2 | 7/2004 |
| WO | 2004/089280 A2 | 10/2004 |
| WO | 2004/089985 A1 | 10/2004 |
| WO | 2004/105781 A2 | 12/2004 |
| WO | 2004/105790 A1 | 12/2004 |
| WO | 2005/000222 A2 | 1/2005 |
| WO | 2005/000360 A2 | 1/2005 |
| WO | 2005/012347 A2 | 2/2005 |
| WO | 2005/021022 A2 | 3/2005 |
| WO | 2005/046716 A1 | 5/2005 |
| WO | 2005/048989 A1 | 6/2005 |
| WO | 2005/049061 A2 | 6/2005 |
| WO | 2005/049069 A1 | 6/2005 |
| WO | 2005/054291 A1 | 6/2005 |
| WO | 2005/077072 A2 | 8/2005 |
| WO | 2005/077094 A2 | 8/2005 |
| WO | 2005/081619 A2 | 9/2005 |
| WO | 2005/102293 A1 | 11/2005 |
| WO | 2005/110425 A1 | 11/2005 |
| WO | 2005/115437 A2 | 12/2005 |
| WO | 2005/117584 A2 | 12/2005 |
| WO | 2005/120492 A1 | 12/2005 |
| WO | 2006/017688 A2 | 2/2006 |
| WO | 2006/024275 A2 | 3/2006 |
| WO | 2006/024631 A2 | 3/2006 |
| WO | 2006/029634 A2 | 3/2006 |
| WO | 2006/037811 A2 | 4/2006 |
| WO | 2006/044531 A2 | 4/2006 |
| WO | 2006/051103 A2 | 5/2006 |
| WO | 2006/051110 A2 | 5/2006 |
| WO | 2006/066024 A2 | 6/2006 |
| WO | 2006/069388 A2 | 6/2006 |
| WO | 2006/073890 A2 | 7/2006 |
| WO | 2006/074600 A1 | 7/2006 |
| WO | 2006/083254 A1 | 8/2006 |
| WO | 2006/086769 A2 | 8/2006 |
| WO | 2006/097535 A2 | 9/2006 |
| WO | 2006/110887 A2 | 10/2006 |
| WO | 2006/114396 A2 | 11/2006 |
| WO | 2006/125763 A1 | 11/2006 |
| WO | WO 2006127948 A2 | 11/2006 |
| WO | 2006/134340 A2 | 12/2006 |
| WO | 2006/138572 A2 | 12/2006 |
| WO | 2007/019331 A2 | 2/2007 |
| WO | 2007/022123 A2 | 3/2007 |
| WO | 2007/024700 A2 | 3/2007 |
| WO | 2007/033316 A2 | 3/2007 |
| WO | 2007/033372 A2 | 3/2007 |
| WO | 2007/035665 A1 | 3/2007 |
| WO | 2007/047834 A2 | 4/2007 |
| WO | 2007/047922 A2 | 4/2007 |
| WO | 2007/056362 A2 | 5/2007 |
| WO | 2007/064691 A1 | 6/2007 |
| WO | 2007/065156 A2 | 6/2007 |
| WO | 2007/067964 A2 | 6/2007 |
| WO | 2007/075534 A2 | 7/2007 |
| WO | 2007/109354 A2 | 9/2007 |
| WO | 2007/120899 A2 | 10/2007 |
| WO | 2007/121411 A2 | 10/2007 |
| WO | 2007/128761 A2 | 11/2007 |
| WO | 2007/133778 A2 | 11/2007 |
| WO | 2007/139941 A2 | 12/2007 |
| WO | 2007/140284 A2 | 12/2007 |
| WO | 2008/021133 A2 | 2/2008 |
| WO | 2008/021560 A2 | 2/2008 |
| WO | 2008/023050 A1 | 2/2008 |
| WO | 2008/038147 A2 | 4/2008 |
| WO | 2008/058461 A1 | 5/2008 |
| WO | 2008/071972 A1 | 6/2008 |
| WO | 2008/073448 A2 | 6/2008 |
| WO | 2008/081418 A1 | 7/2008 |
| WO | 2008/086086 A2 | 7/2008 |
| WO | 2008/098212 A2 | 8/2008 |
| WO | 2008/101017 A2 | 8/2008 |
| WO | 2008/148839 A2 | 12/2008 |
| WO | 2008/152403 A1 | 12/2008 |
| WO | 2009/020802 A2 | 2/2009 |
| WO | 2009/024015 A1 | 2/2009 |
| WO | 2009/029847 A1 | 3/2009 |

(56) References Cited

FOREIGN PATENT DOCUMENTS

| | | |
|---|---|---|
| WO | 2009/030771 A1 | 3/2009 |
| WO | 2009/035540 A2 | 3/2009 |
| WO | 2009/055740 A2 | 4/2009 |
| WO | 2009/055742 A2 | 4/2009 |
| WO | 2009/058662 A2 | 5/2009 |
| WO | 2009/058734 A1 | 5/2009 |
| WO | 2009/063072 A2 | 5/2009 |
| WO | 2009/067268 A1 | 5/2009 |
| WO | WO 2009087081 A2 | 7/2009 |
| WO | 2009/095479 A2 | 8/2009 |
| WO | 2009/099763 A1 | 8/2009 |
| WO | 2009/113099 A2 | 9/2009 |
| WO | 2009/137078 A1 | 11/2009 |
| WO | 2009/137080 A1 | 11/2009 |
| WO | 2009/143014 A1 | 11/2009 |
| WO | 2009/143285 A2 | 11/2009 |
| WO | 2009/152477 A2 | 12/2009 |
| WO | 2009/153960 A1 | 12/2009 |
| WO | 2009/155257 A1 | 12/2009 |
| WO | 2009/155258 A2 | 12/2009 |
| WO | 2009/158704 A2 | 12/2009 |
| WO | 2010/011439 A2 | 1/2010 |
| WO | 2010/013012 A2 | 2/2010 |
| WO | 2010/043566 A2 | 4/2010 |
| WO | 2010/070251 A1 | 6/2010 |
| WO | 2010/070252 A1 | 6/2010 |
| WO | 2010/070253 A1 | 6/2010 |
| WO | 2010/070255 A1 | 6/2010 |
| WO | 2010/071807 A1 | 6/2010 |
| WO | 2010/096052 A1 | 8/2010 |
| WO | 2010/096142 A1 | 8/2010 |
| WO | 2010/102148 A2 | 9/2010 |
| WO | 2010/120476 A2 | 10/2010 |
| WO | 2010/121559 A1 | 10/2010 |
| WO | 2010/123290 A2 | 10/2010 |
| WO | 2010/133675 A1 | 11/2010 |
| WO | 2010/133676 A1 | 11/2010 |
| WO | 2010/138671 A1 | 12/2010 |
| WO | 2010/142665 A1 | 12/2010 |
| WO | 2010/148089 A1 | 12/2010 |
| WO | 2011/000095 A1 | 1/2011 |
| WO | 2011/006497 A1 | 1/2011 |
| WO | 2011/011675 A1 | 1/2011 |
| WO | 2011/012718 A1 | 2/2011 |
| WO | 2011/020319 A1 | 2/2011 |
| WO | 2011/020320 A1 | 2/2011 |
| WO | 2011/024110 A2 | 3/2011 |
| WO | 2011/039096 A1 | 4/2011 |
| WO | 2011/049713 A2 | 4/2011 |
| WO | 2011/052523 A1 | 5/2011 |
| WO | 2011/056713 A2 | 5/2011 |
| WO | 2011/058082 A1 | 5/2011 |
| WO | 2011/058083 A1 | 5/2011 |
| WO | WO 2011051864 A1 | 5/2011 |
| WO | 2011/075393 A1 | 6/2011 |
| WO | 2011/075514 A1 | 6/2011 |
| WO | 2011/075623 A1 | 6/2011 |
| WO | 2011/080103 A1 | 7/2011 |
| WO | 2011/084453 A1 | 7/2011 |
| WO | 2011/084456 A1 | 7/2011 |
| WO | 2011/084459 A1 | 7/2011 |
| WO | 2011/087671 A1 | 7/2011 |
| WO | 2011/087672 A1 | 7/2011 |
| WO | 2011/088837 A1 | 7/2011 |
| WO | 2011/094337 A1 | 8/2011 |
| WO | 2011/109784 A1 | 9/2011 |
| WO | 2011/117415 A1 | 9/2011 |
| WO | 2011/117416 A1 | 9/2011 |
| WO | 2011/119657 A1 | 9/2011 |
| WO | 2011/143208 A1 | 11/2011 |
| WO | 2011/143209 A1 | 11/2011 |
| WO | 2011/144751 A1 | 11/2011 |
| WO | WO 2011144673 A2 | 11/2011 |
| WO | 2011/153965 A1 | 12/2011 |
| WO | 2011/156407 A2 | 12/2011 |
| WO | 2011/160630 A2 | 12/2011 |
| WO | 2011/162830 A2 | 12/2011 |
| WO | 2011/163012 A2 | 12/2011 |
| WO | 2011/163272 A2 | 12/2011 |
| WO | 2011/163473 A1 | 12/2011 |
| WO | 2012/012352 A1 | 1/2012 |
| WO | 2012/012460 A1 | 1/2012 |
| WO | 2012/015975 A2 | 2/2012 |
| WO | 2012/031518 A1 | 3/2012 |
| WO | 2012/035139 A1 | 3/2012 |
| WO | 2012/050923 A2 | 4/2012 |
| WO | 2012/059762 A1 | 5/2012 |
| WO | 2012/064892 A1 | 5/2012 |
| WO | 2012/080471 A1 | 6/2012 |
| WO | 2012/088116 A2 | 6/2012 |
| WO | 2012/088157 A2 | 6/2012 |
| WO | 2012/122535 A2 | 9/2012 |
| WO | 2012/130015 A1 | 10/2012 |
| WO | 2012/138941 A1 | 10/2012 |
| WO | 2012/140647 A2 | 10/2012 |
| WO | 2012/150503 A2 | 11/2012 |
| WO | 2012/158965 A2 | 11/2012 |
| WO | 2012/162547 A2 | 11/2012 |
| WO | 2012/167744 A1 | 12/2012 |
| WO | 2012/169798 A2 | 12/2012 |
| WO | 2012/173422 A1 | 12/2012 |
| WO | 2012/177443 A2 | 12/2012 |
| WO | 2012/177444 A2 | 12/2012 |
| WO | 2012/177929 A2 | 12/2012 |
| WO | 2013/002580 A2 | 1/2013 |
| WO | 2013/004983 A1 | 1/2013 |
| WO | 2013/009545 A1 | 1/2013 |
| WO | 2013/029279 A1 | 3/2013 |
| WO | 2013/041678 A1 | 3/2013 |
| WO | 2012/174478 A9 | 5/2013 |
| WO | 2013/060850 A1 | 5/2013 |
| WO | 2013/074910 A1 | 5/2013 |
| WO | 2013/078500 A1 | 6/2013 |
| WO | 2013/090648 A1 | 6/2013 |
| WO | 2013/092703 A2 | 6/2013 |
| WO | 2013/093720 A2 | 6/2013 |
| WO | 2013/101749 A1 | 7/2013 |
| WO | 2013/104861 A1 | 7/2013 |
| WO | 2013/164483 A1 | 7/2013 |
| WO | 2013/148871 A1 | 10/2013 |
| WO | 2013/148966 A1 | 10/2013 |
| WO | 2013/151663 A1 | 10/2013 |
| WO | 2013/151664 A1 | 10/2013 |
| WO | 2013/151665 A2 | 10/2013 |
| WO | 2013/151666 A2 | 10/2013 |
| WO | 2013/151667 A1 | 10/2013 |
| WO | 2013/151668 A2 | 10/2013 |
| WO | 2013/151669 A1 | 10/2013 |
| WO | 2013/151670 A2 | 10/2013 |
| WO | 2013/151671 A1 | 10/2013 |
| WO | 2013/151672 A2 | 10/2013 |
| WO | 2013/151736 A2 | 10/2013 |
| WO | 2013/160397 A1 | 10/2013 |
| WO | 2013/163162 A1 | 10/2013 |
| WO | 2013/164484 A1 | 11/2013 |
| WO | 2013/171135 A1 | 11/2013 |
| WO | 2013/177565 A1 | 11/2013 |
| WO | 2013/186240 A2 | 12/2013 |
| WO | 2013/192129 A1 | 12/2013 |
| WO | 2013/192130 A1 | 12/2013 |
| WO | 2014/012069 A2 | 1/2014 |
| WO | 2014/016300 A1 | 1/2014 |
| WO | 2014/017843 A1 | 1/2014 |
| WO | 2014/017845 A2 | 1/2014 |
| WO | 2014/017849 A1 | 1/2014 |
| WO | 2014/027253 A1 | 2/2014 |
| WO | 2014/027254 A1 | 2/2014 |
| WO | 2014/041195 A1 | 3/2014 |
| WO | 2014/041375 A1 | 3/2014 |
| WO | 2014/049610 A2 | 4/2014 |
| WO | 2014/056872 A1 | 4/2014 |
| WO | 2014/073842 A1 | 5/2014 |
| WO | 2014/073845 A2 | 5/2014 |
| WO | 2014/081872 A1 | 5/2014 |

(56) References Cited

FOREIGN PATENT DOCUMENTS

| WO | 2014/091316 A2 | 6/2014 |
|---|---|---|
| WO | 2014/096145 A1 | 6/2014 |
| WO | 2014/140222 A1 | 9/2014 |
| WO | 2014/152460 A2 | 9/2014 |
| WO | 2014/158900 A1 | 10/2014 |
| WO | 2014/170496 A1 | 10/2014 |
| WO | 2015/055801 A1 | 4/2015 |
| WO | 2015/055802 A2 | 4/2015 |
| WO | 2015/067716 A1 | 5/2015 |
| WO | 2015/086728 A1 | 6/2015 |
| WO | 2015/086729 A1 | 6/2015 |
| WO | 2015/086730 A1 | 6/2015 |
| WO | 2015/086731 A1 | 6/2015 |
| WO | 2015/086732 A1 | 6/2015 |
| WO | 2015/086733 A1 | 6/2015 |
| WO | 2015/100876 A1 | 7/2015 |
| WO | 2015/104314 A1 | 7/2015 |
| WO | 20151132599 A1 | 9/2015 |
| WO | WO 2015155139 A1 | 10/2015 |
| WO | WO 2015155140 A1 | 10/2015 |
| WO | 2016/065090 A1 | 4/2016 |
| WO | 20161055610 A1 | 4/2016 |
| WO | 2016/198604 A1 | 12/2016 |
| WO | 2016/198624 A1 | 12/2016 |

OTHER PUBLICATIONS

International Preliminary Report on Patentability corresponding to International Patent Application No. PCT/EP2013/077313, dated Feb. 12, 2015.
International Preliminary Report on Patentability corresponding to International Patent Application No. PCT/EP2014/077336, dated Feb. 26, 2016.
International Preliminary Report on Patentability corresponding to International Patent Application No. PCT/EP2014/077337, dated Jun. 14, 2016.
International Preliminary Report on Patentability corresponding to International Patent Application No. PCT/EP2014/077338, dated Jun. 14, 2016.
International Preliminary Report on Patentability corresponding to International Patent Application No. PCT/EP2014/077339, dated Jun. 14, 2016.
International Preliminary Report on Patentability corresponding to International Patent Application No. PCT/EP2014/077340, dated Jun. 14, 2016.
International Preliminary Report on Patentability corresponding to International Patent Application No. PCT/EP2014/077341, dated Jun. 14, 2016.
International Search Report with Written Opinion corresponding to International Patent Application No. PCT/EP2013/062090, dated Feb. 7, 2014.
International Search Report with Written Opinion corresponding to International Patent Application No. PCT/EP2013/070882, dated Dec. 5, 2013.
International Search Report with Written Opinion corresponding to International Patent Application No. PCT/EP2013/077307, dated Feb. 18, 2014.
International Search Report with Written Opinion corresponding to International Patent Application No. PCT/EP2013/077310, dated Feb. 18, 2014.
International Search Report with Written Opinion corresponding to International Patent Application No. PCT/EP2013/077312, dated Feb. 18, 2014.
International Search Report with Written Opinion corresponding to International Patent Application No. PCT/EP2013/077313, dated Feb. 18, 2014.
International Search Report with Written Opinion corresponding to International Patent Application No. PCT/EP2014/077336, dated Mar. 18, 2015
International Search Report with Written Opinion corresponding to International Patent Application No. PCT/EP2014/077337, dated Apr. 1, 2015
International Search Report with Written Opinion corresponding to International Patent Application No. PCT/EP2014/077338, dated Mar. 26, 2015
International Search Report with Written Opinion corresponding to International Patent Application No. PCT/EP2014/077339, dated May 11, 2015
International Search Report with Written Opinion corresponding to International Patent Application No. PCT/EP2014/077340, dated Mar. 18, 2015.
International Search Report with Written Opinion corresponding to International Patent Application No. PCT/EP2014/077341, dated Mar. 18, 2015.
International Search Report with Written Opinion corresponding to International Patent Application No. PCT/EP2015/057416, dated Jun. 22, 2015.
International Search Report with Written Opinion corresponding to International Patent Application No. PCT/EP2015/057417, dated Jun. 17, 2015.
International Search Report with Written Opinion corresponding to International Patent Application No. PCT/EP2015/057418, dated Jun. 19, 2015.
International Search Report with Written Opinion corresponding to International Patent Application No. PCT/EP2015/063607, dated Sep. 23, 2015.
International Search Report with Written Opinion corresponding to International Patent Application No. PCT/EP2016/062496, dated Aug. 3, 2016.
International Search Report with Written Opinion corresponding to International Patent Application No. PCT/EP2016/063332, dated Aug. 10, 2016.
International Search Report with Written Opinion corresponding to International Patent Application No. PCT/EP2016/063339, dated Aug. 8, 2016.
Stoessl et al. (2008) "Potential therapeutic targets for Parkinson's disease," Expert Opinion on Therapeutic Targets. 12(4):425-436.
Aramadhaka et al. (Apr. 18, 2013) "Connectivity maps for biosimilar drug discovery in venoms: The case of Gila Monster Venom and the anti-diabetes drug Byetta®," Toxicon. 69:160-167.
Bhavsar et al. (Mar. 2013) "Evolution of exenatide as a diabetes therapeutic," Curr. Diabetes Rev. 9(2):161-193.
Gao et al. (Jun. 4, 2012) "A site-specific PEGylated analog of exendin-4 with improved pharmacokinetics and pharmacodynamics in vivo," J. Pharm. Pharmacol. 64(11):1646-1653.
Gupta (May 2013) "Glucagon-like peptide-1 analogues: An overview," Indian J. Endocrinol. Metab. 17(3):413-421.
Hou et al. (Jan. 23, 2013) "Long-term treatment with EXf, a peptide analog of Exendin-4, improves β-cell function and survival in diabetic KKAy mice," Peptides. 40:123-132.
Kim et al. (Nov. 9, 2012) "Site-specific PEGylated Exendin-4 modified with a high molecular weight trimeric PEG reduces steric hindrance and increases type 2 antidiabetic therapeutic effects," Bioconjug. Chem. 23(11):2214-2220.
Lee et al. (Oct. 17, 2013) "Decanoic acid-modified glycol chitosan hydrogels containing tightly adsorbed palmityl-acylated exendin-4 as a long-acting sustained-release anti-diabetic system," Acta Biomater. 10(2):812-820.
Parkes et al. (Dec. 12, 2012) "Discovery and development of exenatide: the first antidiabetic agent to leverage the multiple benefits of the incretin hormone, GLP-1," Expert Opin. Drug Discov. 8(2):219-244.
Qian et al. (Jul. 1, 2013) "Characterization of a site-specific PEGylated analog of exendin-4 and determination of the PEGylation site," Int. J. Pharm. 454(1):553-558.
Simonsen et al. (Jan. 11, 2013) "The C-terminal extension of exendin-4 provides additional metabolic stability when added to GLP-1, while there is minimal effect of truncating exendin-4 in anaesthetized pigs," Regul. Pept. 181:17-21.

(56) References Cited

OTHER PUBLICATIONS

Sun et al. (Nov. 6, 2013) "Bifunctional PEGylated exenatide-amylinomimetic hybrids to treat metabolic disorders: an axample of long-acting dual hormonal therapeutics," J. Med. Chem. 56(22):9328-9341.
Yim et al. (Aug. 8, 2013) "Synthesis and preclinical characterization of [64Cu]NODAGA-MAL-exendin-4 with a Nεmaleoyl-L-lysyl-glycine linkage," Nucl. Med. Biol. 40(8):1006-1012.
Yue et al. (Jan. 28, 2013) "Development of a new thiol site-specific prosthetic group and its conjugation with [Cys(40)] exendin-4 for in vivo targeting of insulinomas," Bioconjug. Chem. 24(7):1191-1200.
Lorenz et al. (2013) "Recent progress and future options in the development of GLP-1 receptor agonists for the treatment of diabesity" Bioorg. Med. Chem. Lett. 23(14):4011-4018.
Lozano et al. (2013) "Polyarginine nanocapsules: a new platform for intracellular drug delivery," Journal of Nanoparticle Research. 15:1515. pp. 1-14.
Margolis (2004) "Diagnosis of Huntington Disease," Clin. Chem. 49:1726-1732.
Martin et al. (1998) "Neurodegeneration in excitotoxicity, global cerebral ischemia, and target deprivation: A perspective on the contributions of apoptosis and necrosis," Brain Res. Bull. 46:281-309.
McLaughlin et al. (2010) "Reversible Hyperinsulinemic Hypoglycemia after Gastric Bypass: A Consequence of Altered Nutrient Delivery," J. Clin. Endocrinol. Metabol. 95(4):1851-1855.
Medline Plus "Obesity," National Insitute of Health. Accessible on the Internet at URL: http://www.nlm.nih.gov/medlineplus/obesity.html. [Last Accessed Aug. 22, 2013].
Meier (Sep. 4, 2012) "GLP-1 receptor agonists for individualized treatment of type 2 diabetes mellitus," Nat. Rev. Endocnnol. 8:728-742.
Meier et al. (May 21, 2015) "Incretin-based therapies: where will we be 50 years from now?" Diabetologia. 58:1745-1750.
Miyawaki et al. (2002) "Inhibition of gastric inhibitory polypeptide signaling prevents obesity," Nat. Med. 8(7):738-742.
Murage et al. (2008) "Search for alpha-helical propensity in the receptor-bound conformation of glucagon-like peptide-1," Bioorg. Med. Chem. 16:10106-10112.
Nauck et al. (1993) "Additive insulinotropic effects of exogenous synthetic human gastric inhibitory polypeptide and glucagon-like peptide-1-(7-36) amide infused at near-physiological insulinotropic hormone and glucose concentrations," J. Clin. Endocrinol. Metab. 76:912-917.
Norris et al. (2009) "Exenatide Efficacy and Safety: A Systematic Review," Diabetic Medicine. 26:837-846.
Norwegian Institute of Public Health (Dec. 19, 2013) ATC/DDD Index for Cardiovascular System.
Oh et al. (2010) "Target specific and long-acting delivery of protein, peptide, and nucleotide therapeutics using hyaluronic acid derivatives," Journal of Controlled Release. 141:2-12.
Pan et al. (2006) "Design of a long acting peptide functioning as both a glucagon-like peptide-1 receptor agonist and a glucagon receptor antagonist." Journal of Biological Chemistry. 281(18):12506-12515.
Pedersen et al. (2006) "N- and C-terminal hydrophobic patches are involved in fibrillation of glucagon," Biochemistry. 45:14503-14512.
Pocai (2009) "Glucagon-like peptide 1/glucagon receptor dual agonism reverses obesity in mice," Diabetes. 58(10):2258-2266.
Pocai (Dec. 14, 2013) "Action and therapeutic potential of oxyntomodulin," Molecular Metabolism 3:2412-51.
Rentier et al. (Mar. 26, 2015) "Synthesis of diastereomerically pure Lys(Nε-lipoyl) building blocks and their use in Fmoc/tBu solid phase synthesis of lipoyl-containing peptides for diagnosis of primary biliary cirrhosis," Journal of Peptide Science. 21(5):408-414.
Robberecht et al. (1986) "Comparative efficacy of seven synthetic glucagon analogs, modified in position 1, 2 and/or 12, on liver and heart adenylate cyclase from rat," Peptides. 7(1):109-112.
Rovo et al. (May 2014) "Rational design of a-helix-stabilized exendin-4 analogues," Biochemistry. 53(22):3540-3552.
Seddon (2004) "Pseudopolymorph: A polemic," Crystal Growth and Design. 4(6):1087.
Shiau et al. (1998) "The structural basis of estrogen receptor/coactivator recognition and the antagonism of this interaction by tamoxifen," Cell. 95(7):927-937.
St. John Providence Health System "Preventing Obesity in Children," St. John Providence Health System. Accessible on the Internet at URL: http://www.stjohnprovidence.org/HealthInfoLib/swarticle.aspx?type=85&id=P07863. [Last Accessed Aug. 22, 2013].
Tasyurek et al. (Jul. 2014) "Incretins: Their physiology and application in the treatment of diabetes mellitus," Diabetes Metab. Res. Rev. 30(5):354-371.
Ueda et al. (2010) "Identification of glycosylated exendin-4 analogue with prolonged blood glucose-lowering activity through glycosylation scanning substitution," Bioorg. Med. Chem. Lett. 20(15):4631-4634.
United Healthcare "Diabetes," United Healthcare. Accessible on the Internet at URL: http://www.uhc.com/source4women/health_topics/diabetes/relatedinformation/d0f0417b073bf110VgnVCM1000002f10b10a.htm. [Last Accessed Aug. 22, 2013].
Unison et al. (1993) "The role of histidine-1 in glucagon action," Arch. Biochem. Biophys. 300(2):747-750.
Vippagunta et al. (2001) "Crystalline Solids," Advanced Drug Delivery Reviews. 48:3-26.
Vojkovsky (1995) "Detection of secondary amines on solid phase," Peptide Research 8:236-237.
Ward et al. (Nov. 2013) "Peptide lipidation stabilizes structure to enhance biological function," Mol. Metabol. 2(4):468-479.
World Health Organization (2007) "Prevention of Cardiovascular Disease," WorldHealth Organization. pp. 1-86.
Yun et al. (Feb. 2012) "Solution Structure of LXXLL-related Cofactor Peptide of Orphan Nuclear Receptor FTZ-F1." Bulletin of the Korean Chemical Society, 33(2):583-588.
European Search Report corresponding to European Patent Application No. 12172010, dated Apr. 19, 2013.
European Search Report corresponding to European Patent Application No. 12306232, dated Apr. 19, 2013.
European Search Report corresponding to European Patent Application No. 12306647, dated May 22, 2013.
European Search Report corresponding to European Patent Application No. 13306712, dated May 27, 2014.
European Search Report corresponding to European Patent Application No. 13306713, dated Jun. 12, 2014.
European Search Report corresponding to European Patent Application No. 13306714, dated May 28, 2014.
European Search Report corresponding to European Patent Application No. 13306715, dated Jun. 12, 2014.
European Search Report corresponding to European Patent Application No. 13306716, dated May 27, 2014.
European Search Report corresponding to European Patent Application No. 13306717, dated Jun. 3, 2014.
European Search Report corresponding to European Patent Application No. 13305222, dated Jul. 15, 2013.
European Search Report corresponding to European Patent Application No. 14305501, dated Sep. 23, 2014.
European Search Report corresponding to European Patent Application No. 14305503, dated Sep. 23, 2014.
International Preliminary Report on Patentability corresponding to International Patent Application No. PCT/EP2013/062090, dated Nov. 24, 2014.
International Preliminary Report on Patentability corresponding to International Patent Application No. PCT/EP2013/070882, dated Dec. 1, 2014.
International Preliminary Report on Patentability corresponding to International Patent Application No. PCT/EP2013/077307, dated Feb. 12, 2015.
International Preliminary Report on Patentability corresponding to International Patent Application No. PCT/EP2013/077310, dated Feb. 2, 2015.

(56) References Cited

OTHER PUBLICATIONS

International Preliminary Report on Patentability corresponding to International Patent Application No. PCT/EP2013/077312, dated Feb. 13, 2015.
Guryanov et al. (May 30, 2016) "Innovative chemical synthesis and conformational hints on the lipopeptide liraglutide," J. Pept. Sci. 22:471-479.
Lau et al. (Aug. 26, 2015) "Discovery of the once-weekly Glucagon-like Peptide-1 (GLP-1) analogue Semaglutide," Journal of Medicinal Chemistry. 58:7370-7380.
International Search Report with Written Opinion corresponding to International Patent Application No. PCT/EP2016/063305, dated Oct. 4, 2016.
International Search Report with Written Opinion corresponding to International Patent Application No. PCT/EP2016/066299, dated Jan. 10, 2017.
Amylin Pharmaceuticals, Inc. (2007) "Byetta: Exenatide Injection," Product Information. Accessible on the Internet at URL: http://www.accessdata.fda.gov/drugsatfda_docs/label/2008/021773s012lbl.pdf. [Last Accessed Jun. 2, 2014].
Baggio et al. (2007) "Biology of incretins: GLP-1 and GIP," Gastroenterology. 132:2131-2157.
Bhat et al. (Jun. 1, 2013) "A novel GIP-oxyntomodulin hybrid peptide acting through GIP, glucagon and GLP-1 receptors exhibits weight reducing and anti-diabetic properties," Biochem. Pharmacol. 85:1655-1662.
Bhat et al. (Mar. 17, 2013) "A DPP-IV-resistant triple-acting agonist of GIP, GLP-1 and glucagon receptors with potent glucose-lowering and insulinotropic actions in high-fat-fed mice," Diabetologia. 56:1417-1424.
Biron et al. (2006) "Optimized selective N-methylation of peptides on solid support," J. Peptide Sci. 12:213-219.
Bis et al. (Jun. 27, 2014) "Antimicrobial preservatives induce aggregation of interferon alpha-2a: the order in which preservatives induce protein aggregation is independent of the protein," Int. J. Pharm. 472:356-361.
Braga et al. (2005) "Making Crystals from Crystals: a green route to crystal engineering and polymorphism," Chem. Commun. 2005:3635-3645.
Bromer (1983) "Chemical Characteristics of Glucagon," Handbook of Experimental Pharmacology. 66:1-22.
Bunck et al. (Sep. 2011) "Effects of Exenatide on Measures of B-Cell Function After 3 Years in Metformin-Treated Patients with Type 2 Diabetes," Diabetes Care. 34:2041-2047.
Buse et al. (2009) "Liraglutide once a day versus exenatide twice a day for type 2 diabetes: a 26-week randomised, parallel group, multinational, open-label trial (LEAD-6)," The Lancet. 374:39-47.
Chae et al. (2010) "The fatty acid conjugated exendin-4 analogs for type 2 antidiabetic therapeutics," Journal of Controlled Release. 144:10-16.
Chen et al. (Jan. 2014) "Hyaluronic acid-based drug conjugates: state-of-the-art and perspectives," J. Biomed. Nanotechnol. 10(1):4-16.
Chhabra et al. (1998) "An Appraisal of New Variants of Dde Amine Protecting Group for Solid Phase Peptide Synthesis," Tetrahedron Letters. 39:1603-1606.
Creutzfeld et al. (1978) "Gastric inhibitory polypeptide (GIP) and insulin in obesity: increased response to stimulation and defective feedback control of serum levels," Diabetologia. 14:15-24.
Day et al. (2009) "A New Glucagon and GLP-1 co-agonist Eliminates Obesity in Rodents," Nature Chemical Biology. 5(10):749-757.
Deacon (2004) "Circulation and degradation of GIP and GLP-1," Horm. Metab. Res. 36:761-765.
Donnelly (May 2012) "The structure and function of the glucagon-like peptide-1 receptor and its ligands," Br. J. Pharmacol. 166(1):27-41.
Druce et al. (2009) "Investigation of structure-activity relationships of Oxyntomodulin (Oxm) using Oxm analogs," Endocrinology. 150(4):1712-1722.
Drucker et al. (2010) "Liraglutide," New Reviews—Drug Discovery. 9(4):267-268.
Eng et al. (1990) "Purification and structure of exendin-3, a new pancreatic secretagogue isolated from Heloderma horridum venom," J. Biol. Chem. 265:20259-20262.
Eng et al. (1992) "Isolation and Characterization of Exendin-4, an Exendin-3 Analogue, from Heloderma Suspectum Venom," The Journal of Biological Chemistry. 267(11):7402-7405.
Eng et al. (1996) "Prolonged Effect of Exendin-4 on Hyperglycemia of db/db Mice," Diabetes. 45:152A. Abstract 554.
Ferry, Jr."Diabetes Health (cont.)," MedicineNet. Accessible on the Internet at URL: http://www.onhealth.com/diabetes_health/page3.htm. [Last Accessed Aug. 22, 2013].
Ficht et al. (2008) "Solid-phase Synthesis of Peptide and Glycopeptide Thioesters through Side-Chain-Anchoring Strategies," Chem. Eur. J. 14:3620-3629.
Finan et al. (Dec. 8, 2014) "A rationally designed monomeric peptide triagonist corrects obesity and diabetes in rodents," Nat. Med. 21(1):27-36.—with supplementary information.
Finan et al. (Oct. 30, 2013) "Unimolecular Dual Incretins Maximize Metabolic Benefits in Rodents, Monkeys, and Humans," Sci. Trans. Med. 5:209RA151.
Furman (Mar. 15, 2012) "The development of Byetta (exenatide) from the venom of the Gilo monster as an anti-diabetic agent," Toxicon. 59:464-471.
Gault et al. (2007) "Chemical gastric inhibitory polypeptide receptor antagonism protects against obesity, insulin resistance, glucose intolerance and associated disturbances in mice fed high-fat and cafeteria diets," Diabetologia. 50:1752-1762.
Gault et al. (Aug. 1, 2011) "Administration of an acylated GLP-1 and GIP preparation provides added beneficial glucose-lowering and insulinotropic actions over single incretins in mice with Type 2 diabetes and obesity," Clin Sci (Lond). 121:107-117.
Gentilella et al. (2009) "Exenatide: A Review from Pharmacology to Clinical Practice," Diabetes, Obesity, and Metabolism. 11:544-556.
Göke et al. (1993) "Exendin-4 is a high potency agonist and truncated exendin-(9-39)-amide an antagonist at the glucagon-like peptide 1-(7-36)-amide receptor of insulin-secreting beta-cells," J. Biol. Chem. 268:19650-19655.
Hadji-Georgopoulos et al. (1983) "Increased gastric inhibitory polypeptide levels in patients with symptomatic postprandial hypoglycemia," J. Endocrinol. Metabol. 56(4):648-652.
Hargrove et al. (2007) "Biological Activity of AC3174, A Peptide Analog of Exendin-4," Regulatory Peptides. 141:113-119.
Heppner et al. (2010) "Glucagon regulation of energy metabolism," Physiol. Behav. 100:545-548.
Herling et al. (1998) "Pharmacodynamic profile of a novel inhibitor of the hepatic glucose-6-phosphatase system," Am. J. Physiol. 274(6 Pt 1):G1087-G1093.
Hjorth et al. (1994) "Glucagon and Glucagon-like Peptide 1: Selective Receptor Recognition via Distinct Peptide Epitopes," The Journal of Biological Chemistry. 269(48):30121-30124.
Holst (2007) "The physiology of glucagon-like peptide 1," Physiol. Rev. 87(4):1409-1439.
Joshi et al. (2000) "The degradation pathways of glucagon in acidic solutions," Int. J. Pharm. 203(1-2):115-125.
Kaiser et al. (1970) "Color test for detection of free terminal amino groups in the solid-phase synthesis of peptides." Anal. Biochem. 34:595-598.
Kamerzell et al. (2011) "Protein-excipient interactions: Mechanisms and biophysical characterization applied to protein formulation development," Adv. Drug Deliv. Rev. 63:1118-1159.
Kazakos et al. (2011) "Incretin effect: GLP-1, GIP, DPP4," Diabetes Res Clin Pract. 93(Suppl 1):S32-S36. et al. (2011) "Incretin effect: GLP-1, GIP, DPP4," Diabetes Res Clin Pract. 93(Suppl 1):S32-S36.
King et al. (1990) "A Cleavage Method which Minimizes Side Reactions Following Fmoc Solid Phase Peptide Synthesis," International Journal of Peptide Protein Research. 36:255-266.
Knudsen et al. (2000) "Potent derivatives of glucagon-like peptide-1 with pharmacokinetic properties suitable for once daily administration" J. Med. Chem. 43(9):1664-1669.

(56) References Cited

OTHER PUBLICATIONS

Kong et al. (2010) "Long acting hyaluronate—exendin 4 conjugate for the treatment of type 2 diabetes," Biomaterials. 31:4121-4128.
Korczyn et al. (2002) "Emerging Therapies in the Pharmacological Treatment of Parkinson's Disease," Drugs. 62:775-786.
Kosinski et al. (Mar. 16, 2012) "The glucagon receptor is involved in mediating the body weight-lowering effects of oxyntomodulin," Obesity (Silver Spring). 20:1566-1571.
Krstenansky et al. (1986) "Importance of the 10-13 Region of Glucagon for Its Receptor Interaction and Activation of Adenylate Cyclase," Biochemistry. 25(13):3833-3839.
Lee et al. (May 10, 2013) "Hormonal Response to a Mixed-Meal Challenge After Reversal of Gastric Bypass for Hypoglycemia," J. Clin. Endocrinol. Metab. 98(7):E1208-E1212.
Li et al. (Jul. 25, 2012) "Cloning, expressing of Exendin-4 analogue and bioactivity analysis in vivo," Chinese Journal of Biotechnology. 28(7):877-886.
Liu et al. (2011) "Solid phase peptide synthesis and analysis for exendin-4," China Biotechnology. 31(2):69-73.—English abstract and drawings.
Bayram et al. (Sep. 2014) "Effects of glucagon-like peptide-1 in diabetic rat small resistance arteries," Journal of Cardiovascular Pharmacology. 64(3):277-84.
Brom et al. (Feb. 1, 2014) "Non-invasive quantification of the beta cell mass by SPECT with 111In-labelled exendin," Diabetologia. 57(5):950-959.
Cai et al. (Dec. 2014) "Rb and p107 are required for alpha cell survival, beta cell cycle control and glucagon-like peptide-1 action," Diabetologia. 57(12):2555-2565.
Charokopou et al. (Nov. 2014) "Cost-effectiveness of saxagliptin compared to GLP-1 analogues as an add-on to insulin in the treatment of type 2 diabetes mellitus from a UK health care perspective," Value in Health. 17(7):A347. Abstract No. PDB89.
Chen et al. (Dec. 14, 2013) "Exendin-4 is effective against metabolic disorders induced by intrauterine and postnatal overnutrition in rodents," Diabetologia. 57(3):614-622.
Choi et al. (Jun. 2014) "A long-acting exendin-4 analog conjugate to the human Fc fragment reveals low immunogenic potential," Diabetes. 63(Suppl 1):A259-A260. Abstract No. 1009-P.
Clemmensen et al. (Dec. 30, 2013) "GLP-1/glucagon coagonism restores leptin responsiveness in obese mice chronically maintained on an obesogenic diet," Diabetes. 63(4):1422-1427.
De Marinis et al. (Jun. 2014) "Differential action of GLP-1 and GIP on human pancreatic islet function and viability," Diabetes. 63(Suppl 1):A52. Abstract No. 196-OR.
De Marinis et al. (Sep. 2014) "Differential action of GLP-1 and GIP on human pancreatic islet function and viability," Diabetologia. 57(Suppl 1):S171. Abstract No. 401.
Eriksson et al. (Feb. 10, 2014) "Detection of metastatic insulinoma by positron emission tomography with [(68)ga] exendin-4-a case report," J. Clin. Endocrinol. Metab. 99(5):1519-1524.
Eriksson et al. (May 2014) "Effects of the glucagon-like peptide-1 analog exendin-4 on reendothelialization and intimal hyperplasia formation in an animal model of vascular injury," Arteriosclerosis, Thrombosis, and Vascular Biology. 34(Suppl 1): Abstract No. 515.
Gong et al. (Apr. 18, 2014) "teniposide and its iridoid analogs exhibit antinociception by acting at the spinal GLP-1 receptors," Neuropharmacology. 84:31-45.
Gupta et al. (Sep. 25, 2014) "Mitigation of autophagy ameliorates hepatocellular damage following ischemia reperfusion injury in murine steatotic liver," Am. J. Physiol. Gastrointest. Liver Physiol. 307(11):G1088-G1099.
Jerlhag et al. (Jun. 2014) "A glucagon like peptide-1 analogue reduces alcohol intake and prevents relapse drinking," Alcoholism: Clinical and Experimental Research. 38(Suppl 1):85A. Abstract No. 0339.
Jin et al. (Jun. 24, 2014) "Dipeptidyl peptidase IV inhibitor MK-0626 attenuates pancreatic islet injury in tacrolimus-induced diabetic rats," PloS one. 9(6):e100798. pp. 1-10.

Johnson et al. (Sep. 5, 2014) "A Potent α/β-Peptide Analogue of GLP-1 with Prolonged Action in Vivo," Journal of be American Chemical Society. 136(37):12848-12851.
Kwon et al. (Sep. 2014) "Pharmacological evaluation of once-weekly potentials by combination of long-acting insulin with long-acting exendin4 in an animal model," Diabetologia. 57(Suppl 1):S398-S399. Abstract No. 972.
Li et al. (Apr. 2014) "Vascular protective effect of exendin-4 in experimental models of oxidative stress," Cytotherapy. 16(4 Suppl):S37-S38. Abstract No. 115.
Li et al. (Nov. 5, 2014) "Exendin-4 promotes endothelial barrier enhancement via PKA-and Epac1-dependent Rac1 activation," American Journal of Physiology. 308(2):C164-C175.
Lim et al. (Nov. 18, 2014) "Evaluation of PEGylated Exendin-4 Released from Poly (Lactic-co-Glycolic Acid) Microspheres for Antidiabetic Therapy," Journal of Pharmaceutical Sciences. 104(1):72-80.
Lovshin et al. (Oct. 2014) "Blood pressure-lowering effects of incretin-based diabetes therapies," Canadian Journal of Diabetes. 38(5):364-71.
Lynch et al. (Jun. 24, 2014) "A novel DPP IV-resistant C-terminally extended glucagon analogue exhibits weight-lowering and diabetes-protective effects in high-fat-fed mice mediated through glucagon and GLP-1 receptor activation," Diabetologia. 57(9):1927-1936.
Maas et al. (Oct. 2014) "Impact of the mTOR inhibitor Everolimus on peptide receptor radionuclide therapy in a transgenic neuroendocrine tumor mouse model," European Journal of Nuclear Medicine and Molecular Imaging. 41 (Suppl 2):S529. Abstract No. P593.
Masjkur et al. (Nov. 4, 2014) "Hes3 is Expressed in the Adult Pancreatic Islet and Regulates Gene Expression, Cell Growth, and Insulin Release," The Journal of Biological Chemistry. 289(51):35503-35516.
Mondragon et al. (Aug. 13, 2014) "Divergent effects of liraglutide, exendin-4, and sitagliptin on beta-cell mass and indicators of pancreatitis in a mouse model of hyperglycaemia," PloS one. 9(8):e104873. pp. 1-9.
Nagai et al. (Sep. 2014) "Effects of sitagliptin on body fat and intrahepatic lipid content in Japanese overweight patients with type 2 diabetes," Diabetologia. 57(Suppl 1):S356. Abstract No. 876.
Patel et al. (Sep. 29, 2014) "Cannabinoid receptor 1 antagonist treatment induces glucagon release and shows an additive therapeutic effect with GLP-1 agonist in diet-induced obese mice," Canadian Journal of Physiology and Pharmacology. 92(12):975-983.
Pathak et al. (Nov. 6, 2014) "Antagonism of gastric inhibitory polypeptide (GIP) by palmitoylation of GIP analogues with N- and C-terminal modifications improves obesity and metabolic control in high fat fed mice"; Molecular and Cellular Endocrinology. 401:120-129.
Pi et al. (2014) "胰升血糖素样肽 1 类似物治疗糖尿病的临床研究进展 [Clinical research progress on glucagon-like peptide-1 analogs in treatment of diabetes mellitus]," 检验医学与临床 [Jianyan Yixue Yu Linchuang]. 11(6):830-832.—with English machine translation.
Qian et al. (Jun. 19, 2014) "Analysis of the interferences in quantitation of a site-specifically PEGylated exendin-4 analog by the Bradford method," Analytical Biochemistry. 465C:50-52.
Roed et al. (Nov. 22, 2013) "Real-time trafficking and signaling of the glucagon-like peptide-1 receptor," Mol. Cell Endocrinol. 382(2):938-949.
Russell et al. (Jun. 2014) "The novel GLP-1-GLP-2 dual agonist ZP-GG-72 increases intestinal growth and improves insulin sensitivity in DIO mice," Diabetes. 63(Suppl 1):A98. Abstract No. 374-OR.
Schattauer GMBH (Jun. 12, 2014) Meeting Abstracts of the Swiss Society of Radiology and the Swiss Society of Nuclear Medicine 2014. Nuklearmedizin. 53(2):A111-A126.
Tashiro et al. (Jan. 10, 2014) "A glucagon-like peptide-1 analog liraglutide suppresses macrophage foam cell formation and atherosclerosis," Peptides. 54:19-26.

(56) References Cited

OTHER PUBLICATIONS

Tweedie et al. (May 2014) "Exendin-4, a candidate treatment for the clinical management of traumatic brain injury," Brain Injury. 28(5-6):549-550. Abstract No. 0101.

Vioix et al. (Nov. 2014) "Cost-minimisation analysis of dapagliflozin compared to lixisenatide as an add-on to insulin in the treatment of type 2 diabetes mellitus from a UK health care perspective," Value in Health. 17(7):A348. Abstract No. PDB95.

Wang et al. (Jun. 2014) "Microfluidic multiplexer perifusion device for studying islet immunotoxicity," Diabetes. 63 (Suppl 1):A555. Abstract No. 2181-P.

Wu et al. (May 24, 2014) "(64)Cu labeled sarcophagine exendin-4 for microPET imaging of glucagon like peptide-1 receptor expression," Theranostics. 4(8):770-777.

Xu et al. (Feb. 11, 2014) "Exendin-4 alleviates high glucose-induced rat mesangial cell dysfunction through the AMPK pathway," Cell. Physiol. Biochem. 33(2):423-432.

Xu et al. (Sep. 2014) "Insulinoma imaging with glucagon-like peptide-1 receptor targeting probe (18)F-FBEM-Cys (39)-exendin-4," Journal of Cancer Research and Clinical Oncology. 140(9):1479-1488.

Yang et al. (2014) "Design, synthesis and biological evaluation of novel peptide MC62 analogues as potential antihyperglycemic agents," European Journal of Medicinal Chemistry. 73:105-111.

Yang et al. (Jun. 2014) "Exendin-4, an analogue of glucagon-like peptide-1, attenuates hyperalgesia through serotonergic pathways in rats with neonatal colonic sensitivity," J. Physiol. Pharmacol. 65(3)349-357.

Yosida et al. (May 13, 2014) "Involvement of cAMP/EPAC/TRPM2 activation in glucose- and incretin-induced insulin secretion," Diabetes. 63(10):3394-3403.

Zhang et al. (Aug. 2014) "GLP-1 ameliorates the proliferation activity of INS-1 cells inhibited by intermittent high glucose concentrations through the regulation of cyclins," Molecular Medicine Reports. 10(2):683-688.

Kaydashev, Physiological and pharmacological effects of glucagon-like peptide 1, International Endocrinological Journal, 2012, Nr. 7(47), pp. 45-54 (English abstract).

Fig. 1
a)
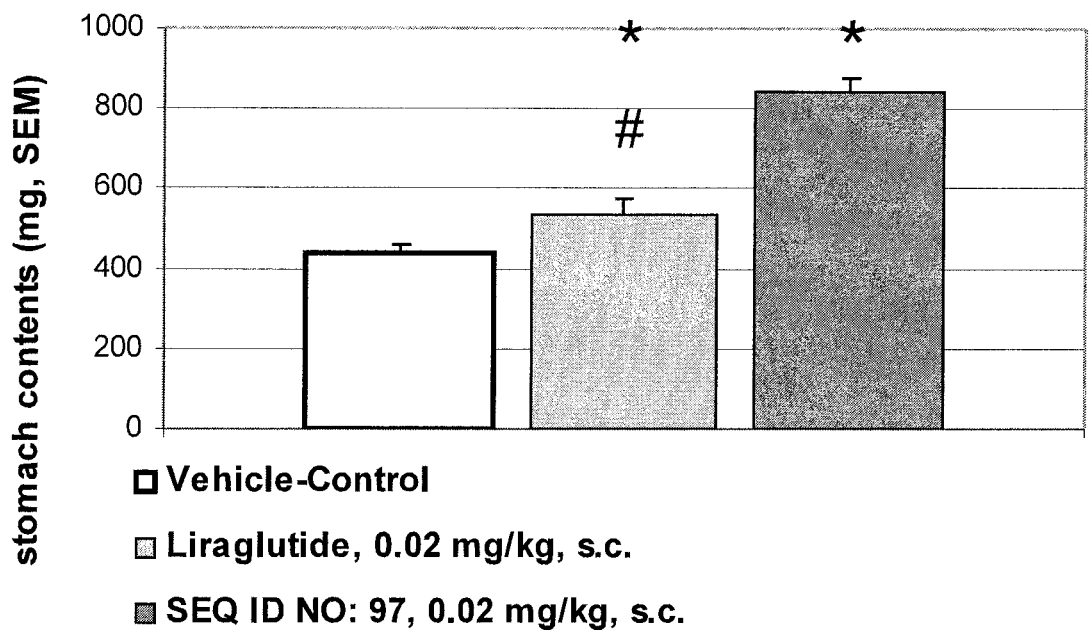
b)
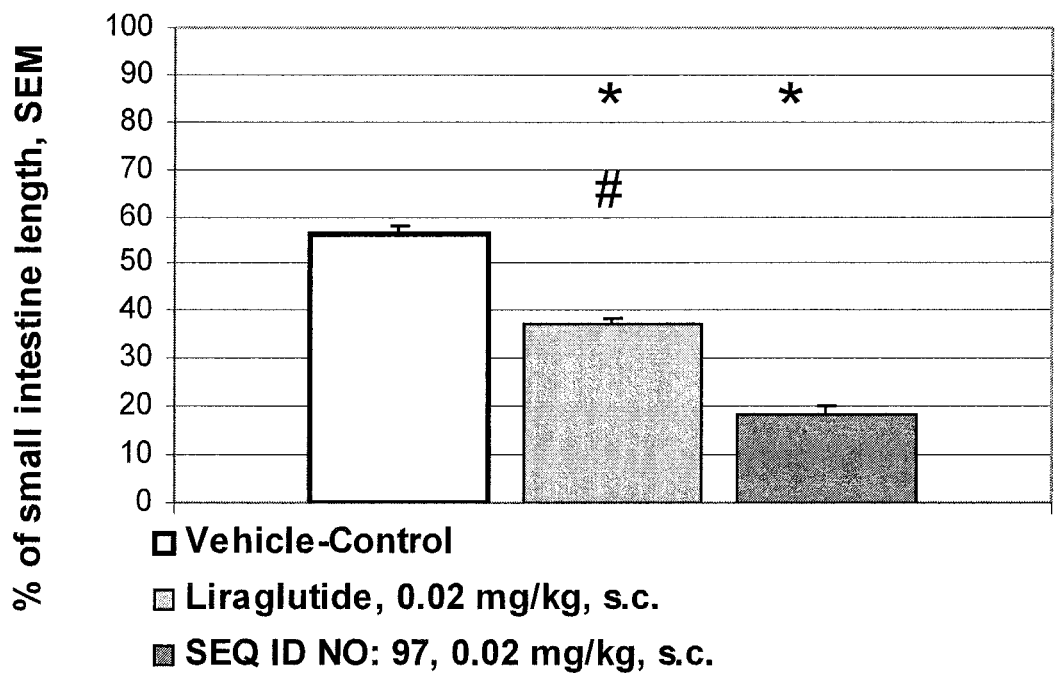

Fig. 1 (cont.)
c)
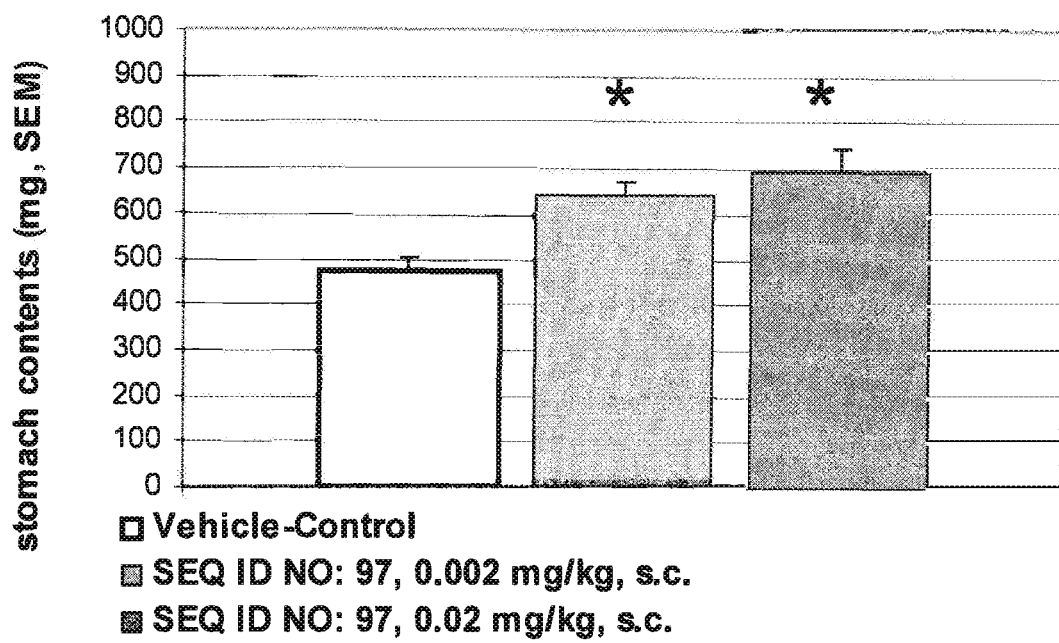
d)
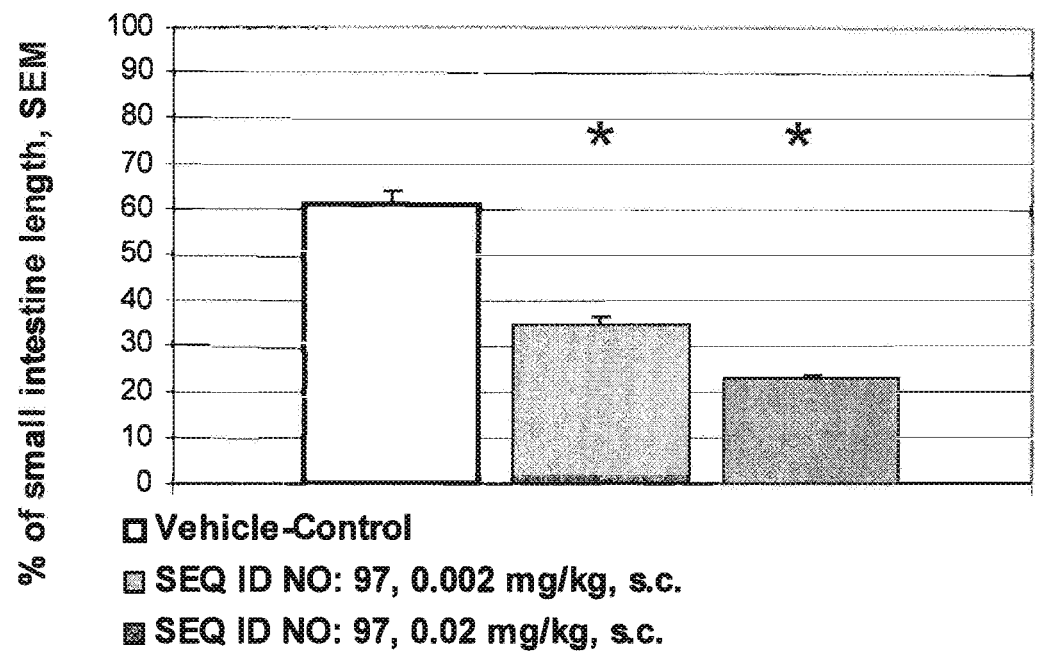

SEQUENCE LISTING

<160> NUMBER OF SEQ ID NOS: 229

<210> SEQ ID NO 1
<211> LENGTH: 39
<212> TYPE: PRT
<213> ORGANISM: Heloderma suspectum

```
<220> FEATURE:
<221> NAME/KEY: MOD_RES
<222> LOCATION: (39)..(39)
<223> OTHER INFORMATION: Ser is modified with an NH2 group

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 2
<211> LENGTH: 29
<212> TYPE: PRT
<213> ORGANISM: Homo sapiens
<220> FEATURE:
<221> NAME/KEY: MOD_RES
<222> LOCATION: (29)..(29)
<223> OTHER INFORMATION: Arg is modified with an NH2 group

<400> SEQUENCE: 2

His Ala Glu Gly Thr Phe Thr Ser Asp Val Ser Ser Tyr Leu Glu Gly
1               5                   10                  15

Gln Ala Ala Lys Glu Ile Ala Trp Leu Val Lys Gly Arg
            20                  25

<210> SEQ ID NO 3
<211> LENGTH: 28
<212> TYPE: PRT
<213> ORGANISM: Homo sapiens
<220> FEATURE:
<221> NAME/KEY: MOD_RES
<222> LOCATION: (28)..(28)
<223> OTHER INFORMATION: Thr is modified with an OH group

<400> SEQUENCE: 3

His Ser Gln Gly Thr Phe Thr Ser Asp Tyr Ser Lys Tyr Leu Asp Ser
1               5                   10                  15

Arg Arg Ala Gln Asp Val Gln Trp Leu Met Asn Thr
            20                  25

<210> SEQ ID NO 4
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 4

His Xaa Gln Gly Thr Phe Thr Ser Asp Leu Ser Lys Gln Lys Glu Ser
1               5                   10                  15

Arg Arg Ala Gln Asp Phe Ile Glu Trp Leu Lys Ala Gly Gly Pro Ser
```

Ser Gly Ala Pro Pro Pro Ser
        35

<210> SEQ ID NO 5
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is an Aib amino acid
<220> FEATURE:
<221> NAME/KEY: MOD_RES
<222> LOCATION: (14)..(14)
<223> OTHER INFORMATION: Lys is functionalized at the amino side chain
      group as Lys(hexadecanoyl)
<220> FEATURE:
<221> NAME/KEY: MOD_RES
<222> LOCATION: (39)..(39)
<223> OTHER INFORMATION: Ser is modified with an NH2 group

<400> SEQUENCE: 5

His Xaa Gln Gly Thr Phe Thr Ser Asp Leu Ser Lys Gln Lys Glu Ser
1               5                   10                  15

Arg Arg Ala Gln Asp Phe Ile Glu Trp Leu Lys Ala Gly Gly Pro Ser
            20                  25                  30

Ser Gly Ala Pro Pro Pro Ser
        35

<210> SEQ ID NO 6
<211> LENGTH: 40
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (40)..(40)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (40)..(40)
<223> OTHER INFORMATION: Lys is modified with an NH2 group

<400> SEQUENCE: 6

His Xaa Gln Gly Thr Phe Thr Ser Asp Leu Ser Lys Gln Lys Glu Ser
1               5                   10                  15

Arg Arg Ala Gln Leu Phe Ile Glu Trp Leu Lys Ala Gly Gly Pro Ser
            20                  25                  30

Ser Gly Ala Pro Pro Pro Ser Lys
        35                  40

<210> SEQ ID NO 7
<211> LENGTH: 39
<212> TYPE: PRT
<213> ORGANISM: Artificial Sequence

```
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalised at the amino side chain
      group as Lys(4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 7

His Xaa Gln Gly Thr Phe Thr Ser Asp Leu Ser Lys Gln Lys Glu Ser
1               5                   10                  15

Lys Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 8
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 8

His Xaa Gln Gly Thr Phe Thr Ser Asp Leu Ser Lys Gln Lys Asp Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
        35

<210> SEQ ID NO 9
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4(4-dodecyloxy-benzoylamino)-butyryl)
<220> FEATURE:
<221> NAME/KEY: MOD_RES
<222> LOCATION: (39)..(39)
<223> OTHER INFORMATION: Ser is modified with an NH2 group
```

<400> SEQUENCE: 9

His Xaa Gln Gly Thr Phe Thr Ser Asp Leu Ser Lys Gln Lys Glu Ser
1               5                   10                  15

Arg Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 10
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH-n-propyl group

<400> SEQUENCE: 10

His Xaa Gln Gly Thr Phe Thr Ser Asp Leu Ser Lys Gln Lys Asp Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
        35

<210> SEQ ID NO 11
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (17)..(17)
<223> OTHER INFORMATION: Xaa is an Aib amino acid
<220> FEATURE:
<221> NAME/KEY: MOD_RES
<222> LOCATION: (39)..(39)
<223> OTHER INFORMATION: Ser is modified with an NH2 group

<400> SEQUENCE: 11

His Xaa Gln Gly Thr Phe Thr Ser Asp Leu Ser Lys Gln Lys Glu Ser
1               5                   10                  15

Xaa Ala Ala Gln Asp Phe Ile Glu Trp Leu Lys Ala Gly Gly Pro Ser
            20                  25                  30

Ser Gly Ala Pro Pro Pro Ser
        35

```
<210> SEQ ID NO 12
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (17)..(17)
<223> OTHER INFORMATION: Xaa is an Aib amino acid
<220> FEATURE:
<221> NAME/KEY: MOD_RES
<222> LOCATION: (20)..(20)
<223> OTHER INFORMATION: Xaa is an Aib amino acid
<220> FEATURE:
<221> NAME/KEY: MOD_RES
<222> LOCATION: (39)..(39)
<223> OTHER INFORMATION: Ser is modified with an NH2 group

<400> SEQUENCE: 12

His Xaa Gln Gly Thr Phe Thr Ser Asp Leu Ser Lys Gln Lys Glu Ser
1               5                   10                  15

Xaa Ala Ala Xaa Leu Phe Ile Glu Trp Leu Lys Ala Gly Gly Pro Ser
            20                  25                  30

Ser Gly Ala Pro Pro Pro Ser
        35

<210> SEQ ID NO 13
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is an Aib amino acid
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (17)..(17)
<223> OTHER INFORMATION: Xaa is an Aib amino acid
<220> FEATURE:
<221> NAME/KEY: MOD_RES
<222> LOCATION: (39)..(39)
<223> OTHER INFORMATION: Ser is modified with an NH2 group

<400> SEQUENCE: 13

His Xaa Gln Gly Thr Phe Thr Ser Asp Leu Ser Lys Gln Lys Glu Ser
1               5                   10                  15

Xaa Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 14
```

```
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (17)..(17)
<223> OTHER INFORMATION: Xaa is an Aib amino acid
<220> FEATURE:
<221> NAME/KEY: MOD_RES
<222> LOCATION: (39)..(39)
<223> OTHER INFORMATION: Ser is modified with an NH2 group

<400> SEQUENCE: 14

His Xaa Gln Gly Thr Phe Thr Ser Asp Leu Ser Lys Gln Lys Glu Ser
1               5                   10                  15

Xaa Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 15
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (17)..(17)
<223> OTHER INFORMATION: Xaa is an Aib amino acid
<220> FEATURE:
<221> NAME/KEY: MOD_RES
<222> LOCATION: (39)..(39)
<223> OTHER INFORMATION: Ser is modified with an NH2 group

<400> SEQUENCE: 15

His Xaa Gln Gly Thr Phe Thr Ser Asp Leu Ser Lys Gln Lys Glu Ser
1               5                   10                  15

Xaa Ala Ala Gln Leu Phe Ile Glu Trp Leu Lys Ala Gly Gly Pro Ser
            20                  25                  30

Ser Gly Ala Pro Pro Pro Ser
        35

<210> SEQ ID NO 16
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
```

```
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 16

His Xaa Gln Gly Thr Phe Thr Ser Asp Leu Ser Lys Gln Lys Glu Glu
1               5                   10                  15

Glu Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 17
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 17

His Xaa Gln Gly Thr Phe Thr Ser Asp Leu Ser Lys Gln Lys Glu Glu
1               5                   10                  15

Glu Ala Ala Lys Asp Phe Ile Glu Trp Leu Lys Ala Gly Gly Pro Ser
            20                  25                  30

Ser Gly Ala Pro Pro Pro Ser
        35

<210> SEQ ID NO 18
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (20)..(20)
<223> OTHER INFORMATION: Xaa is an Aib amino acid
<220> FEATURE:
<221> NAME/KEY: MOD_RES
<222> LOCATION: (39)..(39)
<223> OTHER INFORMATION: Ser is modified with an NH2 group
```

```
<400> SEQUENCE: 18

His Xaa Gln Gly Thr Phe Thr Ser Asp Leu Ser Lys Gln Lys Glu Glu
1               5                   10                  15

Glu Ala Ala Xaa Asp Phe Ile Glu Trp Leu Lys Ala Gly Gly Pro Ser
            20                  25                  30

Ser Gly Ala Pro Pro Pro Ser
        35

<210> SEQ ID NO 19
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 19

His Xaa Gln Gly Thr Phe Thr Ser Asp Leu Ser Lys Gln Lys Glu Glu
1               5                   10                  15

Glu Ala Ala Lys Leu Phe Ile Glu Trp Leu Lys Ala Gly Gly Pro Ser
            20                  25                  30

Ser Gly Ala Pro Pro Pro Ser
        35

<210> SEQ ID NO 20
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 20

His Xaa Gln Gly Thr Phe Thr Ser Asp Leu Ser Lys Gln Lys Glu Ser
1               5                   10                  15

Glu Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 21
<211> LENGTH: 39
```

-continued

```
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 21

His Xaa Gln Gly Thr Phe Thr Ser Asp Leu Ser Lys Gln Lys Glu Ser
1               5                   10                  15

Glu Ala Ala Gln Leu Phe Ile Glu Trp Leu Lys Ala Gly Gly Pro Ser
            20                  25                  30

Ser Gly Ala Pro Pro Pro Ser
        35

<210> SEQ ID NO 22
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 22

His Xaa Gln Gly Thr Phe Thr Ser Asp Leu Ser Lys Gln Lys Asp Glu
1               5                   10                  15

Lys Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 23
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
```

```
<222> LOCATION: (39)..(39)
<223> OTHER INFORMATION: Ser is modified with an NH2 group

<400> SEQUENCE: 23

His Xaa Gln Gly Thr Phe Thr Ser Asp Leu Ser Lys Gln Lys Glu Glu
1               5                   10                  15

Lys Lys Ala Lys Leu Phe Ile Glu Trp Leu Lys Ala Gly Gly Pro Ser
            20                  25                  30

Ser Gly Ala Pro Pro Pro Ser
        35

<210> SEQ ID NO 24
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 24

His Xaa Gln Gly Thr Phe Thr Ser Asp Leu Ser Lys Gln Lys Glu Ser
1               5                   10                  15

Lys Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 25
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is an Aib amino acid
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 25

His Xaa Gln Gly Thr Phe Thr Ser Asp Leu Ser Lys Gln Lys Glu Ser
1               5                   10                  15

Lys Ala Ala Gln Asp Phe Ile Glu Trp Leu Lys Ala Gly Gly Pro Ser
            20                  25                  30

Ser Gly Ala Pro Pro Pro Ser
        35
```

```
<210> SEQ ID NO 26
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 26

His Xaa Gln Gly Thr Phe Thr Ser Asp Leu Ser Lys Gln Lys Glu Ser
1               5                   10                  15

Lys Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 27
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino acid side
      chain group as Lys((S)-4-carboxy-4-octadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 27

His Xaa Gln Gly Thr Phe Thr Ser Asp Leu Ser Lys Gln Lys Glu Ser
1               5                   10                  15

Lys Ala Ala Gln Leu Phe Ile Glu Trp Leu Lys Ala Gly Gly Pro Ser
            20                  25                  30

Ser Gly Ala Pro Pro Pro Ser
        35

<210> SEQ ID NO 28
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
```

```
<220> FEATURE:
<221> NAME/KEY: MOD_RES
<222> LOCATION: (39)..(39)
<223> OTHER INFORMATION: Ser is modified with an NH2 group

<400> SEQUENCE: 28

His Xaa Gln Gly Thr Phe Thr Ser Asp Leu Ser Lys Gln Lys Glu Ser
1               5                   10                  15

Lys Ala Ala Gln Glu Phe Ile Glu Trp Leu Lys Ala Gly Gly Pro Ser
            20                  25                  30

Ser Gly Ala Pro Pro Pro Ser
        35

<210> SEQ ID NO 29
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 29

His Xaa Gln Gly Thr Phe Thr Ser Asp Leu Ser Lys Gln Lys Glu Ser
1               5                   10                  15

Lys Ala Ala Gln Leu Phe Ile Glu Trp Leu Lys Ala Gly Gly Pro Ser
            20                  25                  30

Ser Gly Ala Pro Pro Pro Ser
        35

<210> SEQ ID NO 30
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 30

His Xaa Gln Gly Thr Phe Thr Ser Asp Leu Ser Lys Gln Lys Asp Ser
1               5                   10                  15

Lys Ala Ala Gln Asp Phe Ile Glu Trp Leu Lys Ala Gly Gly Pro Ser
            20                  25                  30

Ser Gly Ala Pro Pro Pro Ser
        35
```

```
<210> SEQ ID NO 31
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is an Aib amino acid
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 31

His Xaa Gln Gly Thr Phe Thr Ser Asp Leu Ser Lys Gln Lys Asp Ser
1               5                   10                  15

Lys Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 32
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys(hexadecanoyl)
<220> FEATURE:
<221> NAME/KEY: MOD_RES
<222> LOCATION: (39)..(39)
<223> OTHER INFORMATION: Ser is modified with an NH2 group

<400> SEQUENCE: 32

His Xaa Gln Gly Thr Phe Thr Ser Asp Leu Ser Lys Gln Lys Glu Ser
1               5                   10                  15

Lys Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 33
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is an Aib amino acid
<220> FEATURE:
<221> NAME/KEY: MOD_RES
<222> LOCATION: (14)..(14)
```

```
<223> OTHER INFORMATION: Lys is functionalized at the amino side chain
      group as Lys(hexadecanoyl)
<220> FEATURE:
<221> NAME/KEY: MOD_RES
<222> LOCATION: (39)..(39)
<223> OTHER INFORMATION: Ser is modified with an NH2 group

<400> SEQUENCE: 33

His Xaa Gln Gly Thr Phe Thr Ser Asp Leu Ser Lys Gln Lys Glu Ser
1               5                   10                  15

Lys Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 34
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 34

His Xaa Gln Gly Thr Phe Thr Ser Asp Leu Ser Lys Gln Lys Asp Glu
1               5                   10                  15

Gln Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 35
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 35

His Xaa Gln Gly Thr Phe Thr Ser Asp Leu Ser Lys Gln Lys Glu Ser
1               5                   10                  15

Gln Ala Ala Gln Asp Phe Ile Glu Trp Leu Lys Ala Gly Gly Pro Ser
            20                  25                  30
```

```
Ser Gly Ala Pro Pro Pro Ser
        35

<210> SEQ ID NO 36
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is an Aib amino acid
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 36

His Xaa Gln Gly Thr Phe Thr Ser Asp Leu Ser Lys Gln Lys Glu Ser
1               5                   10                  15

Gln Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 37
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 37

His Xaa Gln Gly Thr Phe Thr Ser Asp Leu Ser Lys Gln Lys Glu Ser
1               5                   10                  15

Gln Ala Ala Gln Glu Phe Ile Glu Trp Leu Lys Ala Gly Gly Pro Ser
            20                  25                  30

Ser Gly Ala Pro Pro Pro Ser
        35

<210> SEQ ID NO 38
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is an Aib amino acid
<220> FEATURE:
```

```
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 38

His Xaa Gln Gly Thr Phe Thr Ser Asp Leu Ser Lys Gln Lys Glu Ser
1               5                   10                  15

Gln Ala Ala Gln Glu Phe Ile Glu Trp Leu Lys Ala Gly Gly Pro Ser
            20                  25                  30

Ser Gly Ala Pro Pro Pro Ser
        35

<210> SEQ ID NO 39
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 39

His Xaa Gln Gly Thr Phe Thr Ser Asp Leu Ser Lys Gln Lys Asp Ser
1               5                   10                  15

Gln Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 40
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 40

His Xaa Gln Gly Thr Phe Thr Ser Asp Leu Ser Lys Gln Lys Glu Ser
1               5                   10                  15

Gln Ala Ala Gln Asp Phe Ile Glu Trp Leu Lys Ala Gly Gly Pro Ser
```

Ser Gly Ala Pro Pro Pro Ser
        35

<210> SEQ ID NO 41
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is an Aib amino acid
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 41

His Xaa Gln Gly Thr Phe Thr Ser Asp Leu Ser Lys Gln Lys Glu Ser
1               5                   10                  15

Gln Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 42
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino acid chain
      group as Lys(hexadecanoyl)
<220> FEATURE:
<221> NAME/KEY: MOD_RES
<222> LOCATION: (39)..(39)
<223> OTHER INFORMATION: Ser is modified with an NH2 group

<400> SEQUENCE: 42

His Xaa Gln Gly Thr Phe Thr Ser Asp Leu Ser Lys Gln Lys Glu Ser
1               5                   10                  15

Gln Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 43
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)

```
<223> OTHER INFORMATION: Xaa is an Aib amino acid
<220> FEATURE:
<221> NAME/KEY: MOD_RES
<222> LOCATION: (14)..(14)
<223> OTHER INFORMATION: Lys is functionalized at the amino acid chain
      group as Lys(hexadecanoyl)
<220> FEATURE:
<221> NAME/KEY: MOD_RES
<222> LOCATION: (39)..(39)
<223> OTHER INFORMATION: Ser is modified with an NH2 group

<400> SEQUENCE: 43

His Xaa Gln Gly Thr Phe Thr Ser Asp Leu Ser Lys Gln Lys Glu Ser
1               5                   10                  15

Gln Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 44
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 44

His Xaa Gln Gly Thr Phe Thr Ser Asp Leu Ser Lys Gln Lys Glu Ser
1               5                   10                  15

Arg Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 45
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 45

His Xaa Gln Gly Thr Phe Thr Ser Asp Leu Ser Lys Gln Lys Glu Ser
1               5                   10                  15
```

Arg Ala Ala Gln Leu Phe Ile Glu Trp Leu Lys Ala Gly Gly Pro Ser
            20                  25                  30

Ser Gly Ala Pro Pro Pro Ser
        35

<210> SEQ ID NO 46
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      as Lys((S)-4-carboxy-4-hexadecanoylamino-butyryl)
<220> FEATURE:
<221> NAME/KEY: MOD_RES
<222> LOCATION: (20)..(20)
<223> OTHER INFORMATION: Xaa is an Aib amino acid
<220> FEATURE:
<221> NAME/KEY: MOD_RES
<222> LOCATION: (39)..(39)
<223> OTHER INFORMATION: Ser is modified with an NH2 group

<400> SEQUENCE: 46

His Xaa Gln Gly Thr Phe Thr Ser Asp Leu Ser Lys Gln Lys Glu Ser
1               5                   10                  15

Arg Ala Ala Xaa Leu Phe Ile Glu Trp Leu Lys Ala Gly Gly Pro Ser
            20                  25                  30

Ser Gly Ala Pro Pro Pro Ser
        35

<210> SEQ ID NO 47
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys ((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 47

His Xaa Gln Gly Thr Phe Thr Ser Asp Leu Ser Lys Gln Lys Glu Ser
1               5                   10                  15

Arg Ala Ala Gln Glu Phe Ile Glu Trp Leu Lys Ala Gly Gly Pro Ser
            20                  25                  30

Ser Gly Ala Pro Pro Pro Ser
        35

<210> SEQ ID NO 48
<211> LENGTH: 39
<212> TYPE: PRT

```
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 48

His Xaa Gln Gly Thr Phe Thr Ser Asp Leu Ser Lys Gln Lys Glu Ser
1               5                   10                  15

Arg Ala Ala Gln Leu Phe Ile Glu Trp Leu Lys Ala Gly Gly Pro Ser
            20                  25                  30

Ser Gly Ala Pro Pro Pro Ser
        35

<210> SEQ ID NO 49
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-((S)-4-carboxy-4-hexadecanoylamino-
      butyrylamino)-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 49

His Xaa Gln Gly Thr Phe Thr Ser Asp Leu Ser Lys Gln Lys Glu Ser
1               5                   10                  15

Arg Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 50
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys(4-hexadecanoylamino-butyryl)
<220> FEATURE:
<221> NAME/KEY: MOD_RES
```

```
<222> LOCATION: (39)..(39)
<223> OTHER INFORMATION: Ser is modified with an NH2 group

<400> SEQUENCE: 50

His Xaa Gln Gly Thr Phe Thr Ser Asp Leu Ser Lys Gln Lys Glu Ser
1               5                   10                  15

Arg Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 51
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 51

His Xaa Gln Gly Thr Phe Thr Ser Asp Leu Ser Lys Gln Lys Glu Ser
1               5                   10                  15

Arg Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 52
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-((S)-4-carboxy-4-octadecanoylamino-
      butyrylamino)-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 52

His Xaa Gln Gly Thr Phe Thr Ser Asp Leu Ser Lys Gln Lys Glu Ser
1               5                   10                  15

Arg Ala Ala Gln Asp Phe Ile Glu Trp Leu Lys Ala Gly Gly Pro Ser
            20                  25                  30

Ser Gly Ala Pro Pro Pro Ser
        35
```

```
<210> SEQ ID NO 53
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys(4-octadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 53

His Xaa Gln Gly Thr Phe Thr Ser Asp Leu Ser Lys Gln Lys Glu Ser
1               5                   10                  15

Arg Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 54
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys(3-(3-octadecanoylamino-propionylamino)-propionyl)
<220> FEATURE:
<221> NAME/KEY: MOD_RES
<222> LOCATION: (39)..(39)
<223> OTHER INFORMATION: Ser is modified with an NH2 group

<400> SEQUENCE: 54

His Xaa Gln Gly Thr Phe Thr Ser Asp Leu Ser Lys Gln Lys Glu Ser
1               5                   10                  15

Arg Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 55
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
```

```
    group as Lys((S)-4-carboxy-4-((Z)-octadec-9-enoylamino)-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 55

His Xaa Gln Gly Thr Phe Thr Ser Asp Leu Ser Lys Gln Lys Glu Ser
1               5                  10                  15

Arg Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 56
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
    group as Lys(4-((Z)-octadec-9-enoylamino)-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 56

His Xaa Gln Gly Thr Phe Thr Ser Asp Leu Ser Lys Gln Lys Glu Ser
1               5                  10                  15

Arg Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 57
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
    group as Lys((S)-4-carboxy-4-(3-[(R)-2,5,7,8-tetramethyl-2-
    ((4R,8R)-4,8,12-trimethyl-tridecyl)-chroman-6-yloxycarbonyl]-
    propionylamino]-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 57

His Xaa Gln Gly Thr Phe Thr Ser Asp Leu Ser Lys Gln Lys Glu Ser
1               5                  10                  15

Arg Ala Ala Gln Asp Phe Ile Glu Trp Leu Lys Ala Gly Gly Pro Ser
            20                  25                  30
```

```
Ser Gly Ala Pro Pro Pro Ser
        35

<210> SEQ ID NO 58
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys(4-(3-[(R)-2,5,7,8-tetramethyl-2-((4R,8R)-4,8,12-
      trimethyl-tridecyl)-chroman-6-yloxycarbonyl]-propionylamino
-
      butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 58

His Xaa Gln Gly Thr Phe Thr Ser Asp Leu Ser Lys Gln Lys Glu Ser
1               5                   10                  15

Arg Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 59
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-henicosanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 59

His Xaa Gln Gly Thr Phe Thr Ser Asp Leu Ser Lys Gln Lys Glu Ser
1               5                   10                  15

Arg Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 60
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
```

```
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-docosanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 60

His Xaa Gln Gly Thr Phe Thr Ser Asp Leu Ser Lys Gln Lys Glu Ser
1               5                   10                  15

Arg Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 61
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino acid side
      chain group as Lys((S)-4-carboxy-4-((Z)-nonadec-10-enoylamino)-
      butyryl)
<220> FEATURE:
<221> NAME/KEY: MOD_RES
<222> LOCATION: (39)..(39)
<223> OTHER INFORMATION: Ser is modfied with an NH2 group

<400> SEQUENCE: 61

His Xaa Gln Gly Thr Phe Thr Ser Asp Leu Ser Lys Gln Lys Glu Ser
1               5                   10                  15

Arg Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 62
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-(4-decyloxy-benzoylamino)-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 62
```

His Xaa Gln Gly Thr Phe Thr Ser Asp Leu Ser Lys Gln Lys Glu Ser
1               5                   10                  15

Arg Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 63
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-[(4'-octyloxy-biphenyl-4-carbonyl)-
      amino]-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 63

His Xaa Gln Gly Thr Phe Thr Ser Asp Leu Ser Lys Gln Lys Glu Ser
1               5                   10                  15

Arg Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 64
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-(12-phenyl-dodecanoylamino)-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 64

His Xaa Gln Gly Thr Phe Thr Ser Asp Leu Ser Lys Gln Lys Glu Ser
1               5                   10                  15

Arg Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 65
<211> LENGTH: 39
<212> TYPE: PRT
<213> ORGANISM: Artificial Sequence

```
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 65

His Xaa Gln Gly Thr Phe Thr Ser Asp Leu Ser Lys Gln Lys Glu Ser
 1               5                  10                  15

Arg Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 66
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys(hexadecanoyl)
<220> FEATURE:
<221> NAME/KEY: MOD_RES
<222> LOCATION: (39)..(39)
<223> OTHER INFORMATION: Ser is modified with an NH2 group

<400> SEQUENCE: 66

His Xaa Gln Gly Thr Phe Thr Ser Asp Leu Ser Lys Gln Lys Glu Ser
 1               5                  10                  15

Arg Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 67
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (20)..(20)
<223> OTHER INFORMATION: Xaa is an Aib amino acid
```

```
<220> FEATURE:
<221> NAME/KEY: MOD_RES
<222> LOCATION: (39)..(39)
<223> OTHER INFORMATION: Ser is modified with an NH2 group

<400> SEQUENCE: 67

His Xaa Gln Gly Thr Phe Thr Ser Asp Leu Ser Lys Gln Lys Asp Ser
1               5                   10                  15

Arg Arg Ala Xaa Asp Phe Ile Glu Trp Leu Lys Ala Gly Gly Pro Ser
            20                  25                  30

Ser Gly Ala Pro Pro Pro Ser
        35

<210> SEQ ID NO 68
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 68

His Xaa Gln Gly Thr Phe Thr Ser Asp Leu Ser Lys Gln Lys Glu Ser
1               5                   10                  15

Arg Arg Ala Gln Leu Phe Ile Glu Trp Leu Lys Ala Gly Gly Pro Ser
            20                  25                  30

Ser Gly Ala Pro Pro Pro Ser
        35

<210> SEQ ID NO 69
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys(hexadecanoyl)
<220> FEATURE:
<221> NAME/KEY: MOD_RES
<222> LOCATION: (39)..(39)
<223> OTHER INFORMATION: Ser is modified with an NH2 group

<400> SEQUENCE: 69

His Xaa Gln Gly Thr Phe Thr Ser Asp Leu Ser Lys Gln Lys Glu Ser
1               5                   10                  15

Arg Arg Ala Gln Leu Phe Ile Glu Trp Leu Lys Ala Gly Gly Pro Ser
            20                  25                  30

Ser Gly Ala Pro Pro Pro Ser
        35
```

```
<210> SEQ ID NO 70
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 70

His Xaa Gln Gly Thr Phe Thr Ser Asp Leu Ser Lys Gln Lys Glu Ser
1               5                   10                  15

Arg Ala Ala Gln Leu Phe Ile Glu Trp Leu Lys Ala Gly Gly Pro Ser
            20                  25                  30

Ser Gly Ala Pro Pro Pro Ser
        35

<210> SEQ ID NO 71
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Xaa is an Orn amino acid
<220> FEATURE:
<221> NAME/KEY: MOD_RES
<222> LOCATION: (14)..(14)
<223> OTHER INFORMATION: Orn is functionalized at the amino side chain
      group as Orn(S)-4-carboxy-4-hexadecanoylamino-butyryl
<220> FEATURE:
<221> NAME/KEY: MOD_RES
<222> LOCATION: (39)..(39)
<223> OTHER INFORMATION: Ser is modified with an NH2 group

<400> SEQUENCE: 71

His Xaa Gln Gly Thr Phe Thr Ser Asp Leu Ser Lys Gln Xaa Glu Ser
1               5                   10                  15

Arg Arg Ala Gln Asp Phe Ile Glu Trp Leu Lys Ala Gly Gly Pro Ser
            20                  25                  30

Ser Gly Ala Pro Pro Pro Ser
        35

<210> SEQ ID NO 72
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
```

```
<223> OTHER INFORMATION: Xaa is a D-Ser
<220> FEATURE:
<221> NAME/KEY: MOD_RES
<222> LOCATION: (14)..(14)
<223> OTHER INFORMATION: Xaa is an alpha,gamma-diaminobutyricacid (Dab)
      amino acid
<220> FEATURE:
<221> NAME/KEY: MOD_RES
<222> LOCATION: (14)..(14)
<223> OTHER INFORMATION: Dab is functionalized at the amino side chain
      group as Dab(S)-4-carboxy-4-hexadecanoylamino-butyryl
<220> FEATURE:
<221> NAME/KEY: MOD_RES
<222> LOCATION: (39)..(39)
<223> OTHER INFORMATION: Ser is modified with an NH2 group

<400> SEQUENCE: 72

His Xaa Gln Gly Thr Phe Thr Ser Asp Leu Ser Lys Gln Xaa Glu Ser
1               5                   10                  15

Arg Arg Ala Gln Asp Phe Ile Glu Trp Leu Lys Ala Gly Gly Pro Ser
            20                  25                  30

Ser Gly Ala Pro Pro Pro Ser
            35

<210> SEQ ID NO 73
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 73

His Xaa His Gly Thr Phe Thr Ser Asp Leu Ser Lys Gln Lys Glu Ser
1               5                   10                  15

Arg Arg Ala Gln Asp Phe Ile Glu Trp Leu Lys Ala Gly Gly Pro Ser
            20                  25                  30

Ser Gly Ala Pro Pro Pro Ser
            35

<210> SEQ ID NO 74
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group
```

```
<400> SEQUENCE: 74

His Xaa Gln Gly Thr Phe Thr Ser Asp Leu Ser Lys Gln Lys Asp Ser
1               5                   10                  15

Arg Arg Ala Gln Asp Phe Ile Glu Trp Leu Lys Ala Gly Gly Pro Ser
            20                  25                  30

Ser Gly Ala Pro Pro Pro Ser
        35

<210> SEQ ID NO 75
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (20)..(20)
<223> OTHER INFORMATION: Xaa is an Aib amino acid
<220> FEATURE:
<221> NAME/KEY: MOD_RES
<222> LOCATION: (39)..(39)
<223> OTHER INFORMATION: Ser is modified with an NH2 group

<400> SEQUENCE: 75

His Xaa Gln Gly Thr Phe Thr Ser Asp Leu Ser Lys Gln Lys Glu Ser
1               5                   10                  15

Arg Arg Ala Xaa Asp Phe Ile Glu Trp Leu Lys Ala Gly Gly Pro Ser
            20                  25                  30

Ser Gly Ala Pro Pro Pro Ser
        35

<210> SEQ ID NO 76
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys(hexadecanoyl)
<220> FEATURE:
<221> NAME/KEY: MOD_RES
<222> LOCATION: (20)..(20)
<223> OTHER INFORMATION: Xaa is an Aib amino acid
<220> FEATURE:
<221> NAME/KEY: MOD_RES
<222> LOCATION: (39)..(39)
<223> OTHER INFORMATION: Ser is modified with an NH2 group

<400> SEQUENCE: 76

His Xaa Gln Gly Thr Phe Thr Ser Asp Leu Ser Lys Gln Lys Glu Ser
1               5                   10                  15

Arg Arg Ala Xaa Asp Phe Ile Glu Trp Leu Lys Ala Gly Gly Pro Ser
```

Ser Gly Ala Pro Pro Pro Ser
        35

<210> SEQ ID NO 77
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is an Aib amino acid
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 77

His Xaa Gln Gly Thr Phe Thr Ser Asp Leu Ser Lys Gln Lys Glu Ser
1               5                   10                  15

Arg Arg Ala Gln Asp Phe Ile Glu Trp Leu Lys Ala Gly Gly Pro Ser
            20                  25                  30

Ser Gly Ala Pro Pro Pro Ser
        35

<210> SEQ ID NO 78
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (28)..(28)
<223> OTHER INFORMATION: Xaa is an Aib amino acid
<220> FEATURE:
<221> NAME/KEY: MOD_RES
<222> LOCATION: (39)..(39)
<223> OTHER INFORMATION: Ser is modified with an NH2 group

<400> SEQUENCE: 78

His Xaa Gln Gly Thr Phe Thr Ser Asp Leu Ser Lys Gln Lys Asp Ser
1               5                   10                  15

Arg Arg Ala Gln Asp Phe Ile Glu Trp Leu Lys Xaa Gly Gly Pro Ser
            20                  25                  30

Ser Gly Ala Pro Pro Pro Ser
        35

<210> SEQ ID NO 79
<211> LENGTH: 39
<212> TYPE: PRT
<213> ORGANISM: Artificial Sequence
<220> FEATURE:

```
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (28)..(28)
<223> OTHER INFORMATION: Xaa is an Aib amino acid
<220> FEATURE:
<221> NAME/KEY: MOD_RES
<222> LOCATION: (39)..(39)
<223> OTHER INFORMATION: Ser is modified with an NH2 group

<400> SEQUENCE: 79

His Xaa Gln Gly Thr Phe Thr Ser Asp Leu Ser Lys Gln Lys Glu Ser
1               5                   10                  15

Arg Arg Ala Gln Asp Phe Ile Glu Trp Leu Lys Xaa Gly Gly Pro Ser
            20                  25                  30

Ser Gly Ala Pro Pro Pro Ser
        35

<210> SEQ ID NO 80
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 80

His Xaa Gln Gly Thr Phe Thr Ser Asp Leu Ser Lys Gln Lys Asp Ser
1               5                   10                  15

Arg Arg Ala Gln Asp Phe Ile Glu Trp Leu Lys Asp Gly Gly Pro Ser
            20                  25                  30

Ser Gly Ala Pro Pro Pro Ser
        35

<210> SEQ ID NO 81
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys(hexadecanoyl)
<220> FEATURE:
```

```
<221> NAME/KEY: MOD_RES
<222> LOCATION: (39)..(39)
<223> OTHER INFORMATION: Ser is modified with an NH2 group

<400> SEQUENCE: 81

His Xaa Gln Gly Thr Phe Thr Ser Asp Leu Ser Lys Gln Lys Asp Ser
1               5                   10                  15

Arg Arg Ala Gln Asp Phe Ile Glu Trp Leu Lys Asp Gly Gly Pro Ser
            20                  25                  30

Ser Gly Ala Pro Pro Pro Ser
        35

<210> SEQ ID NO 82
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 82

His Xaa Gln Gly Thr Phe Thr Ser Asp Leu Ser Lys Gln Lys Glu Ser
1               5                   10                  15

Arg Arg Ala Gln Asp Phe Ile Glu Trp Leu Lys Glu Gly Gly Pro Ser
            20                  25                  30

Ser Gly Arg Pro Pro Pro Ser
        35

<210> SEQ ID NO 83
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys(hexadecanoyl)
<220> FEATURE:
<221> NAME/KEY: MOD_RES
<222> LOCATION: (39)..(39)
<223> OTHER INFORMATION: Ser is modified with an NH2 group

<400> SEQUENCE: 83

His Xaa Gln Gly Thr Phe Thr Ser Asp Leu Ser Lys Gln Lys Glu Ser
1               5                   10                  15

Arg Arg Ala Gln Asp Phe Ile Glu Trp Leu Lys Glu Gly Gly Pro Ser
            20                  25                  30

Ser Gly Arg Pro Pro Pro Ser
        35
```

```
<210> SEQ ID NO 84
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 84

His Xaa Gln Gly Thr Phe Thr Ser Asp Leu Ser Lys Gln Lys Asp Ser
1               5                   10                  15

Arg Arg Ala Gln Asp Phe Ile Glu Trp Leu Lys Lys Gly Gly Pro Ser
            20                  25                  30

Ser Gly Ala Pro Pro Pro Ser
        35

<210> SEQ ID NO 85
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 85

His Xaa Gln Gly Thr Phe Thr Ser Asp Leu Ser Lys Gln Lys Glu Ser
1               5                   10                  15

Arg Arg Ala Gln Asp Phe Ile Glu Trp Leu Lys Lys Gly Gly Pro Ser
            20                  25                  30

Ser Gly Ala Pro Pro Pro Ser
        35

<210> SEQ ID NO 86
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
```

```
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 86

His Xaa Gln Gly Thr Phe Thr Ser Asp Leu Ser Lys Gln Lys Asp Ser
1               5                   10                  15

Gln Ala Ala Gln Asp Phe Ile Glu Trp Leu Lys Asn Thr Gly Pro Ser
            20                  25                  30

Ser Gly Ala Pro Pro Pro Ser
        35

<210> SEQ ID NO 87
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified withn an NH2 group

<400> SEQUENCE: 87

His Xaa Gln Gly Thr Phe Thr Ser Asp Leu Ser Lys Gln Lys Asp Glu
1               5                   10                  15

Arg Arg Ala Lys Asp Phe Ile Glu Trp Leu Lys Asn Gly Gly Pro Ser
            20                  25                  30

Ser Gly Ala Pro Pro Pro Ser
        35

<210> SEQ ID NO 88
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 88

His Xaa Gln Gly Thr Phe Thr Ser Asp Leu Ser Lys Gln Lys Glu Lys
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
```

-continued

```
<210> SEQ ID NO 89
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-(3-[(R)-2,5,7,8-tetramethyl-2-
      ((4R,8R)-4,8,12-trimethyl-tridecyl)-chroman-6-yloxycarbonyl]-
      propionylamino)-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 89

His Xaa Gln Gly Thr Phe Thr Ser Asp Leu Ser Lys Gln Lys Asp Ser
 1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
        35

<210> SEQ ID NO 90
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-tetradecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 90

His Xaa Gln Gly Thr Phe Thr Ser Asp Leu Ser Lys Gln Lys Asp Ser
 1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
        35

<210> SEQ ID NO 91
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
```

```
<220> FEATURE:
<221> NAME/KEY: MOD_RES
<222> LOCATION: (14)..(14)
<223> OTHER INFORMATION: Lys is functionalized at the amino side chain
      group as Lys((S)-4-(11-benzyloxycarbonyl-undecanoylamino)-4-
      carboxy-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 91

His Xaa Gln Gly Thr Phe Thr Ser Asp Leu Ser Lys Gln Lys Asp Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
        35

<210> SEQ ID NO 92
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 92

His Xaa Gln Gly Thr Phe Thr Ser Asp Leu Ser Lys Gln Lys Asp Ser
1               5                   10                  15

Arg Arg Ala Gln Asp Phe Ile Glu Trp Leu Lys Asn Thr Gly Pro Ser
            20                  25                  30

Ser Gly Ala Pro Pro Pro Ser
        35

<210> SEQ ID NO 93
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 93

His Xaa Gln Gly Thr Phe Thr Ser Asp Leu Ser Lys Gln Lys Asp Ser
1               5                   10                  15
```

```
Arg Arg Ala Gln Asp Phe Ile Glu Trp Leu Lys Asn Ala Gly Pro Ser
            20                  25                  30

Ser Gly Ala Pro Pro Pro Ser
        35

<210> SEQ ID NO 94
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (29)..(29)
<223> OTHER INFORMATION: Xaa is a D-Ala
<220> FEATURE:
<221> NAME/KEY: MOD_RES
<222> LOCATION: (39)..(39)
<223> OTHER INFORMATION: Ser is modified with an NH2 group

<400> SEQUENCE: 94

His Xaa Gln Gly Thr Phe Thr Ser Asp Leu Ser Lys Gln Lys Asp Ser
1               5                   10                  15

Arg Arg Ala Gln Asp Phe Ile Glu Trp Leu Lys Asn Xaa Gly Pro Ser
            20                  25                  30

Ser Gly Ala Pro Pro Pro Ser
        35

<210> SEQ ID NO 95
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 95

His Xaa Gln Gly Thr Phe Thr Ser Asp Leu Ser Lys Gln Lys Glu Ser
1               5                   10                  15

Arg Arg Ala Gln Asp Phe Ile Glu Trp Leu Lys Asn Ala Gly Pro Ser
            20                  25                  30

Ser Gly Ala Pro Pro Pro Ser
        35

<210> SEQ ID NO 96
<211> LENGTH: 39
<212> TYPE: PRT
```

```
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 96

His Xaa Gln Gly Thr Phe Thr Ser Asp Leu Ser Lys Gln Lys Glu Ser
1               5                   10                  15

Arg Arg Ala Gln Asp Phe Ile Glu Trp Leu Lys Asn Thr Gly Pro Ser
            20                  25                  30

Ser Gly Ala Pro Pro Pro Ser
        35

<210> SEQ ID NO 97
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 97

His Xaa Gln Gly Thr Phe Thr Ser Asp Leu Ser Lys Gln Lys Asp Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
        35

<210> SEQ ID NO 98
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butytyl)
<220> FEATURE:
<221> NAME/KEY: MOD_RES
<222> LOCATION: (39)..(39)
```

<223> OTHER INFORMATION: Ser is modified with an NH-pyrrolidin group

<400> SEQUENCE: 98

His Xaa Gln Gly Thr Phe Thr Ser Asp Leu Ser Lys Gln Lys Asp Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
        35

<210> SEQ ID NO 99
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH-benzyl group

<400> SEQUENCE: 99

His Xaa Gln Gly Thr Phe Thr Ser Asp Leu Ser Lys Gln Lys Asp Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
        35

<210> SEQ ID NO 100
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH-tert.butyl group

<400> SEQUENCE: 100

His Xaa Gln Gly Thr Phe Thr Ser Asp Leu Ser Lys Gln Lys Asp Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
        35

<210> SEQ ID NO 101

```
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized ath the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an N-diethyl group

<400> SEQUENCE: 101

His Xaa Gln Gly Thr Phe Thr Ser Asp Leu Ser Lys Gln Lys Asp Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
        35

<210> SEQ ID NO 102
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an N-morpholin group

<400> SEQUENCE: 102

His Xaa Gln Gly Thr Phe Thr Ser Asp Leu Ser Lys Gln Lys Asp Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
        35

<210> SEQ ID NO 103
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
```

```
<221> NAME/KEY: MOD_RES
<222> LOCATION: (39)..(39)
<223> OTHER INFORMATION: Ser is modified with an NH-CH2-CF3 group

<400> SEQUENCE: 103

His Xaa Gln Gly Thr Phe Thr Ser Asp Leu Ser Lys Gln Lys Asp Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
        35

<210> SEQ ID NO 104
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH-(CH2-CH2-O)4-CH2-
      CH2-COOH group

<400> SEQUENCE: 104

His Xaa Gln Gly Thr Phe Thr Ser Asp Leu Ser Lys Gln Lys Asp Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
        35

<210> SEQ ID NO 105
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH-(CH2-CH2-O)24-CH2-
      CH2-COOH group

<400> SEQUENCE: 105

His Xaa Gln Gly Thr Phe Thr Ser Asp Leu Ser Lys Gln Lys Asp Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
```

<210> SEQ ID NO 106
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH-(CH2)15-CH3 group

<400> SEQUENCE: 106

His Xaa Gln Gly Thr Phe Thr Ser Asp Leu Ser Lys Gln Lys Asp Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
        35

<210> SEQ ID NO 107
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH-(CH2)12-OH group

<400> SEQUENCE: 107

His Xaa Gln Gly Thr Phe Thr Ser Asp Leu Ser Lys Gln Lys Asp Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
        35

<210> SEQ ID NO 108
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES

```
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH-(CH2)14-CH3 group

<400> SEQUENCE: 108

His Xaa Gln Gly Thr Phe Thr Ser Asp Leu Ser Lys Gln Lys Asp Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
        35

<210> SEQ ID NO 109
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH-(CH2)17-CH3 group

<400> SEQUENCE: 109

His Xaa Gln Gly Thr Phe Thr Ser Asp Leu Ser Lys Gln Lys Asp Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
        35

<210> SEQ ID NO 110
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH-(CH2)13-CH3 group

<400> SEQUENCE: 110

His Xaa Gln Gly Thr Phe Thr Ser Asp Leu Ser Lys Gln Lys Asp Ser
1               5                   10                  15

Arg Arg Ala Gln Asp Phe Ile Glu Trp Leu Lys Asn Gly Gly Pro Ser
            20                  25                  30
```

```
Ser Gly Ala Pro Pro Pro Ser
        35

<210> SEQ ID NO 111
<211> LENGTH: 40
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (40)..(40)
<223> OTHER INFORMATION: Ser is modified with an NH2 group

<400> SEQUENCE: 111

His Xaa Gln Gly Thr Phe Thr Ser Asp Leu Ser Lys Gln Lys Glu Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser Lys
        35                  40

<210> SEQ ID NO 112
<211> LENGTH: 40
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys(hexadecanoyl)
<220> FEATURE:
<221> NAME/KEY: MOD_RES
<222> LOCATION: (40)..(40)
<223> OTHER INFORMATION: Ser is modified with an NH2 group

<400> SEQUENCE: 112

His Xaa Gln Gly Thr Phe Thr Ser Asp Leu Ser Lys Gln Lys Glu Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser Lys
        35                  40

<210> SEQ ID NO 113
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
```

```
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 113

His Xaa Gln Gly Thr Phe Thr Ser Asp Leu Ser Lys Gln Lys Glu Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Lys
        35

<210> SEQ ID NO 114
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys(hexadecanoyl)
<220> FEATURE:
<221> NAME/KEY: MOD_RES
<222> LOCATION: (39)..(39)
<223> OTHER INFORMATION: Ser is modified with an NH2 group

<400> SEQUENCE: 114

His Xaa Gln Gly Thr Phe Thr Ser Asp Leu Ser Lys Gln Lys Glu Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Lys
        35

<210> SEQ ID NO 115
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is an Aib amino acid
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 115

His Xaa Gln Gly Thr Phe Thr Ser Asp Leu Ser Lys Gln Lys Asp Ser
1               5                   10                  15
```

Arg Arg Ala Gln Asp Phe Ile Glu Trp Leu Lys Asn Gly Gly Pro Ser
            20                  25                  30

Ser Gly Ala Pro Pro Ser
        35

<210> SEQ ID NO 116
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: SITE
<222> LOCATION: (39)..(39)
<223> OTHER INFORMATION: Ser is modified with an NH2 group

<400> SEQUENCE: 116

His Xaa Gln Gly Thr Phe Thr Ser Asp Leu Ser Lys Gln Lys Glu Ser
1               5                   10                  15

Arg Arg Ala Gln Asp Phe Ile Glu Trp Leu Lys Asn Gly Gly Pro Ser
            20                  25                  30

Ser Gly Ala Pro Pro Ser
        35

<210> SEQ ID NO 117
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is an Aib amino acid
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl-)
<220> FEATURE:
<221> NAME/KEY: MOD_RES
<222> LOCATION: (39)..(39)
<223> OTHER INFORMATION: Ser is modified with an NH2 group

<400> SEQUENCE: 117

His Xaa Gln Gly Thr Phe Thr Ser Asp Leu Ser Lys Gln Lys Glu Ser
1               5                   10                  15

Arg Arg Ala Gln Asp Phe Ile Glu Trp Leu Lys Asn Gly Gly Pro Ser
            20                  25                  30

Ser Gly Ala Pro Pro Ser
        35

<210> SEQ ID NO 118
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES

```
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (20)..(20)
<223> OTHER INFORMATION: Xaa is an Aib amino acid
<220> FEATURE:
<221> NAME/KEY: MOD_RES
<222> LOCATION: (39)..(39)
<223> OTHER INFORMATION: Ser is modified with an NH2 group

<400> SEQUENCE: 118

His Xaa Gln Gly Thr Phe Thr Ser Asp Leu Ser Lys Gln Lys Asp Ser
1               5                   10                  15

Arg Arg Ala Xaa Asp Phe Ile Glu Trp Leu Lys Asn Gly Gly Pro Ser
            20                  25                  30

Ser Gly Ala Pro Pro Pro Ser
        35

<210> SEQ ID NO 119
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys(hexadecanoyl)
<220> FEATURE:
<221> NAME/KEY: MOD_RES
<222> LOCATION: (20)..(20)
<223> OTHER INFORMATION: Xaa is an Aib amino acid
<220> FEATURE:
<221> NAME/KEY: MOD_RES
<222> LOCATION: (39)..(39)
<223> OTHER INFORMATION: Ser is modified with an NH2 group

<400> SEQUENCE: 119

His Xaa Gln Gly Thr Phe Thr Ser Asp Leu Ser Lys Gln Lys Glu Ser
1               5                   10                  15

Arg Arg Ala Xaa Asp Phe Ile Glu Trp Leu Lys Asn Gly Gly Pro Ser
            20                  25                  30

Ser Gly Ala Pro Pro Pro Ser
        35

<210> SEQ ID NO 120
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
```

```
<220> FEATURE:
<221> NAME/KEY: MOD_RES
<222> LOCATION: (20)..(20)
<223> OTHER INFORMATION: Xaa is an Aib amino acid
<220> FEATURE:
<221> NAME/KEY: MOD_RES
<222> LOCATION: (39)..(39)
<223> OTHER INFORMATION: Ser is modified with an NH2 group

<400> SEQUENCE: 120

His Xaa Gln Gly Thr Phe Thr Ser Asp Leu Ser Lys Gln Lys Glu Ser
1               5                   10                  15

Arg Arg Ala Xaa Asp Phe Ile Glu Trp Leu Lys Asn Gly Gly Pro Ser
            20                  25                  30

Ser Gly Ala Pro Pro Pro Ser
        35

<210> SEQ ID NO 121
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (20)..(20)
<223> OTHER INFORMATION: Xaa is an Aib amino acid
<220> FEATURE:
<221> NAME/KEY: MOD_RES
<222> LOCATION: (39)..(39)
<223> OTHER INFORMATION: Ser is modified with an NH2 group

<400> SEQUENCE: 121

His Xaa Gln Gly Thr Phe Thr Ser Asp Leu Ser Lys Gln Lys Glu Ser
1               5                   10                  15

Arg Ala Ala Xaa Leu Phe Ile Glu Trp Leu Lys Asn Gly Gly Pro Ser
            20                  25                  30

Ser Gly Ala Pro Pro Pro Ser
        35

<210> SEQ ID NO 122
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys(hexadecanoyl)
<220> FEATURE:
<221> NAME/KEY: MOD_RES
<222> LOCATION: (20)..(20)
<223> OTHER INFORMATION: Xaa is an Aib amino acid
<220> FEATURE:
<221> NAME/KEY: MOD_RES
<222> LOCATION: (39)..(39)
```

<223> OTHER INFORMATION: Ser is modified with an NH2 group

<400> SEQUENCE: 122

His Xaa Gln Gly Thr Phe Thr Ser Asp Leu Ser Lys Gln Lys Glu Ser
1               5                   10                  15

Arg Ala Ala Xaa Leu Phe Ile Glu Trp Leu Lys Asn Gly Gly Pro Ser
            20                  25                  30

Ser Gly Ala Pro Pro Pro Ser
            35

<210> SEQ ID NO 123
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 123

His Xaa Gln Gly Thr Phe Thr Ser Asp Leu Ser Lys Gln Lys Asp Ser
1               5                   10                  15

Gln Ala Ala Gln Asp Phe Ile Glu Trp Leu Lys Arg Gly Gly Pro Ser
            20                  25                  30

Ser Gly Ala Pro Pro Pro Ser
            35

<210> SEQ ID NO 124
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 124

His Xaa Gln Gly Thr Phe Thr Ser Asp Leu Ser Lys Gln Lys Asp Ser
1               5                   10                  15

Gln Ala Ala Gln Asp Phe Ile Glu Trp Leu Lys Arg Ala Gly Pro Ser
            20                  25                  30

Ser Gly Ala Pro Pro Pro Ser
            35

<210> SEQ ID NO 125

-continued

```
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 125

His Xaa Gln Gly Thr Phe Thr Ser Asp Leu Ser Lys Gln Lys Asp Ser
1               5                   10                  15

Arg Arg Ala Gln Asp Phe Ile Glu Trp Leu Lys Arg Gly Gly Pro Ser
            20                  25                  30

Ser Gly Ala Pro Pro Pro Ser
        35

<210> SEQ ID NO 126
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (29)..(29)
<223> OTHER INFORMATION: Xaa is a D-Ala
<220> FEATURE:
<221> NAME/KEY: MOD_RES
<222> LOCATION: (39)..(39)
<223> OTHER INFORMATION: Ser is modified with an NH2 group

<400> SEQUENCE: 126

His Xaa Gln Gly Thr Phe Thr Ser Asp Leu Ser Lys Gln Lys Glu Ser
1               5                   10                  15

Arg Arg Ala Gln Asp Phe Ile Glu Trp Leu Lys Arg Xaa Gly Pro Ser
            20                  25                  30

Ser Gly Ala Pro Pro Pro Ser
        35

<210> SEQ ID NO 127
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
```

```
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 127

His Xaa Gln Gly Thr Phe Thr Ser Asp Leu Ser Lys Gln Lys Glu Ser
1               5                   10                  15

Arg Arg Ala Gln Asp Phe Ile Glu Trp Leu Lys Arg Gly Gly Pro Ser
            20                  25                  30

Ser Gly Ala Pro Pro Pro Ser
        35

<210> SEQ ID NO 128
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 128

His Xaa Gln Gly Thr Phe Thr Ser Asp Leu Ser Lys Gln Lys Asp Ser
1               5                   10                  15

Arg Arg Ala Gln Asp Phe Ile Glu Trp Leu Lys Ser Gly Gly Pro Ser
            20                  25                  30

Ser Gly Ala Pro Pro Pro Ser
        35

<210> SEQ ID NO 129
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 129

His Xaa Gln Gly Thr Phe Thr Ser Asp Leu Ser Lys Gln Lys Glu Ser
1               5                   10                  15

Arg Arg Ala Gln Asp Phe Ile Glu Trp Leu Lys Ser Gly Gly Pro Ser
            20                  25                  30
```

Ser Gly Ala Pro Pro Pro Ser
        35

<210> SEQ ID NO 130
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (17)..(17)
<223> OTHER INFORMATION: Xaa is an Aib amino acid
<220> FEATURE:
<221> NAME/KEY: MOD_RES
<222> LOCATION: (39)..(39)
<223> OTHER INFORMATION: Ser is modified with an NH2 group

<400> SEQUENCE: 130

His Xaa Gln Gly Thr Phe Thr Ser Asp Leu Ser Lys Gln Lys Glu Ser
1               5                   10                  15

Xaa Ala Ala Gln Leu Phe Ile Glu Trp Leu Lys Ala Gly Gly Pro Ser
            20                  25                  30

Ser Gly Ala Pro Pro Pro Ser
        35

<210> SEQ ID NO 131
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys(4-octadecanoylamino-butyryl)
<220> FEATURE:
<221> NAME/KEY: MOD_RES
<222> LOCATION: (17)..(17)
<223> OTHER INFORMATION: Xaa is an Aib amino acid
<220> FEATURE:
<221> NAME/KEY: MOD_RES
<222> LOCATION: (39)..(39)
<223> OTHER INFORMATION: Ser is modified with an NH2 group

<400> SEQUENCE: 131

His Xaa Gln Gly Thr Phe Thr Ser Asp Leu Ser Lys Gln Lys Glu Ser
1               5                   10                  15

Xaa Ala Ala Gln Leu Phe Ile Glu Trp Leu Lys Ala Gly Gly Pro Ser
            20                  25                  30

Ser Gly Ala Pro Pro Pro Ser
        35

<210> SEQ ID NO 132
<211> LENGTH: 39

```
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is an Aib amino acid
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (17)..(17)
<223> OTHER INFORMATION: Xaa is an Aib amino acid
<220> FEATURE:
<221> NAME/KEY: MOD_RES
<222> LOCATION: (39)..(39)
<223> OTHER INFORMATION: Ser is modified with an NH2 group

<400> SEQUENCE: 132

His Xaa Gln Gly Thr Phe Thr Ser Asp Leu Ser Lys Gln Lys Glu Ser
1               5                   10                  15
Xaa Ala Ala Gln Leu Phe Ile Glu Trp Leu Lys Ala Gly Gly Pro Ser
            20                  25                  30
Ser Gly Ala Pro Pro Pro Ser
        35

<210> SEQ ID NO 133
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is an Aib amino acid
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (29)..(29)
<223> OTHER INFORMATION: Xaa is a D-Ala
<220> FEATURE:
<221> NAME/KEY: MOD_RES
<222> LOCATION: (39)..(39)
<223> OTHER INFORMATION: Ser is modified with an NH2 group

<400> SEQUENCE: 133

His Xaa Gln Gly Thr Phe Thr Ser Asp Leu Ser Lys Gln Lys Asp Glu
1               5                   10                  15
Lys Ala Ala Lys Leu Phe Ile Glu Trp Leu Lys Ala Xaa Gly Pro Ser
            20                  25                  30
Ser Gly Ala Pro Pro Pro Ser
        35

<210> SEQ ID NO 134
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
```

<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-(15-carboxy-pentadecanoylamino)-
      butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 134

His Xaa Gln Gly Thr Phe Thr Ser Asp Leu Ser Lys Gln Lys Glu Ser
1               5                   10                  15

Lys Ala Ala Gln Asp Phe Ile Glu Trp Leu Lys Ala Gly Gly Pro Ser
                20                  25                  30

Ser Gly Ala Pro Pro Pro Ser
                35

<210> SEQ ID NO 135
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-(15-carboxy-pentadecanoylamino)-
      butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 135

His Xaa Gln Gly Thr Phe Thr Ser Asp Leu Ser Lys Gln Lys Glu Ser
1               5                   10                  15

Lys Ala Ala Gln Glu Phe Ile Glu Trp Leu Lys Ala Gly Gly Pro Ser
                20                  25                  30

Ser Gly Ala Pro Pro Pro Ser
                35

<210> SEQ ID NO 136
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-(15-carboxy-pentadecanoylamino)-
      butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 136

```
His Xaa Gln Gly Thr Phe Thr Ser Asp Leu Ser Lys Gln Lys Glu Ser
1               5                   10                  15

Lys Ala Ala Gln Leu Phe Ile Glu Trp Leu Lys Ala Gly Gly Pro Ser
            20                  25                  30

Ser Gly Ala Pro Pro Pro Ser
            35

<210> SEQ ID NO 137
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 137

His Xaa His Gly Thr Phe Thr Ser Asp Leu Ser Lys Gln Lys Asp Ser
1               5                   10                  15

Lys Ala Ala Gln Asp Phe Ile Glu Trp Leu Lys Ala Gly Gly Pro Ser
            20                  25                  30

Ser Gly Ala Pro Pro Pro Ser
            35

<210> SEQ ID NO 138
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (29)..(29)
<223> OTHER INFORMATION: Xaa is a D-Ala
<220> FEATURE:
<221> NAME/KEY: MOD_RES
<222> LOCATION: (39)..(39)
<223> OTHER INFORMATION: Ser is modified with an NH2 group

<400> SEQUENCE: 138

His Xaa His Gly Thr Phe Thr Ser Asp Leu Ser Lys Gln Lys Asp Ser
1               5                   10                  15

Lys Ala Ala Gln Leu Phe Ile Glu Trp Leu Lys Ala Xaa Gly Pro Ser
            20                  25                  30

Ser Gly Ala Pro Pro Pro Ser
            35
```

```
<210> SEQ ID NO 139
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-henicosanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 139

His Xaa Gln Gly Thr Phe Thr Ser Asp Leu Ser Lys Gln Lys Asp Ser
1               5                   10                  15

Lys Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 140
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-((S)-4-carboxy-4-hexadecanoylamino-
      butyrylamino)-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 140

His Xaa Gln Gly Thr Phe Thr Ser Asp Leu Ser Lys Gln Lys Asp Ser
1               5                   10                  15

Lys Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 141
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
``` group as Lys(6-[(4,4-diphenyl-cyclohexyloxy)-hydroxy-
phosphoryloxy]-hexanoyl)
<220> FEATURE:
<221> NAME/KEY: MOD_RES
<222> LOCATION: (39)..(39)
<223> OTHER INFORMATION: Ser is modified with an NH2 group

<400> SEQUENCE: 141

His Xaa Gln Gly Thr Phe Thr Ser Asp Leu Ser Lys Gln Lys Asp Ser
1               5                   10                  15

Lys Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 142
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-icosanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 142

His Xaa Gln Gly Thr Phe Thr Ser Asp Leu Ser Lys Gln Lys Asp Ser
1               5                   10                  15

Lys Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 143
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (29)..(29)
<223> OTHER INFORMATION: Xaa is a D-Ala
<220> FEATURE:
<221> NAME/KEY: MOD_RES
<222> LOCATION: (39)..(39)
<223> OTHER INFORMATION: Ser is modified with an NH2 group

<400> SEQUENCE: 143

His Xaa Gln Gly Thr Phe Thr Ser Asp Leu Ser Lys Gln Lys Asp Ser
1               5                   10                  15

Lys Ala Ala Gln Asp Phe Ile Glu Trp Leu Lys Ala Xaa Gly Pro Ser
            20                  25                  30

Ser Gly Ala Pro Pro Pro Ser
        35

<210> SEQ ID NO 144
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (19)..(19)
<223> OTHER INFORMATION: Xaa is an Aib amino acid
<220> FEATURE:
<221> NAME/KEY: MOD_RES
<222> LOCATION: (39)..(39)
<223> OTHER INFORMATION: Ser is modified with an NH2 group

<400> SEQUENCE: 144

His Xaa Gln Gly Thr Phe Thr Ser Asp Leu Ser Lys Gln Lys Asp Ser
1               5                   10                  15

Lys Ala Xaa Gln Asp Phe Ile Glu Trp Leu Lys Ala Gly Gly Pro Ser
            20                  25                  30

Ser Gly Ala Pro Pro Pro Ser
        35

<210> SEQ ID NO 145
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 145

His Xaa Gln Gly Thr Phe Thr Ser Asp Leu Ser Lys Gln Lys Asp Ser
1               5                   10                  15

Lys Ala Ser Gln Asp Phe Ile Glu Trp Leu Lys Ala Gly Gly Pro Ser
            20                  25                  30

Ser Gly Ala Pro Pro Pro Ser
        35

<210> SEQ ID NO 146
<211> LENGTH: 39
<212> TYPE: PRT

```
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 146

His Xaa Gln Gly Thr Phe Thr Ser Asp Leu Ser Lys Gln Lys Asp Ser
 1               5                  10                  15

Lys Ala Leu Gln Asp Phe Ile Glu Trp Leu Lys Ala Gly Gly Pro Ser
                20                  25                  30

Ser Gly Ala Pro Pro Pro Ser
                35

<210> SEQ ID NO 147
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 147

His Xaa Gln Gly Thr Phe Thr Ser Asp Leu Ser Lys Gln Lys Asp Ser
 1               5                  10                  15

Lys Ala Ala Gln Asp Phe Ile Glu Trp Lys Lys Ala Gly Gly Pro Ser
                20                  25                  30

Ser Gly Ala Pro Pro Pro Ser
                35

<210> SEQ ID NO 148
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is an Aib amino acid
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (29)..(29)
```

<223> OTHER INFORMATION: Xaa is a D-Ala
<220> FEATURE:
<221> NAME/KEY: MOD_RES
<222> LOCATION: (39)..(39)
<223> OTHER INFORMATION: Ser is modified with an NH2 group

<400> SEQUENCE: 148

His Xaa Gln Gly Thr Phe Thr Ser Asp Leu Ser Lys Gln Lys Asp Ser
1               5                   10                  15

Lys Ala Ala Gln Leu Phe Ile Glu Trp Leu Lys Ala Xaa Gly Pro Ser
            20                  25                  30

Ser Gly Ala Pro Pro Pro Ser
        35

<210> SEQ ID NO 149
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is an Aib amino acid
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-henicosanoylamino-butyryl)
<220> FEATURE:
<221> NAME/KEY: MOD_RES
<222> LOCATION: (29)..(29)
<223> OTHER INFORMATION: Xaa is a D-Ala
<220> FEATURE:
<221> NAME/KEY: MOD_RES
<222> LOCATION: (39)..(39)
<223> OTHER INFORMATION: Ser is modified with an NH2 group

<400> SEQUENCE: 149

His Xaa Gln Gly Thr Phe Thr Ser Asp Leu Ser Lys Gln Lys Asp Ser
1               5                   10                  15

Lys Ala Ala Gln Leu Phe Ile Glu Trp Leu Lys Ala Xaa Gly Pro Ser
            20                  25                  30

Ser Gly Ala Pro Pro Pro Ser
        35

<210> SEQ ID NO 150
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 150

His Xaa Gln Gly Thr Phe Thr Ser Asp Leu Ser Lys Gln Lys Glu Ser
1               5                   10                  15

Leu Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 151
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 151

His Xaa Gln Gly Thr Phe Thr Ser Asp Leu Ser Lys Gln Lys Asp Glu
1               5                   10                  15

Gln Ala Ala Lys Asp Phe Ile Glu Trp Leu Lys Ala Gly Gly Pro Ser
            20                  25                  30

Ser Gly Ala Pro Pro Pro Ser
        35

<210> SEQ ID NO 152
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is an Aib amino acid
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 152

His Xaa Gln Gly Thr Phe Thr Ser Asp Leu Ser Lys Gln Lys Asp Glu
1               5                   10                  15

Gln Arg Ala Lys Glu Phe Ile Glu Trp Leu Lys Ala Gly Gly Pro Ser
            20                  25                  30

Ser Gly Ala Pro Pro Pro Ser
        35

<210> SEQ ID NO 153
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES

```
<222> LOCATION: (2)..(2)
<223> OTHER INFORMATION: Xaa is an Aib amino acid
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (29)..(29)
<223> OTHER INFORMATION: Xaa is a D-Ala
<220> FEATURE:
<221> NAME/KEY: MOD_RES
<222> LOCATION: (39)..(39)
<223> OTHER INFORMATION: Ser is modified with an NH2 group

<400> SEQUENCE: 153

His Xaa Gln Gly Thr Phe Thr Ser Asp Leu Ser Lys Gln Lys Asp Glu
 1               5                  10                  15

Gln Ala Ala Lys Leu Phe Ile Glu Trp Leu Lys Ala Xaa Gly Pro Ser
            20                  25                  30

Ser Gly Ala Pro Pro Pro Ser
        35

<210> SEQ ID NO 154
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is an Aib amino acid
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 154

His Xaa Gln Gly Thr Phe Thr Ser Asp Leu Ser Lys Gln Lys Glu Ser
 1               5                  10                  15

Gln Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 155
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is an Aib amino acid
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group
```

<400> SEQUENCE: 155

His Xaa Gln Gly Thr Phe Thr Ser Asp Leu Ser Lys Gln Lys Asp Ser
1               5                   10                  15

Gln Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 156
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is an Aib amino acid
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 156

His Xaa Gln Gly Thr Phe Thr Ser Asp Leu Ser Lys Gln Lys Asp Ser
1               5                   10                  15

Gln Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 157
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 157

His Xaa Gln Gly Thr Phe Thr Ser Asp Leu Ser Lys Gln Lys Asp Ser
1               5                   10                  15

Gln Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 158
<211> LENGTH: 39

```
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is an Aib amino acid
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (29)..(29)
<223> OTHER INFORMATION: Xaa is a D-Ala
<220> FEATURE:
<221> NAME/KEY: MOD_RES
<222> LOCATION: (39)..(39)
<223> OTHER INFORMATION: Ser is modified with an NH2 group

<400> SEQUENCE: 158

His Xaa Gln Gly Thr Phe Thr Ser Asp Leu Ser Lys Gln Lys Asp Ser
1               5                   10                  15

Gln Ala Ala Gln Leu Phe Ile Glu Trp Leu Lys Ala Xaa Gly Pro Ser
            20                  25                  30

Ser Gly Ala Pro Pro Pro Ser
            35

<210> SEQ ID NO 159
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is an Aib amino acid
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-henicosanoylamino-butyryl)
<220> FEATURE:
<221> NAME/KEY: MOD_RES
<222> LOCATION: (29)..(29)
<223> OTHER INFORMATION: Xaa is a D-Ala
<220> FEATURE:
<221> NAME/KEY: MOD_RES
<222> LOCATION: (39)..(39)
<223> OTHER INFORMATION: Ser is modified with an NH2 group

<400> SEQUENCE: 159

His Xaa Gln Gly Thr Phe Thr Ser Asp Leu Ser Lys Gln Lys Asp Ser
1               5                   10                  15

Gln Ala Ala Gln Leu Phe Ile Glu Trp Leu Lys Ala Xaa Gly Pro Ser
            20                  25                  30

Ser Gly Ala Pro Pro Pro Ser
            35

<210> SEQ ID NO 160
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
```

<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-((9Z,12Z)-octadeca-9,12-
      dienoylamino)-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 160

His Xaa Gln Gly Thr Phe Thr Ser Asp Leu Ser Lys Gln Lys Glu Ser
1               5                   10                  15

Arg Ala Ala Gln Asp Phe Ile Glu Trp Leu Lys Ala Gly Gly Pro Ser
            20                  25                  30

Ser Gly Ala Pro Pro Pro Ser
            35

<210> SEQ ID NO 161
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (29)..(29)
<223> OTHER INFORMATION: Xaa is a D-Ala
<220> FEATURE:
<221> NAME/KEY: MOD_RES
<222> LOCATION: (39)..(39)
<223> OTHER INFORMATION: Ser is modified with an NH2 group

<400> SEQUENCE: 161

His Xaa Gln Gly Thr Phe Thr Ser Asp Leu Ser Lys Gln Lys Asp Ser
1               5                   10                  15

Arg Arg Ala Gln Asp Phe Ile Glu Trp Leu Lys Ala Xaa Gly Pro Ser
            20                  25                  30

Ser Gly Ala Pro Pro Pro Ser
            35

<210> SEQ ID NO 162
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is an Aib amino acid
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 162

His Xaa Gln Gly Thr Phe Thr Ser Asp Leu Ser Lys Gln Lys Asp Ser
1               5                   10                  15

Arg Arg Ala Gln Asp Phe Ile Glu Trp Leu Lys Ala Gly Gly Pro Ser
            20                  25                  30

Ser Gly Ala Pro Pro Pro Ser
        35

<210> SEQ ID NO 163
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 163

His Xaa Gln Gly Thr Phe Thr Ser Asp Leu Ser Lys Gln Lys Asp Ser
1               5                   10                  15

Arg Arg Ala Gln Asp Phe Ile Glu Trp Leu Lys Ala Gly Gly Pro Ser
            20                  25                  30

Ser Gly Ala Pro Pro Pro Ser
        35

<210> SEQ ID NO 164
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (28)..(28)
<223> OTHER INFORMATION: Xaa is an Aib amino acid
<220> FEATURE:
<221> NAME/KEY: MOD_RES
<222> LOCATION: (39)..(39)
<223> OTHER INFORMATION: Ser is modified with an NH2 group

<400> SEQUENCE: 164

His Xaa Gln Gly Thr Phe Thr Ser Asp Leu Ser Lys Gln Lys Asp Ser
1               5                   10                  15

Lys Ala Ala Gln Asp Phe Ile Glu Trp Leu Lys Xaa Gly Gly Pro Ser
            20                  25                  30

Ser Gly Ala Pro Pro Pro Ser
        35

```
<210> SEQ ID NO 165
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 165

His Xaa Gln Gly Thr Phe Thr Ser Asp Leu Ser Lys Gln Lys Glu Ser
 1               5                  10                  15

Arg Arg Ala Gln Asp Phe Ile Glu Trp Leu Lys Glu Gly Gly Pro Ser
            20                  25                  30

Ser Gly Lys Pro Pro Pro Ser
        35

<210> SEQ ID NO 166
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 166

His Xaa Gln Gly Thr Phe Thr Ser Asp Leu Ser Lys Gln Lys Asp Ser
 1               5                  10                  15

Gln Ala Ala Gln Asp Phe Ile Glu Trp Leu Lys Asn Thr Gly Pro Ser
            20                  25                  30

Ser Gly Ala Pro Pro Pro Ser
        35

<210> SEQ ID NO 167
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
```

```
<223> OTHER INFORMATION: Lys is functionalized at the amino side chain
      group as Lys((S)-4-carboxy-4-(3-[3-((2S,3R,4S,5R)-5-carboxy-
      2,3,4,5-tetrahydroxy-pentanoylamino-)-propionylamino]-
      propionylamino)-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 167

His Xaa Gln Gly Thr Phe Thr Ser Asp Leu Ser Lys Gln Lys Asp Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
            35

<210> SEQ ID NO 168
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-((9Z,12Z)-octadeca-9,12-
      dienoylamino)-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 168

His Xaa Gln Gly Thr Phe Thr Ser Asp Leu Ser Lys Gln Lys Asp Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
            35

<210> SEQ ID NO 169
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-[6-((2S,3R,4S,5R)-5-carboxy-2,3,4,5-
      tetrahydroxy-pentanoylamino)-hexanoylamino]-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 169

His Xaa Gln Gly Thr Phe Thr Ser Asp Leu Ser Lys Gln Lys Asp Ser
1               5                   10                  15
```

Arg Arg Ala Gln Asp Phe Ile Glu Trp Leu Lys Asn Gly Gly Pro Ser
            20                  25                  30

Ser Gly Ala Pro Pro Pro Ser
            35

<210> SEQ ID NO 170
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-((2S,3R,4S,5R)-5-carboxy-2,3,4,5-
      tetrahydroxy-pentanoylamino)-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 170

His Xaa Gln Gly Thr Phe Thr Ser Asp Leu Ser Lys Gln Lys Asp Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
            35

<210> SEQ ID NO 171
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-[11-((2S,3R,4R,5R)-2,3,4,5,6-
      pentahydroxy-hexylcarbamoyl)-undecanoylamino]-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 171

His Xaa Gln Gly Thr Phe Thr Ser Asp Leu Ser Lys Gln Lys Asp Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
            35

<210> SEQ ID NO 172
<211> LENGTH: 39
<212> TYPE: PRT
<213> ORGANISM: Artificial Sequence
<220> FEATURE:

```
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 172

His Xaa Gln Gly Thr Phe Thr Ser Asp Leu Ser Lys Gln Lys Glu Ser
1               5                   10                  15

Arg Arg Ala Gln Asp Phe Ile Glu Trp Leu Lys Arg Gly Gly Pro Ser
            20                  25                  30

Ser Gly Glu Pro Pro Pro Ser
        35

<210> SEQ ID NO 173
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 173

His Xaa Gln Gly Thr Phe Thr Ser Asp Leu Ser Lys Gln Lys Asp Ser
1               5                   10                  15

Lys Ala Ala Gln Asp Phe Ile Glu Trp Leu Lys Ser Gly Gly Pro Ser
            20                  25                  30

Ser Gly Ala Pro Pro Pro Ser
        35

<210> SEQ ID NO 174
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is an Aib amino acid
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (39)..(39)
<223> OTHER INFORMATION: Ser is modified with an NH2 group
```

<400> SEQUENCE: 174

His Xaa Gln Gly Thr Phe Thr Ser Asp Leu Ser Lys Gln Lys Asp Glu
1               5                   10                  15

Gln Arg Ala Lys Glu Phe Ile Glu Trp Leu Lys Ser Gly Gly Pro Ser
            20                  25                  30

Ser Gly Ala Pro Pro Pro Ser
        35

<210> SEQ ID NO 175
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is an Aib amino acid
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 175

His Xaa Gln Gly Thr Phe Thr Ser Asp Leu Ser Lys Gln Lys Asp Glu
1               5                   10                  15

Gln Arg Ala Lys Asp Phe Ile Glu Trp Leu Lys Ser Gly Gly Pro Ser
            20                  25                  30

Ser Gly Ala Pro Pro Pro Ser
        35

<210> SEQ ID NO 176
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is an Aib amino acid
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 176

His Xaa Gln Gly Thr Phe Thr Ser Asp Leu Ser Lys Gln Lys Asp Glu
1               5                   10                  15

Gln Arg Ala Lys Glu Phe Ile Glu Trp Leu Lys Ser Gly Gly Pro Ser
            20                  25                  30

Ser Gly Ala Pro Pro Pro Ser
        35

<210> SEQ ID NO 177
<211> LENGTH: 39
<212> TYPE: PRT

```
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH-(CH2-CH2-O)24-CH2-
      CH2-COOH group

<400> SEQUENCE: 177

His Xaa Gln Gly Thr Phe Thr Ser Asp Leu Ser Lys Gln Lys Glu Ser
1               5                   10                  15

Lys Ala Ala Gln Asp Phe Ile Glu Trp Leu Lys Ala Gly Gly Pro Ser
            20                  25                  30

Ser Gly Ala Pro Pro Pro Ser
            35

<210> SEQ ID NO 178
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH-(CH2-CH2-O)4-CH2-
      CH2-COOH group

<400> SEQUENCE: 178

His Xaa Gln Gly Thr Phe Thr Ser Asp Leu Ser Lys Gln Lys Glu Ser
1               5                   10                  15

Lys Ala Ala Gln Asp Phe Ile Glu Trp Leu Lys Ala Gly Gly Pro Ser
            20                  25                  30

Ser Gly Ala Pro Pro Pro Ser
            35

<210> SEQ ID NO 179
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (3)..(3)
<223> OTHER INFORMATION: Gln is an alpha-N-MeGln
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
```

```
<221> NAME/KEY: MOD_RES
<222> LOCATION: (39)..(39)
<223> OTHER INFORMATION: Ser is modified with an NH2 group

<400> SEQUENCE: 179

His Ser Gln Gly Thr Phe Thr Ser Asp Leu Ser Lys Gln Lys Glu Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
        35

<210> SEQ ID NO 180
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (3)..(3)
<223> OTHER INFORMATION: Gln is an alpha-N-MeGln
<220> FEATURE:
<221> NAME/KEY: MOD_RES
<222> LOCATION: (14)..(14)
<223> OTHER INFORMATION: Lys is functionalized at the amino side chain
     group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 180

His Ser Gln Gly Thr Phe Thr Ser Asp Leu Ser Lys Gln Lys Glu Ser
1               5                   10                  15

Arg Arg Ala Gln Asp Phe Ile Glu Trp Leu Lys Ala Gly Gly Pro Ser
            20                  25                  30

Ser Gly Ala Pro Pro Pro Ser
        35

<210> SEQ ID NO 181
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is an Aib amino acid
<220> FEATURE:
<221> NAME/KEY: MOD_RES
<222> LOCATION: (14)..(14)
<223> OTHER INFORMATION: Lys is functionalized at the amino side chain
     group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 181

His Xaa Gln Gly Thr Phe Thr Ser Asp Leu Ser Lys Gln Lys Asp Ser
1               5                   10                  15

Arg Arg Ala Gln Asp Phe Ile Glu Trp Leu Lys Ala Gly Gly Pro Ser
            20                  25                  30

Ser Gly Ala Pro Pro Pro Ser
        35
```

<210> SEQ ID NO 182
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is an Aib amino acid
<220> FEATURE:
<221> NAME/KEY: MOD_RES
<222> LOCATION: (39)..(39)
<223> OTHER INFORMATION: Ser is modified with an NH2 group

<400> SEQUENCE: 182

His Xaa Gln Gly Thr Phe Thr Ser Asp Leu Ser Lys Gln Met Asp Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
        35

<210> SEQ ID NO 183
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (39)..(39)
<223> OTHER INFORMATION: Ser is modified with an NH2 group

<400> SEQUENCE: 183

His Xaa Gln Gly Thr Phe Thr Ser Asp Leu Ser Lys Gln Lys Asp Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
        35

<210> SEQ ID NO 184
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (39)..(39)
<223> OTHER INFORMATION: Ser is modified with an NH2 group

<400> SEQUENCE: 184

His Xaa Gln Gly Thr Phe Thr Ser Asp Leu Ser Lys Gln Met Glu Ser
1               5                   10                  15

Arg Arg Ala Gln Asp Phe Ile Glu Trp Leu Lys Ala Gly Gly Pro Ser
            20                  25                  30

Ser Gly Ala Pro Pro Pro Ser

<210> SEQ ID NO 185
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (39)..(39)
<223> OTHER INFORMATION: Ser is modified with an NH2 group

<400> SEQUENCE: 185

His Xaa Gln Gly Thr Phe Thr Ser Asp Leu Ser Lys Gln Met Asp Ser
1               5                   10                  15

Arg Arg Ala Gln Asp Phe Ile Glu Trp Leu Lys Arg Gly Gly Pro Ser
            20                  25                  30

Ser Gly Ala Pro Pro Pro Ser
        35

<210> SEQ ID NO 186
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (39)..(39)
<223> OTHER INFORMATION: Ser is modified with an NH2 group

<400> SEQUENCE: 186

His Xaa Gln Gly Thr Phe Thr Ser Asp Leu Ser Lys Gln Met Asp Ser
1               5                   10                  15

Arg Arg Ala Gln Asp Phe Ile Glu Trp Leu Lys Lys Gly Gly Pro Ser
            20                  25                  30

Ser Gly Ala Pro Pro Pro Ser
        35

<210> SEQ ID NO 187
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (28)..(28)
<223> OTHER INFORMATION: Xaa is an Aib amino acid
<220> FEATURE:
<221> NAME/KEY: MOD_RES
<222> LOCATION: (39)..(39)
<223> OTHER INFORMATION: Ser is modified with an NH2 group

<400> SEQUENCE: 187

His Xaa Gln Gly Thr Phe Thr Ser Asp Leu Ser Lys Gln Met Asp Ser

```
1               5                   10                  15
Arg Arg Ala Gln Asp Phe Ile Glu Trp Leu Lys Xaa Gly Gly Pro Ser
            20                  25                  30

Ser Gly Ala Pro Pro Pro Ser
        35

<210> SEQ ID NO 188
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (39)..(39)
<223> OTHER INFORMATION: Ser is modified with an NH2 group

<400> SEQUENCE: 188

His Xaa Gln Gly Thr Phe Thr Ser Asp Leu Ser Lys Gln Met Asp Ser
1               5                   10                  15

Arg Arg Ala Gln Asp Phe Ile Glu Trp Leu Lys Ala Gly Gly Pro Ser
            20                  25                  30

Ser Gly Ala Pro Pro Pro Ser
        35

<210> SEQ ID NO 189
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (39)..(39)
<223> OTHER INFORMATION: Ser is modified with an NH2 group

<400> SEQUENCE: 189

His Xaa Gln Gly Thr Phe Thr Ser Asp Leu Ser Lys Gln Met Glu Ser
1               5                   10                  15

Lys Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 190
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (20)..(20)
<223> OTHER INFORMATION: Xaa is an Aib amino acid
<220> FEATURE:
<221> NAME/KEY: MOD_RES
```

```
<222> LOCATION: (39)..(39)
<223> OTHER INFORMATION: Ser is modified with an NH2 group

<400> SEQUENCE: 190

His Xaa Gln Gly Thr Phe Thr Ser Asp Leu Ser Lys Gln Met Glu Ser
1               5                   10                  15

Arg Arg Ala Xaa Asp Phe Ile Glu Trp Leu Lys Ala Gly Gly Pro Ser
            20                  25                  30

Ser Gly Ala Pro Pro Pro Ser
        35

<210> SEQ ID NO 191
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Xaa is an Nle amino acid
<220> FEATURE:
<221> NAME/KEY: MOD_RES
<222> LOCATION: (39)..(39)
<223> OTHER INFORMATION: Ser is modified with an NH2 group

<400> SEQUENCE: 191

His Xaa Gln Gly Thr Phe Thr Ser Asp Leu Ser Lys Gln Xaa Glu Ser
1               5                   10                  15

Gln Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 192
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Xaa is a Nle amino acid
<220> FEATURE:
<221> NAME/KEY: MOD_RES
<222> LOCATION: (39)..(39)
<223> OTHER INFORMATION: Ser is modified with an NH2 group

<400> SEQUENCE: 192

His Xaa Gln Gly Thr Phe Thr Ser Asp Leu Ser Lys Gln Xaa Asp Ser
1               5                   10                  15

Lys Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 193
<211> LENGTH: 39
```

```
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Xaa is an Nle amino acid
<220> FEATURE:
<221> NAME/KEY: MOD_RES
<222> LOCATION: (39)..(39)
<223> OTHER INFORMATION: Ser is modified with an NH2 group

<400> SEQUENCE: 193

His Xaa Gln Gly Thr Phe Thr Ser Asp Leu Ser Lys Gln Xaa Asp Ser
1               5                   10                  15

Gln Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 194
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is an alpha-N-AcLys
<220> FEATURE:
<221> NAME/KEY: MOD_RES
<222> LOCATION: (39)..(39)
<223> OTHER INFORMATION: Ser is modified with an NH2 group

<400> SEQUENCE: 194

His Xaa Gln Gly Thr Phe Thr Ser Asp Leu Ser Lys Gln Lys Glu Ser
1               5                   10                  15

Arg Arg Ala Gln Asp Phe Ile Glu Trp Leu Lys Ala Gly Gly Pro Ser
            20                  25                  30

Ser Gly Ala Pro Pro Pro Ser
        35

<210> SEQ ID NO 195
<211> LENGTH: 30
<212> TYPE: PRT
<213> ORGANISM: Artificial Sequence
<220> FEATURE:
<223> OTHER INFORMATION: Liraglutide
<220> FEATURE:
<221> NAME/KEY: MOD_RES
<222> LOCATION: (20)..(20)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (30)..(30)
<223> OTHER INFORMATION: Gly is modified with an OH group

<400> SEQUENCE: 195

His Ala Glu Gly Thr Phe Thr Ser Asp Val Ser Ser Tyr Leu Glu Gly
```

```
                1               5                  10                 15
Gln Ala Ala Lys Glu Ile Ala Trp Leu Val Arg Gly Arg Gly
                20                 25                 30

<210> SEQ ID NO 196
<211> LENGTH: 39
<212> TYPE: PRT
<213> ORGANISM: Artificial
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (20)..(20)
<223> OTHER INFORMATION: Xaa is Aib
<220> FEATURE:
<221> NAME/KEY: MOD_RES
<222> LOCATION: (39)..(39)
<223> OTHER INFORMATION: Ser is modified with an NH2 group

<400> SEQUENCE: 196

His Xaa Gln Gly Thr Phe Thr Ser Asp Leu Ser Lys Gln Lys Asp Ser
1               5                  10                 15

Lys Arg Ala Xaa Asp Phe Ile Glu Trp Leu Lys Ala Gly Gly Pro Ser
                20                 25                 30

Ser Gly Ala Pro Pro Pro Ser
        35

<210> SEQ ID NO 197
<211> LENGTH: 39
<212> TYPE: PRT
<213> ORGANISM: Artificial
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 197

His Xaa Gln Gly Thr Phe Thr Ser Asp Leu Ser Lys Gln Lys Asp Glu
1               5                  10                 15

Gln Arg Ala Lys Leu Phe Ile Glu Trp Leu Lys Ala Gly Gly Pro Ser
                20                 25                 30

Ser Gly Ala Pro Pro Pro Ser
        35

<210> SEQ ID NO 198
<211> LENGTH: 39
<212> TYPE: PRT
<213> ORGANISM: Artificial
<220> FEATURE:
```

```
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 198

His Xaa Gln Gly Thr Phe Thr Ser Asp Leu Ser Lys Gln Lys Asp Ser
1               5                   10                  15

Arg Arg Ala Gln Leu Phe Ile Glu Trp Leu Lys Ala Gly Gly Pro Ser
            20                  25                  30

Ser Gly Ala Pro Pro Pro Ser
        35

<210> SEQ ID NO 199
<211> LENGTH: 39
<212> TYPE: PRT
<213> ORGANISM: Artificial
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (29)..(29)
<223> OTHER INFORMATION: Xaa is D-Ala
<220> FEATURE:
<221> NAME/KEY: MOD_RES
<222> LOCATION: (39)..(39)
<223> OTHER INFORMATION: Ser is modified with an NH2 group

<400> SEQUENCE: 199

His Xaa Gln Gly Thr Phe Thr Ser Asp Leu Ser Lys Gln Lys Asp Glu
1               5                   10                  15

Gln Arg Ala Lys Asp Phe Ile Glu Trp Leu Lys Ala Xaa Gly Pro Ser
            20                  25                  30

Ser Gly Ala Pro Pro Pro Ser
        35

<210> SEQ ID NO 200
<211> LENGTH: 39
<212> TYPE: PRT
<213> ORGANISM: Artificial
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
```

```
<221> NAME/KEY: MOD_RES
<222> LOCATION: (29)..(29)
<223> OTHER INFORMATION: Xaa is D-Ala
<220> FEATURE:
<221> NAME/KEY: MOD_RES
<222> LOCATION: (39)..(39)
<223> OTHER INFORMATION: Ser is modified with an NH2 group

<400> SEQUENCE: 200

His Xaa Gln Gly Thr Phe Thr Ser Asp Leu Ser Lys Gln Lys Asp Glu
1               5                   10                  15

Gln Arg Ala Lys Leu Phe Ile Glu Trp Leu Lys Ala Xaa Gly Pro Ser
            20                  25                  30

Ser Gly Ala Pro Pro Pro Ser
        35

<210> SEQ ID NO 201
<211> LENGTH: 39
<212> TYPE: PRT
<213> ORGANISM: Artificial
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-henicosanoylamino-butyryl)
<220> FEATURE:
<221> NAME/KEY: MOD_RES
<222> LOCATION: (29)..(29)
<223> OTHER INFORMATION: Xaa is D-Ala
<220> FEATURE:
<221> NAME/KEY: MOD_RES
<222> LOCATION: (39)..(39)
<223> OTHER INFORMATION: Ser is modified with an NH2 group

<400> SEQUENCE: 201

His Xaa Gln Gly Thr Phe Thr Ser Asp Leu Ser Lys Gln Lys Asp Glu
1               5                   10                  15

Gln Ala Ala Lys Leu Phe Ile Glu Trp Leu Lys Ala Xaa Gly Pro Ser
            20                  25                  30

Ser Gly Ala Pro Pro Pro Ser
        35

<210> SEQ ID NO 202
<211> LENGTH: 39
<212> TYPE: PRT
<213> ORGANISM: Artificial
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-henicosanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 202

His Xaa Gln Gly Thr Phe Thr Ser Asp Leu Ser Lys Gln Lys Glu Ser
```

```
                1               5                  10                  15
Arg Ala Ala Gln Asp Phe Ile Glu Trp Leu Lys Ala Gly Gly Pro Ser
                20                  25                  30

Ser Gly Ala Pro Pro Ser
                35

<210> SEQ ID NO 203
<211> LENGTH: 39
<212> TYPE: PRT
<213> ORGANISM: Artificial
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-henicosanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 203

His Xaa Gln Gly Thr Phe Thr Ser Asp Leu Ser Lys Gln Lys Glu Ser
1               5                  10                  15

Arg Ala Ala Gln Leu Phe Ile Glu Trp Leu Lys Ala Gly Gly Pro Ser
                20                  25                  30

Ser Gly Ala Pro Pro Ser
                35

<210> SEQ ID NO 204
<211> LENGTH: 39
<212> TYPE: PRT
<213> ORGANISM: Artificial
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-henicosanoylamino-butyryl)
<220> FEATURE:
<221> NAME/KEY: MOD_RES
<222> LOCATION: (29)..(29)
<223> OTHER INFORMATION: Xaa is D-Ala
<220> FEATURE:
<221> NAME/KEY: MOD_RES
<222> LOCATION: (39)..(39)
<223> OTHER INFORMATION: Ser is modified with an NH2 group

<400> SEQUENCE: 204

His Xaa Gln Gly Thr Phe Thr Ser Asp Leu Ser Lys Gln Lys Glu Ser
1               5                  10                  15

Arg Ala Ala Gln Leu Phe Ile Glu Trp Leu Lys Ala Xaa Gly Pro Ser
                20                  25                  30

Ser Gly Ala Pro Pro Ser
                35

<210> SEQ ID NO 205
<211> LENGTH: 39
```

```
<212> TYPE: PRT
<213> ORGANISM: Artificial
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (29)..(29)
<223> OTHER INFORMATION: Xaa is D-Ala
<220> FEATURE:
<221> NAME/KEY: MOD_RES
<222> LOCATION: (39)..(39)
<223> OTHER INFORMATION: Ser is modified with an NH2 group

<400> SEQUENCE: 205

His Xaa Gln Gly Thr Phe Thr Ser Asp Leu Ser Lys Gln Lys Glu Ser
1               5                  10                  15

Arg Arg Ala Gln Leu Phe Ile Glu Trp Leu Lys Ala Xaa Gly Pro Ser
            20                  25                  30

Ser Gly Ala Pro Pro Pro Ser
        35

<210> SEQ ID NO 206
<211> LENGTH: 39
<212> TYPE: PRT
<213> ORGANISM: Artificial
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 206

His Xaa Gln Gly Thr Phe Thr Ser Asp Leu Ser Lys Gln Lys Asp Glu
1               5                  10                  15

Gln Lys Ala Lys Leu Phe Ile Glu Trp Leu Lys Ser Gly Gly Pro Ser
            20                  25                  30

Ser Gly Ala Pro Pro Pro Ser
        35

<210> SEQ ID NO 207
<211> LENGTH: 39
<212> TYPE: PRT
<213> ORGANISM: Artificial
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (14)..(14)
```

```
<223> OTHER INFORMATION: Lys is functionalized at the amino side chain
      group as Lys((S)-4-carboxy-4-((S)-4-carboxy-4-hexadecanoylamino-
      butyrylamino)-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 207

His Xaa Gln Gly Thr Phe Thr Ser Asp Leu Ser Lys Gln Lys Asp Glu
1               5                   10                  15

Gln Arg Ala Lys Glu Phe Ile Glu Trp Leu Lys Ser Gly Gly Pro Ser
            20                  25                  30

Ser Gly Ala Pro Pro Pro Ser
            35

<210> SEQ ID NO 208
<211> LENGTH: 39
<212> TYPE: PRT
<213> ORGANISM: Artificial
<220> FEATURE:
<223> OTHER INFORMATION: Exendin-4-analogue
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 208

His Ser His Gly Thr Phe Thr Ser Asp Leu Ser Lys Gln Lys Glu Ser
1               5                   10                  15

Arg Arg Ala Gln Asp Phe Ile Glu Trp Leu Lys Ala Gly Gly Pro Ser
            20                  25                  30

Ser Gly Ala Pro Pro Pro Ser
            35

<210> SEQ ID NO 209
<211> LENGTH: 39
<212> TYPE: PRT
<213> ORGANISM: Artificial
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (29)..(29)
<223> OTHER INFORMATION: Xaa is D-Ala
<220> FEATURE:
<221> NAME/KEY: MOD_RES
<222> LOCATION: (39)..(39)
<223> OTHER INFORMATION: Ser is modified with an NH2 group

<400> SEQUENCE: 209

His Xaa Gln Gly Thr Phe Thr Ser Asp Leu Ser Lys Gln Lys Asp Lys
1               5                   10                  15

Arg Arg Ala Gln Asp Phe Ile Glu Trp Leu Lys Ala Xaa Gly Pro Ser
            20                  25                  30
```

-continued

Ser Gly Ala Pro Pro Pro Ser
        35

<210> SEQ ID NO 210
<211> LENGTH: 39
<212> TYPE: PRT
<213> ORGANISM: Artificial
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (29)..(29)
<223> OTHER INFORMATION: Xaa is D-Ala
<220> FEATURE:
<221> NAME/KEY: MOD_RES
<222> LOCATION: (39)..(39)
<223> OTHER INFORMATION: Ser is modified with an NH2 group

<400> SEQUENCE: 210

His Xaa Gln Gly Thr Phe Thr Ser Asp Leu Ser Lys Gln Lys Asp Lys
1               5                   10                  15

Arg Arg Ala Gln Leu Phe Ile Glu Trp Leu Lys Ala Xaa Gly Pro Ser
            20                  25                  30

Ser Gly Ala Pro Pro Pro Ser
        35

<210> SEQ ID NO 211
<211> LENGTH: 39
<212> TYPE: PRT
<213> ORGANISM: Artificial
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (29)..(29)
<223> OTHER INFORMATION: Xaa is D-Ala
<220> FEATURE:
<221> NAME/KEY: MOD_RES
<222> LOCATION: (39)..(39)
<223> OTHER INFORMATION: Ser is modified with an NH2 group

<400> SEQUENCE: 211

His Xaa Gln Gly Thr Phe Thr Ser Asp Leu Ser Lys Gln Lys Asp Lys
1               5                   10                  15

Arg Ala Ala Gln Leu Phe Ile Glu Trp Leu Lys Ala Xaa Gly Pro Ser
            20                  25                  30

Ser Gly Ala Pro Pro Pro Ser
        35

<210> SEQ ID NO 212
<211> LENGTH: 39

```
<212> TYPE: PRT
<213> ORGANISM: Artificial
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-henicosanoylamino-butyryl)
<220> FEATURE:
<221> NAME/KEY: MOD_RES
<222> LOCATION: (29)..(29)
<223> OTHER INFORMATION: Xaa is D-Ala
<220> FEATURE:
<221> NAME/KEY: MOD_RES
<222> LOCATION: (39)..(39)
<223> OTHER INFORMATION: Ser is modified with an NH2 group

<400> SEQUENCE: 212

His Xaa Gln Gly Thr Phe Thr Ser Asp Leu Ser Lys Gln Lys Asp Lys
1               5                   10                  15

Arg Ala Ala Gln Leu Phe Ile Glu Trp Leu Lys Ala Xaa Gly Pro Ser
            20                  25                  30

Ser Gly Ala Pro Pro Pro Ser
        35

<210> SEQ ID NO 213
<211> LENGTH: 39
<212> TYPE: PRT
<213> ORGANISM: Artificial
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 213

His Xaa Gln Gly Thr Phe Thr Ser Asp Leu Ser Lys Gln Lys Asp Glu
1               5                   10                  15

Glu Ala Ala Lys Leu Phe Ile Glu Trp Leu Lys Ala Gly Gly Pro Ser
            20                  25                  30

Ser Gly Ala Pro Pro Pro Ser
        35

<210> SEQ ID NO 214
<211> LENGTH: 39
<212> TYPE: PRT
<213> ORGANISM: Artificial
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (14)..(14)
```

<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 214

His Xaa Gln Gly Thr Phe Thr Ser Asp Leu Ser Lys Gln Lys Asp Glu
1               5                   10                  15

Glu Ala Ala Arg Leu Phe Ile Glu Trp Leu Lys Ala Gly Gly Pro Ser
            20                  25                  30

Ser Gly Ala Pro Pro Pro Ser
        35

<210> SEQ ID NO 215
<211> LENGTH: 39
<212> TYPE: PRT
<213> ORGANISM: Artificial
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 215

His Xaa Gln Gly Thr Phe Thr Ser Asp Leu Ser Lys Gln Lys Glu Glu
1               5                   10                  15

Glu Ala Ala Arg Leu Phe Ile Glu Trp Leu Lys Ala Gly Gly Pro Ser
            20                  25                  30

Ser Gly Ala Pro Pro Pro Ser
        35

<210> SEQ ID NO 216
<211> LENGTH: 39
<212> TYPE: PRT
<213> ORGANISM: Artificial
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 216

His Xaa Gln Gly Thr Phe Thr Ser Asp Leu Ser Lys Gln Lys Asp Glu
1               5                   10                  15

Glu Ala Ala Arg Leu Phe Ile Glu Trp Leu Lys Ala Gly Gly Pro Ser
            20                  25                  30

```
Ser Gly Ala Pro Pro Pro Ser
        35

<210> SEQ ID NO 217
<211> LENGTH: 39
<212> TYPE: PRT
<213> ORGANISM: Artificial
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 217

His Xaa His Gly Thr Phe Thr Ser Asp Leu Ser Lys Gln Lys Glu Glu
1               5                   10                  15

Glu Ala Ala Arg Leu Phe Ile Glu Trp Leu Lys Ala Gly Gly Pro Ser
            20                  25                  30

Ser Gly Ala Pro Pro Pro Ser
        35

<210> SEQ ID NO 218
<211> LENGTH: 39
<212> TYPE: PRT
<213> ORGANISM: Artificial
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 218

His Xaa His Gly Thr Phe Thr Ser Asp Leu Ser Lys Gln Lys Asp Glu
1               5                   10                  15

Glu Ala Ala Arg Leu Phe Ile Glu Trp Leu Lys Ala Gly Gly Pro Ser
            20                  25                  30

Ser Gly Ala Pro Pro Pro Ser
        35

<210> SEQ ID NO 219
<211> LENGTH: 39
<212> TYPE: PRT
<213> ORGANISM: Artificial
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is D-Ser
<220> FEATURE:
```

```
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 219

His Xaa His Gly Thr Phe Thr Ser Asp Leu Ser Lys Gln Lys Glu Glu
1               5                   10                  15

Glu Ala Ala Arg Leu Phe Ile Glu Trp Leu Lys Ala Gly Gly Pro Ser
            20                  25                  30

Ser Gly Ala Pro Pro Pro Ser
        35

<210> SEQ ID NO 220
<211> LENGTH: 39
<212> TYPE: PRT
<213> ORGANISM: Artificial
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 220

His Xaa His Gly Thr Phe Thr Ser Asp Leu Ser Lys Gln Lys Asp Glu
1               5                   10                  15

Glu Ala Ala Arg Leu Phe Ile Glu Trp Leu Lys Ala Gly Gly Pro Ser
            20                  25                  30

Ser Gly Ala Pro Pro Pro Ser
        35

<210> SEQ ID NO 221
<211> LENGTH: 39
<212> TYPE: PRT
<213> ORGANISM: Artificial
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 221

His Xaa Gln Gly Thr Phe Thr Ser Asp Leu Ser Lys Gln Lys Asp Glu
1               5                   10                  15

Glu Ala Ala Arg Leu Phe Ile Glu Trp Leu Lys Ala Gly Gly Pro Ser
```

Ser Gly Ala Pro Pro Pro Ser
        35

<210> SEQ ID NO 222
<211> LENGTH: 39
<212> TYPE: PRT
<213> ORGANISM: Artificial
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 222

His Xaa Gln Gly Thr Phe Thr Ser Asp Leu Ser Lys Gln Lys Asp Glu
1               5                   10                  15

Glu Ala Ala Arg Leu Phe Ile Glu Trp Leu Lys Ala Gly Gly Pro Ser
            20                  25                  30

Ser Gly Ala Pro Pro Pro Ser
        35

<210> SEQ ID NO 223
<211> LENGTH: 39
<212> TYPE: PRT
<213> ORGANISM: Artificial
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 223

His Xaa Gln Gly Thr Phe Thr Ser Asp Leu Ser Lys Gln Lys Glu Glu
1               5                   10                  15

Glu Ala Ala Arg Leu Phe Ile Glu Trp Leu Lys Ala Gly Gly Pro Ser
            20                  25                  30

Ser Gly Ala Pro Pro Pro Ser
        35

<210> SEQ ID NO 224
<211> LENGTH: 39
<212> TYPE: PRT
<213> ORGANISM: Artificial
<220> FEATURE:
<223> OTHER INFORMATION: Exendin-4-analogue
<220> FEATURE:
<221> NAME/KEY: MOD_RES
<222> LOCATION: (2)..(2)

```
<223> OTHER INFORMATION: Xaa is Aib
<220> FEATURE:
<221> NAME/KEY: MOD_RES
<222> LOCATION: (39)..(39)
<223> OTHER INFORMATION: Ser is modified with an NH2 group

<400> SEQUENCE: 224

His Xaa Gln Gly Thr Phe Thr Ser Asp Leu Ser Lys Gln Leu Asp Glu
1               5                   10                  15

Glu Ala Ala Arg Leu Phe Ile Glu Trp Leu Lys Ala Gly Gly Pro Ser
            20                  25                  30

Ser Gly Ala Pro Pro Pro Ser
        35

<210> SEQ ID NO 225
<211> LENGTH: 39
<212> TYPE: PRT
<213> ORGANISM: Artificial
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (39)..(39)
<223> OTHER INFORMATION: Ser is modified with an NH2 group

<400> SEQUENCE: 225

His Xaa Gln Gly Thr Phe Thr Ser Asp Leu Ser Lys Gln Leu Glu Glu
1               5                   10                  15

Glu Ala Ala Arg Leu Phe Ile Glu Trp Leu Lys Ala Gly Gly Pro Ser
            20                  25                  30

Ser Gly Ala Pro Pro Pro Ser
        35

<210> SEQ ID NO 226
<211> LENGTH: 39
<212> TYPE: PRT
<213> ORGANISM: Artificial
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-((S)-4-carboxy-4-hexadecanoylamino-
      butyrylamino)-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 226

His Xaa Gln Gly Thr Phe Thr Ser Asp Leu Ser Lys Gln Lys Asp Glu
1               5                   10                  15

Glu Ala Ala Arg Leu Phe Ile Glu Trp Leu Lys Ala Gly Gly Pro Ser
            20                  25                  30

Ser Gly Ala Pro Pro Pro Ser
        35
```

```
<210> SEQ ID NO 227
<211> LENGTH: 39
<212> TYPE: PRT
<213> ORGANISM: Artificial
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-((S)-4-carboxy-4-hexadecanoylamino-
      butyrylamino)-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 227

His Xaa His Gly Thr Phe Thr Ser Asp Leu Ser Lys Gln Lys Asp Glu
1               5                   10                  15

Glu Ala Ala Arg Leu Phe Ile Glu Trp Leu Lys Ala Gly Gly Pro Ser
            20                  25                  30

Ser Gly Ala Pro Pro Pro Ser
        35

<210> SEQ ID NO 228
<211> LENGTH: 39
<212> TYPE: PRT
<213> ORGANISM: Artificial
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-((S)-4-carboxy-4-hexadecanoylamino-
      butyrylamino)-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 228

His Xaa Gln Gly Thr Phe Thr Ser Asp Leu Ser Lys Gln Lys Glu Glu
1               5                   10                  15

Glu Ala Ala Arg Leu Phe Ile Glu Trp Leu Lys Ala Gly Gly Pro Ser
            20                  25                  30

Ser Gly Ala Pro Pro Pro Ser
        35

<210> SEQ ID NO 229
<211> LENGTH: 39
<212> TYPE: PRT
<213> ORGANISM: Artificial
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (14)..(14)
```

```
<223> OTHER INFORMATION: Lys is functionalized at the amino side chain
      group as Lys((S)-4-carboxy-4-((S)-4-carboxy-4-hexadecanoylamino-
      butyrylamino)-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 229

His Xaa His Gly Thr Phe Thr Ser Asp Leu Ser Lys Gln Lys Glu Glu
1               5                   10                  15

Glu Ala Ala Arg Leu Phe Ile Glu Trp Leu Lys Ala Gly Gly Pro Ser
            20                  25                  30

Ser Gly Ala Pro Pro Pro Ser
        35
```

EXENDIN-4 DERIVATIVES AS DUAL GLP1/GLUCAGON AGONISTS

RELATED APPLICATIONS

This application is a continuation of U.S. patent application Ser. No. 15/130,647, filed Apr. 15, 2016, which is a division of U.S. patent application Ser. No. 14/049,597, filed Oct. 9, 2013, now U.S. Pat. No. 9,365,632, which claims priority to European Patent Application No. 13305222.5, filed Feb. 27, 2013, and European Patent Application No. 12306232.5, filed Oct. 19, 2012, the entire disclosures of which are hereby incorporated herein by reference.

FIELD OF THE INVENTION

The present invention relates to exendin-4 peptide analogues which—in contrast to the pure GLP-1 agonist exendin-4—activate both the GLP1 and the Glucagon receptor and their medical use, for example in the treatment of disorders of the metabolic syndrome, including diabetes and obesity, as well as for reduction of excess food intake.

BACKGROUND OF THE INVENTION

Exendin-4 is a 39 amino acid peptide which is produced by the salivary glands of the Gila monster (*Heloderma suspectum*) (Eng, J. et al., J. Biol. Chem., 267:7402-05, 1992). Exendin-4 is an activator of the glucagon-like peptide-1 (GLP-1) receptor, whereas it does not activate significantly the glucagon receptor.

Exendin-4 shares many of the glucoregulatory actions observed with GLP-1. Clinical and non-clinical studies have shown that exendin-4 has several beneficial antidiabetic properties including a glucose dependent enhancement in insulin synthesis and secretion, glucose dependent suppression of glucagon secretion, slowing down gastric emptying, reduction of food intake and body weight, and an increase in beta-cell mass and markers of beta cell function (Gentilella R et al., Diabetes Obes Metab., 11:544-56, 2009; Norris S L et al., Diabet Med., 26:837-46, 2009; Bunck M C et al., Diabetes Care., 34:2041-7, 2011).

These effects are beneficial not only for diabetics but also for patients suffering from obesity. Patients with obesity have a higher risk of getting diabetes, hypertension, hyperlipidemia, cardiovascular and musculoskeletal diseases.

Relative to GLP-1, exendin-4 is resistant to cleavage by dipeptidyl peptidase-4 (DPP4) resulting in a longer half-life and duration of action in vivo (Eng J., Diabetes, 45 (Suppl 2):152A (abstract 554), 1996).

Nevertheless, exendin-4 is chemically labile due to methionine oxidation in position 14 (Hargrove D M et al., Regul. Pept., 141: 113-9, 2007) as well as deamidation and isomerization of asparagine in position 28 (WO 2004/035623).

The amino acid sequence of exendin-4 is shown as SEQ ID NO: 1

HGEGTFTSDLSKQMEEEAVRLFIEWLKNGGPSSGAPPPS-NH$_2$

The amino acid sequence of GLP-1(7-36)-amide is shown as SEQ ID NO: 2

HAEGTFTSDVSSYLEGQAAKEFIAWLVKGR-NH$_2$

Liraglutide is a marketed chemically modified GLP-1 analog in which, among other modifications, a fatty acid is linked to a lysine in position 20 leading to a prolonged duration of action (Drucker D J et al., Nature Drug Disc. Rev. 9, 267-268, 2010; Buse, J. B. et al., Lancet, 374:39-47, 2009).

The amino acid sequence of Liraglutide is shown as SEQ ID NO: 195.

HAEGTFTSDVSSYLEGQAAK((S)-4-Carboxy-4-hexadecanoylamino-butyryl-) EFIAWLVRGRG-OH

Glucagon is a 29-amino acid peptide which is released into the bloodstream when circulating glucose is low. Glucagon's amino acid sequence is shown in SEQ ID NO: 3.

HSQGTFTSDYSKYLDSRRAQDFVQWLMNT-OH

During hypoglycemia, when blood glucose levels drop below normal, glucagon signals the liver to break down glycogen and release glucose, causing an increase of blood glucose levels to reach a normal level. Hypoglycemia is a common side effect of insulin treated patients with hyperglycemia (elevated blood glucose levels) due to diabetes. Thus, glucagon's most predominant role in glucose regulation is to counteract insulin action and maintain blood glucose levels.

Holst (Holst, J. J. Physiol. Rev. 2007, 87, 1409) and Meier (Meier, J. J. Nat. Rev. Endocrinol. 2012, 8, 728) describe that GLP-1 receptor agonists, such as GLP-1, liraglutide and exendin-4, have 3 major pharmacological activities to improve glycemic control in patients with T2DM by reducing fasting and postprandial glucose (FPG and PPG): (i) increased glucose-dependent insulin secretion (improved first- and second-phase), (ii) glucagon suppressing activity under hyperglycemic conditions, (iii) delay of gastric emptying rate resulting in retarded absorption of meal-derived glucose.

Pocai et al. (Obesity 2012; 20: 1566-1571; Diabetes 2009, 58, 2258) and Day et al. (Nat Chem Biol 2009; 5: 749) describe that dual activation of the GLP-1 and glucagon receptors, e.g. by combining the actions of GLP-1 and glucagon in one molecule, leads to a therapeutic principle with anti-diabetic action and a pronounced weight lowering effect.

Peptides which bind and activate both the glucagon and the GLP-1 receptor (Hjort et al., Journal of Biological Chemistry, 269, 30121-30124, 1994; Day J W et al., Nature Chem Biol, 5: 749-757, 2009) and suppress body weight gain and reduce food intake are described in patent applications WO 2008/071972, WO 2008/101017, WO 2009/155258, WO 2010/096052, WO 2010/096142, WO 2011/075393, WO 2008/152403, WO 2010/070251, WO 2010/070252, WO 2010/070253, WO 2010/070255, WO 2011/160630, WO 2011/006497, WO 2011/152181, WO 2011/152182, WO 2011/117415, WO 2011/117416 and WO 2006/134340, the contents of which are herein incorporated by reference.

In addition, triple co-agonist peptides which not only activate the GLP-1 and the glucagon receptor but also the GIP receptor are described in WO 2012/088116 and by V A Gault et al. (Biochem Pharmacol, 85, 16655-16662, 2013; Diabetologia, 56, 1417-1424, 2013).

Bloom et al. (WO 2006/134340) disclose that peptides which bind and activate both the glucagon and the GLP-1 receptor can be constructed as hybrid molecules from glucagon and exendin-4, where the N-terminal part (e.g. residues 1-14 or 1-24) originates from glucagon and the C-terminal part (e.g. residues 15-39 or 25-39) originates from exendin-4.

D E Otzen et al. (Biochemistry, 45, 14503-14512, 2006) disclose that N- and C-terminal hydrophobic patches are involved in fibrillation of glucagon due to the hydrophobicity and/or high β-sheet propensity of the underlying residues.

Krstenansky et al. (Biochemistry, 25, 3833-3839, 1986) show the importance of the residues 10-13 of glucagon for its receptor interactions and activation of adenylate cyclase. In the exendin-4 derivatives described in this invention, several of the underlying residues are different from glucagon. In particular residues Tyr10 and Tyr13, which are known to contribute to the fibrillation of glucagon (D E Otzen, Biochemistry, 45, 14503-14512, 2006) are replaced by Leu in position 10 and Gln, a non-aromatic polar amino acid, in position 13, leading to exendin-4 derivatives with potentially improved biophysical properties.

Furthermore, compounds of this invention are exendin-4 derivatives with fatty acid acylated residues in position 14. This fatty acid functionalization in position 14 results in exendin-4 derivatives with high activity not only at the GLP-1 receptor but also at the glucagon receptor when compared to the corresponding non-acylated exendin-4 derivatives. In addition, this modification results in an improved pharmacokinetic profile.

Compounds of this invention are more resistant to cleavage by neutral endopeptidase (NEP) and dipeptidyl peptidase-4 (DPP4), resulting in a longer half-life and duration of action in vivo when compared with GLP-1 and glucagon. Furthermore, the compounds are stabilized versus other proteases, among those cathepsin D.

Compounds of this invention are preferably soluble not only at neutral pH, but also at pH 4.5. This property potentially allows co-formulation for a combination therapy with an insulin or insulin derivative and preferably with a basal insulin like insulin glargine/Lantus®.

BRIEF SUMMARY OF THE INVENTION

Provided herein are exendin-4 derivatives which potently activate the GLP1 and the glucagon receptor. In these exendin-4 derivatives—among other substitutions—methionine at position 14 is replaced by an amino acid carrying an —NH$_2$ group in the side chain, which is further substituted with an unpolar residue (e.g. a fatty acid optionally combined with a linker).

The invention provides a peptidic compound having the formula (I):

$$R^1\text{—}Z\text{—}R^2 \quad (I)$$

wherein Z is a peptide moiety having the formula (II)

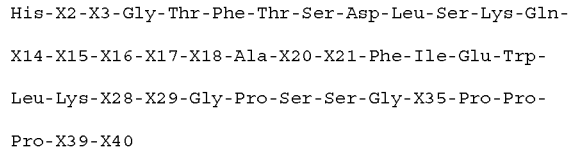

X2 represents an amino acid residue selected from Ser, D-Ser and Aib,

X3 represents an amino acid residue selected from Gln, His and α-amino-functionalized Gln, wherein Gln may be functionalized in that an H of the α-NH$_2$ group is substituted by (C$_1$-C$_4$)-alkyl, X14 represents an amino acid residue having a side chain with an —NH$_2$ group, wherein the —NH$_2$ side chain group is functionalized by —C(O)—R$^5$, —C(O)O—R$^5$, —C(O)NH—R$^5$, —S(O)$_2$—R$^5$ or R$^5$, preferably by —C(O)—R$^5$, wherein R$^5$ may be a moiety comprising up to 50 or up to 100 carbon atoms and optionally heteroatoms selected from halogen, N, O, S and/or P, X15 represents an amino acid residue selected from Glu and Asp, X16 represents an amino acid residue selected from Ser, Glu and Lys, X17 represents an amino acid residue selected from Arg, Glu, Gln, Leu, Aib and Lys, X18 represents an amino acid residue selected from Arg, Ala and Lys, X20 represents an amino acid residue selected from Gln, Arg, Lys, His, Glu and Aib, X21 represents an amino acid residue selected from Asp, Leu and Glu, X28 represents an amino acid residue selected from Asn, Arg, Lys, Aib, Ser, Glu, Ala and Asp, X29 represents an amino acid residue selected from Gly, Ala, D-Ala and Thr, X35 represents an amino acid residue selected from Ala, Glu, Arg and Lys, X39 represents Ser or is absent and X40 is absent or represents an amino acid residue having a side chain with an —NH$_2$ group, wherein the —NH$_2$ side chain group is optionally functionalized by —C(O)—R$^5$, —C(O)O—R$^5$, —C(O)NH—R$^5$, —S(O)$_2$—R$^5$ or R$^5$, preferably by —C(O)—R$^5$, wherein R$^5$ may be a moiety comprising up to 50 or up to 100 carbon atoms and optionally heteroatoms selected from halogen, N, O, S and/or P, R$^1$ represents the N-terminal group of the peptidic compound and is selected from NH$_2$ and mono- or bisfunctionalized NH$_2$, R$^2$ represents the C-terminal group of the peptidic compound and is selected from
(i) OH or functionalized OH and
(ii) NH$_2$ or mono- or bisfunctionalized NH$_2$,
or a salt or solvate thereof.

The compounds of the invention are GLP-1 and glucagon receptor agonists as determined by the observation that they are capable of stimulating intracellular cAMP formation.

According to another embodiment, the compounds of the invention, particularly with a lysine at position 14 which is further substituted with a lipophilic residue, exhibit at least a relative activity of 0.1%, more preferably of 0.2%, more preferably of 0.3% and even more preferably of 0.4% compared to that of GLP-1(7-36) at the GLP-1 receptor. Furthermore, the compounds exhibit at least a relative activity of 0.1%, more preferably of 0.2% or of 0.3% or of 0.4% and even more preferably of 0.5% compared to that of natural glucagon at the glucagon receptor.

The term "activity" as used herein preferably refers to the capability of a compound to activate the human GLP-1 receptor and the human glucagon receptor. More preferably the term "activity" as used herein refers to the capability of a compound to stimulate intracellular cAMP formation. The term "relative activity" as used herein is understood to refer to the capability of a compound to activate a receptor in a certain ratio as compared to another receptor agonist or as compared to another receptor. The activation of the receptors by the agonists (e.g. by measuring the cAMP level) is determined as described herein, e.g. as described in the examples.

According to one embodiment, the compounds of the invention have an $EC_{50}$ for hGLP-1 receptor of 450 pmol or less, preferably of 200 pmol or less; more preferably of 150 pmol or less, more preferably of 100 pmol or less, more preferably of 90 pmol or less, more preferably of 80 pmol or less, more preferably of 70 pmol or less, more preferably of 60 pmol or less, more preferably of 50 pmol or less, more preferably of 40 pmol or less, more preferably of 30 pmol or less, more preferably of 25 pmol or less, more preferably of 20 pmol or less, more preferably of 15 pmol or less, more preferably of 10 pmol or less, more preferably of 9 pmol or less, more preferably of 8 pmol or less, more preferably of 7 pmol or less, more preferably of 6 pmol or less, and more preferably of 5 pmol or less.

According to another embodiment, the compounds of the invention have an $EC_{50}$ for hGlucagon receptor of 500 pmol or less, preferably of 200 pmol or less; more preferably of 150 pmol or less, more preferably of 100 pmol or less, more preferably of 90 pmol or less, more preferably of 80 pmol or less, more preferably of 70 pmol or less, more preferably of 60 pmol or less, more preferably of 50 pmol or less, more preferably of 40 pmol or less, more preferably of 30 pmol or less, more preferably of 25 pmol or less, more preferably of 20 pmol or less, more preferably of 15 pmol or less, more preferably of 10 pmol or less.

According to another embodiment, the compounds of the invention have an $EC_{50}$ for hGLP-1 receptor of 450 pmol or less, preferably of 200 pmol or less; more preferably of 150 pmol or less, more preferably of 100 pmol or less, more preferably of 90 pmol or less, more preferably of 80 pmol or less, more preferably of 70 pmol or less, more preferably of 60 pmol or less, more preferably of 50 pmol or less, more preferably of 40 pmol or less, more preferably of 30 pmol or less, more preferably of 25 pmol or less, more preferably of 20 pmol or less, more preferably of 15 pmol or less, more preferably of 10 pmol or less, more preferably of 9 pmol or less, more preferably of 8 pmol or less, more preferably of 7 pmol or less, more preferably of 6 pmol or less, and more preferably of 5 pmol or less, and/or an $EC_{50}$ for hGlucagon receptor of 500 pmol or less, preferably of 200 pmol or less; more preferably of 150 pmol or less, more preferably of 100 pmol or less, more preferably of 90 pmol or less, more preferably of 80 pmol or less, more preferably of 70 pmol or less, more preferably of 60 pmol or less, more preferably of 50 pmol or less, more preferably of 40 pmol or less, more preferably of 30 pmol or less, more preferably of 25 pmol or less, more preferably of 20 pmol or less, more preferably of 15 pmol or less, more preferably of 10 pmol or less.

In still another embodiment, the $EC_{50}$ for both receptors i.e. for the hGLP-1 receptor and the hGlucagon receptor, is 100 pmol or less, more preferably 90 pmol or less, more preferably 80 pmol or less, more preferably 70 pmol or less, more preferably 60 pmol or less, more preferably 50 pmol or less, more preferably 40 pmol or less, more preferably 30 pmol or less, more preferably 25 pmol or less, more preferably 20 pmol or less, more preferably 15 pmol or less, more preferably 10 pmol or less. The $EC_{50}$ for hGLP-1 receptor and hGlucagon receptor may be determined as described in the Methods herein and as used to generate the results described in Example 9.

The compounds of the invention have the ability to reduce the intestinal passage, to increase the gastric content and/or to reduce the food intake of a patient. These activities of the compounds of the invention can be assessed in animal models known to the skilled person and also described herein in the Methods. The results of such experiments are described in Examples 11 and 12. Preferred compounds of the invention may increase the gastric content of mice, preferably of female NMRI-mice, if administered as a single dose, preferably subcutaneous dose, of 0.02 mg/kg body weight by at least 25%, more preferably by at least 30%, more preferably by at least 40%, more preferably by at least 50%, more preferably by at least 60%, more preferably by at least 70%, more preferably by at least 80%.

Preferably, this result is measured 1 h after administration of the respective compound and 30 mins after administration of a bolus, and/or reduces intestinal passage of mice, preferably of female NMRI-mice, if administered as a single dose, preferably subcutaneous dose, of 0.02 mg/kg body weight at least by 45%; more preferably by at least 50%, more preferably by at least 55%, more preferably by at least 60%, and more preferably at least 65%; and/or reduces food intake of mice, preferably of female NMRI-mice, over a period of 22 h, if administered as a single dose, preferably subcutaneous dose of 0.01 mg/kg body weight by at least 10%, more preferably 15%, and more preferably 20%.

The compounds of the invention have the ability to reduce blood glucose level, and/or to reduce HbA1c levels of a patient. These activities of the compounds of the invention can be assessed in animal models known to the skilled person and also described herein in the Methods. The results of such experiments are described in Examples 14 and 17.

Preferred compounds of the invention may reduce blood glucose level of mice, preferably in female leptin-receptor deficient diabetic db/db mice over a period of 24 h, if administered as a single dose, preferably subcutaneous dose, of 0.01 mg/kg body weight by at least 4 mmol/L; more preferably by at least 6 mmol/L, more preferably by at least 8 mmol/L. If the dose is increased to 0.1 mg/kg body weight a more pronounced reduction of blood glucose levels can be observed in mice over a period of 24 h, if administered as a single dose, preferably subcutaneous dose. Preferably the compounds of the invention lead to a reduction by at least 7 mmol/L; more preferably by at least 9 mmol/L, more preferably by at least 11 mmol/L. The compounds of the invention preferably reduce the increase of HbA1c levels of mice over a period of 4 weeks, if administered at a daily dose of 0.01 mg/kg to about the ignition value.

The compounds of the invention also have the ability to reduce body weight of a patient. These activities of the compounds of the invention can be assessed in animal models known to the skilled person and also described herein in the Methods and in Examples 13 and 16.

It was found that peptidic compounds of the formula (I), particularly those with a lysine at position 14 which is further substituted with a lipophilic residue, showed increased glucagon receptor activation compared to derivatives having the original methionine (from exendin-4) at position 14. Furthermore, oxidation (in vitro or in vivo) of methionine is not possible anymore.

In one embodiment the compounds of the invention have a high solubility at acidic and/or physiological pH values, e.g., at pH 4.5 and/or at pH 7.4 at 25° C., in another embodiment at least 0.5 mg/ml and in a particular embodiment at least 1.0 mg/ml.

Furthermore, according to one embodiment, the compounds of the invention preferably have a high stability when stored in solution. Preferred assay conditions for determining the stability is storage for 7 days at 25° C. in solution at pH 4.5 or pH 7. The remaining amount of peptide is determined by chromatographic analyses as described in the Examples. Preferably, after 7 days at 25° C. in solution at pH 4.5 or pH 7, the remaining peptide amount is at least 80%, more preferably at least 85%, even more preferably at least 90% and even more preferably at least 95%.

Preferably, the compounds of the present invention comprise a peptide moiety Z (II) which is a linear sequence of 39-40 amino carboxylic acids, particularly α-amino carboxylic acids linked by peptide, i.e. carboxamide bonds.

In an embodiment $R^1$ is selected from —$NH_2$, —$NH[(C_1$-$C_5)$alkyl], —$N[(C_1$-$C_5)$alkyl]$_2$, —$NH[(C_0$-$C_4)$alkylene-$(C_3$-$C_8)$cycloalkyl], $NH$—$C(O)$—$H$, $NH$—$C(O)$—$(C_1$-$C_5)$-alkyl, $NH$—$C(O)$—$(C_0$-$C_3)$alkylene-$(C_3$-$C_8)$cycloalkyl, in which alkyl or cycloalkyl is unsubstituted or up to 5-fold substituted by —OH or halogen selected from F, Cl, Br and I, preferably F.

In an embodiment $R^2$ is selected from —OH, —O—$(C_1$-$C_{20})$alkyl, —$O(C_0$-$C_8)$alkylene-$(C_3$-$C_8)$cycloalkyl, —$NH_2$, —$NH[(C_1$-$C_{30})$alkyl], —$N[(C_1$-$C_{30})$alkyl]$_2$, —$NH[(C0$-$C8)$alkylene-$(C_3$-$C_8)$cycloalkyl], —$N[(C0$-$C8)$alkylene-$(C_3$-$C_8)$cycloalkyl]$_2$, —$NH[(CH_2$—$CH_2$—$O)_{1-40}$—$(C_1$-$C_4)$alkyl], —$NH$—$(C_3$-$C_8)$heterocyclyl or —$NH$—$(C_0$-$C_8)$alkylene-aryl, wherein aryl is selected from phenyl and naphthyl, preferably phenyl, or a $(C_3$-$C_8)$-heterocyclyl containing 1 N-atom and optionally two additional heteroatoms selected from O, N or S, particularly selected from azetidinyl, pyrrolidinyl, piperidinyl, morpholinyl und homopiperidinyl. Moreover alkyl or cycloalkyl as described above is unsubstituted or up to 5-fold substituted by —OH or halogen selected from F, Cl, Br and I, preferably F.

In one embodiment, the N-terminal group $R^1$ is $NH_2$. In a further embodiment, the C-terminal group $R^2$ is $NH_2$. In still a further embodiment the N-terminal group $R^1$ and the C-terminal group $R^2$ are $NH_2$.

In one embodiment position X14 represents an amino acid residue with a functionalized —$NH_2$ side chain group, such as functionalized Lys, Orn, Dab, or Dap, more preferably functionalized Lys, and X40 represents an amino acid residue with a functionalized —$NH_2$ side chain group, such as functionalized Lys, Orn, Dab, or Dap, more preferably functionalized Lys.

An amino acid residue with an —$NH_2$ side chain group, e.g. Lys, Orn, Dab or Dap, may be functionalized in that at least one H atom of the —$NH_2$ side chain group is replaced by —$C(O)$—$R^5$, —$C(O)O$—$R^5$, —$C(O)NH$—R5, —$S(O)$ 2-R5 or $R^5$, preferably by —$C(O)$—$R^5$, wherein $R^5$ may be a moiety comprising up to 50 or up to 100 carbon atoms and optionally heteroatoms selected from halogen, N, O, S and/or P.

In certain embodiments, $R^5$ may comprise a lipophilic moiety, e.g. an acyclic linear or branched saturated hydrocarbon group, wherein $R^5$ particularly comprises an acyclic linear or branched $(C_4$-$C_{30})$ saturated or unsaturated hydrocarbon group, and/or a cyclic saturated, unsaturated or aromatic group, particularly a mono-, bi-, or tricyclic group comprising 4 to 14 carbon atoms and 0, 1, or 2 heteroatoms selected from N, O, and S, e.g. cyclohexyl, phenyl, biphenyl, chromanyl, phenanthrenyl or naphthyl, wherein the acyclic or cyclic group may be unsubstituted or substituted e.g. by halogen, —OH and/or $CO_2H$.

More preferred groups $R^5$ may comprise a lipophilic moiety, e.g. an acyclic linear or branched $(C_{12}$-$C_{22})$ saturated or unsaturated hydrocarbon group. The lipophilic moiety may be attached to the —$NH_2$ side chain group by a linker in all stereoisomeric forms, e.g. a linker comprising one or more, e.g. 2, amino acid linker groups such as γ-aminobutyric acid (GABA), ε-aminohexanoic acid (ε-Ahx), γ-Glu and/or β-Ala. In one embodiment the lipophilic moiety is attached to the —$NH_2$ side chain group by a linker. In another embodiment the lipophilic moiety directly attached to the —$NH_2$ side chain group. Specific examples of amino acid linker groups are (β-Ala)$_{1-4}$, (γ-Glu)$_{1-4}$, (ε-Ahx)$_{1-4}$, or (GABA)$_{1-4}$. Preferred amino acid linker groups are ß-Ala, γ-Glu, ß-Ala-ß-Ala and γ-Glu-γ-Glu.

Specific preferred examples for —$C(O)$—$R^5$ groups are listed in the following Table 1, which are selected from the group consisting of (S)-4-Carboxy-4-hexadecanoylamino-butyryl-, (S)-4-Carboxy-4-octadecanoylamino-butyryl-, 4-Hexadecanoylamino-butyryl-, 4-{3-[(R)-2,5,7,8-tetramethyl-2-((4R,8R)-4,8,12-trimethyl-tridecyl)-chroman-6-yloxycarbonyl]-propionylamino}-butyryl-, 4-octadecanoylamino-butyryl-, 4-((Z)-octadec-9-enoylamino)-butyryl-, 6-[(4,4-Diphenyl-cyclohexyloxy)-hydroxy-phosphoryloxy]-hexanoyl-, Hexadecanoyl-, (S)-4-Carboxy-4-(15-carboxy-pentadecanoylamino)-butyryl-, (S)-4-Carboxy-4-{3-[3-((2S,3R,4S,5R)-5-carboxy-2,3,4,5-tetrahydroxy-pentanoylamino)-propionylamino]-propionylamino}-butyryl-, (S)-4-Carboxy-4-{3-[(R)-2,5,7,8-tetramethyl-2-((4R,8R)-4,8,12-trimethyl-tridecyl)-chroman-6-yloxycarbonyl]-propionylamino}-butyryl-, (S)-4-Carboxy-4-((9Z,12Z)-octadeca-9,12-dienoylamino)-butyryl-, (S)-4-Carboxy-4-[6-((2S,3R,4S,5R)-5-carboxy-2,3,4,5-tetrahydroxy-pentanoylamino)-hexanoylamino]-butyryl-, (S)-4-Carboxy-4-((2S,3R,4S,5R)-5-carboxy-2,3,4,5-tetrahydroxy-pentanoylamino)-butyryl-, (S)-4-Carboxy-4-tetradecanoylamino-butyryl-, (S)-4-(11-Benzyloxycarbonyl-undecanoylamino)-4-carboxy-butyryl-, (S)-4-Carboxy-4-[11-((2S,3R,4R,5R)-2,3,4,5,6-pentahydroxy-hexylcarbamoyl)-undecanoylamino]-butyryl-, (S)-4-Carboxy-4-((Z)-octadec-9-enoylamino)-butyryl-, (S)-4-Carboxy-4-(4-dodecyloxy-benzoylamino)-butyryl-, (S)-4-Carboxy-4-henicosanoylamino-butyryl-, (S)-4-Carboxy-4-docosanoylamino-butyryl-, (S)-4-Carboxy-4-((Z)-nonadec-10-enoylamino)-butyryl-, (S)-4-Carboxy-4-(4-decyloxy-benzoylamino)-butyryl-, (S)-4-Carboxy-4-[(4'-octyloxy-biphenyl-4-carbonyl)-amino]-butyryl-, (S)-4-Carboxy-4-(12-phenyl-dodecanoylamino)-butyryl-, (S)-4-Carboxy-4-icosanoylamino-butyryl-, (S)-4-Carboxy-4-((S)-4-carboxy-4-hexadecanoylamino-butyrylamino)-butyryl-, (S)-4-Carboxy-4-((S)-4-carboxy-4-octadecanoylamino-butyrylamino)-butyryl-, 3-(3-Octadecanoylamino-propionylamino)-propionyl-, 3-(3-Hexadecanoylamino-propionylamino)-propionyl-, 3-Hexadecanoylamino-propionyl-, (S)-4-Carboxy-4-[(R)-4-((3R,5S,7R,8R,9R,10S,12S,13R,14R,17R)-3,7,12-trihydroxy-8,10,13-trimethyl-hexadecahydro-cyclopenta[a]phenanthren-17-yl)-pentanoylamino]-butyryl-, (S)-4-Carboxy-4-[(R)-4-((3R,5R,8R,9S,10S,13R,14S,17R)-3-hydroxy-10,13-dimethyl-hexadecahydro-cyclopenta[a]phenanthren-17-yl)-pentanoylamino]-butyryl-, (S)-4-Carboxy-4-((9S,10R)-9,10,16-trihydroxy-hexadecanoylamino)-butyryl-, Tetradecanoyl-, 11-Carboxy-undecanoyl-, 11-Benzyloxycarbonyl-undecanoyl-, (S)-4-Carboxy-4-((S)-4-carboxy-4-tetradecanoylamino-butyrylamino)-butyryl-, 6-[Hydroxy-(naphthalene-2-yloxy)-phosphoryloxy]-hexanoyl-, 6-[Hydroxy-(5-phenyl-pentyloxy)-phosphoryloxy]-hexanoyl-, 4-(Naphthalene-2-sulfonylamino)-4-oxo-butyryl-, 4-(Biphenyl-4-sulfonylamino)-4-oxo-butyryl-, (S)-4-Carboxy-4-{(S)-4-carboxy-4-[2-(2-{2-[2-(2-{[(S)-4-carboxy-4-(17-carboxy-heptadecanoylamino)-butyrylamino]-ethoxy}-ethoxy)-acetylamino]-ethoxy}-ethoxy)-acetylamino]-butyrylamino}-butyryl-, (S)-4-Carboxy-4-[2-(2-{2-[2-(2-{[(S)-4-carboxy-4-(17-carboxyheptadecanoylamino)-butyrylamino]-ethoxy}-ethoxy)-acetylamino]-ethoxy}-ethoxy)-acetylamino-butyryl-, (S)-4-Carboxy-2-{(S)-4-carboxy-2-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetylamino]-butyrylamino}-butyryl-, (S)-4-Carboxy-2-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetylamino]-butyryl-, (S)-4-Carboxy-4-{(S)-4-carboxy-4-[2-(2-{2-[(S)-4-carboxy-4-(17-carboxy-heptadecanoylamino)-butyrylamino]-ethoxy}-ethoxy)-acetylamino]-butyrylamino}-butyryl-, (S)-4-Carboxy-4-[2-(2-{2-[(S)-4-carboxy-4-(17-carboxy-heptadecanoylamino)-butyrylamino]-ethoxy}-ethoxy)-acetylamino]-butyryl-, (S)-4-Carboxy-2-{(S)-4-carboxy-2-[2-(2-{2-[(S)-4-carboxy-4-(17-carboxy-heptadecanoylamino)-butyrylamino]-ethoxy}-ethoxy)-acetylamino]-butyrylamino}-butyryl-, (S)-4-Carboxy-2-[2-(2-{2-[(S)-4-carboxy-4-(17-carboxy-heptadecanoylamino)-butyrylamino]-ethoxy}-ethoxy)-acetylamino]-butyryl-, 2-(2-{2-[2-(2-{2-[(S)-4-Carboxy-4-(17-carboxy-heptadecanoylamino)-butyrylamino]-ethoxy}-ethoxy)-acetylamino]-ethoxy}-ethoxy)-acetyl-, 2-(2-{2-[(S)-4-Carboxy-4-(17-carboxy-heptadecanoylamino)-butyrylamino]-ethoxy}-ethoxy)-acetyl, (S)-4-Carboxy-4-((S)-4-carboxy-4-{(S)-4-carboxy-4-[(S)-4-carboxy-4-(19-carboxy-nonadecanoylamino)-butyrylamino]-butyrylamino}-butyrylamino)-butyryl, 2-(2-{2-[2-(2-{2-[(S)-4-Carboxy-4-(16-1H-tetrazol-5-yl-hexadecanoylamino)-butyrylamino]-ethoxy}-ethoxy)-acetylamino]-ethoxy}-ethoxy)-acetyl-, 2-(2-{2-[2-(2-{2-[(S)-4-Carboxy-4-(16-carboxy-hexadecanoylamino)-butyrylamino]-ethoxy}-ethoxy)-acetylamino]-ethoxy}-ethoxy)-acetylamino]-ethoxy}-ethoxy)-acetyl-, (S)-4-Carboxy-4-{(S)-4-carboxy-4-[(S)-4-carboxy-4-(17-carboxy-heptadecanoylamino)-butyrylamino]-butyrylamino}-butyryl-, (S)-4-Carboxy-4-((S)-4-carboxy-4-{2-[2-(2-{2-[2-(2-{(S)-4-carboxy-4-[10-(4-carboxy-phenoxy)-decanoylamino]-butyrylamino}-ethoxy)-ethoxy]-acetylamino}-ethoxy)-ethoxy]-acetylamino}-butyryl-, (S)-4-Carboxy-4-{(S)-4-carboxy-4-[2-(2-{2-[2-(2-{2-[(S)-4-carboxy-4-(7-carboxy-heptanoylamino)-butyrylamino]-ethoxy}-ethoxy)-acetylamino]-ethoxy}-ethoxy)-acetylamino]-butyrylamino}-butyryl-, (S)-4-Carboxy-4-{(S)-4-carboxy-4-[2-(2-{2-[2-(2-{2-[(S)-4-carboxy-4-(11-carboxy-undecanoylamino)-butyrylamino]-ethoxy}-ethoxy)-acetylamino]-ethoxy}-ethoxy)-acetylamino]-butyrylamino}-butyryl-, (S)-4-Carboxy-4-{(S)-4-carboxy-4-[2-(2-{2-[2-(2-{2-[(S)-4-carboxy-4-(13-carboxy-tridecanoylamino)-butyrylamino]-ethoxy}-ethoxy)-acetylamino]-ethoxy}-ethoxy)-acetylamino]-butyrylamino}-butyryl-, (S)-4-Carboxy-4-{(S)-4-carboxy-4-[2-(2-{2-[2-(2-{2-[(S)-4-carboxy-4-(15-carboxy-pentadecanoylamino)-butyrylamino]-ethoxy}-ethoxy)-acetylamino]-ethoxy}-ethoxy)-acetylamino]-butyrylamino}-butyryl-, and (S)-4-Carboxy-4-{(S)-4-carboxy-4-[2-(2-{2-[2-(2-{2-[(S)-4-carboxy-4-(19-carboxy-nonadecanoylamino)-butyrylamino]-ethoxy}-ethoxy)-acetylamino]-ethoxy}-ethoxy)-acetylamino]-butyrylamino}-butyryl-.

Further preferred are stereoisomers, particularly enantiomers of these groups, either S- or R-enantiomers. The term "R" in Table 1 is intended to mean the attachment site of —C(O)—$R^5$ at the peptide back bone, i.e. particularly the ε-amino group of Lys.

TABLE 1

| structure | IUPAC | name |
|---|---|---|
| 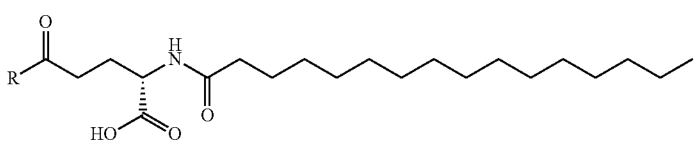 | (S)-4-Carboxy-4-hexadecanoylamino-butyryl- | γE-x53 |
| 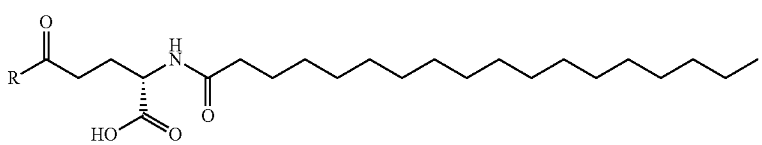 | (S)-4-Carboxy-4-octadecanoylamino-butyryl- | γE-x70 |
| 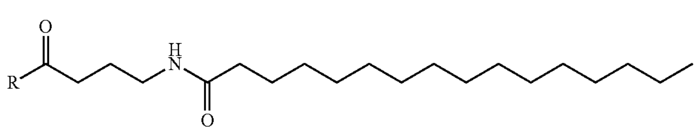 | 4-Hexadecanoylamino-butyryl- | GABA-x53 |
| 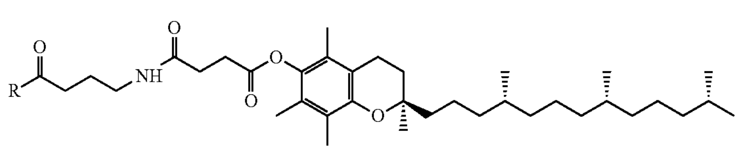 | 4-{3-[(R)-2,5,7,8-tetramethyl-2-(4R,8R)-4,8,12-trimethyl-tridecyl)-chroman-6-yloxycarbonyl]-propionylamino}-butyryl | GABA-x60 |
| 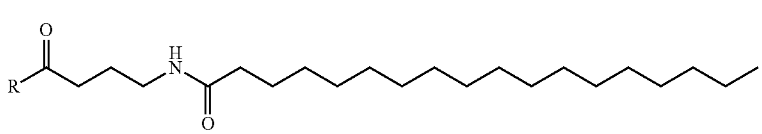 | 4-octadecanoylamino-butyryl- | GABA-x70 |

TABLE 1-continued

| structure | IUPAC | name |
|---|---|---|
| 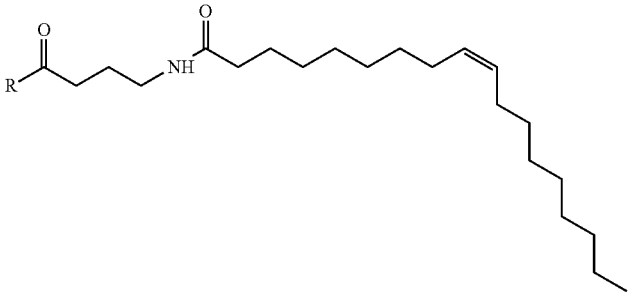 | 4-((Z)-octadec-9-enoylamino)-butyryl- | GABA-x74 |
| 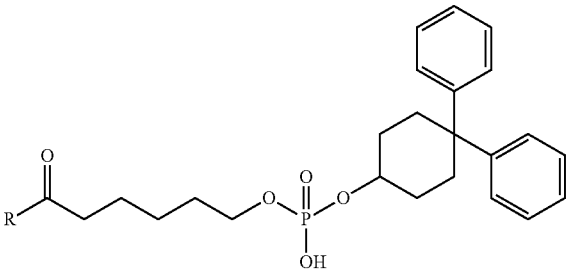 | 6-[(4,4-Diphenyl-cyclohexyloxy)-hydroxy-phosphoryloxy]-hexanoyl- | Phospho1 |
| 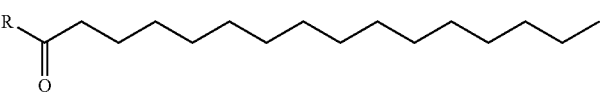 | Hexadecanoyl- | x53 |
| 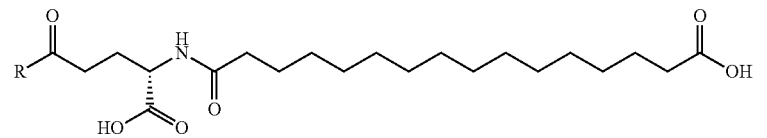 | (S)-4-Carboxy-4-(15-carboxy-pentadecanoylamino)-butyryl- | x52 |
| 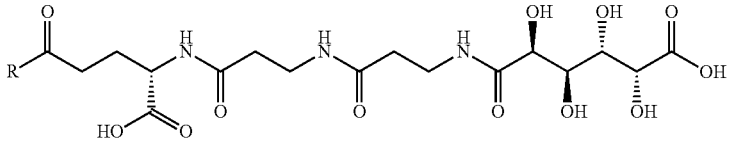 | (S)-4-Carboxy-4-{3-[3-((2S,3R,4S,5R)-5-carboxy-2,3,4,5-tetrahydroxy-pentanoylamino)-propionylamino]-propionylamino}-butyryl | γE-x59 |
| 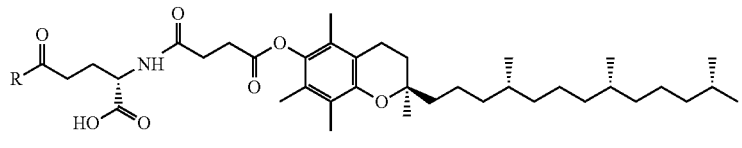 | (S)-4-Carboxy-4-{3-[(R)-2,5,7,8-tetramethyl-2-((4R,8R)-4,8,12-trimethyl-tridecyl)-chroman-6-yloxycarbonyl]-propionylamino}-butyryl | γE-x60 |
| 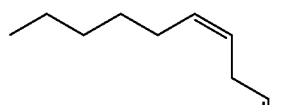 | (S)-4-Carboxy-4-((9Z,12Z)-octadeca-9,12-dienoylamino)-butyryl- | γE-x61 |
| 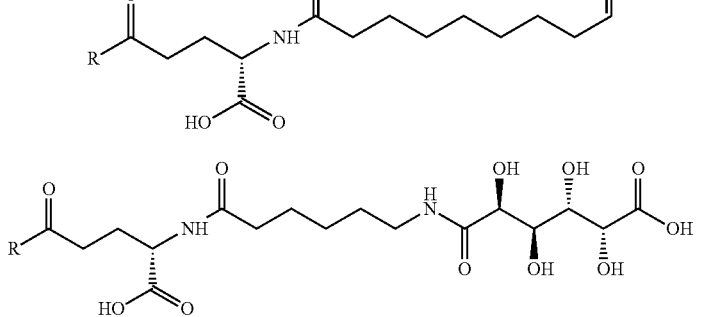 | (S)-4-Carboxy-4-[6-((2S,3R,4S,5R)-5-carboxy-2,3,4,5-tetrahydroxy-pentanoylamino)-hexanoylamino]-butyryl | γE-x64 |

TABLE 1-continued

| structure | IUPAC | name |
|---|---|---|
| 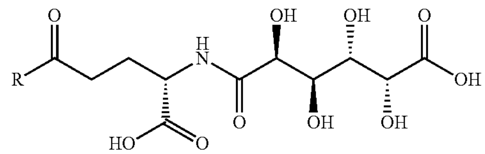 | (S)-4-Carboxy-4-((2S,3R,4S,5R)-5-carboxy-2,3,4,5-tetrahydroxy-pentanoylamino)-butyryl | γE-x65 |
| 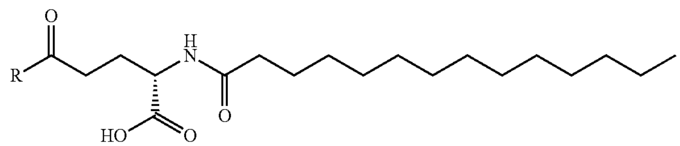 | (S)-4-Carboxy-4-tetradecanoylamino-butyryl- | γE-x69 |
| 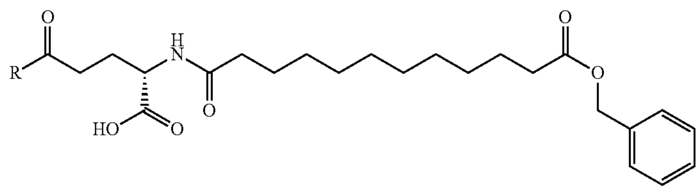 | (S)-4-(11-Benzyl-oxycarbonyl-undecanoylamino)-carboxy-butyryl | γE-x72 |
| 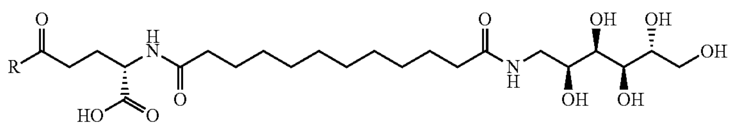 | (S)-4-Carboxy-4-[11-((2S,3R,4R,5R)-2,3,4,5,6-pentahydroxy-hexylcarbamoyl)undecanoylamino]-butyryl- | γE-x73 |
| 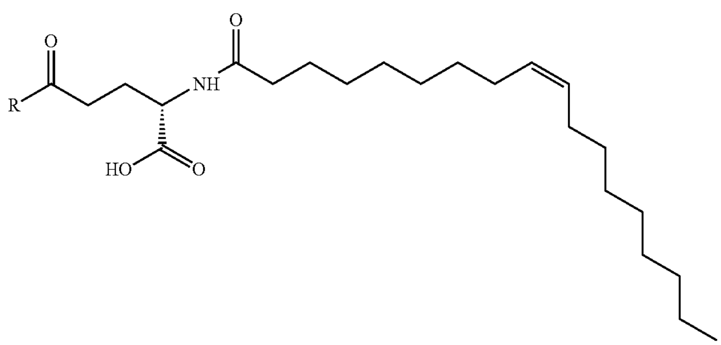 | (S)-4-Carboxy-4-((Z)-octadec-9-enoylamino)-butyryl- | γE-x74 |
| 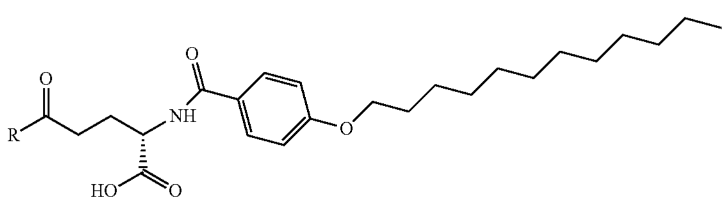 | (S)-4-Carboxy-4-(4-dodecyloxy-benzoylamino)-butyryl- | γE-x75 |
| 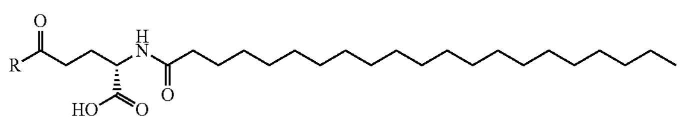 | (S)-4-Carboxy-4-henicosanoylamino-butyryl- | γE-x76 |
| 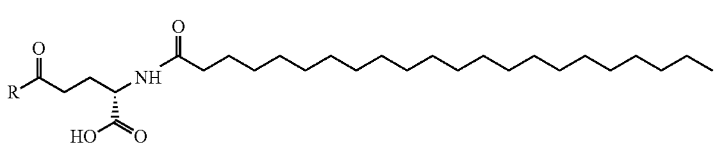 | (S)-4-Carboxy-4-docosanoylamino-butyryl- | γE-x77 |

TABLE 1-continued
| structure | IUPAC | name |
|---|---|---|
| 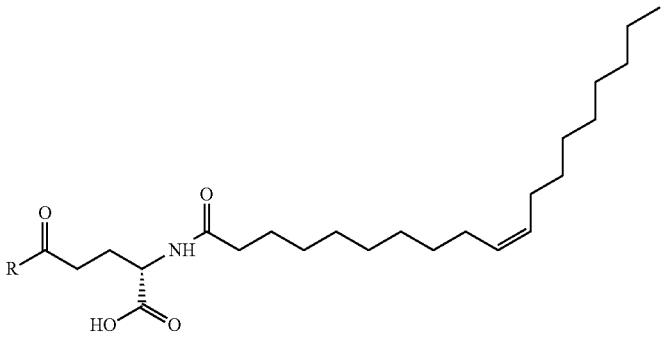 | (S)-4-Carboxy-4-((Z)-nonadec-10-enoylamino)-butyryl- | γE-x79 |
| 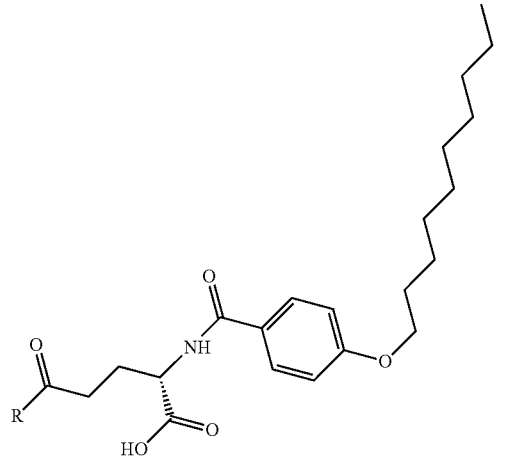 | (S)-4-Carboxy-4-(4-decyloxy-benzoylamino)-butyryl- | γE-x80 |
| 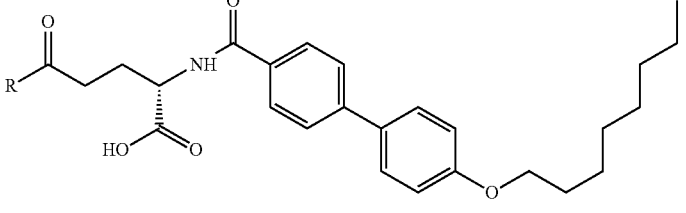 | (S)-4-Carboxy-4-[(4'-octyloxy-biphenyl-4 carbonyl)-amino]-butyryl- | γE-x81 |
| 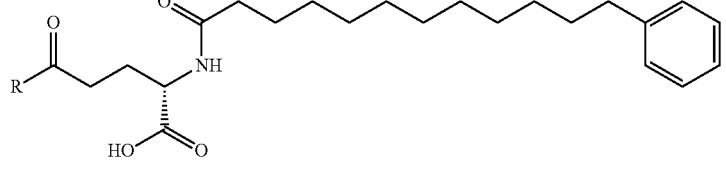 | (S)-4-Carboxy-4-(12-phenyl-dodecanoylamino)-butyryl- | γE-x82 |
| 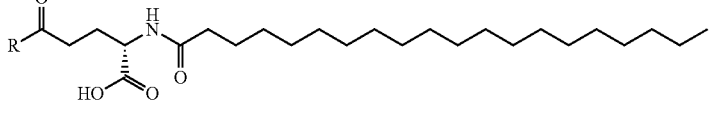 | (S)-4-Carboxy-4-icosanoylamino-butyryl- | γE-x95 |
| 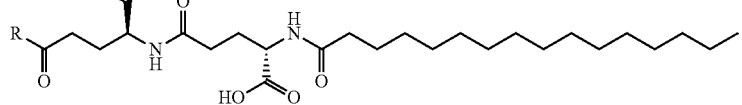 | (S)-4-Carboxy-4-((S)-4-carboxy-4-hexadecanoylamino-butyrylamino)-butyryl- | γE-γE-x53 |

TABLE 1-continued

| structure | IUPAC | name |
|---|---|---|
| 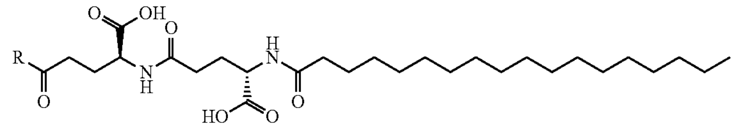 | (S)-4-Carboxy-4-((S)-4-carboxy-4-octadecanoylamino-butyrylamino)-butyryl- | γE-γE-x70 |
| 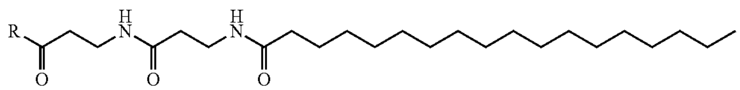 | 3-(3-Octadecanoylamino-propionyl-amino)-propionyl | β-Ala-β-Ala-x70 |
| | 3-(3-Hexadecanoylamino-propionyl-amino)-propionyl | β-Ala-β-Ala-x53 |
| 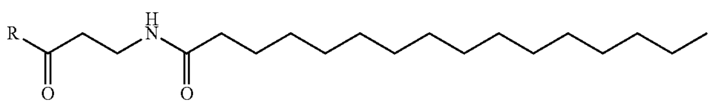 | 3-Hexadecanoylamino-propionyl- | β-Ala-x53 |
| 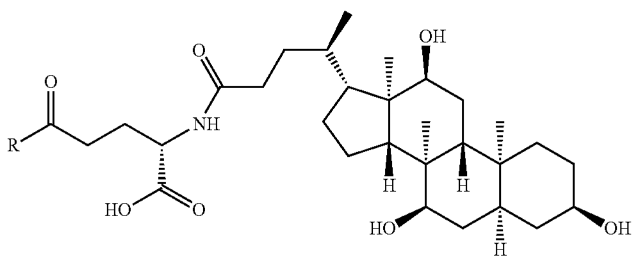 | (S)-4-Carboxy-4-[(R)-4-((3R,5S,7R,8R,9R,10S,12S,13R,14R,17R)3,7,12-trihydroxy-8,10,13-trimethyl-hexadecahydro-cyclopenta[a]phenanthren-17-yl)-pentanoylamino]-butyryl- | γE-x16 |
| 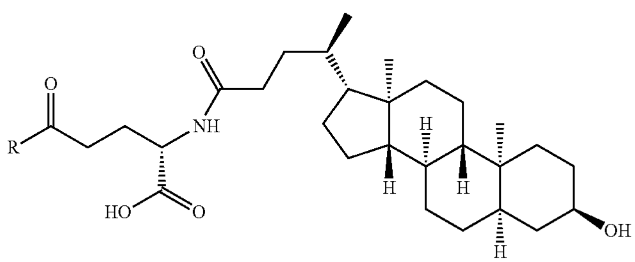 | (S)-4-Carboxy-4-[(R)-4-((3R,5R,8R,9S,10S,13R,14S,17R)-3-hydroxy-10,13-dimethyl-hexadecahydro-cyclopenta[a]phenanthren-17-yl)-pentanoylamino]-butyryl- | γE-x19 |
| 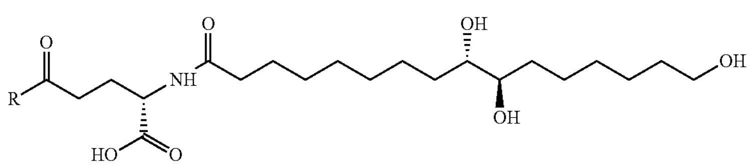 | (S)-4-Carboxy-4-((9S,10R)-9,10,16-trihydroxy-hexadecanoylamino)-butyryl- | γE-x25 |
| 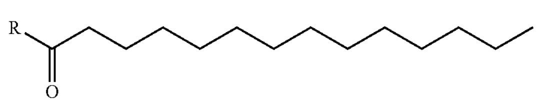 | tetradecanoyl- | x69 |
| 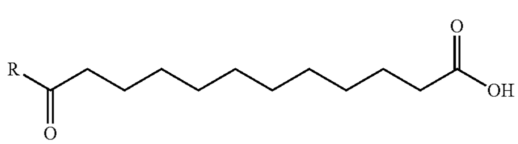 | 11-Carboxy-undecanoyl- | x71 |
| 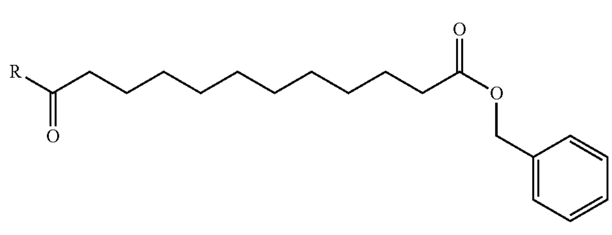 | 11-Benzyloxycaronyl-undecanoyl- | x72 |

TABLE 1-continued

| structure | IUPAC | name |
| --- | --- | --- |
| 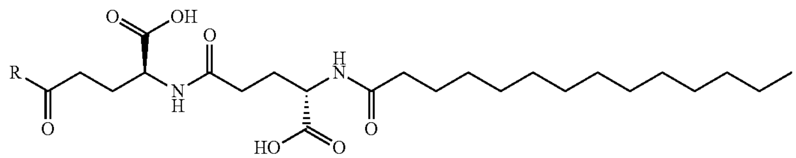 | (S)-4-Carboxy-4-((S)-4-carboxy-4-tetradecanoylamino-butyrylamino)-butyryl- | γE-γE-x69 |
| 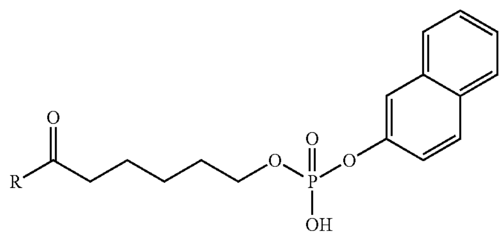 | 6-[Hydroxy-(naphthalen-2-yloxy)-phosphoryloxy]-hexanoyl- | Phospho2 |
| 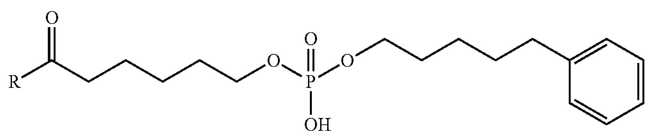 | 6-[Hydroxy-(5-phenyl-pentyloxy)-phosphoryloxy]-hexanoyl- | Phospho3 |
| 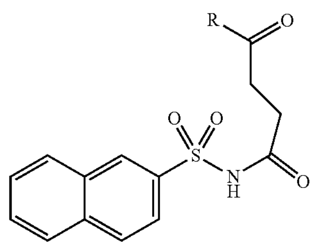 | 4-(Naphthalene-2-sulfonylamino)-4-oxo-butyryl- | Sulfona-mid 1 |
| 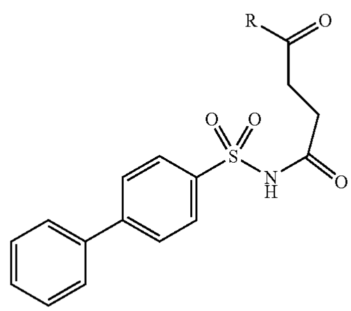 | 4-(Biphenyl-4-sulfonylamino)-4-oxo-butyryl- | Sulfona-mid 2 |
| | (S)-4-Carboxy-4-{(S)-4-carboxy-4-[2-(2-{2-[2-(2-(2-[(S)-4-carboxy-4-(17-carboxy-heptadecanoylamino)-butyrylamino]-ethoxy}-ethoxy)-acetylamino]-ethoxy}-ethoxy)-acetylamino]-butyrylamino}-butyryl- | x100 |
| 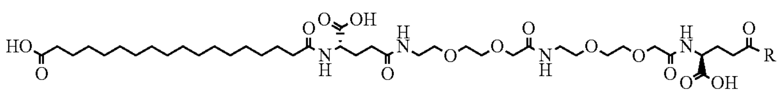 | (S)-4-Carboxy-4-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetylamino]-butyryl | x101 |

TABLE 1-continued

| structure | IUPAC | name |
|---|---|---|
| 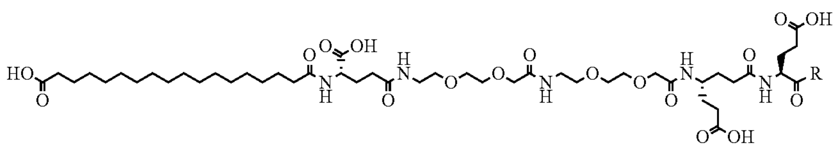 | (S)-4-Carboxy-2-{(S)-4-carboxy-2-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetylamino]-butyrylamino}-butyryl | x102 |
| 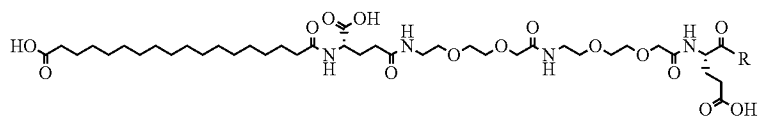 | (S)-4-Carboxy-2-[2-(2-{2-[2-(2-{2-[(S)-((4-carboxy-4-(17-carboxy-heptadecanoylamino)-butyrylamino]-ethoxy}-ethoxy)-acetylamino]-ethoxy}-ethoxy)-acetylamino]-butyryl | x103 |
| 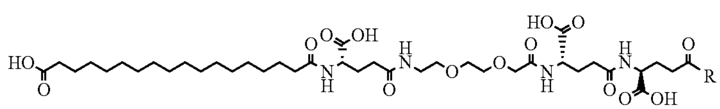 | (S)-4-Carboxy-4-{(S)-4-carboxy-4-[2-(2-{2-[(S)-4-carboxy-4-(17-carboxy-heptadecanoylamino)-butyrylamino]-ethoxy}-ethoxy)-acetylamino]-butyrylamino}-butyryl | x104 |
| 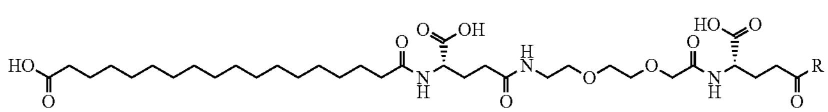 | (S)-4-Carboxy-4-[2-(2-{2-[(S)-4-carboxy-4-(17-carboxy-heptadecanoylamino)-butyrylamino]-ethoxy}-ethoxy)-acetylamino]-butyryl | x105 |
| 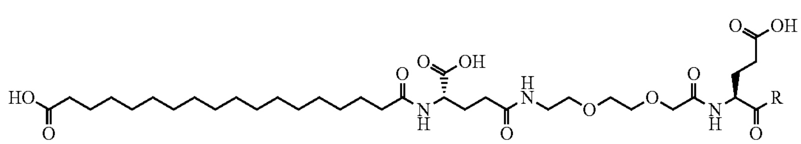 | (S)-4-Carboxy-2-{(S)-4-carboxy-2-[2-(2-{2-[(S)-4-carboxy-4-(17-carboxy-heptadecanoylamino)-butyrylamino]-ethoxy}-ethoxy)-acetylamino]-butyrylamino}-butyryl | x106 |
| 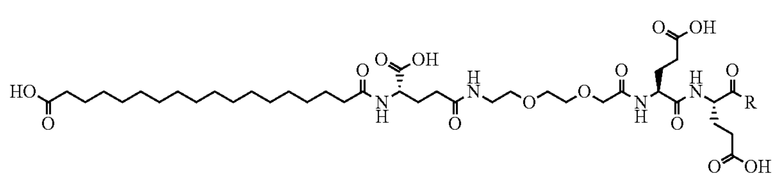 | (S)-4-Carboxy-2-[2-(2-{2-[(S)-4-carboxy-4-(17-carboxy-heptadecanoylamino)-butyrylamino]-ethoxy}-ethoxy)-acetylamino]-butyryl | x107 |
| | 2-(2-{2-[2-(2-{2-[(S)-Carboxy-4-(17-carboxy-heptadecanoylamino)-butyrylamino]-ethoxy}-ethoxy)-acetylamino]-ethoxy}-ethoxy)-acetyl- | x108 |
| 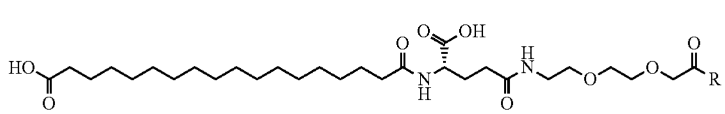 | 2-(2-{2-[(S)-4-Carboxy-4-(17-carboxy-heptadecanoylamino)-butyrylamino]-ethoxy}-ethoxy)-acetyl | x109 |

TABLE 1-continued

| structure | IUPAC | name |
|---|---|---|
| 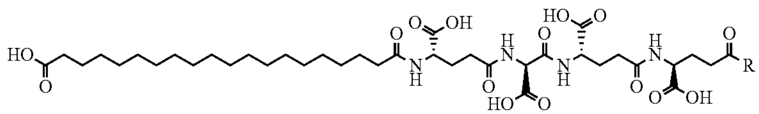 | (S)-4-Carboxy-4-((S)-4-carboxy-4-{(S)-4-carboxy-4-[(S)-4-carboxy-4-(19-carboxy-nonadecanoylamino)-butyrylamino]-butyrylamino}-butyrylamino)-butyryl | x110 |
| 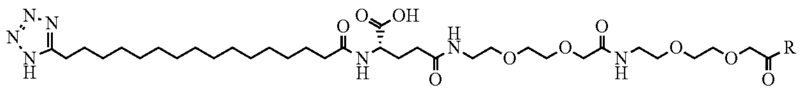 | 2-(2-{2-[2-(2-{2-[(S)-4-Carboxy-4-(16-1H-tetrazol-5-yl-hexadecanoylamino)-butyrylamino]-ethoxy}-ethoxy)-acetylamino]-ethoxy}-ethoxy)-acetyl | x111 |
| 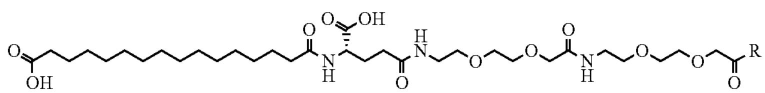 | 2-(2-{2-[2-(2-{2-[(S)-4-Carboxy-4-(16-carboxy-hexadecanoylamino)-butyrylamino]-ethoxy}-ethoxy)-acetylamino]-ethoxy}-ethoxy)-acetyl | x112 |
| 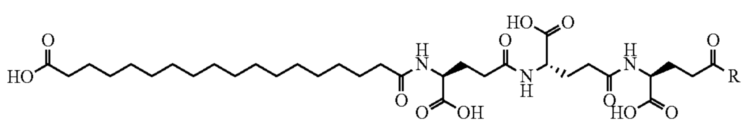 | (S)-4-Carboxy-4-{(S)-4-carboxy-4-[(S)-4-carboxy-4-(17-carboxy-heptadecanoylamino)-butyrylamino]-butyrylamino}-butyryl | x113 |
| 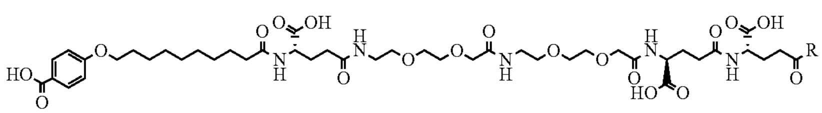 | (S)-4-Carboxy-4-((S)-4-carboxy-4-{2-[2-(2-{2-[2-(2-{(S)-4-carboxy-4-[10-(4-carboxy-phenoxy)-decanoylamino]-butyrylamino}-ethoxy)-ethoxy]-acetylamino}-ethoxy)-ethoxy]-acetylamino}-butyryl | x114 |
| 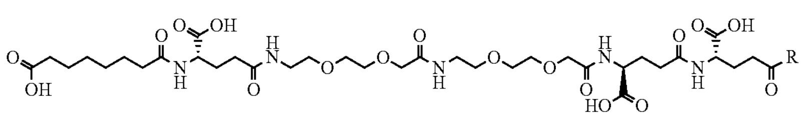 | (S)-4-Carboxy-4-{(S)-4-carboxy-4-[2-(2-{2-[2-(2-{2-[(S)-4-carboxy-4-(7-carboxy-heptanoylamino)-butyrylamino]-ethoxy}-ethoxy)-acetylamino]-ethoxy}-ethoxy)-acetylamino]-butyrylamino}-butyryl | x115 |
| 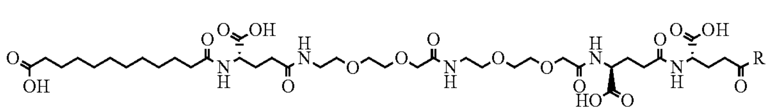 | (S)-4-Carboxy-4-{(S)-4-carboxy-4-[2-(2-{2-[2-(2-{2-[(S)-4-carboxy-4-(11-carboxy-undecanoylamino)-butyrylamino]-ethoxy}-ethoxy)-acetylamino]-ethoxy}-ethoxy)-acetylamino]-butyrylamino}-butyryl | x116 |

TABLE 1-continued

| structure | IUPAC | name |
|---|---|---|
| 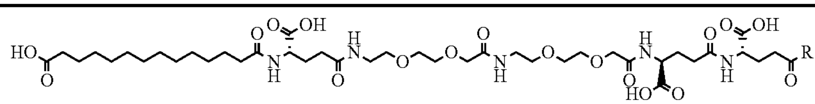 | (S)-4-Carboxy-4-{(S)-4-carboxy-4-[2-(2-{2-[2-(2-{2-[(S)-4-carboxy-4-(13-carboxy-tridecanoylamino)-butyrylamino]-ethoxy}-ethoxy)-acetylamino]-ethoxy}-ethoxy)-acetylamino]-butyrylamino}-butyryl | x117 |
| 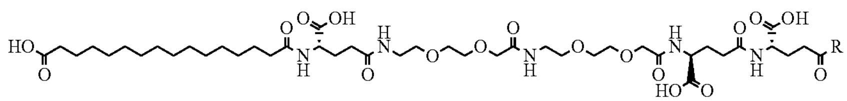 | (S)-4-Carboxy-4-{(S)-4-carboxy-4-[2-(2-{2-[2-(2-{2-[(S)-4-carboxy-4-(15-carboxy-pentadecanoylamino)-butyrylamino]-ethoxy}-ethoxy)-acetylamino]-ethoxy}-ethoxy)-acetylamino]-butyrylamino}-butyryl | x118 |
| 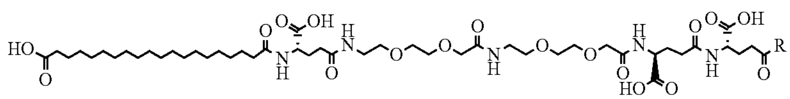 | (S)-4-Carboxy-4-{(S)-4-carboxy-4-[2-(2-{2-[2-(2-{2-[(S)-4-carboxy-4-(19-carboxy-nonadecanoylamino)-butyrylamino]-ethoxy}-ethoxy)-acetylamino]-ethoxy}-ethoxy)-acetylamino]-butyrylamino}-butyryl | x119 |

According to one embodiment, $R^5$ is selected from the group consisting of (S)-4-carboxy-4-hexadecanoylamino-butyryl (γE-x53), (S)-4-carboxy-4-octadecanoylamino-butyryl (γE-x70) 4-hexadecanoylamino-butyryl (GABA-x53) 4-{3-[(R)-2,5,7,8-tetramethyl-2-((4R,8R)-4,8,12-trimethyl-tridecyl)-chroman-6-yloxycarbonyl]-propionylamino}-butyryl- (GABA-x60), 4-octadecanoylamino-butyryl (GABA-x70), 4-((Z)-octadec-9-enoylamino)-butyryl (GABA-x74), 6-[(4,4-Diphenyl-cyclohexyloxy)-hydroxy-phosphoryloxy]-hexanoyl (Phospho1), Hexadecanoyl (x53), (S)-4-Carboxy-4-(15-carboxy-pentadecanoylamino)-butyryl (x52), (S)-4-Carboxy-4-{3-[3-((2S,3R,4S,5R)-5-carboxy-2,3,4,5-tetrahydroxy-pentanoylamino)-propionylamino]-propionylamino}-butyryl (γE-x59), (S)-4-Carboxy-4-{3-[(R)-2,5,7,8-tetramethyl-2-((4R,8R)-4,8,12-trimethyl-tridecyl)-chroman-6-yloxycarbonyl]-propionylamino}-butyryl (γE-x60), (S)-4-Carboxy-4-((9Z,12Z)-octadeca-9,12-dienoylamino)-butyryl (γE-x61), (S)-4-Carboxy-4-[6-((2S,3R,4S,5R)-5-carboxy-2,3,4,5-tetrahydroxy-pentanoylamino)-hexanoylamino]-butyryl (γE-x64), (S)-4-Carboxy-4-((2S,3R,4S,5R)-5-carboxy-2,3,4,5-tetrahydroxy-pentanoylamino)-butyryl (γE-x65), (S)-4-carboxy-4-tetradecanoylamino-butyryl (γE-x69), (S)-4-(11-Benzyloxycarbonyl-undecanoylamino)-4-carboxy-butyryl (γE-x72), (S)-4-carboxy-4-[11-((2S,3R,4R,5R)-2,3,4,5,6-pentahydroxy-hexylcarbamoyl)-undecanoylamino]-butyryl (γE-x73), (S)-4-Carboxy-4-((Z)-octadec-9-enoylamino)-butyryl (γE-x74), (S)-4-Carboxy-4-(4-dodecyloxy-benzoylamino)-butyryl (γE-x75), (S)-4-Carboxy-4-henicosanoylamino-butyryl (γE-x76), (S)-4-Carboxy-4-docosanoylamino-butyryl (γE-x77), (S)-4-Carboxy-4-((Z)-nonadec-10-enoylamino)-butyryl (γE-x79), (S)-4-Carboxy-4-(4-decyloxy-benzoylamino)-butyryl (γE-x80), (S)-4-Carboxy-4-[(4'-octyloxy-biphenyl-4-carbonyl)-amino]-butyryl (γE-x81), (S)-4-Carboxy-4-(12-phenyl-dodecanoylamino)-butyryl (γE-x82), (S)-4-Carboxy-4-icosanoylamino-butyryl (γE-x95), (S)-4-Carboxy-4-((S)-4-carboxy-4-hexadecanoylamino-butyrylamino)-butyryl (γE-γE-x53), (S)-4-Carboxy-4-((S)-4-carboxy-4-octadecanoylamino-butyrylamino)-butyryl (γE-γE-x70), and 3-(3-Octadecanoylamino-propionylamino)-propionyl (β-Ala-β-Ala-x70).

According to another embodiment, $R^5$ is selected from the group consisting of (S)-4-carboxy-4-octadecanoylamino-butyryl (γE-x70), (S)-4-carboxy-4-hexadecanoylamino-butyryl (γE-x53), and hexadecanoyl (x53).

According to yet another embodiment, $R^5$ is (S)-4-carboxy-4-hexadecanoylamino-butyryl (γE-x53).

In some embodiments of the invention, position X14 and/or X40 represents Lysine (Lys). According to some embodiments, Lys at position 14 and optionally at position 40 is functionalized, e.g. with a group —C(O)R$^5$ as described above. In other embodiments, X40 is absent and X14 is Lys functionalized with —C(O)—R$^5$, —C(O)O—R$^5$, —C(O)NH—R5, —S(O)2-R5 or R5, preferably by —C(O)—R$^5$, wherein R$^5$ is as defined above. In particular, X14 is Lys functionalized with C(O)—R$^5$, wherein R$^5$ is selected from the group consisting of (S)-4-carboxy-4-hexadecanoylamino-butyryl (γE-x53), (S)-4-carboxy-4-octadecanoylamino-butyryl (γE-x70), 4-hexadecanoylamino-butyryl (GABA-x53), 4-{3-[(R)-2,5,7,8-tetramethyl-2-((4R,8R)-4,8,12-trimethyl-tridecyl)-chroman-6-yloxycarbonyl]-propionylamino}-butyryl-(GABA-x60), 4-octadecanoylamino-butyryl (GABA-x70), 4-((Z)-octadec-9-enoylamino)-butyryl (GABA-x74), 6-[(4,4-Diphenyl-cyclohexyloxy)-hydroxy-phosphoryloxy]-hexanoyl (Phospho1), Hexadecanoyl (x53), (S)-4-Carboxy-4-(15-carboxy-pentadecanoylamino)-butyryl (x52), (S)-4-Carboxy-4-{3-[3-((2S,3R,4S,5R)-5-carboxy-2,3,4,5-tetrahydroxy-pentanoylamino)-propionylamino]-propionylamino}-butyryl (γE-x59), (S)-4-Carboxy-4-{3-[(R)-2,5,7,8-tetramethyl-2-((4R,8R)-4,8,12-trimethyl-tridecyl)-chroman-6-yloxycarbonyl]-propionylamino}-butyryl (γE-x60), (S)-4-Carboxy-4-((9Z,12Z)-octadeca-9,12-dienoylamino)-butyryl (γE-x61), (S)-4-Carboxy-4-[6-((2S,3R,4S,5R)-5-carboxy-2,3,4,5-tetrahydroxy-pentanoylamino)-hexanoylamino]-butyryl (γE-x64), (S)-4-Carboxy-4-((2S,3R,4S,5R)-5-carboxy-2,3,4,5-tetrahydroxy-pentanoylamino)-butyryl (γE-x65), (S)-4-carboxy-4-tetradecanoylamino-butyryl (γE-x69), (S)-4-(11-Benzyloxycarbonyl-undecanoylamino)-4-carboxy-butyryl (γE-x72), (S)-4-carboxy-4-[11-((2S,3R,4R,5R)-2,3,4,5,6-pentahydroxy-hexylcarbamoyl)-undecanoylamino]-butyryl (γE-x73), (S)-4-Carboxy-4-((Z)-octadec-9-enoylamino)-butyryl (γE-x74), (S)-4-Carboxy-4-(4-dodecyloxy-benzoylamino)-butyryl (γE-x75), (S)-4-Carboxy-4-henicosanoylamino-butyryl (γE-x76), (S)-4-Carboxy-4-docosanoylamino-butyryl (γE-x77), (S)-4-Carboxy-4-((Z)-nonadec-10-enoylamino)-butyryl (γE-x79), (S)-4-Carboxy-4-(4-decyloxy-benzoylamino)-butyryl (γE-x80), (S)-4-Carboxy-4-[(4'-octyloxy-biphenyl-4-carbonyl)-amino]-butyryl (γE-x81), (S)-4-Carboxy-4-(12-phenyl-dodecanoylamino)-butyryl (γE-x82), (S)-4-Carboxy-4-icosanoylamino-butyryl (γE-x95), (S)-4-Carboxy-4-((S)-4-carboxy-4-hexadecanoylamino-butyrylamino)-butyryl (γE-γE-x53), (S)-4-Carboxy-4-((S)-4-carboxy-4-octadecanoylamino-butyrylamino)-butyryl (γE-γE-x70), and 3-(3-Octadecanoylamino-propionylamino)-propionyl (β-Ala-β-Ala-x70).

A further embodiment relates to a group of compounds, wherein
$R^1$ is $NH_2$,
$R^2$ is $NH_2$ or
$R^1$ and $R^2$ are $NH_2$.

A further embodiment relates to a group of compounds, wherein
X2 represents an amino acid residue selected from Ser, D-Ser and Aib,
X3 represents an amino acid residue selected from Gln, His and α-amino-functionalized Gln, wherein Gln may be functionalized in that an H of the α-$NH_2$ group is substituted by $(C_1-C_4)$-alkyl,
X14 represents an amino acid residue selected from Lys, Orn, Dab and Dap, wherein the —$NH_2$ side chain group is functionalized by —C(O)—$R^5$,
X15 represents an amino acid residue selected from Glu and Asp,
X16 represents an amino acid residue selected from Ser, Lys and Glu,
X17 represents an amino acid residue selected from Arg, Glu, Gln, Leu and Lys,
X18 represents an amino acid residue selected from Arg and Ala,
X20 represents an amino acid residue selected from Gln, Arg, Lys and Aib,
X21 represents an amino acid residue selected from Asp, Leu and Glu,
X28 represents an amino acid residue selected from Asn, Arg, Lys, Aib, Ser, Glu, Asp and Ala,
X29 represents an amino acid residue selected from Gly, Ala, D-Ala and Thr,
X35 represents an amino acid residue selected from Ala or Glu,
X39 is Ser or is absent,
X40 is either absent or represents Lys, wherein the —$NH_2$ side chain group can be functionalized by —C(O)—$R^5$ and
—C(O)—$R^5$ is as defined above.

A further embodiment relates to a group of compounds, wherein
X2 represents an amino acid residue selected from D-Ser and Aib,
X3 represents Gln,
X14 represents an amino acid residue selected from Lys and Orn, wherein the —$NH_2$ side chain group is functionalized by —C(O)—$R^5$,
X15 represents an amino acid residue selected from Glu and Asp,
X16 represents an amino acid residue selected from Ser and Glu,
X17 represents an amino acid residue selected from Arg, Gln and Lys,
X18 represents an amino acid residue selected from Arg and Ala,
X20 represents an amino acid residue selected from Gln, Arg, Lys and Aib,
X21 represents an amino acid residue selected from Asp, Leu and Glu,
X28 represents an amino acid residue selected from Asn, Arg, Lys, Aib, Ser and Ala,
X29 represents an amino acid residue selected from Gly, Ala or Thr,
X35 represents Ala,
X39 is Ser or is absent,
X40 is either absent or represents Lys, wherein the —$NH_2$ side chain group can be functionalized by —C(O)—$R^5$ and
—C(O)—$R^5$ is as defined above.

A further embodiment relates to a group of compounds, wherein
X20 represents an amino acid residue selected from Gln, Lys and Aib.

A further embodiment relates to a group of compounds, wherein
X2 represents an amino acid residue selected from D-Ser and Aib,
X3 represents Gln,
X14 represents Lys, wherein the —$NH_2$ side chain group is functionalized by one of the groups selected from 3-(3-octadecanoylamino-propionyl-amino)-propionyl-, 4-hexadecanoylamino-butyryl-, 4-{3-[(R)-2,5,7,8-tetramethyl-2-((4R,8R)-4,8,12-trimethyl-tridecyl)-chroman-6-yloxycarbonyl]-propionylamino}-butyryl-, 4-octadecanoylamino-butyryl-, 4-((Z)-octadec-9-enoylamino)-butyryl-, hexadecanoyl-, (S)-4-carboxy-4-((Z)-octadec-9-enoylamino)-butyryl-, (S)-4-carboxy-4-(4-dodecyloxy-benzoylamino)-butyryl-, (S)-4-carboxy-4-henicosanoylamino-butyryl-, (S)-4-carboxy-4-docosanoylamino-butyryl-, (S)-4-carboxy-4-((Z)-nonadec-10-enoylamino)-butyryl-, (S)-4-carboxy-4-(4-decyloxy-benzoylamino)-butyryl-, (S)-4-carboxy-4-[(4'-octyloxy-biphenyl-4-carbonyl)-amino]-butyryl-, (S)-4-carboxy-4-(12-phenyl-dodecanoylamino)-butyryl-, (S)-4-carboxy-4-((S)-4-carboxy-4-hexadecanoylamino-butyrylamino)-butyryl-, (S)-4-carboxy-4-((S)-4-carboxy-4-octadecanoylamino-butyrylamino)-butyryl-, (S)-carboxy-4-{3-[(R)-2,5,7,8-tetramethyl-2-((4R,8R)-4,8,12-trimethyl-tridecyl)-chroman-6-yloxycarbonyl]-propionylamino}-butyryl-, (S)-4-carboxy-4-((9Z,12Z)- octadeca-9,12-dienoylamino)-butyryl-, (S)-4-carboxy-4-octadecanoylamino-butyryl- and (S)-4-carboxy-4-hexadecanoylamino-butyryl-, X15 represents Glu,
X16 represents Ser,
X17 represents an amino acid residue selected from Arg, Gln and Lys,
X18 represents Ala,
X20 represents Gln,
X21 represents Asp,
X28 represents Ala,
X29 represents Gly,
X35 represents Ala,
X39 is Ser
X40 is absent.

A further embodiment relates to a group of compounds of formula (I), wherein
X2 represents Aib,
X3 represents Gln,
X14 represents Lys, wherein the —NH$_2$ side chain group is functionalized, particularly by (S)-4-Carboxy-4-hexadecanoylamino-butyryl- and (S)-4-Carboxy-4-octadecanoylamino-butyryl-;
X15 represents an amino acid residue selected from Asp and Glu,
X16 represents an amino acid residue selected from Ser and Glu,
X17 represents an amino acid residue selected from Gln and Lys,
X18 represents Ala,
X20 represents an amino acid residue selected from Gln and Lys,
X21 represents an amino acid residue selected from Asp and Leu,
X28 represents Ala,
X29 represents an amino acid residue selected from Gly and D-Ala,
X35 represents Ala,
X39 is Ser,
X40 is absent.

A further embodiment relates to a group of compounds, wherein
X2 represents an amino acid residue selected from D-Ser and Aib,
X3 represents Gln,
X14 represents Lys, wherein the —NH$_2$ side chain group is functionalized, particularly by (S)-4-Carboxy-4-octadecanoylamino-butyryl-;
X15 represents Asp,
X16 represents Ser,
X17 represents Arg,
X18 represents Arg,
X20 represents Gln,
X21 represents Asp,
X28 represents Ala,
X29 represents an amino acid residue selected from Gly and D-Ala,
X35 represents Ala,
X39 is Ser,
X40 is absent.

A further embodiment relates to a group of compounds, wherein
X2 represents D-Ser,
X3 represents Gln,
X14 represents Lys, wherein the —NH$_2$ side chain group can be functionalized, particularly by (S)-4-carboxy-4-{3-[(R)-2,5,7,8-tetramethyl-2-((4R,8R)-4,8,12-trimethyl-tridecyl)-chroman-6-yloxycarbonyl]-propionylamino}-butyryl-, (S)-4-carboxy-4-((9Z,12Z)-octadeca-9,12-dienoylamino)-butyryl-, (S)-4-carboxy-4-tetradecanoylamino-butyryl-, (S)-4-carboxy-4-octadecanoylamino-butyryl-, 2-((S)-4-carboxy-4-{3-[3-((2S,3R,4S,5R)-5-carboxy-2,3,4,5-tetrahydroxy-pentanoylamino)-propionylamino]-propionylamino}-butyryl-, 2-{(S)-4-carboxy-4-[6-((2S,3R,4S,5R)-5-carboxy-2,3,4,5-tetrahydroxy-pentanoylamino)-hexanoylamino]-butyryl-, 2-[(S)-4-carboxy-4-((2S,3R,4S,5R)-5-carboxy-2,3,4,5-tetrahydroxy-pentanoylamino)-butyryl-, 2-[(S)-4-(11-benzyloxycarbonyl-undecanoylamino)-4-carboxy-butyryl-, 2-{(S)-4-carboxy-4-[11-((2S,3R,4R,5R)-2,3,4,5,6-pentahydroxy-hexylcarbamoyl)-undecanoylamino]-butyryl-;

X15 represents Asp,
X16 represents Ser,
X17 represents Arg,
X18 represents Arg,
X20 represents Gln,
X21 represents Asp,
X28 represents Asn,
X29 represents Gly,
X35 represents Ala,
X39 is Ser,
X40 is absent.

A further embodiment relates to a group of compounds, wherein
X2 represents D-Ser,
X3 represents Gln,
X14 represents Lys, wherein the —NH$_2$ side chain group is functionalized, particularly by (S)-4-carboxy-4-hexadecanoylamino-butyryl- or hexadecanoyl-;
X15 represents an amino acid residue selected from Glu or Asp,
X16 represents Ser,
X17 represents Arg,
X18 represents Arg,
X20 represents Gln,
X21 represents Asp,
X28 represents an amino acid residue selected from Asn, Arg, Lys, Aib, Ser, Glu and Asp,
X29 represents an amino acid residue selected from Gly, Ala, D-Ala and Thr,
X35 represents an amino acid residue selected from Ala, Glu, Arg and Lys,
X39 is Ser,
X40 is absent.

A further embodiment relates to a group of compounds, wherein
X2 represents D-Ser,
X3 represents Gln,
X14 represents Lys, wherein the —NH$_2$ side chain group is functionalized, particularly by (S)-4-carboxy-4-hexadecanoylamino-butyryl- or hexadecanoyl-;
X15 represents an amino acid residue selected from Glu and Asp,
X16 represents an amino acid residue selected from Ser and Glu,
X17 represents an amino acid residue selected from Arg, Glu, Lys and Aib,
X18 represents an amino acid residue selected from Arg, Lys and Ala,
X20 represents an amino acid residue selected from Gln, Lys and Aib, X21 represents an amino acid residue selected from Asp and Leu, X28 represents an amino acid residue selected from Ala and Asn, X29 represents Gly, X35 represents Ala, X39 is Ser, X40 is absent.

A further embodiment relates to a group of compounds, wherein

X2 represents D-Ser,

X3 represents Gln,

X14 represents Orn or Dab, wherein the —NH$_2$ side chain group is functionalized, particularly by (S)-4-carboxy-4-hexadecanoylamino-butyryl-;

X15 represents Glu,

X16 represents Ser,

X17 represents Arg,

X18 represents Arg,

X20 represents Gln,

X21 represents Asp,

X28 represents Ala,

X29 represents Gly,

X35 represents Ala,

X39 is Ser,

X40 is absent.

A further embodiment relates to a group of compounds, wherein

X2 represents D-Ser,

X3 represents Gln,

X14 represents Lys, wherein the —NH$_2$ side chain group is functionalized, particularly by (S)-4-carboxy-4-hexadecanoylamino-butyryl- or hexadecanoyl-;

X15 represents an amino acid residue selected from Glu and Asp,

X16 represents Ser,

X17 represents an amino acid residue selected from Arg and Lys,

X18 represents an amino acid residue selected from Arg and Ala,

X20 represents Gln,

X21 represents an amino acid residue selected from Asp and Leu,

X28 represents an amino acid residue selected from Ala and Asn,

X29 represents Gly,

X35 represents Ala,

X39 represents Ser or is absent,

X40 is absent or represents Lys, wherein the —NH$_2$ side chain group is optionally functionalized, particularly by (S)-4-carboxy-4-hexadecanoylamino-butyryl- and R$^2$ is NH$_2$, NH(C$_1$-C$_{18}$) alkyl, which are unsubstituted or monosubstituted by OH or 3-fold-substituted by F, N[(C$_1$-C$_6$) alkyl]$_2$, NH(CH$_2$—CH$_2$—O)$_{1-24}$—(C$_1$-C$_4$) alkyl-COOH, NH-pyrrolidine (N-pyrrolidin-1-yl-amido), NH-benzyl (N-benzyl-amido) or N-morpholine (1-morpholin-4-yl), particularly by NH$_2$, NH—CH$_2$—CH$_3$, NH—(CH$_2$)$_2$—CH$_3$, NH—C(CH$_3$)$_3$, NH—CH$_2$—CF$_3$, NH—(CH$_2$)$_{12}$—OH, NH—(CH$_2$)$_{13}$—CH$_3$, NH—(CH$_2$)$_{14}$—CH$_3$, NH—(CH$_2$)$_{15}$—CH$_3$, NH—(CH$_2$)$_{17}$—CH$_3$, NH(CH$_2$—CH$_2$—O)$_4$—CH$_2$—COOH, NH(CH$_2$—CH$_2$—O)$_{24}$—CH$_2$—COOH, NH—N(CH$_2$)$_4$, NH—CH$_2$—C$_6$H$_5$, N(CH$_2$—CH$_2$)$_2$O.

A further embodiment relates to a group of compounds, wherein

X2 represents an amino acid residue selected from Ser, D-Ser and Aib,

X3 represents an amino acid residue selected from Gln, His, Asn and N$^\alpha$-methylated Gln [Gln (α-NHCH$_3$)], X14 represents Lys, wherein the —NH$_2$ side chain group is functionalized, particularly by (S)-4-carboxy-4-hexadecanoylamino-butyryl- or hexadecanoyl-;

X15 represents an amino acid residue selected from Glu and Asp,

X16 represents an amino acid residue selected from Ser and Lys,

X17 represents an amino acid residue selected from Arg and Glu,

X18 represents an amino acid residue selected from Arg and Ala,

X20 represents an amino acid residue selected from Gln, Arg and Aib,

X21 represents an amino acid residue selected from Asp and Leu,

X28 represents an amino acid residue selected from Ala and Asn,

X29 represents Gly,

X35 represents Ala,

X39 is Ser,

X40 is absent.

A further embodiment relates to a group of compounds of formula (I), wherein

X2 represents an amino acid residue selected from Ser, D-Ser and Aib,

X3 represents an amino acid residue selected from Gln, His and N$^\alpha$-methylated Gln [Gln (α-NHCH$_3$)], X14 represents Lys, wherein the —NH$_2$ side chain group is functionalized, particularly by (S)-4-carboxy-4-hexadecanoylamino-butyryl- or hexadecanoyl-;

X15 represents an amino acid residue selected from Glu and Asp,

X16 represents an amino acid residue selected from Ser and Lys,

X17 represents Arg,

X18 represents an amino acid residue selected from Arg and Ala,

X20 represents an amino acid residue selected from Gln and Aib,

X21 represents an amino acid residue selected from Asp and Leu,

X28 represents an amino acid residue selected from Ala and Asn,

X29 represents Gly,

X35 represents Ala,

X39 is Ser,

X40 is absent.

A further embodiment relates to a group of compounds of formula (I), wherein

X2 represents an amino acid residue selected from D-Ser and Aib,

X3 represents an amino acid residue selected from Gln and His,

X14 represents Lys, wherein the —NH$_2$ side chain group is functionalized, particularly by (S)-4-carboxy-4-hexadecanoylamino-butyryl-, (S)-4-carboxy-4-((S)-4-carboxy hexadecanoylamino-butyrylamino)-butyryl-, or (S)-4-carboxy-4-octadecanoyl-amino-butyryl-;

X15 represents an amino acid residue selected from Glu and Asp,

X16 represents Glu,

X17 represents Glu,
X18 represents Ala,
X20 represents an amino acid residue selected from Arg and Lys,
X21 represents Leu,
X28 represents Ala,
X29 represents Gly,
X35 represents Ala,
X39 is Ser,
X40 is absent.

A still further preferred embodiment relates to a group of compounds wherein
X40 is absent.

A still further preferred embodiment relates to a group of compounds, wherein
the functionalized Lys in position 14 is functionalized at its ε-amino group with —C(O)—R$^5$, and —C(O)—R$^5$ is (S)-4-carboxy-4-hexadecanoyl-amino-butyryl, (S)-4-carboxy-4-octadecanoylamino-butyryl, hexadecanoyl or octadecanoyl.

A still further preferred embodiment relates to a group of compounds wherein
X2 represents an amino acid residue selected from Aib and D-Ser;
X3 represents an amino acid residue selected from Gln and His;
X14 represents Lys, wherein the —NH$_2$ side chain group is functionalized by one of the groups selected from (S)-4-Carboxy-4-hexadecanoylamino-butyryl-, (S)-4-Carboxy-4-octadecanoylamino-butyryl-, (S)-4-Carboxy-4-((S)-4-carboxy-4-hexadecanoylamino-butyrylamino)-butyryl-, (S)-4-Carboxy-4-((S)-4-carboxy-4-octadecanoylamino-butyrylamino)-butyryl-, 3-(3-Octadecanoylamino-propionylamino)-propionyl-, 3-(3-Hexadecanoylamino-propionylamino)-propionyl-, (S)-4-Carboxy-4-henicosanoylamino-butyryl-, 4-Hexadecanoylamino-butyryl- and 4-octadecanoylamino-butyryl-;
X15 represents an amino acid residue selected from Asp and Glu;
X16 represents an amino acid residue selected from Ser and Glu;
X17 represents an amino acid residue selected from Arg, Gln, Lys, Aib and Leu;
X18 represents an amino acid residue selected from Arg and Ala;
X20 represents an amino acid residue selected from Gln, Aib and Lys;
X21 represents an amino acid residue selected from Asp, Glu and Lys;
X28 represents an amino acid residue selected from Asn, Ser, Aib, Ala and Arg;
X29 represents an amino acid residue selected from Gly, Thr, Ala and D-Ala;
X35 represents Ala;
X39 represents Ser and
X40 is absent.

A still further preferred embodiment relates to a group of compounds wherein
X2 represents an amino acid residue selected from Aib and D-Ser;
X3 represents Gln;
X14 represents Lys, wherein the —NH$_2$ side chain group is functionalized by one of the groups selected from (S)-4-carboxy-4-hexadecanoyl-amino-butyryl, (S)-4-carboxy-4-octadecanoylamino-butyryl, hexadecanoyl and octadecanoyl;
X15 represents Glu;
X16 represents Ser;
X17 represents an amino acid residue selected from Arg, Gln and Lys;
X18 represents Ala;
X20 represents Gln;
X21 represents Asp;
X28 represents Ala;
X29 represents Gly;
X35 represents Ala;
X39 represents Ser and
X40 is absent.

A further embodiment relates to a group of compounds, wherein
X2 represents Aib,
X3 represents Gln,
X14 represents Lys, wherein the —NH$_2$ side chain group is functionalized, particularly by (S)-4-Carboxy-4-henicosanoylamino-butyryl- and (S)-4-Carboxy-4-octadecanoylamino-butyryl-;
X15 represents Asp,
X16 represents an amino acid residue selected from Lys and Glu,
X17 represents an amino acid residue selected from Arg and Glu,
X18 represents an amino acid residue selected from Ala and Arg,
X20 represents an amino acid residue selected from Gln and Lys,
X21 represents an amino acid residue selected from Asp and Leu,
X28 represents Ala,
X29 represents an amino acid residue selected from Gly and D-Ala,
X35 represents Ala,
X39 is Ser,
X40 is absent.

In one embodiment, the invention provides a peptidic compound having the formula (I):

$$R^1\text{—}Z\text{—}R^2 \quad (I),$$

wherein Z is a peptide moiety having the formula (IIa)

(IIa)
H-dSer-Q-G-T-F-T-S-D-L-S-K-Q-K(γE-x53)-D-S-K-A-Aib-Q-D-F-I-E-W-L-K-A-G-G-P-S-S-G-A-P-P-S-NH$_2$.

In another embodiment, the invention provides a peptidic compound having the formula (I):

$$R^1\text{—}Z\text{—}R^2 \quad (I),$$

wherein Z is a peptide moiety having the formula (IIb)

(IIb)
H-dSer-Q-G-T-F-T-S-D-L-S-K-Q-K(γE-x53)-D-S-K-A-S-Q-D-F-I-E-W-L-K-A-G-G-P-S-S-G-A-P-P-S-NH$_2$.

In another embodiment, the invention provides a peptidic compound having the formula (I):

$$R^1\text{—}Z\text{—}R^2 \quad (I),$$

wherein Z is a peptide moiety having the formula (IIc)

(IIc)
H-dSer-Q-G-T-F-T-S-D-L-S-K-Q-K(γE-x53)-D-S-K-A-L-Q-D-F-I-E-W-L-K-A-G-G-P-S-S-G-A-P-P-S-NH$_2$.

In another embodiment, the invention provides a peptidic compound having the formula (I):

R¹—Z—R² (I), wherein Z is a peptide moiety having the formula (IId)

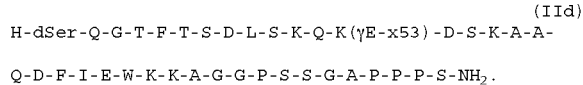

(IId)
H-dSer-Q-G-T-F-T-S-D-L-S-K-Q-K(γE-x53)-D-S-K-A-A-Q-D-F-I-E-W-K-K-A-G-G-P-S-S-G-A-P-P-P-S-NH₂.

Specific examples of peptidic compounds of the invention are the compounds of SEQ ID NO: 4-181, as well as salts and solvates thereof.

Further specific examples of peptidic compounds of the invention are the compounds of SEQ ID NO: 4-181 and 196-223 as well as salts and solvates thereof.

Further specific examples of peptidic compounds of the invention are the compounds of SEQ ID NO: 7, 11-13, 22, 24-31, 34-39, 44-48, 86, 97, 123-124, 130-159, 164, 166, 173-176, as well as salts and solvates thereof.

Further specific examples of peptidic compounds of formula (I) are the compounds of SEQ ID NO: 7, 11-13, 22, 24-31, 34-39, 44-48, 86, 97, 123-124, 130-159, 164, 166, 173-176, 196-223, 226-229 as well as salts and solvates thereof.

In some embodiments, the compound of the invention is selected from the group consisting of SEQ ID NOs.: 25, 31, 133, 148, 153, 155 and 158. In other embodiments, the compound of the invention is selected from the group consisting of SEQ ID NOs.: 209, 210, 211, 212 and 213.

According to one particular embodiment, the compound of the invention is represented by SEQ ID NO.: 97 (see Table 10). In another particular embodiment, the compound of formula (I) is represented by SEQ ID NO.: 24 (see Table 10).

In certain embodiments, i.e. when the compound of formula (I) comprises genetically encoded amino acid residues, the invention further provides a nucleic acid (which may be DNA or RNA) encoding said compound, an expression vector comprising such a nucleic acid, and a host cell containing such a nucleic acid or expression vector.

In a further aspect, the present invention provides a composition comprising a compound of the invention in admixture with a carrier. In preferred embodiments, the composition is a pharmaceutically acceptable composition and the carrier is a pharmaceutically acceptable carrier. The compound of the invention may be in the form of a salt, e.g. a pharmaceutically acceptable salt or a solvate, e.g. a hydrate. In still a further aspect, the present invention provides a composition for use in a method of medical treatment, particularly in human medicine.

In certain embodiments, the nucleic acid or the expression vector may be used as therapeutic agents, e.g. in gene therapy.

The compounds of formula (I) are suitable for therapeutic application without an additionally therapeutically effective agent. In other embodiments, however, the compounds are used together with at least one additional therapeutically active agent, as described in "combination therapy".

The compounds of formula (I) are particularly suitable for the treatment or prevention of diseases or disorders caused by, associated with and/or accompanied by disturbances in carbohydrate and/or lipid metabolism, e.g. for the treatment or prevention of hyperglycemia, type 2 diabetes, impaired glucose tolerance, type 1 diabetes, obesity and metabolic syndrome. Further, the compounds of the invention are particularly suitable for the treatment or prevention of degenerative diseases, particularly neurodegenerative diseases.

The compounds described find use, inter alia, in preventing weight gain or promoting weight loss. By "preventing" is meant inhibiting or reducing when compared to the absence of treatment, and is not necessarily meant to imply complete cessation of a disorder.

The compounds of the invention may cause a decrease in food intake and/or increase in energy expenditure, resulting in the observed effect on body weight.

Independently of their effect on body weight, the compounds of the invention may have a beneficial effect on circulating cholesterol levels, being capable of improving lipid levels, particularly LDL, as well as HDL levels (e.g. increasing HDL/LDL ratio).

Thus, the compounds of the invention can be used for direct or indirect therapy of any condition caused or characterised by excess body weight, such as the treatment and/or prevention of obesity, morbid obesity, obesity linked inflammation, obesity linked gallbladder disease, obesity induced sleep apnea. They may also be used for treatment and prevention of the metabolic syndrome, diabetes, hypertension, atherogenic dyslipidemia, atherosclerosis, arteriosclerosis, coronary heart disease, or stroke. Their effects in these conditions may be as a result of or associated with their effect on body weight, or may be independent thereof.

Preferred medical uses include delaying or preventing disease progression in type 2 diabetes, treating metabolic syndrome, treating obesity or preventing overweight, for decreasing food intake, increase energy expenditure, reducing body weight, delaying the progression from impaired glucose tolerance (IGT) to type 2 diabetes; delaying the progression from type 2 diabetes to insulin-requiring diabetes; regulating appetite; inducing satiety; preventing weight regain after successful weight loss; treating a disease or state related to overweight or obesity; treating bulimia; treating binge eating; treating atherosclerosis, hypertension, type 2 diabetes, IGT, dyslipidemia, coronary heart disease, hepatic steatosis, treatment of beta-blocker poisoning, use for inhibition of the motility of the gastrointestinal tract, useful in connection with investigations of the gastrointestinal tract using techniques such as X-ray, CT- and NMR-scanning.

Further preferred medical uses include treatment or prevention of degenerative disorders, particularly neurodegenerative disorders such as Alzheimer's disease, Parkinson's disease, Huntington's disease, ataxia, e.g spinocerebellar ataxia, Kennedy disease, myotonic dystrophy, Lewy body dementia, multi-systemic atrophy, amyotrophic lateral sclerosis, primary lateral sclerosis, spinal muscular atrophy, prion-associated diseases, e.g. Creutzfeldt-Jacob disease, multiple sclerosis, telangiectasia, Batten disease, corticobasal degeneration, subacute combined degeneration of spinal cord, Tabes dorsalis, Tay-Sachs disease, toxic encephalopathy, infantile Refsum disease, Refsum disease, neuroacanthocytosis, Niemann-Pick disease, Lyme disease, Machado-Joseph disease, Sandhoff disease, Shy-Drager syndrome, wobbly hedgehog syndrome, proteopathy, cerebral β-amyloid angiopathy, retinal ganglion cell degeneration in glaucoma, synucleinopathies, tauopathies, frontotemporal lobar degeneration (FTLD), dementia, cadasil syndrome, hereditary cerebral hemorrhage with amyloidosis, Alexander disease, seipinopathies, familial amyloidotic neuropathy, senile systemic amyloidosis, serpinopathies, AL (light chain) amyloidosis (primary systemic amyloidosis), AH (heavy chain) amyloidosis, AA (secondary) amyloidosis, aortic medial amyloidosis, ApoAI amyloidosis, ApoAII amyloidosis, ApoAIV amyloidosis, familial amyloidosis of the Finnish type (FAF), Lysozyme amyloidosis, Fibrinogen amyloidosis, Dialysis amyloidosis, Inclusion body myositis/myopathy, Cataracts, Retinitis pigmentosa with rhodopsin mutations, medullary thyroid carcinoma, cardiac atrial amyloidosis, pituitary prolactinoma, Hereditary lattice corneal dystrophy, Cutaneous lichen amyloidosis, Mallory bodies, corneal lactoferrin amyloidosis, pulmonary alveolar proteinosis, odontogenic (Pindborg) tumor amyloid, cystic fibrosis, sickle cell disease or critical illness myopathy (CIM).

DETAILED DESCRIPTION OF THE INVENTION

Definitions

The amino acid sequences of the present invention contain the conventional one letter and three letter codes for naturally occurring amino acids, as well as generally accepted three letter codes for other amino acids, such as Aib (α-aminoisobutyric acid), Orn (ornithin), Dab (2,4-diamino butyric acid), Dap (2,3-diamino propionic acid), Nle (norleucine), GABA (γ-aminobutyric acid) or Ahx (ε-aminohexanoic acid).

The term "native exendin-4" refers to native exendin-4 having the sequence HGEGTFTSDLSKQMEEEAVR-LFIEWLKNGGPSSGAPPPS-NH$_2$ (SEQ ID NO: 1).

The invention provides peptidic compounds as defined above.

The peptidic compounds of the present invention comprise a linear backbone of amino carboxylic acids linked by peptide, i.e. carboxamide bonds. Preferably, the amino carboxylic acids are α-amino carboxylic acids and more preferably L-α-amino carboxylic acids, unless indicated otherwise. The peptidic compounds preferably comprise a backbone sequence of 39-40 amino carboxylic acids.

The peptidic compounds may be functionalized (covalently linked) with chemical moieties at their N-terminus, C-terminus and at least one side chain. The N-terminus of the peptidic compound may be unmodified, i.e. an NH$_2$ group or a mono- or bisfunctionalized NH$_2$ group.

At the C-terminus, the peptidic compounds may be unmodified, i.e. have a OH group or be modified, e.g. with functionalized OH group or an NH$_2$ group or a monofunctionalized or bisfunctionalized NH$_2$ group as described above (see R)

The term "alkyl", as used herein, refers to saturated, monovalent hydrocarbon radicals. The alkyl groups can be linear, i.e. straight-chain, or branched.

The term "alkanediyl" or "alkylene", as used herein, refers to saturated, divalent hydrocarbon radicals. As far as applicable, the preceding explanations regarding alkyl groups apply correspondingly to alkanediyl groups, which thus can likewise be linear and branched. Examples of divalent alkyl groups are —CH$_2$— (=methylene), —CH$_2$—CH$_2$—, —CH$_2$—CH$_2$—CH$_2$—, —CH$_2$—CH$_2$—CH$_2$—CH$_2$—, —CH(CH$_3$)—, —C(CH$_3$)$_2$—, —CH(CH$_3$)—CH$_2$—, —CH$_2$—CH(CH$_3$)—, —C(CH$_3$)$_2$—CH$_2$—, —CH$_2$—C(CH$_3$)$_2$—.

The term "cycloalkyl", as used herein, unless otherwise indicated, refers to a monovalent radical of a saturated or partially saturated hydrocarbon ring system, which can be monocyclic. Examples of cycloalkyl groups are cyclopropyl, cyclobutyl, cyclopentyl, cyclohexyl, cycloheptyl and cyclooctyl.

The term "heterocycloalkyl" or "heterocyclyl", as used herein unless otherwise indicated, refers to a cycloalkyl as defined above, in which 1, 2 or 3 carbon atoms are replaced by nitrogen, oxygen or sulfur atoms, provided that the heterocycloalkyl system is stable and suitable as a subgroup for the desired purpose of the compound of the formula (I) such as use as a drug substance. Depending on the definition of the respective heterocyclic group, in one embodiment of the invention the number of ring heteroatoms which can be present in a heterocyclic group, independently of the number of ring heteroatoms in any other heterocyclic group, is 1, 2, 3 or 4, in another embodiment 1, 2 or 3, in another embodiment 1 or 2, in another embodiment 2, in another embodiment 1, wherein the ring heteroatoms can be identical or different. The heterocycloalkyl group can be attached by any ring carbon atom or saturated ring nitrogen atom.

Halogen is fluorine, chlorine, bromine or iodine.

The peptidic compounds of the present invention may have unmodified side chains or carry at least one modification at one of the side chains.

For the avoidance of doubt, in the definitions provided herein, it is generally intended that the sequence of the peptidic moiety (II) differs from native exendin-4 at least at one of those positions which are stated to allow variation. Amino acids within the peptide moiety (II) can be considered to be numbered consecutively from 0 to 40 in the conventional N-terminal to C-terminal direction. Reference to a "position" within peptidic moiety (II) should be constructed accordingly, as should reference to positions within native exendin-4 and other molecules.

The amino acid residues at position 14 and optionally at position 40, having a side chain with an —NH$_2$ group, e.g. Lys, Orn, Dab or Dap are conjugated to a functional group, e.g. acyl groups. Thus, one or more selected amino acids of the peptides in the present invention may carry a covalent attachment at their side chains. In some cases those attachments may be lipophilic. These lipophilic side chain attachments have the potential to reduce in vivo clearance of the peptides thus increasing their in vivo half-lives.

The lipophilic attachment may consist of a lipophilic moiety which can be a branched or unbranched, aliphatic or unsaturated acyclic moiety and/or a cyclic moiety selected from one or several aliphatic or unsaturated homocycles or heterocycles, aromatic condensed or non-condensed homocycles or heterocycles, ether linkages, unsaturated bonds and substituents, e.g. hydroxy and/or carboxy groups. The lipophilic moiety may be attached to the peptide either by alkylation, reductive amination or by an amide bond or a sulfonamide bond in case of amino acids carrying an amino group at their side chain, an ester bond in case of amino acids carrying a hydroxy group at their side chain or thioether or thioester linkages in case of amino acids carrying a thiol group at their side chain or it may be attached to a modified side chain of an amino acid thus allowing the introduction of a lipophilic moiety by click-chemistry or Michael-addition.

Nonlimiting examples of lipophilic moieties that can be attached to amino acid side chains include fatty acids, e.g. $C_{8-30}$ fatty acids such as palmitic acid, myristic acid, stearic acid and oleic acid, and/or cyclic groups as described above or derivatives thereof.

There might be one or several linkers between the amino acid of the peptide and the lipophilic attachment. Nonlimiting examples of those linkers are β-alanine, γ-glutamic acid, γ-aminobutyric acid and/or ε-aminohexanoic acid or dipeptides, such as β-Ala-β-Ala and/or γ-Glu-γ-Glu in all their stereo-isomer forms (S and R enantiomers).

Thus, one nonlimiting example of a side chain attachment is palmitic acid which is covalently linked to the α-amino group of glutamic acid forming an amide bond. The γ-carboxy group of this substituted glutamic acid can form an amide bond with the side chain amino group of a lysine within the peptide.

In a further aspect, the present invention provides a composition comprising a compound of the invention as described herein, or a salt or solvate thereof, in admixture with a carrier.

The invention also provides the use of a compound of the present invention for use as a medicament, particularly for the treatment of a condition as described below.

The invention also provides a composition wherein the composition is a pharmaceutically acceptable composition, and the carrier is a pharmaceutically acceptable carrier.

Peptide Synthesis

The skilled person is aware of a variety of different methods to prepare peptides that are described in this invention. These methods include but are not limited to synthetic approaches and recombinant gene expression. Thus, one way of preparing these peptides is the synthesis in solution or on a solid support and subsequent isolation and purification. A different way of preparing the peptides is gene expression in a host cell in which a DNA sequence encoding the peptide has been introduced. Alternatively, the gene expression can be achieved without utilizing a cell system. The methods described above may also be combined in any way.

A preferred way to prepare the peptides of the present invention is solid phase synthesis on a suitable resin. Solid phase peptide synthesis is a well established methodology (see for example: Stewart and Young, Solid Phase Peptide Synthesis, Pierce Chemical Co., Rockford, Ill., 1984; E. Atherton and R. C. Sheppard, Solid Phase Peptide Synthesis. A Practical Approach, Oxford-IRL Press, New York, 1989). Solid phase synthesis is initiated by attaching an N-terminally protected amino acid with its carboxy terminus to an inert solid support carrying a cleavable linker. This solid support can be any polymer that allows coupling of the initial amino acid, e.g. a trityl resin, a chlorotrityl resin, a Wang resin or a Rink resin in which the linkage of the carboxy group (or carboxamide for Rink resin) to the resin is sensitive to acid (when Fmoc strategy is used). The polymer support must be stable under the conditions used to deprotect the α-amino group during the peptide synthesis.

After the first amino acid has been coupled to the solid support, the α-amino protecting group of this amino acid is removed. The remaining protected amino acids are then coupled one after the other in the order represented by the peptide sequence using appropriate amide coupling reagents, for example BOP (benzotriazol-1-yl-oxy-tris-(dimethylamino)-phosphonium), HBTU (2-(1H-benzotriazol-1-yl)-1,1,3,3-tetramethyl-uronium), HATU (O-(7-azabenztriazol-1-yl-oxy-tris-(dimethylamino)-phosphonium) or DIC (N,N'-diisopropylcarbodiimide)/HOBt (1-hydroxybenzotriazol), wherein BOP, HBTU and HATU are used with tertiary amine bases. Alternatively, the liberated N-terminus can be functionalized with groups other than amino acids, for example carboxylic acids, etc.

Usually, reactive side chain groups of the amino acids are protected with suitable blocking groups. These protecting groups are removed after the desired peptides have been assembled. They are removed concomitantly with the cleavage of the desired product from the resin under the same conditions. Protecting groups and the procedures to introduce protecting groups can be found in Protective Groups in Organic Synthesis, 3d ed., Greene, T. W. and Wuts, P. G. M., Wiley & Sons (New York: 1999).

In some cases it might be desirable to have side chain protecting groups that can selectively be removed while other side chain protecting groups remain intact. In this case the liberated functionality can be selectively functionalized. For example, a lysine may be protected with an ivDde protecting group (S. R. Chhabra et al., Tetrahedron Lett. 39, (1998), 1603) which is labile to a very nucleophilic base, for example 4% hydrazine in DMF (dimethyl formamide). Thus, if the N-terminal amino group and all side chain functionalities are protected with acid labile protecting groups, the ivDde ([1-(4,4-dimethyl-2,6-dioxocyclohex-1-ylidene)-3-methylbutyl) group can be selectively removed using 4% hydrazine in DMF and the corresponding free amino group can then be further modified, e.g. by acylation. The lysine can alternatively be coupled to a protected amino acid and the amino group of this amino acid can then be deprotected resulting in another free amino group which can be acylated or attached to further amino acids.

Finally the peptide is cleaved from the resin. This can be achieved by using King's cocktail (D. S. King, C. G. Fields, G. B. Fields, Int. J. Peptide Protein Res. 36, 1990, 255-266). The raw material can then be purified by chromatography, e.g. preparative RP-HPLC, if necessary.

Potency

As used herein, the term "potency" or "in vitro potency" is a measure for the ability of a compound to activate the receptors for GLP-1 or glucagon in a cell-based assay. Numerically, it is expressed as the "EC50 value", which is the effective concentration of a compound that induces a half maximal increase of response (e.g. formation of intracellular cAMP) in a dose-response experiment.

Therapeutic Uses

According to one aspect, the compounds of the invention are for use in medicine, particularly human medicine.

The compounds of the invention are agonists for the receptors for GLP-1 and for glucagon (e.g. "dual agonists") and may provide an attractive option for targeting the metabolic syndrome by allowing simultaneous treatment of obesity and diabetes.

Metabolic syndrome is a combination of medical disorders that, when occurring together, increase the risk of developing type 2 diabetes, as well as atherosclerotic vascular disease, e.g. heart disease and stroke. Defining medical parameters for the metabolic syndrome include diabetes mellitus, impaired glucose tolerance, raised fasting glucose, insulin resistance, urinary albumin secretion, central obesity, hypertension, elevated triglycerides, elevated LDL cholesterol and reduced HDL cholesterol.

Obesity is a medical condition in which excess body fat has accumulated to the extent that it may have an adverse effect on health and life expectancy and due to its increasing prevalence in adults and children it has become one of the leading preventable causes of death in modern world. It increases the likelihood of various other diseases, including heart disease, type 2 diabetes, obstructive sleep apnoe, certain types of cancer, as well as osteoarthritis, and it is most commonly caused by a combination of excess food intake, reduced energy expenditure, as well as genetic susceptibility.

Diabetes mellitus, often simply called diabetes, is a group of metabolic diseases in which a person has high blood sugar levels, either because the body does not produce enough insulin, or because cells do not respond to the insulin that is produced. The most common types of diabetes are: (1) type 1 diabetes, where the body fails to produce insulin; (2) type 2 diabetes, where the body fails to use insulin properly, combined with an increase in insulin deficiency over time, and (3) gestational diabetes, where women develop diabetes due to their pregnancy. All forms of diabetes increase the risk of long-term complications, which typically develop after many years. Most of these long-term complications are based on damage to blood vessels and can be divided into the two categories "macrovascular" disease, arising from atherosclerosis of larger blood vessels and "microvascular" disease, arising from damage of small blood vessels. Examples for macrovascular disease conditions are ischemic heart disease, myocardial infarction, stroke and peripheral vascular disease. Examples for microvascular diseases are diabetic retinopathy, diabetic nephropathy, as well as diabetic neuropathy.

The receptors for GLP-1 and glucagon are both members of the family B of G-protein coupled receptors. They are highly related to each other and share not only a significant level of sequence identity, but have also similar mechanisms of ligand recognition and intracellular signaling pathways.

Similarly, the peptides GLP-1 and glucagon are homologous to each other, with similar length and regions of high sequence identity. Both are produced from a common precursor, preproglucagon, which is differentially processed in a tissue-specific manner to yield e.g. GLP-1 in intestinal endocrine cells and glucagon in alpha cells of pancreatic islets.

The incretin hormone GLP-1 is secreted by intestinal endocrine cells in response to food and enhances meal-stimulated insulin secretion. Evidence suggests that GLP-1 secretion is reduced in subjects with impaired glucose tolerance or type 2 diabetes, whereas responsiveness to GLP-1 is still preserved in these patients. Thus, targeting of the GLP-1 receptor with suitable agonists offers an attractive approach for treatment of metabolic disorders, including diabetes. The receptor for GLP-1 is distributed widely, being found mainly in pancreatic islets, brain, heart, kidney and the gastrointestinal tract. In the pancreas, GLP-1 acts in a strictly glucose-dependent manner by increasing secretion of insulin from beta cells. This glucose-dependency shows that activation of GLP-1 receptors is unlikely to cause hypoglycemia.

At the beta cell level, GLP-1 has been shown to promote glucose sensitivity, neogenesis, proliferation, transcription of proinsulin and hypertrophy, as well as antiapoptosis. Other relevant effects of GLP-1 beyond the pancreas include delayed gastric emptying, increased satiety, decreased food intake, reduction of body weight, as well as neuroprotective and cardioprotective effects. In patients with type 2 diabetes, such extrapancreatic effects could be particularly important considering the high rates of comorbidities like obesity and cardiovascular disease.

Glucagon is a 29-amino acid peptide hormone that is produced by pancreatic alpha cells and released into the bloodstream when circulating glucose is low. An important physiological role of glucagon is to stimulate glucose output in the liver, which is a process providing the major counterregulatory mechanism for insulin in maintaining glucose homeostasis in vivo.

Glucagon receptors are however also expressed in extra-hepatic tissues such as kidney, heart, adipocytes, lymphoblasts, brain, retina, adrenal gland and gastrointestinal tract, suggesting a broader physiological role beyond glucose homeostasis. Accordingly, recent studies have reported that glucagon has therapeutically positive effects on energy management, including stimulation of energy expenditure and thermogenesis, accompanied by reduction of food intake and body weight loss. Altogether, stimulation of glucagon receptors might be useful in the treatment of obesity and the metabolic syndrome.

Oxyntomodulin is a 37-amino acid peptide hormone consisting of glucagon with an eight amino acids encompassing C-terminal extension. Like GLP-1 and glucagon, it is preformed in preproglucagon and cleaved and secreted in a tissue-specific manner by endocrinal cells of the small bowel. Oxyntomodulin is known to stimulate both, the receptors for GLP-1 and glucagon and is therefore the prototype of a dual agonist.

As GLP-1 is known for its anti-diabetic effects, GLP-1 and glucagon are both known for their food intake-suppressing effects and glucagon is also a mediator of additional energy expenditure, it is conceivable that a combination of the activities of the two hormones in one molecule can yield a powerful medication for treatment of the metabolic syndrome and in particular its components diabetes and obesity.

Accordingly, the compounds of the invention may be used for treatment of glucose intolerance, insulin resistance, pre-diabetes, increased fasting glucose, type 2 diabetes, hypertension, dyslipidemia, arteriosclerosis, coronary heart disease, peripheral artery disease, stroke or any combination of these individual disease components.

In addition, they may be used for control of appetite, feeding and calorie intake, increase of energy expenditure, prevention of weight gain, promotion of weight loss, reduction of excess body weight and altogether treatment of obesity, including morbid obesity.

Further disease states and health conditions which could be treated with the compounds of the invention are obesity-linked inflammation, obesity-linked gallbladder disease and obesity-induced sleep apnea.

Although all these conditions could be associated directly or indirectly with obesity, the effects of the compounds of the invention may be mediated in whole or in part via an effect on body weight, or independent thereof.

Further, diseases to be treated are neurodegenerative diseases such as Alzheimer's disease or Parkinson's disease, or other degenerative diseases as described above.

Pharmaceutical Compositions

The term "pharmaceutical composition" indicates a mixture containing ingredients that are compatible when mixed and which may be administered. A pharmaceutical composition may include one or more medicinal drugs. Additionally, the pharmaceutical composition may include carriers, buffers, acidifying agents, alkalizing agents, solvents, adjuvants, tonicity adjusters, emollients, expanders, preservatives, physical and chemical stabilizers e.g. surfactants, antioxidants and other components, whether these are considered active or inactive ingredients. Guidance for the skilled in preparing pharmaceutical compositions may be found, for example, in Remington: The Science and Practice of Pharmacy, (20th ed.) ed. A. R. Gennaro A. R., 2000, Lippencott Williams & Wilkins and in R. C. Rowe et al (Ed), Handbook of Pharmaceutical Excipients, PhP, May 2013 update.

The exendin-4 peptide derivatives of the present invention, or salts thereof, are administered in conjunction with an acceptable pharmaceutical carrier, diluent, or excipient as part of a pharmaceutical composition. A "pharmaceutically acceptable carrier" is a carrier which is physiologically acceptable (e.g. physiologically acceptable pH) while retaining the therapeutic properties of the substance with which it is administered. Standard acceptable pharmaceutical carriers and their formulations are known to one skilled in the art and described, for example, in Remington: The Science and Practice of Pharmacy, (20th ed.) ed. A. R. Gennaro A. R., 2000, Lippencott Williams & Wilkins and in R. C. Rowe et al (Ed), Handbook of Pharmaceutical excipients, PhP, May 2013 update. One exemplary pharmaceutically acceptable carrier is physiological saline solution.

In one embodiment carriers are selected from the group of buffers (e.g. citrate/citric acid), acidifying agents (e.g. hydrochloric acid), alkalizing agents (e.g. sodium hydroxide), preservatives (e.g. phenol), co-solvents (e.g. polyethylene glycol 400), tonicity adjusters (e.g. mannitol), stabilizers (e.g. surfactant, antioxidants, amino acids).

Concentrations used are in a range that is physiologically acceptable.

Acceptable pharmaceutical carriers or diluents include those used in formulations suitable for oral, rectal, nasal or parenteral (including subcutaneous, intramuscular, intravenous, intradermal, and transdermal) administration. The compounds of the present invention will typically be administered parenterally.

The term "pharmaceutically acceptable salt" means salts of the compounds of the invention which are safe and effective for use in mammals. Pharmaceutically acceptable salts may include, but are not limited to, acid addition salts and basic salts. Examples of acid addition salts include chloride, sulfate, hydrogen sulfate, (hydrogen) phosphate, acetate, citrate, tosylate or mesylate salts. Examples of basic salts include salts with inorganic cations, e.g. alkaline or alkaline earth metal salts such as sodium, potassium, magnesium or calcium salts and salts with organic cations such as amine salts. Further examples of pharmaceutically acceptable salts are described in Remington: The Science and Practice of Pharmacy, (20th ed.) ed. A. R. Gennaro A. R., 2000, Lippencott Williams & Wilkins or in Handbook of Pharmaceutical Salts, Properties, Selection and Use, e.d. P. H. Stahl, C. G. Wermuth, 2002, jointly published by Verlag Helvetica Chimica Acta, Zurich, Switzerland, and Wiley-VCH, Weinheim, Germany.

The term "solvate" means complexes of the compounds of the invention or salts thereof with solvent molecules, e.g. organic solvent molecules and/or water.

In the pharmaceutical composition, the exendin-4 derivative can be in monomeric or oligomeric form.

The term "therapeutically effective amount" of a compound refers to a nontoxic but sufficient amount of the compound to provide the desired effect. The amount of a compound of the formula I necessary to achieve the desired biological effect depends on a number of factors, for example the specific compound chosen, the intended use, the mode of administration and the clinical condition of the patient. An appropriate "effective" amount in any individual case may be determined by one of ordinary skill in the art using routine experimentation For example the "therapeutically effective amount" of a compound of the formula (I) is about 0.01 to 50 mg/dose, preferably 0.1 to 10 mg/dose.

Pharmaceutical compositions of the invention are those suitable for parenteral (for example subcutaneous, intramuscular, intradermal or intravenous), oral, rectal, topical and peroral (for example sublingual) administration, although the most suitable mode of administration depends in each individual case on the nature and severity of the condition to be treated and on the nature of the compound of formula I used in each case.

Suitable pharmaceutical compositions may be in the form of separate units, for example capsules, tablets and powders in vials or ampoules, each of which contains a defined amount of the compound; as powders or granules; as solution or suspension in an aqueous or nonaqueous liquid; or as an oil-in-water or water-in-oil emulsion. It may be provided in single or multiple dose injectable form, for example in the form of a pen. The compositions may, as already mentioned, be prepared by any suitable pharmaceutical method which includes a step in which the active ingredient and the carrier (which may consist of one or more additional ingredients) are brought into contact.

In certain embodiments the pharmaceutical composition may be provided together with a device for application, for example together with a syringe, an injection pen or an autoinjector. Such devices may be provided separate from a pharmaceutical composition or prefilled with the pharmaceutical composition.

Combination Therapy

The compounds of the present invention, dual agonists for the GLP-1 and glucagon receptors, can be widely combined with other pharmacologically active compounds, such as all drugs mentioned in the Rote Liste 2012 and/or the Rote Liste 2013, e.g. with all antidiabetics mentioned in the Rote Liste 2012, chapter 12, and/or the Rote Liste 2013, chapter 12, all weight-reducing agents or appetite suppressants mentioned in the Rote Liste 2012, chapter 1, and/or the Rote Liste 2013, chapter 1, all lipid-lowering agents mentioned in the Rote Liste 2012, chapter 58, and/or the Rote Liste 2013, chapter 58, all antihypertensives and nephroprotectives, mentioned in the Rote Liste 2012 and/or the Rote Liste 2013, or all diuretics mentioned in the Rote Liste 2012, chapter 36, and/or the Rote Liste 2013, chapter 36.

The active ingredient combinations can be used especially for a synergistic improvement in action. They can be applied either by separate administration of the active ingredients to the patient or in the form of combination products in which a plurality of active ingredients are present in one pharmaceutical preparation. When the active ingredients are administered by separate administration of the active ingredients, this can be done simultaneously or successively.

Most of the active ingredients mentioned hereinafter are disclosed in the USP Dictionary of USAN and International Drug Names, US Pharmacopeia, Rockville 2011.

Other active substances which are suitable for such combinations include in particular those which for example potentiate the therapeutic effect of one or more active substances with respect to one of the indications mentioned and/or which allow the dosage of one or more active substances to be reduced.

Therapeutic agents which are suitable for combinations include, for example, antidiabetic agents such as:

Insulin and Insulin derivatives, for example: Glargine/Lantus®, 270-330 U/mL of insulin glargine (EP 2387989 A), 300 U/mL of insulin glargine (EP 2387989 A), Glulisin/Apidra®, Detemir/Levemir®, Lispro/Humalog®/Liprolog®, Degludec/DegludecPlus, Aspart, basal insulin and analogues (e.g. LY-2605541, LY2963016, NN1436), PEGylated insulin Lispro, Humulin®, Linjeta, SuliXen®, NN1045, Insulin plus Symlin, PE0139, fast-acting and short-acting insulins (e.g. Linjeta, PH20, NN1218, HinsBet), (APC-002)hydrogel, oral, inhalable, transdermal and sublingual insulins (e.g. Exubera®, Nasulin®, Afrezza, Tregopil, TPM 02, Capsulin, Oral-lyn®, Cobalamin® oral insulin, ORMD-0801, NN1953, NN1954, NN1956, VIAtab, Oshadi oral insulin). Additionally included are also those insulin derivatives which are bonded to albumin or another protein by a bifunctional linker.

GLP-1, GLP-1 analogues and GLP-1 receptor agonists, for example: Lixisenatide/AVE0010/ZP10/Lyxumia, Exenatide/Exendin-4/Byetta/Bydureon/ITCA 650/AC-2993, Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

DPP-4 inhibitors, for example: Alogliptin/Nesina, Trajenta/Linagliptin/BI-1356/Ondero/Trajenta/Tradjenta/Trayenta/Tradzenta, Saxagliptin/Onglyza, Sitagliptin/Januvia/Xelevia/Tesave/Janumet/Velmetia, Galvus/Vildagliptin, Anagliptin, Gemigliptin, Teneligliptin, Melogliptin, Trelagliptin, DA-1229, Omarigliptin/MK-3102, KM-223, Evogliptin, ARI-2243, PBL-1427, Pinoxacin.

SGLT2 inhibitors, for example: Invokana/Canaglifozin, Forxiga/Dapagliflozin, Remoglifozin, Sergliflozin, Empagliflozin, Ipragliflozin, Tofogliflozin, Luseogliflozin, LX-4211, Ertuglifozin/PF-04971729, RO-4998452, EGT-0001442, KGA-3235/DSP-3235, LIK066, SBM-TFC-039, Biguanides (e.g. Metformin, Buformin, Phenformin), Thiazolidinediones (e.g. Pioglitazone, Rivoglitazone, Rosiglitazone, Troglitazone), dual PPAR agonists (e.g. Aleglitazar, Muraglitazar, Tesaglitazar), Sulfonylureas (e.g. Tolbutamide, Glibenclamide, Glimepiride/Amaryl, Glipizide), Meglitinides (e.g. Nateglinide, Repaglinide, Mitiglinide), Alpha-glucosidase inhibitors (e.g. Acarbose, Miglitol, Voglibose), Amylin and Amylin analogues (e.g. Pramlintide, Symlin).

GPR119 agonists (e.g. GSK-263A, PSN-821, MBX-2982, APD-597, ZYG-19, DS-8500), GPR40 agonists (e.g. Fasiglifam/TAK-875, TUG-424, P-1736, JTT-851, GW9508).

Other suitable combination partners are: Cycloset, inhibitors of 11-beta-HSD (e.g. LY2523199, BMS770767, RG-4929, BMS816336, AZD-8329, HSD-016, BI-135585), activators of glucokinase (e.g. TTP-399, AMG-151, TAK-329, GKM-001), inhibitors of DGAT (e.g. LCQ-908), inhibitors of protein tyrosinephosphatase 1 (e.g. Trodusquemine), inhibitors of glucose-6-phosphatase, inhibitors of fructose-1,6-bisphosphatase, inhibitors of glycogen phosphorylase, inhibitors of phosphoenol pyruvate carboxykinase, inhibitors of glycogen synthase kinase, inhibitors of pyruvate dehydrokinase, alpha2-antagonists, CCR-2 antagonists, SGLT-1 inhibitors (e.g. LX-2761).

One or more lipid lowering agents are also suitable as combination partners, such as for example: HMG-CoA-reductase inhibitors (e.g. Simvastatin, Atorvastatin), fibrates (e.g. Bezafibrate, Fenofibrate), nicotinic acid and the derivatives thereof (e.g. Niacin), PPAR-(alpha, gamma or alpha/gamma) agonists or modulators (e.g. Aleglitazar), PPAR-delta agonists, ACAT inhibitors (e.g. Avasimibe), cholesterol absorption inhibitors (e.g. Ezetimibe), Bile acid-binding substances (e.g. Cholestyramine), ileal bile acid transport inhibitors, MTP inhibitors, or modulators of PCSK9.

HDL-raising compounds such as: CETP inhibitors (e.g. Torcetrapib, Anacetrapid, Dalcetrapid, Evacetrapid, JTT-302, DRL-17822, TA-8995) or ABC1 regulators.

Other suitable combination partners are one or more active substances for the treatment of obesity, such as for example: Sibutramine, Tesofensine, Orlistat, antagonists of the cannabinoid-1 receptor, MCH-1 receptor antagonists, MC4 receptor agonists, NPY5 or NPY2 antagonists (e.g. Velneperit), beta-3-agonists, leptin or leptin mimetics, agonists of the 5HT2c receptor (e.g. Lorcaserin), or the combinations of bupropione/naltrexone, bupropione/zonisamide, bupropione/phentermine or pramlintide/metreleptin.

Other suitable combination partners are:

Further gastrointestinal peptides such as Peptide YY 3-36 (PYY3-36) or analogues thereof, pancreatic polypeptide (PP) or analogues thereof.

Glucagon receptor agonists or antagonists, GIP receptor agonists or antagonists, ghrelin antagonists or inverse agonists, Xenin and analogues thereof.

Moreover, combinations with drugs for influencing high blood pressure, chronic heart failure or atherosclerosis, such as e.g.: Angiotensin II receptor antagonists (e.g. telmisartan, candesartan, valsartan, losartan, eprosartan, irbesartan, olmesartan, tasosartan, azilsartan), ACE inhibitors, ECE inhibitors, diuretics, beta-blockers, calcium antagonists, centrally acting hypertensives, antagonists of the alpha-2-adrenergic receptor, inhibitors of neutral endopeptidase, thrombocyte aggregation inhibitors and others or combinations thereof are suitable.

In another aspect, this invention relates to the use of a compound according to the invention or a physiologically acceptable salt thereof combined with at least one of the active substances described above as a combination partner, for preparing a medicament which is suitable for the treatment or prevention of diseases or conditions which can be affected by binding to the receptors for GLP-1 and glucagon and by modulating their activity. This is preferably a disease in the context of the metabolic syndrome, particularly one of the diseases or conditions listed above, most particularly diabetes or obesity or complications thereof.

The use of the compounds according to the invention, or a physiologically acceptable salt thereof, in combination with one or more active substances may take place simultaneously, separately or sequentially.

The use of the compound according to the invention, or a physiologically acceptable salt thereof, in combination with another active substance may take place simultaneously or at staggered times, but particularly within a short space of time. If they are administered simultaneously, the two active substances are given to the patient together; if they are used at staggered times, the two active substances are given to the patient within a period of less than or equal to 12 hours, but particularly less than or equal to 6 hours.

Consequently, in another aspect, this invention relates to a medicament which comprises a compound according to the invention or a physiologically acceptable salt of such a compound and at least one of the active substances described above as combination partners, optionally together with one or more inert carriers and/or diluents.

The compound according to the invention, or physiologically acceptable salt or solvate thereof, and the additional active substance to be combined therewith may both be present together in one formulation, for example a tablet or capsule, or separately in two identical or different formulations, for example as so-called kit-of-parts.

LEGENDS TO THE FIGURES

FIG. 1. Effect of s.c. administration of compound SEQ ID NO: 97 and comparators on gastric emptying and intestinal passage in female NMRI-mice. Data are mean+SEM. "*" indicates statistical significance versus vehicle, "#" versus comparators, respectively.

a) Effect of SEQ ID NO: 97 and Liraglutide (all 0.02 mg/kg, s.c.) on remaining gastric contents (as indicator for gastric emptying)

b) Effect of SEQ ID NO: 97 and Liraglutide all 0.02 mg/kg, s.c., on small intestinal motility c) Effect of SEQ ID NO: 97, at 0.02 and 0.002 mg/kg, s.c., on remaining gastric contents (as indicator for gastric emptying)

d) Effect of SEQ ID NO: 97, at 0.02 and 0.002 mg/kg, s.c., on small intestinal motility FIG. 2. Effect of SEQ ID NO: 97, 0.1 and 0.01 mg/kg, s.c., on 22-hours food intake in female NMRI-mice. Data are mean+SEM. *p<0.05.

Figure 3:
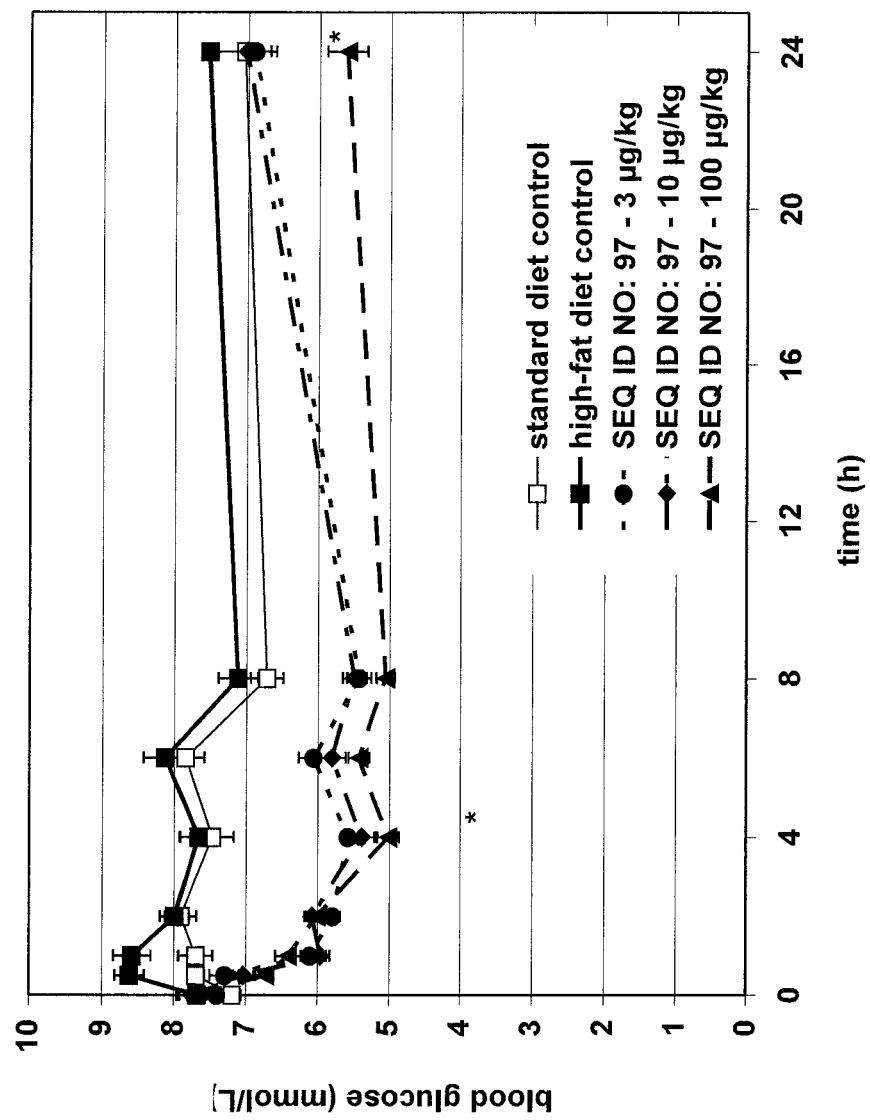

FIG. 3. Acute effect of s.c. administration of compound SEQ ID NO: 97 on blood glucose in female diet-induced obese C57BL/6NCrl mice (9 months on high-fat diet). Data are mean+SEM. *p<0.05.

Figure 4:
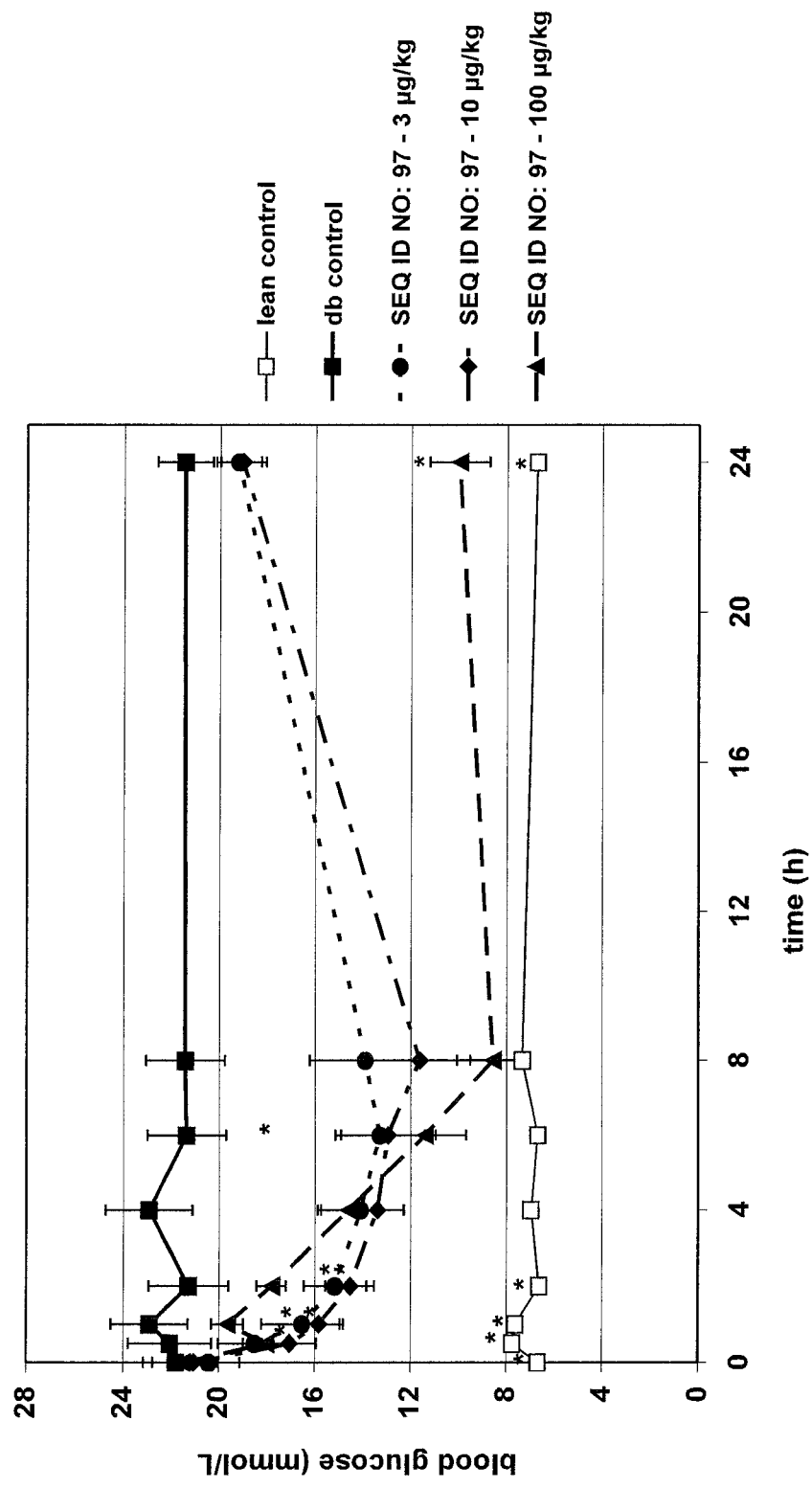

FIG. 4. Acute effect of s.c. administration of compound SEQ ID NO: 97 on blood glucose in female leptin-receptor deficient diabetic db/db mice. Data are mean+SEM. *p<0.05.

Figure 5:
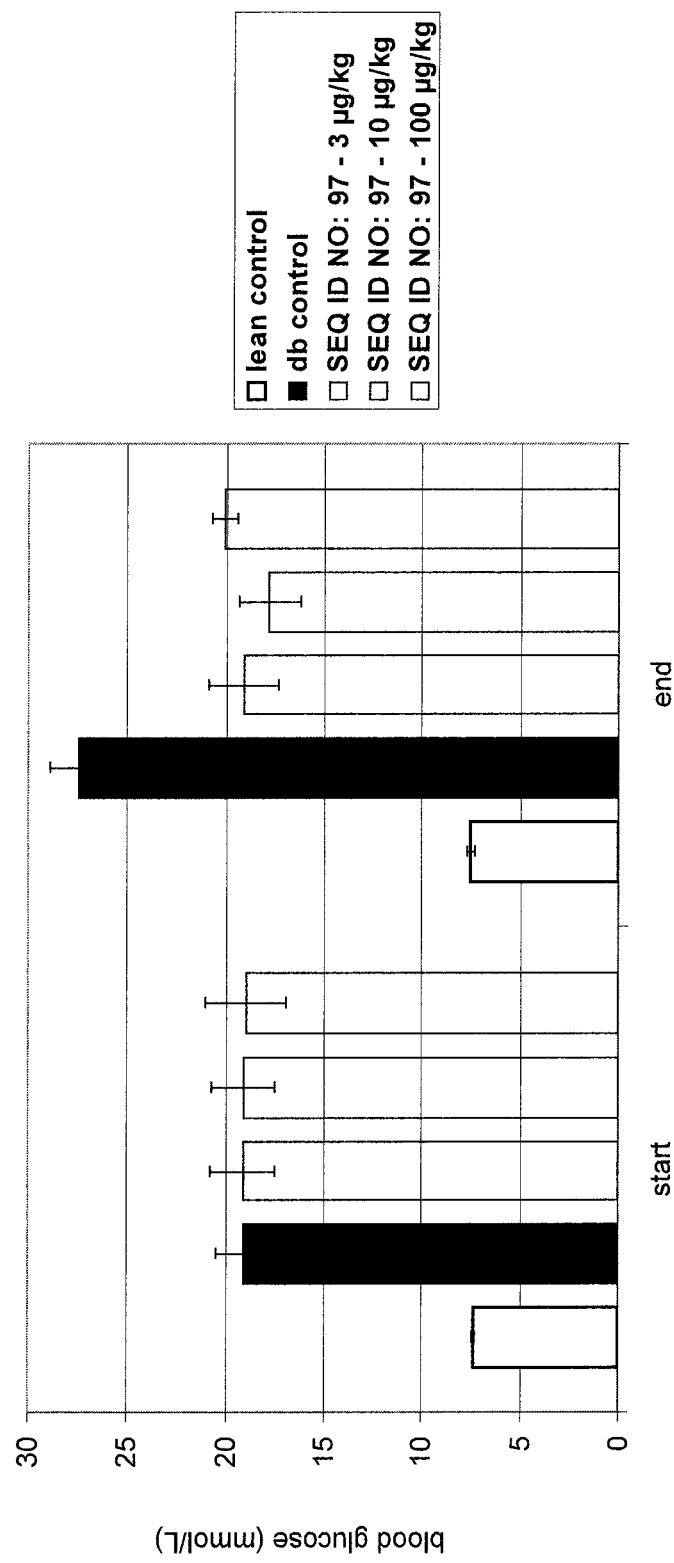

FIG. 5. Glucose level before and after 4 weeks of subcutaneous treatment with SEQ ID NO: 97 in female leptin-receptor deficient diabetic db/db mice. Data are mean+SEM.

Figure 6:
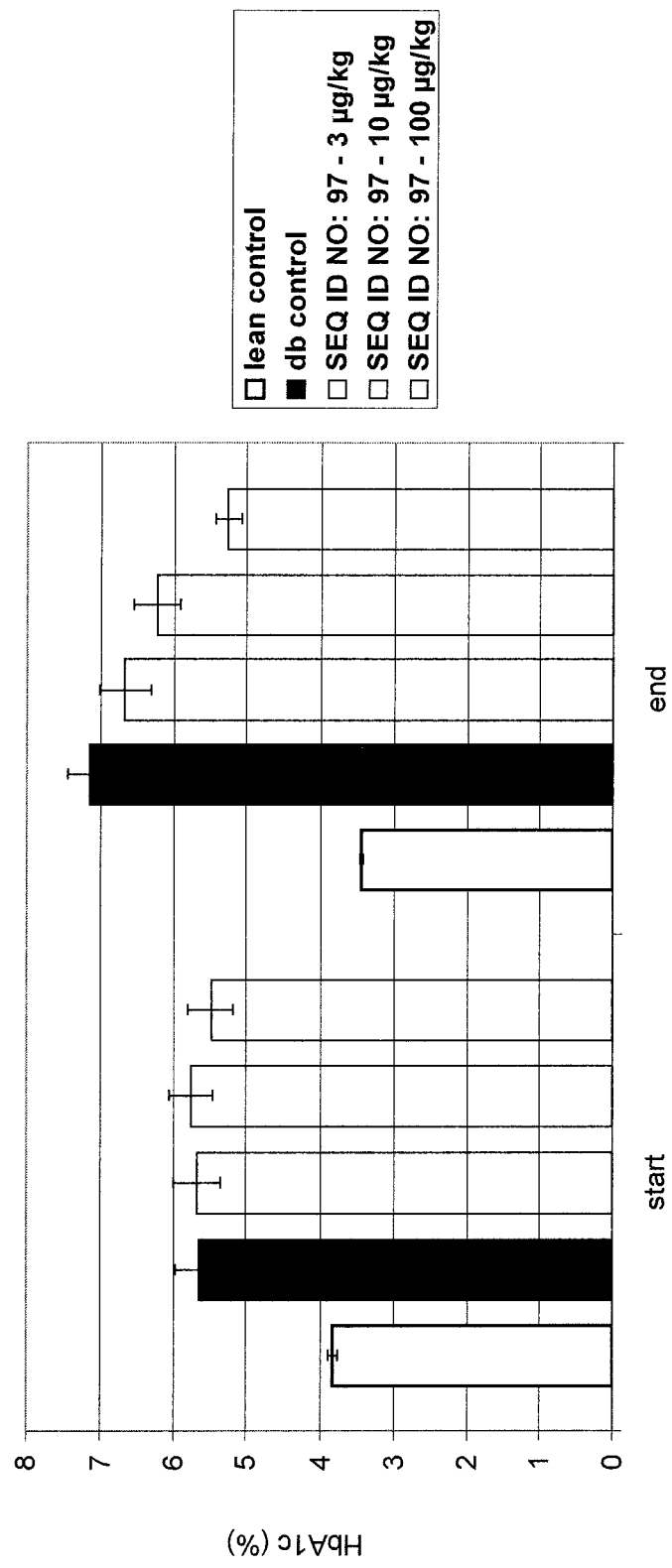

FIG. 6. HbA1c level before and after 4 weeks of subcutaneous treatment with SEQ ID NO: 97 in female leptin-receptor deficient diabetic db/db mice. Data are mean+SEM.

Figure 7:
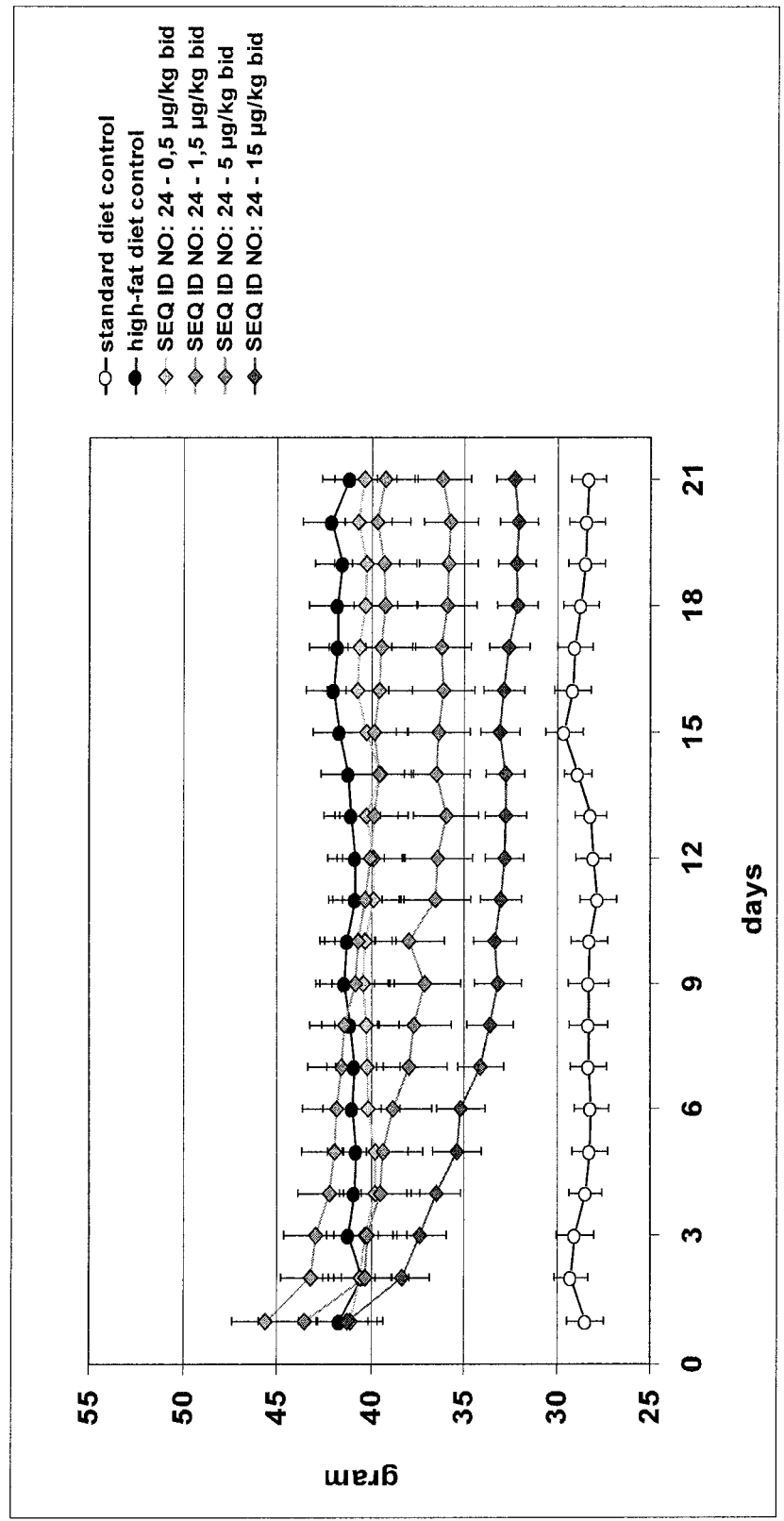

FIG. 7. Body weight development during 3 weeks of subcutaneous treatment with SEQ ID NO: 24 in male high-fat fed C57BL/6N Crl mice. Data are mean+SEM.

Figure 8:
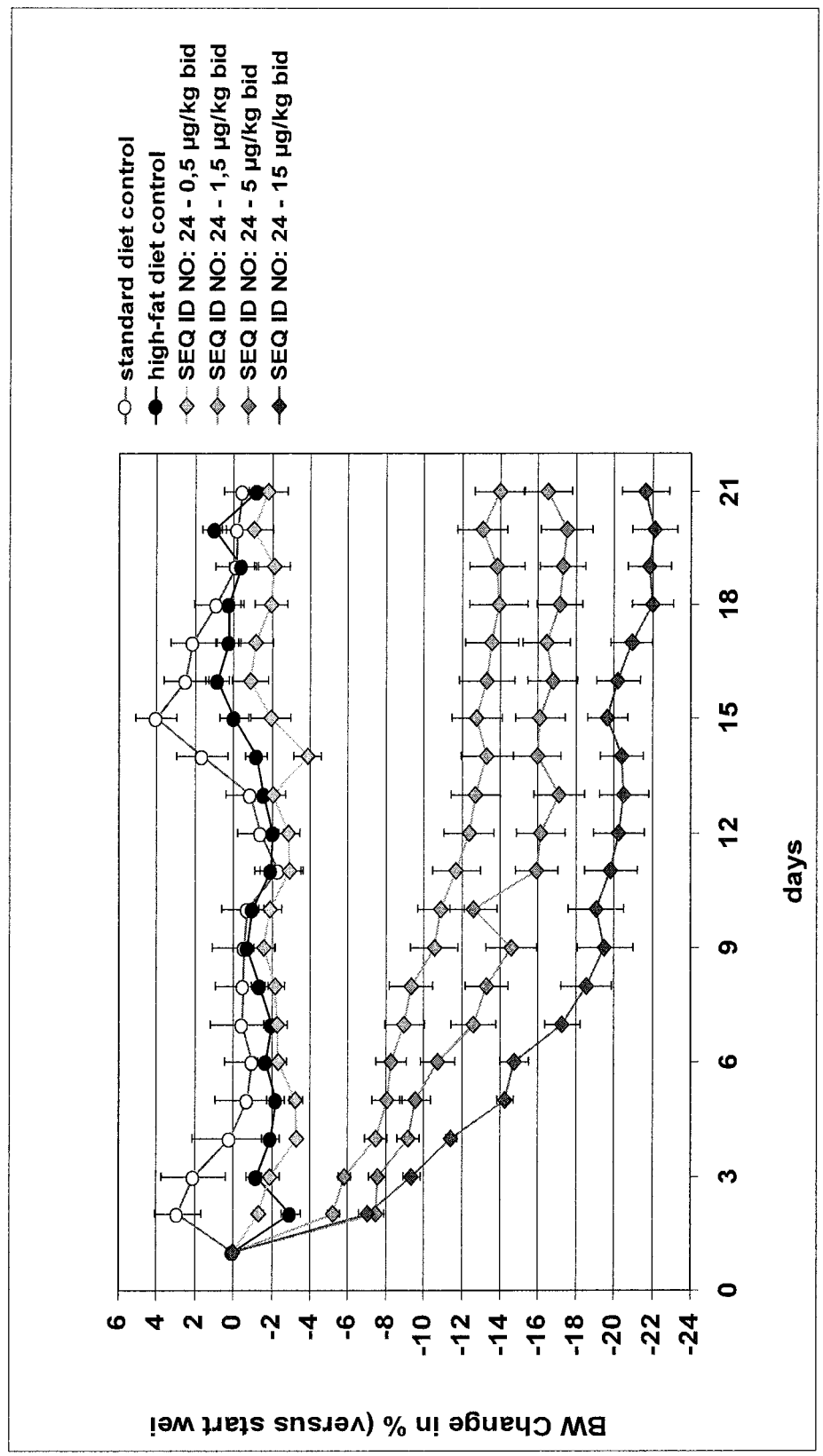

FIG. 8. Relative body weight change in % during 3 weeks of subcutaneous treatment with SEQ ID NO: 24 in male high-fat fed C57BL/6N Crl mice. Data are mean+SEM.

Figure 9:
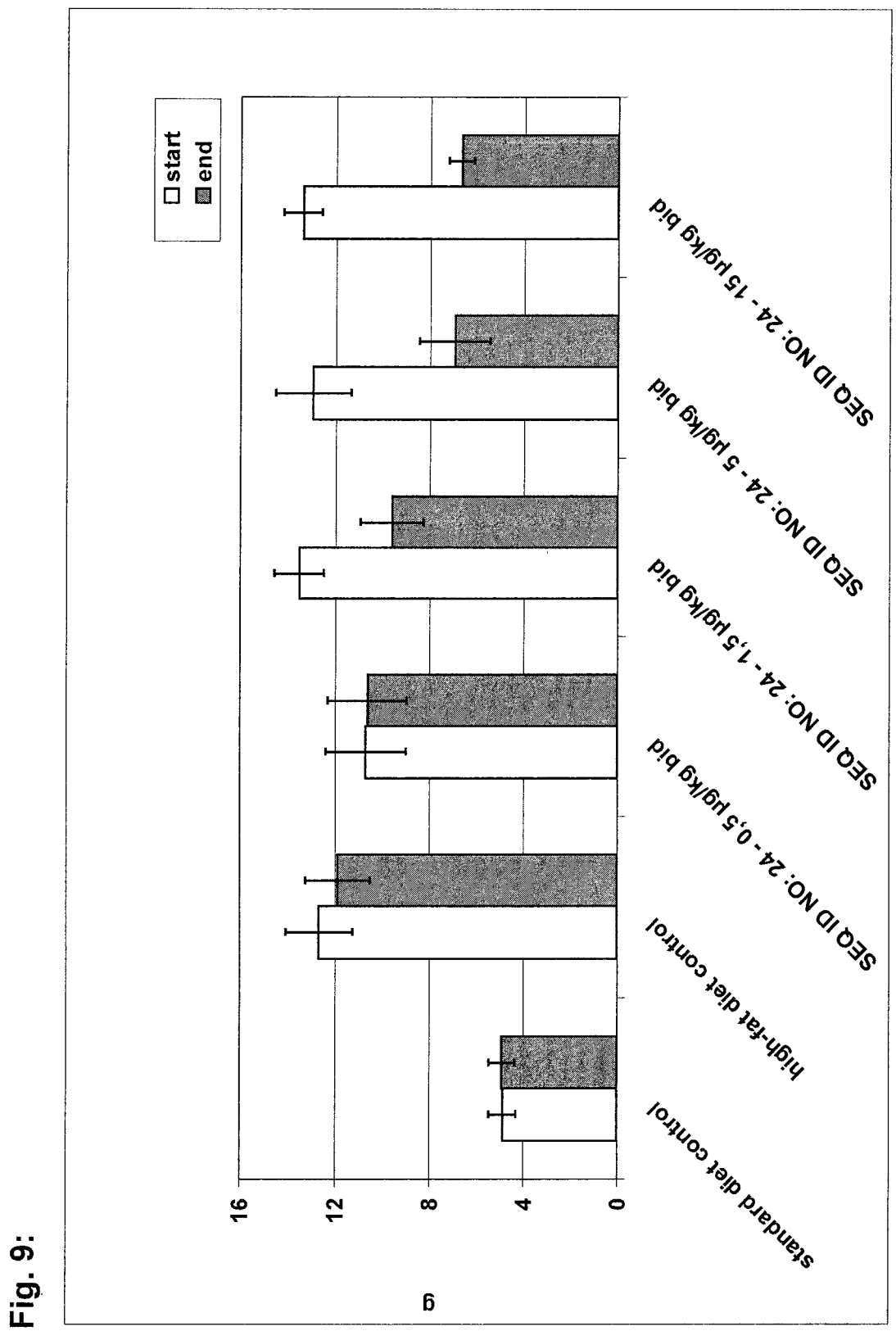

FIG. 9. Determination of total fat mass measured by nuclear magnetic resonance (NMR) using a Bruker minispec, before and after 3 weeks of treatment with SEQ ID NO: 24 in male high-fat fed C57BL/6N Crl mice. Data are mean+SEM.

Figure 10:
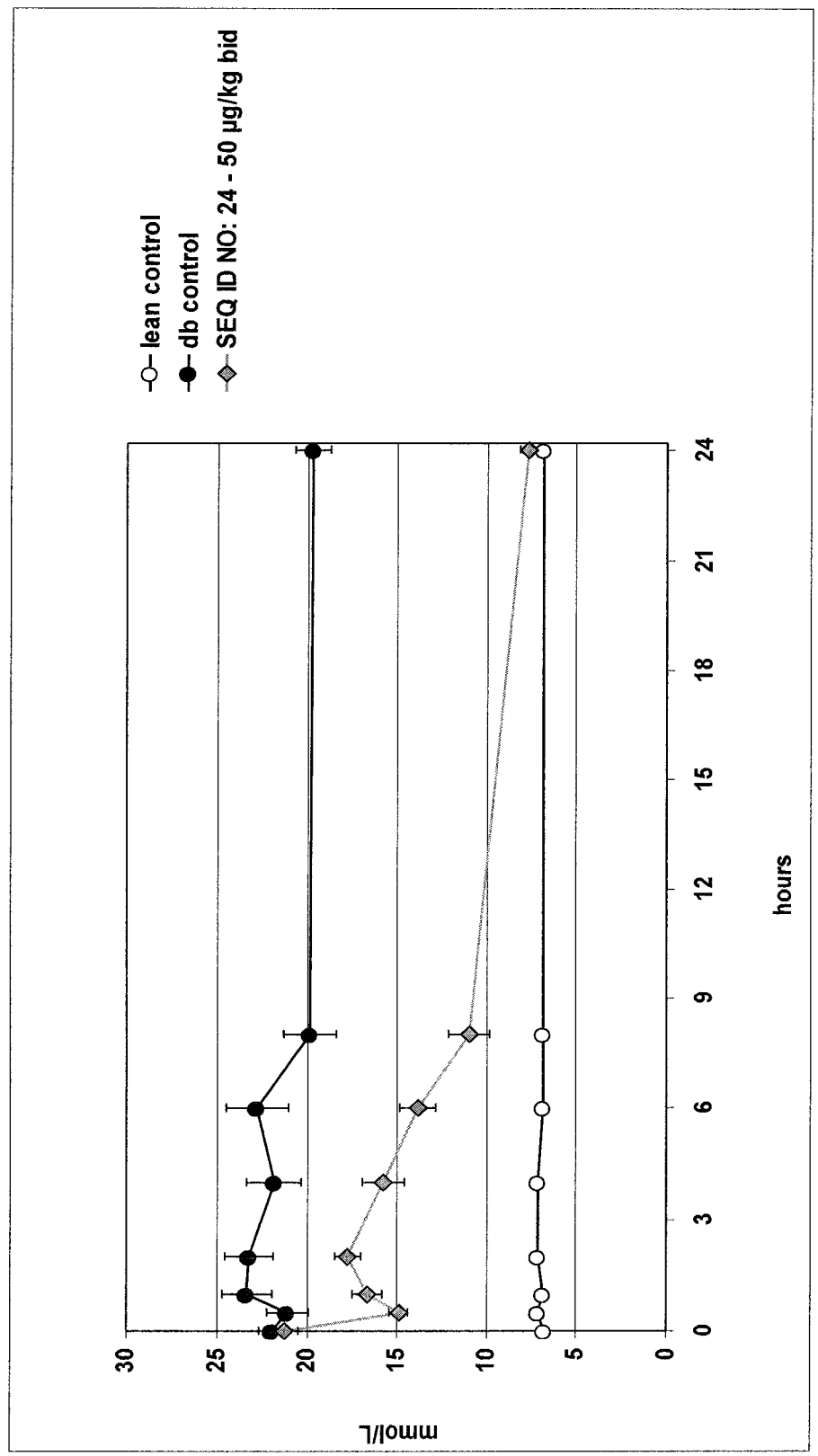

FIG. 10. Acute effect of s.c. administration of compound SEQ ID NO: 24 on blood glucose in female leptin-receptor deficient diabetic db/db mice. Data are mean+SEM.

Figure 11:
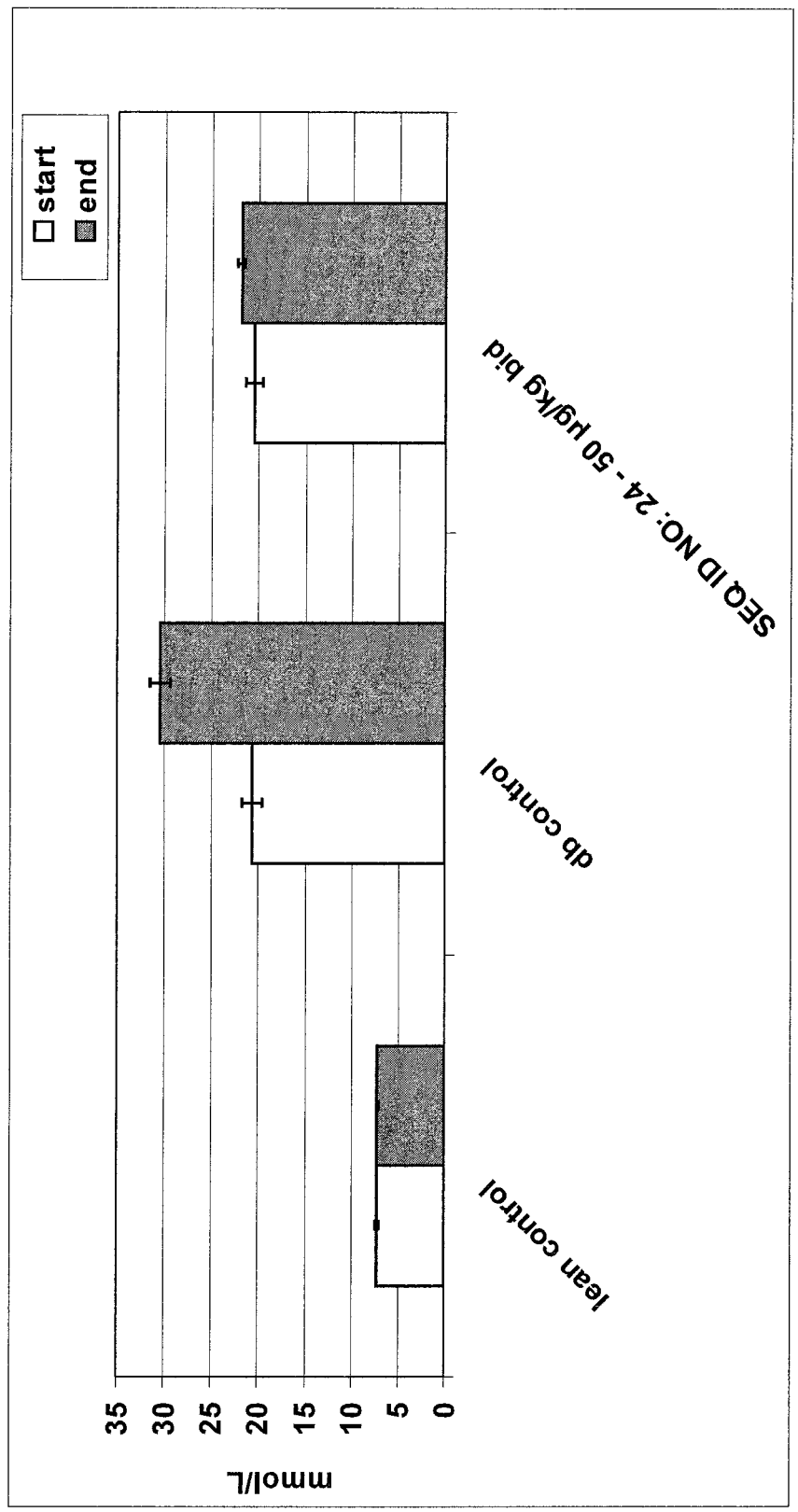

FIG. 11. Glucose level before and after 4 weeks of subcutaneous treatment with SEQ ID NO: 24 in female leptin-receptor deficient diabetic db/db mice. Data are mean+SEM.

Figure 12:
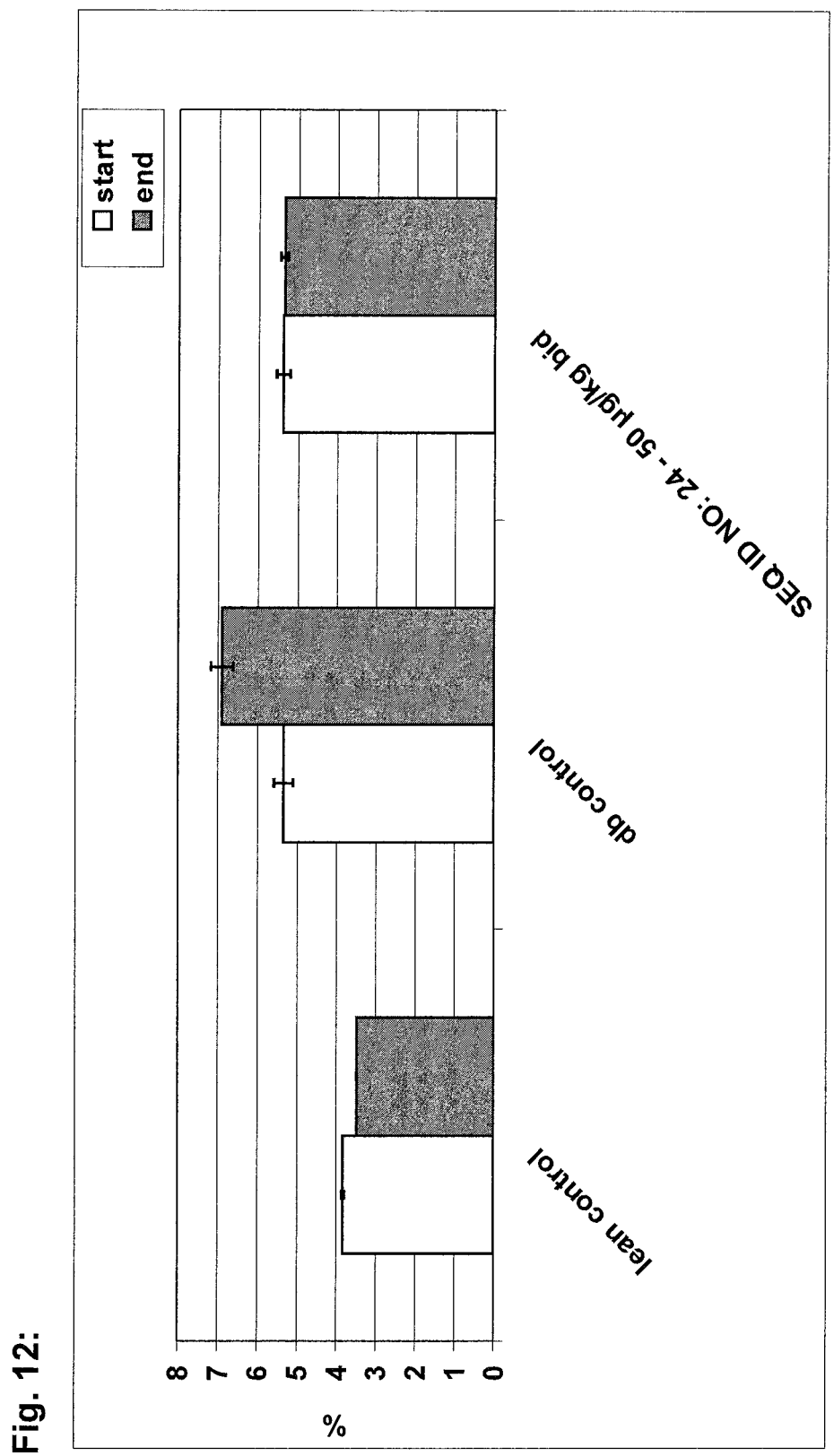

FIG. 12. HbA1c level before and after 4 weeks of subcutaneous treatment with SEQ ID NO: 24 in female leptin-receptor deficient diabetic db/db mice. Data are mean+SEM.

METHODS

Abbreviations employed are as follows:
ivDde: 1-(4,4-dimethyl-2,6-dioxocyclohexylidene)3-methyl-butyl
Dde: 1-(4,4-dimethyl-2,6-dioxocyclohexylidene)-ethyl
TFA: trifluoroacetic acid
BOP benzotriazol-1-yl-oxy-tris-(dimethylamino)-phosphonium hexafluorophosphate
HBTU 2-(1H-benzotriazol-1-yl)-1,1,3,3-tetramethyl-uronium hexafluorophosphate
HATU O-(7-azabenzotriazol-1-yl)-N,N,N',N'-tetramethyluronium hexafluorophosphate
DIC N,N'-diisopropylcarbodiimide
HOBt 1-hydroxybenzotriazol
DMF dimethyl formamide
EDT ethanedithiol
HPLC High Performance Liquid Chromatography
Boc tert-butyloxycarbonyl
Fmoc fluorenyloxycarbonyl
PEG Polyethylene Glycol
HTRF Homogenous Time Resolved Fluorescence
BSA bovine serum albumin
FBS fetal bovine serum
DMEM Dulbecco's modified Eagle's medium
PBS phosphate buffered saline
HEPES 2-[4-(2-hydroxyethyl)piperazin-1-yl]ethanesulfonic acid
IBMX 3-Isobutyl-1-methylxanthine General Synthesis of Peptidic Compounds Materials:

Different Rink-Amide resins (4-(2',4'-Dimethoxyphenyl-Fmoc-aminomethyl)-phenoxyacetamido-norleucylaminomethyl resin, Merck Biosciences; 4-[(2,4-Dimethoxyphenyl)(Fmoc-amino)methyl]phenoxy acetamido methyl resin, Agilent Technologies) were used for the synthesis of peptide amides with loadings in the range of 0.3-0.4 mmol/g. Suppliers were Merck Biosciences and Agilent Technologies. From the same suppliers 2-chloro-trityl-chloride polystyrene resins with loadings up to 1.4 mmol/g were purchased and used for the synthesis of peptide acids.

Fmoc protected natural amino acids were purchased from Protein Technologies Inc., Senn Chemicals, Merck Biosciences, Novabiochem, Iris Biotech or Bachem. The following standard amino acids were used throughout the syntheses: Fmoc-L-Ala-OH, Fmoc-L-Asn(Trt)-OH, Fmoc-L-Asp(OtBu)-OH, Fmoc-L-Cys(Trt)-OH, Fmoc-L-Gln(Trt)-OH, Fmoc-L-Glu(OtBu)-OH, Fmoc-Gly-OH, Fmoc-L-His(Trt)-OH, Fmoc-L-Ile-OH, Fmoc-L-Leu-OH, Fmoc-L-Lys(Boc)-OH, Fmoc-L-Met-OH, Fmoc-L-Phe-OH, Fmoc-L-Pro-OH, Fmoc-L-Ser(tBu)-OH, Fmoc-L-Thr(tBu)-OH, Fmoc-L-Trp(Boc)-OH, Fmoc-L-Tyr(tBu)-OH, Fmoc-L-Val-OH.

In addition, the following special amino acids were purchased from the same suppliers as above: Fmoc-L-Lys(ivDde)-OH, Fmoc-Aib-OH, Fmoc-D-Ser(tBu)-OH, Fmoc-D-Ala-OH, Boc-L-His(Boc)-OH (available as toluene solvate) and Boc-L-His(Trt)-OH.

The solid phase peptide syntheses were performed on a Prelude Peptide Synthesizer (Protein Technologies Inc) using standard Fmoc chemistry and HBTU/DIPEA activation. DMF was used as the solvent. Deprotection: 20% piperidine/DMF for 2×2.5 min. Washes: 7×DMF. Coupling 2:5:10 200 mM AA/500 mM HBTU/2M DIPEA in DMF 2× for 20 min. Washes: 5×DMF.

In cases where a Lys-side chain was modified, Fmoc-L-Lys(ivDde)-OH was used in the corresponding position. After completion of the synthesis, the ivDde group was removed according to a modified literature procedure (S. R. Chhabra et al., Tetrahedron Lett. 39, (1998), 1603), using 4% hydrazine hydrate in DMF. The following acylations were carried out by treating the resin with the N-hydroxy succinimide esters of the desired acid or using coupling reagents like HBTU/DIPEA or HOBt/DIC.

All the peptides that had been synthesized were cleaved from the resin with King's cleavage cocktail consisting of 82.5% TFA, 5% phenol, 5% water, 5% thioanisole, 2.5% EDT. The crude peptides were then precipitated in diethyl or diisopropyl ether, centrifuged, and lyophilized. Peptides were analysed by analytical HPLC and checked by ESI mass spectrometry. Crude peptides were purified by a conventional preparative HPLC purification procedure.

Analytical HPLC was performed on an Agilent 1100 Series HPLC system with a Waters XBridge BEH130 3.5 μm C18 column (2.1×150 mm) at 40° C. with a gradient elution at a flow rate of 0.5 mL/min and monitored at 215 and 280 nm. The gradients were set up as 10% B to 90% B over 15 min and then 90% B for 1 min or as 15% B to 50% B over 12.5 min and then 50% B to 90% B over 3 min. Buffer A=0.1% formic acid in water and B=0.1% formic acid in acetonitrile.

General Preparative HPLC Purification Procedure:

The crude peptides were purified either on an Äkta Purifier System or on a Jasco semiprep HPLC System. Preparative RP-C18-HPLC columns of different sizes and with different flow rates were used depending on the amount of crude peptide to be purified. Acetonitrile+0.1% TFA (B) and water+0.1% TFA (A) were employed as eluents. Product-containing fractions were collected and lyophilized to obtain the purified product.

Solubility and Stability-Testing of Exendin-4 Derivatives

Prior to the testing of solubility and stability of a peptide batch, its content was determined. Therefore, two parameters were investigated, its purity (HPLC-UV) and the amount of salt load of the batch (ion chromatography). Since synthesized peptides contain primarily trifluoroacetate anions, only anion chromatography was performed.

For solubility testing, the target concentration was 1.0 mg/mL pure compound. Therefore, solutions from solid samples were prepared in different buffer systems with a concentration of 1.0 mg/mL compound based on the previously determined content. HPLC-UV was performed after 2 h of gentle agitation from the supernatant, which was obtained by 20 min of centrifugation at 4000 rpm.

The solubility was then determined by comparison with the UV peak areas obtained with a stock solution of the peptide at a concentration of 2 mg/mL in pure water or a variable amount of acetonitrile (optical control that all of the compound was dissolved). This analysis also served as starting point (t0) for the stability testing.

For stability testing, an aliquot of the supernatant obtained for solubility was stored for 7 days at 25° C. After that time course, the sample was centrifuged for 20 min at 4000 rpm and the supernatant was analysed with HPLC-UV.

For determination of the amount of the remaining peptide, the peak areas of the target compound at t0 and t7 were compared, resulting in "% remaining peptide", following the equation $$\% \text{ remaining peptide} = [(\text{peak area peptide } t7) \times 100] / \text{peak area peptide } t0.$$

The amount of soluble degradation products was calculated from the comparison of the sum of the peak areas from all observed impurities reduced by the sum of peak areas observed at t0 (i.e. to determine the amount of newly formed peptide-related species). This value was given in percentual relation to the initial amount of peptide at t0, following the equation:

$$\% \text{ soluble degradation products} = \{[(\text{peak area sum of impurities } t7) - (\text{peak area sum of impurities } t0)] \times 100\} / \text{peak area peptide } t0$$

The potential difference from the sum of "% remaining peptide" and "% soluble degradation products" to 100% reflects the amount of peptide which did not remain soluble upon stress conditions following the equation $$\% \text{ precipitate} = 100 - ([\% \text{ remaining peptide}] + [\% \text{ soluble degradation products}])$$

This precipitate includes non-soluble degradation products, polymers and/or fibrils, which have been removed from analysis by centrifugation.

Anion Chromatography

Instrument: Dionex ICS-2000, pre/column: Ion Pac AG-18 2×50 mm (Dionex)/AS18 2×250 mm (Dionex), eluent: aqueous sodium hydroxide, flow: 0.38 mL/min, gradient: 0-6 min: 22 mM KOH, 6-12 min: 22-28 mM KOH, 12-15 min: 28-50 mM KOH, 15-20 min: 22 mM, suppressor: ASRS 300 2 mm, detection: conductivity.

HPLC-UV

Instrument: Agilent 1100, column: X-Bridge C18 3.5 μm 2.1×150 mm (Waters), eluent: A: H20+500 ppm TFA/B: Methanol, flow: 0.55 mL/min, gradient: 0-5 min: 10-60% B; 5-15 min: 60-99% B; detection: 214 nm.

In Vitro Cellular Assays for GLP-1 Receptor and Glucagon Receptor Efficacy

Agonism of compounds for the two receptors was determined by functional assays measuring cAMP response of HEK-293 cell lines stably expressing human GLP-1 or glucagon receptor.

cAMP content of cells was determined using a kit from Cisbio Corp. (cat. no. 62AM4PEC) based on HTRF (Homogeneous Time Resolved Fluorescence). For preparation, cells were split into T175 culture flasks and grown overnight to near confluency in medium (DMEM/10% FBS). Medium was then removed and cells washed with PBS lacking calcium and magnesium, followed by proteinase treatment with accutase (Sigma-Aldrich cat. no. A6964). Detached cells were washed and resuspended in assay buffer (1×HBSS; 20 mM HEPES, 0.1% BSA, 2 mM IBMX) and cellular density determined. They were then diluted to 400000 cells/ml and 25 μl-aliquots dispensed into the wells of 96-well plates. For measurement, 25 μl of test compound in assay buffer was added to the wells, followed by incubation for 30 minutes at room temperature. After addition of HTRF reagents diluted in lysis buffer (kit components), the plates were incubated for 1 hr, followed by measurement of the fluorescence ratio at 665/620 nm. In vitro potency of agonists was quantified by determining the concentrations that caused 50% activation of maximal response (EC50).

Bioanalytical Screening Method for Quantification of Peptide GLP1-GCG Receptor Agonists in Mice Mice were dosed 1 mg/kg subcutaneously (s.c.). The mice were sacrificed and blood samples were collected after 0.25, 1, 2, 4, 8, 16 and 24 hours post application. Plasma samples were analysed after protein precipitation via liquid chromatography mass spectrometry (LC/MS). PK parameters and half-life were calculated using WinonLin Version 5.2.1 (non-compartment model).

Gastric Emptying and Intestinal Passage in Mice

Female NMRI-mice of a body weight between 20 and 30 g were used. Mice were adapted to housing conditions for at least one week.

Mice were overnight fasted, while water remained available all the time. On the study day, mice were weighed, single-caged and allowed access to 500 mg of feed for 30 min, while water was removed. At the end of the 30 min feeding period, remaining feed was removed and weighed. 60 min later, a coloured, non-caloric bolus was instilled via gavage into the stomach. The test compound/reference compound or its vehicle in the control group was administered subcutaneously, to reach C max when coloured bolus was administered. After another 30 min, the animals were sacrificed and the stomach and the small intestine prepared. The filled stomach was weighed, emptied, carefully cleaned and dried and reweighed. The calculated stomach content indicated the degree of gastric emptying. The small intestine was straightened without force and measured in length. Then the distance from the gastric beginning of the gut to the tip of the farthest travelled intestinal content bolus was measured. The intestinal passage was given as relation in percent of the latter distance and the total length of the small intestine.

Statistical analyses were performed with Everstat 6.0 by 1-way-ANOVA, followed by Dunnetts or Newman-Keuls as post-hoc test, respectively. Differences were considered statistically significant at the $p<0.05$ level. As post hoc test Dunnet's Test was applied to compare versus vehicle control, only. Newman-Keul's Test was applied for all pairwise comparisons (i.e. versus vehicle and reference groups).

Automated Assessment of Feed Intake in Mice

Female NMRI-mice of a body weight between 20 and 30 g were used. Mice were adapted to housing conditions for at least one week and for at least one day single-caged in the assessment equipment, when basal data were recorded simultaneously. On the study day, test product was administered subcutaneously close to the lights-off phase (12 h lights off) and assessment of feed consumption was directly started afterwards.

Assessment included continued monitoring (every 30 min) over 22 hours. Repetition of this procedure over several days was possible. Restriction of assessment to 22 hours was for practical reasons to allow for reweighing of animals, refilling of feed and water and drug administration between procedures. Results could be assessed as cumulated data over 22 hours or differentiated to 30 min intervals.

Statistical analyses were performed with Everstat 6.0 by two-way ANOVA on repeated measures and Dunnetts post-hoc analyses. Differences were considered statistically significant at the $p<0.05$ level.

Acute and Subchronic Effects of Exendin-4 Derivatives after Subcutaneous Treatment on Blood Glucose and Body Weight in Female Diet-Induced Obese (DIO) C57BL/6NCrl Mice (10 Months on High-Fat Diet)

Female C57BL/6NCrl mice were housed in groups in a specific pathogen-free barrier facility on a 12-h light/dark cycle with free access to water and high-fat diet. After 10 months on high-fat diet, mice were stratified to treatment groups (n=8), so that each group had similar mean body weight.

An aged-matched group with ad-libitum access to standard chow was included as standard control group.

Before the experiment, mice were subcutaneously (s.c.) injected with vehicle solution and weighed for 3 days to acclimate them to the procedures.

1) Acute effect on blood glucose in fed DIO mice: initial blood samples were taken just before first administration (s.c.) of vehicle (phosphate buffer solution) or the exendin-4 derivatives at doses of 3, 10, and 100 µg/kg (dissolved in phosphate puffer), respectively. The volume of administration was 5 mL/kg. The animals had access to water and their corresponding diet during the experiment, food consumption was determined at all time points of blood sampling. Blood glucose levels were measured at t=0.5 h, t=1 h, t=2 h, t=4 h, t=6 h, t=8 h, and t=24 h (method: d-glucose hexokinase, hemolysate, AU640 Beckman Coulter). Blood sampling was performed by tail incision without anaesthesia.

Comparable data can also be obtained when using male mice.

2) Subchronic effect on body weight: all animals were treated once daily s.c. in the morning, at the beginning of the light phase (12 h lights on) with either vehicle or exendin-4 derivatives at the abovementioned doses for 4 weeks. Body weight was recorded daily. On days 6 and 28, total fat mass was measured by nuclear magnetic resonance (NMR) using a Bruker minispec (Ettlingen, Germany).

Comparable data can be obtained for both female and male mice.

Statistical analyses were performed with Everstat 6.0 by repeated measures two-way ANOVA and Dunnetts post-hoc analyses (glucose profile) and 1-way-ANOVA, followed by Dunnetts post-hoc test (body weight, body fat). Differences versus vehicle-treated DIO control mice were considered statistically significant at the $p<0.05$ level.

Acute and Subchronic Effects of Exendin-4 Derivatives after Subcutaneous Treatment on Blood Glucose and HbA1c in Female Leptin-Receptor Deficient Diabetic db/db Mice Female BKS.Cg-m+/+Leprdb/J (db/db) and BKS.Cg-m+/+Leprdb/+ (lean control) mice were obtained from Charles River Laboratories, Germany, at an age of 9-10 weeks. The animals were housed in groups in a specific pathogen-free barrier facility on a 12-h light/dark cycle with free access to water and rodent-standard chow. After 1 week of acclimatization, blood samples were drawn from the tail without anaesthesia and blood glucose (method: d-glucose hexokinase, hemolysate, AU640 Beckman Coulter) and HbA1c level (method: hemolysate, Cobas6000 c501, Roche Diagnostics, Germany) were determined.

HbA1c is a glycosylated form of haemoglobin whose level reflects the average level of glucose to which the erythrocyte has been exposed during its lifetime. In mice, HbA1c is a relevant biomarker for the average blood glucose level during the preceding 4 weeks (erythrocyte life span in mouse~47 days).

Db/db mice were stratified to treatment groups (n=8), so that each group had similar baseline blood glucose and HbA1c levels.

1) Acute effect on blood glucose in fed db/db mice: initial blood samples were taken just before first administration (s.c.) of vehicle (phosphate buffer solution) or exendin-4 derivatives at doses of 3, 10, and 100 µg/kg (dissolved in phosphate puffer), respectively. The volume of administration was 5 mL/kg. The animals had access to water and chow during the experiment, food consumption was determined at all time points of blood sampling. Blood glucose levels were measured at t=0.5 h, t=1 h, t=2 h, t=4 h, t=6 h, t=8 h, and t=24 h. Blood sampling was performed by tail incision without anaesthesia.

Comparable data can also be obtained when using male mice.

2) Subchronic effect on blood glucose and HbA1c: all animals were treated once daily s.c. with either vehicle or exendin-4 derivatives at the abovementioned doses for 4 weeks. At the end of the study, blood samples (tail, no anaesthesia) were analyzed for glucose and HbA1c.

Comparable data can be obtained for both female and male mice.

Statistical analyses were performed with Everstat 6.0 by repeated measures two-way ANOVA and Dunnetts post-hoc analyses. Differences versus vehicle-treated db/db control mice were considered statistically significant at the $p<0.05$ level.

EXAMPLES

The invention is further illustrated by the following examples.

Example 1

Synthesis of SEQ ID NO: 4

The solid phase synthesis was carried out on Novabiochem Rink-Amide resin (4-(2',4'-Dimethoxyphenyl-Fmoc-aminomethyl)-phenoxyacetamido-norleucylaminomethyl resin), 100-200 mesh, loading of 0.34 mmol/g. The Fmoc-synthesis strategy was applied with HBTU/DIPEA-activation. In position 14 Fmoc-Lys(ivDde)-OH and in position 1 Boc-His(Boc)-OH were used in the solid phase synthesis protocol. The ivDde-group was cleaved from the peptide on resin according to a modified literature procedure (S. R. Chhabra et al., Tetrahedron Lett. 39, (1998), 1603), using 4% hydrazine hydrate in DMF. Hereafter Palm-Glu(γOSu)-OtBu was coupled to the liberated amino-group. The peptide was cleaved from the resin with King's cocktail (D. S. King, C. G. Fields, G. B. Fields, Int. J. Peptide Protein Res. 36, 1990, 255-266). The crude product was purified via preparative HPLC on a Waters column (Sunfire, Prep C18) using an acetonitrile/water gradient (both buffers with 0.1% TFA).

Finally, the molecular mass of the purified peptide was confirmed by LC-MS.

Example 2

Synthesis of SEQ ID NO: 5

The solid phase synthesis was carried out on Novabiochem Rink-Amide resin (4-(2',4'-Dimethoxyphenyl-Fmoc-aminomethyl)-phenoxyacetamido-norleucylaminomethyl resin), 100-200 mesh, loading of 0.34 mmol/g. The Fmoc-synthesis strategy was applied with HBTU/DIPEA-activation. In position 14 Fmoc-Lys(ivDde)-OH and in position 1 Boc-His(Boc)-OH were used in the solid phase synthesis protocol. The ivDde-group was cleaved from the peptide on resin according to a modified literature procedure (S. R. Chhabra et al., Tetrahedron Lett. 39, (1998), 1603), using 4% hydrazine hydrate in DMF. Hereafter Palm (γOSu) was coupled to the liberated amino-group. The peptide was cleaved from the resin with King's cocktail (D. S. King, C. G. Fields, G. B. Fields, Int. J. Peptide Protein Res. 36, 1990, 255-266). The crude product was purified via preparative HPLC on a Waters column (Sunfire, Prep C18) using an acetonitrile/water gradient (both buffers with 0.1% TFA).

Finally, the molecular mass of the purified peptide was confirmed by LC-MS.

Example 3

Synthesis of SEQ ID NO: 6

The solid phase synthesis was carried out on Novabiochem Rink-Amide resin (4-(2',4'-Dimethoxyphenyl-Fmoc-aminomethyl)-phenoxyacetamido-norleucylaminomethyl resin), 100-200 mesh, loading of 0.34 mmol/g. The Fmoc-synthesis strategy was applied with HBTU/DIPEA-activation. In position 14 and in position 40 Fmoc-Lys(ivDde)-OH and in position 1 Boc-His(Boc)-OH were used in the solid phase synthesis protocol. The ivDde-group was cleaved from the peptide on resin according to a modified literature procedure (S. R. Chhabra et al., Tetrahedron Lett. 39, (1998), 1603), using 4% hydrazine hydrate in DMF. Hereafter Palm-Glu(γOSu)-OtBu was coupled to the liberated amino-group. The peptide was cleaved from the resin with King's cocktail (D. S. King, C. G. Fields, G. B. Fields, Int. J. Peptide Protein Res. 36, 1990, 255-266). The crude product was purified via preparative HPLC on a Waters column (Sunfire, Prep C18) using an acetonitrile/water gradient (both buffers with 0.1% TFA).

Finally, the molecular mass of the purified peptide was confirmed by LC-MS.

Example 4

Synthesis of SEQ ID NO: 7

The solid phase synthesis was carried out on Novabiochem Rink-Amide resin (4-(2',4'-Dimethoxyphenyl-Fmoc-aminomethyl)-phenoxyacetamido-norleucylaminomethyl resin), 100-200 mesh, loading of 0.34 mmol/g. The Fmoc-synthesis strategy was applied with HBTU/DIPEA-activation. In position 14 Fmoc-Lys(ivDde)-OH and in position 1 Boc-His(Boc)-OH were used in the solid phase synthesis protocol. The ivDde-group was cleaved from the peptide on resin according to a modified literature procedure (S. R. Chhabra et al., Tetrahedron Lett. 39, (1998), 1603), using 4% hydrazine hydrate in DMF. Hereafter Fmoc-GABA was coupled to the liberated amino-group employing the coupling reagents HBTU/DIPEA followed by Fmoc-deprotection with 20% piperidine in DMF. Finally palmitic acid was coupled to the amino-group of GABA using HBTU/DIPEA. The peptide was cleaved from the resin with King's cocktail (D. S. King, C. G. Fields, G. B. Fields, Int. J. Peptide Protein Res. 36, 1990, 255-266). The crude product was purified via preparative HPLC on a Waters column (Sunfire, Prep C18) using an acetonitrile/water gradient (both buffers with 0.1% TFA).

Finally, the molecular mass of the purified peptide was confirmed by LC-MS.

Example 5

Synthesis of SEQ ID NO: 8

The solid phase synthesis was carried out on Agilent Technologies Rink-Amide resin (4-[(2,4-Dimethoxyphenyl)(Fmoc-amino)methyl]phenoxyacetomido methyl resin), 75-150 μm, loading of 0.38 mmol/g. The Fmoc-synthesis strategy was applied with HBTU/DIPEA-activation. In position 14 Fmoc-Lys(ivDde)-OH and in position 1 Boc-His(Boc)-OH were used in the solid phase synthesis protocol. The ivDde-group was cleaved from the peptide on resin according to a modified literature procedure (S. R. Chhabra et al., Tetrahedron Lett. 39, (1998), 1603), using 4% hydrazine hydrate in DMF. Hereafter Fmoc-Glu-OtBu was coupled to the liberated amino-group using HBTU/DIPEA for activation followed by the removal of the Fmoc-group with 20% piperidine in DMF. Stearic acid was coupled onto the resulting amino group after activation with HBTU/DIPEA. The peptide was cleaved from the resin with King's cocktail (D. S. King, C. G. Fields, G. B. Fields, Int. J. Peptide Protein Res. 36, 1990, 255-266). The crude product was purified via preparative HPLC on a Waters column (Sunfire, Prep C18) using an acetonitrile/water gradient (both buffers with 0.1% TFA).

Finally, the molecular mass of the purified peptide was confirmed by LC-MS.

Example 6

Synthesis of SEQ ID NO: 9

The solid phase synthesis was carried out on Agilent Technologies Rink-Amide resin (4-[(2,4-Dimethoxyphenyl)(Fmoc-amino)methyl]phenoxyacetomido methyl resin), 75-150 μm, loading of 0.38 mmol/g. The Fmoc-synthesis strategy was applied with HBTU/DIPEA-activation. In position 14 Fmoc-Lys(ivDde)-OH and in position 1 Boc-His (Boc)-OH were used in the solid phase synthesis protocol. The ivDde-group was cleaved from the peptide on resin according to a modified literature procedure (S. R. Chhabra et al., Tetrahedron Lett. 39, (1998), 1603), using 4% hydrazine hydrate in DMF. Hereafter Fmoc-Glu-OtBu was coupled to the liberated amino-group using HBTU/DIPEA for activation followed by the removal of the Fmoc-group with 20% piperidine in DMF. 4-Dodecyloxy benzoic acid was coupled onto the resulting amino group after activation with HBTU/DIPEA. The peptide was cleaved from the resin with King's cocktail (D. S. King, C. G. Fields, G. B. Fields, Int. J. Peptide Protein Res. 36, 1990, 255-266). The crude product was purified via preparative HPLC on a Waters column (Sunfire, Prep C18) using an acetonitrile/water gradient (both buffers with 0.1% TFA).

Finally, the molecular mass of the purified peptide was confirmed by LC-MS.

Example 7

Synthesis of SEQ ID NO: 10

The solid phase synthesis was carried out on Agilent Technologies Cl-Trt-Cl resin (2,α-Dichlorobenzhydryl-polystyrene crosslinked with divinylbenzene), 75-150 m, loading of 1.4 mmol/g. Fmoc-Ser-OAllyl was synthesized according to literature (S. Ficht, R. J. Payne, R. T. Guy, C.-H. Wong, Chem. Eur. J. 14, 2008, 3620-3629) and coupled via the side chain hydroxyl function onto Cl-Trt-Cl-resin using DIPEA in dichloromethane. The Fmoc-synthesis strategy was applied with HBTU/DIPEA-activation. In position 14 Fmoc-Lys(ivDde)-OH and in position 1 Boc-His(Boc)-OH were used in the solid phase synthesis protocol. The ivDde-group was cleaved from the peptide on resin according to a modified literature procedure (S. R. Chhabra et al., Tetrahedron Lett. 39, (1998), 1603), using 4% hydrazine hydrate in DMF. Hereafter Fmoc-Glu-OtBu was coupled to the liberated amino-group using HBTU/DIPEA for activation followed by the removal of the Fmoc-group with 20% piperidine in DMF. Palmitic acid was coupled onto the resulting amino group after activation with HBTU/DIPEA. The allyl-ester group was removed employing the procedure described in literature (S. Ficht, R. J. Payne, R. T. Guy, C.-H. Wong, Chem. Eur. J. 14, 2008, 3620-3629) followed by activation of the C-terminus with HOBt/DIC in DMF and addition of n-propylamin. The peptide was cleaved from the resin with King's cocktail (D. S. King, C. G. Fields, G. B. Fields, Int. J. Peptide Protein Res. 36, 1990, 255-266). The crude product was purified via preparative HPLC on a Waters column (Sunfire, Prep C18) using an acetonitrile/water gradient (both buffers with 0.1% TFA).

Finally, the molecular mass of the purified peptide was confirmed by LC-MS.

In an analogous way, the other peptides listed in Table 2 were synthesized.

TABLE 2

List of synthesized peptides and comparison of calculated vs. found molecular weight

| SEQ ID NO | calc. mass | found mass |
|---|---|---|
| 4 | 4553.1 | 4552.4 |
| 5 | 4422.0 | 4421.4 |
| 6 | 5046.9 | 5046.8 |
| 7 | 4396.0 | 4395.1 |
| 8 | 4610.2 | 4609.8 |
| 9 | 4518.1 | 4518.2 |
| 10 | 4624.2 | 4624.6 |
| 11 | 4425.0 | 4424.4 |
| 12 | 4352.0 | 4351.2 |
| 13 | 4395.0 | 4394.1 |
| 14 | 4396.9 | 4396.0 |
| 15 | 4395.0 | 4394.4 |
| 16 | 4483.0 | 4482.0 |
| 17 | 4483.0 | 4483.2 |
| 18 | 4439.9 | 4439.1 |
| 19 | 4481.1 | 4480.5 |
| 20 | 4440.9 | 4440.0 |
| 21 | 4439.0 | 4438.2 |
| 22 | 4468.0 | 4467.9 |
| 23 | 4537.2 | 4536.5 |
| 24 | 4440.0 | 4439.5 |

TABLE 2-continued

List of synthesized peptides and comparison of calculated vs. found molecular weight

| SEQ ID NO | calc. mass | found mass |
|---|---|---|
| 25 | 4438.0 | 4437.4 |
| 26 | 4468.1 | 4467.2 |
| 27 | 4466.1 | 4465.3 |
| 28 | 4454.0 | 4454.0 |
| 29 | 4438.1 | 4437.3 |
| 30 | 4426.0 | 4425.9 |
| 31 | 4424.0 | 4423.9 |
| 32 | 4310.9 | 4310.3 |
| 33 | 4308.9 | 4308.3 |
| 34 | 4468.0 | 4467.9 |
| 35 | 4439.9 | 4439.4 |
| 36 | 4438.0 | 4437.3 |
| 37 | 4454.0 | 4453.9 |
| 38 | 4452.0 | 4451.9 |
| 39 | 4425.9 | 4425.9 |
| 40 | 4468.0 | 4467.4 |
| 41 | 4466.0 | 4465.4 |
| 42 | 4310.8 | 4310.3 |
| 43 | 4308.9 | 4308.3 |
| 44 | 4468.0 | 4467.4 |
| 45 | 4494.1 | 4493.4 |
| 46 | 4423.0 | 4422.3 |
| 47 | 4482.0 | 4482.0 |
| 48 | 4466.1 | 4465.4 |
| 49 | 4597.1 | 4596.4 |
| 50 | 4424.0 | 4423.5 |
| 51 | 4496.1 | 4495.2 |
| 52 | 4625.2 | 4626.0 |
| 53 | 4452.1 | 4452.0 |
| 54 | 4509.1 | 4509.0 |
| 55 | 4494.0 | 4493.7 |
| 56 | 4450.0 | 4449.6 |
| 57 | 4742.4 | 4741.6 |
| 58 | 4698.4 | 4698.0 |
| 59 | 4538.2 | 4538.3 |
| 60 | 4552.2 | 4552.1 |
| 61 | 4508.1 | 4507.7 |
| 62 | 4490.0 | 4490.2 |
| 63 | 4474.0 | 4474.3 |
| 64 | 4474.0 | 4474.3 |
| 65 | 4496.1 | 4495.5 |
| 66 | 4338.9 | 4338.4 |
| 67 | 4496.1 | 4495.7 |
| 68 | 4551.2 | 4550.5 |
| 69 | 4422.1 | 4421.5 |
| 70 | 4466.1 | 4465.5 |
| 71 | 4539.1 | 4538.8 |
| 72 | 4525.0 | 4524.8 |
| 73 | 4562.1 | 4561.5 |
| 74 | 4539.1 | 4538.4 |
| 75 | 4510.1 | 4509.4 |
| 76 | 4381.0 | 4380.3 |
| 77 | 4551.1 | 4550.5 |
| 78 | 4553.1 | 4552.7 |
| 79 | 4567.1 | 4566.7 |
| 80 | 4583.1 | 4582.4 |
| 81 | 4454.0 | 4453.5 |
| 82 | 4696.3 | 4695.8 |
| 83 | 4567.1 | 4566.7 |
| 84 | 4596.2 | 4595.4 |
| 85 | 4610.2 | 4609.7 |
| 86 | 4513.0 | 4512.8 |
| 87 | 4624.2 | 4623.4 |
| 88 | 4623.2 | 4622.5 |
| 89 | 4856.5 | 4856.3 |
| 90 | 4554.1 | 4553.7 |
| 91 | 4646.1 | 4645.8 |
| 92 | 4626.2 | 4625.5 |
| 93 | 4596.1 | 4595.4 |
| 94 | 4596.1 | 4595.3 |
| 95 | 4610.2 | 4609.5 |
| 96 | 4640.2 | 4639.8 |
| 97 | 4582.1 | 4581.7 |
| 98 | 4651.3 | 4651.1 |
| 99 | 4672.3 | 4672.1 |

TABLE 2-continued

List of synthesized peptides and comparison of calculated vs. found molecular weight

| SEQ ID NO | calc. mass | found mass |
|---|---|---|
| 100 | 4638.3 | 4638.0 |
| 101 | 4638.3 | 4638.2 |
| 102 | 4652.2 | 4652.2 |
| 103 | 4664.2 | 4663.7 |
| 104 | 4830.4 | 4830.3 |
| 105 | 5711.5 | 5711.2 |
| 106 | 4806.6 | 4806.5 |
| 107 | 4766.5 | 4766.0 |
| 108 | 4792.6 | 4792.6 |
| 109 | 4834.6 | 4834.5 |
| 110 | 4778.5 | 4778.9 |
| 111 | 4724.3 | 4723.9 |
| 112 | 4595.2 | 4594.7 |
| 113 | 4637.2 | 4636.7 |
| 114 | 4508.1 | 4507.7 |
| 115 | 4580.1 | 4579.4 |
| 116 | 4596.1 | 4595.4 |
| 117 | 4594.2 | 4593.4 |
| 118 | 4539.1 | 4538.6 |
| 119 | 4424.0 | 4423.4 |
| 120 | 4553.1 | 4552.5 |
| 121 | 4466.1 | 4466.0 |
| 122 | 4337.0 | 4336.5 |
| 123 | 4511.0 | 4511.0 |
| 124 | 4525.1 | 4525.0 |
| 125 | 4624.2 | 4623.7 |
| 126 | 4652.2 | 4651.7 |
| 127 | 4638.2 | 4637.7 |
| 128 | 4555.1 | 4554.3 |
| 129 | 4569.1 | 4568.6 |
| 131 | 4381.0 | 4380.9 |
| 133 | 4506.2 | 4505.4 |
| 134 | 4470.0 | 4470.0 |
| 135 | 4484.0 | 4484.0 |
| 136 | 4468.1 | 4468.0 |
| 137 | 4463.0 | 4462.4 |
| 138 | 4475.2 | 4475.8 |
| 139 | 4495.2 | 4495.6 |
| 140 | 4555.1 | 4554.0 |
| 142 | 4482.1 | 4481.4 |
| 143 | 4468.0 | 4467.0 |
| 144 | 4440.0 | 4439.1 |
| 145 | 4442.0 | 4440.0 |
| 146 | 4468.0 | 4466.1 |
| 147 | 4441.0 | 4438.8 |
| 148 | 4464.1 | 4462.2 |
| 149 | 4506.2 | 4505.4 |
| 150 | 4453.1 | 4453.6 |
| 151 | 4468.0 | 4467.9 |
| 152 | 4593.2 | 4592.1 |
| 153 | 4506.2 | 4505.1 |
| 155 | 4423.9 | 4423.9 |
| 156 | 4452.0 | 4451.9 |
| 157 | 4454.0 | 4453.9 |
| 158 | 4464.1 | 4462.8 |
| 159 | 4506.2 | 4504.8 |
| 161 | 4581.2 | 4580.7 |
| 162 | 4565.2 | 4564.2 |
| 163 | 4567.1 | 4566.4 |
| 164 | 4468.1 | 4468.0 |
| 166 | 4541.1 | 4540.8 |
| 173 | 4442.0 | 4441.9 |
| 174 | 4609.2 | 4608.3 |
| 175 | 4595.2 | 4594.8 |
| 183 | 4214.6 | 4214.1 |
| 184 | 4188.6 | 4190.7 |
| 185 | 4259.7 | 4259.0 |
| 186 | 4231.7 | 4231.0 |
| 187 | 4188.6 | 4188.4 |
| 188 | 4174.6 | 4172.0 |
| 189 | 4075.5 | 4074.8 |
| 190 | 4145.6 | 4145.1 |
| 191 | 4057.4 | 4056.2 |
| 192 | 4043.4 | 4043.4 |
| 193 | 4043.4 | 4043.2 |

TABLE 2-continued

List of synthesized peptides and comparison of calculated vs. found molecular weight

| SEQ ID NO | calc. mass | found mass |
|---|---|---|
| 196 | 4496.1 | 4494.4 |
| 197 | 4577.3 | 4575.6 |
| 198 | 4563.2 | 4561.2 |
| 199 | 4593.2 | 4591.2 |
| 200 | 4591.3 | 4589.7 |
| 201 | 4548.3 | 4546.2 |
| 202 | 4536.2 | 4534.0 |
| 203 | 4534.2 | 4532.4 |
| 204 | 4548.3 | 4546.2 |
| 205 | 4591.3 | 4590.4 |
| 206 | 4565.3 | 4567.0 |
| 207 | 4710.3 | 4710.6 |
| 208 | 4562.1 | 4559.6 |
| 209 | 4620.3 | 4618.8 |
| 210 | 4618.4 | 4616.1 |
| 211 | 4533.3 | 4532.4 |
| 212 | 4575.3 | 4573.5 |
| 213 | 4493.1 | 4493.4 |
| 214 | 4521.1 | 4523.4 |
| 215 | 4535.2 | 4536.9 |
| 217 | 4544.2 | 4545.0 |
| 219 | 4546.2 | 4545.3 |
| 221 | 4495.1 | 4494.4 |
| 222 | 4523.1 | 4522.4 |
| 226 | 4622.2 | 4621.6 |
| 227 | 4631.2 | 4629.6 |

In an analogous way, the following peptides of Table 3 can be synthesized:

TABLE 3

List of peptides that can be synthesized in an analogous way.
SEQ ID NO 130
132
141
154
160
165
167
168
169
170
171
172
176
177
178
179
180
181
182
218
223
228
229

Example 8: Chemical Stability and Solubility

Solubility and chemical stability of peptidic compounds were assessed as described in Methods. The results are given in Table 4.

TABLE 4

Chemical stability and solubility

| SEQ ID NO | Stability pH 4.5 | Stability pH 7.4 | Solubility [mg/ml] pH 4.5 | Solubility [mg/ml] pH 7.4 |
|---|---|---|---|---|
| 35 | 100 | 100 | >1000 | >1000 |
| 36 | 99.7 | 100 | >1000 | >1000 |
| 44 | 99.1 | 99.4 | >1000 | >1000 |
| 24 | 100 | 100 | >1000 | >1000 |
| 25 | 99.6 | 99.6 | >1000 | >1000 |
| 66 | 100 | 98.1 | >1000 | >1000 |
| 82 | 98.4 | 99.9 | >1000 | >1000 |
| 126 | 99.5 | 91.4 | >1000 | >1000 |
| 85 | 95.9 | 85.8 | >1000 | >968.6 |
| 97 | 99.5 | 96.5 | >2000 | >2000 |
| 70 | 98.2 | 97.5 | >1000 | >1000 |
| 4 | 99.5 | 98.8 | >815 | >910 |
| 117 | 98.3 | 87.2 | >1000 | >1000 |
| 121 | 100 | 90.5 | >1000 | >980 |
| 195 |  |  | 0 | >985 |

Example 9: In Vitro Data on GLP-1 and Glucagon Receptor

Potencies of peptidic compounds at the GLP-1 and glucagon receptors were determined by exposing cells expressing human glucagon receptor (hGlucagon R) or human GLP-1 receptor (hGLP-1 R) to the listed compounds at increasing concentrations and measuring the formed cAMP as described in Methods.

The results are shown in Table 5:

TABLE 5

EC50 values of exendin-4 derivatives at GLP-1 and Glucagon receptors (indicated in pM)

| SEQ ID NO | EC50 hGLP-1R | EC50 hGlucagon-R |
|---|---|---|
| 2 | 0.7 | >10000000 |
| 3 | 56.6 | 1.0 |
| 4 | 5 | 4 |
| 5 | 11 | 109 |
| 6 | 141 | 18.9 |
| 7 | 3.5 | 20.7 |
| 8 | 6.3 | 2.3 |
| 9 | 2.2 | 4.1 |
| 10 | 9.2 | 1.7 |
| 11 | 3.6 | 25.7 |
| 12 | 4.6 | 263 |
| 13 | 3.1 | 281 |
| 14 | 4.6 | 94.7 |
| 15 | 6.6 | 176 |
| 16 | 2.8 | 117 |
| 17 | 1.7 | 93.1 |
| 18 | 2.6 | 152 |
| 19 | 1.9 | 104 |
| 20 | 3.8 | 104 |
| 21 | 3.8 | 144 |
| 22 | 1.1 | 2.4 |
| 23 | 5.6 | 126 |
| 24 | 1.9 | 9.4 |
| 25 | 4.2 | 40.6 |
| 26 | 5.1 | 5.4 |
| 27 | 7.7 | 25.1 |
| 28 | 5.5 | 12.6 |
| 29 | 5.9 | 87.9 |
| 30 | 3.2 | 7 |
| 31 | 1.7 | 9.3 |
| 32 | 10.2 | 188 |
| 33 | 11.2 | 473 |
| 34 | 1.5 | 6.7 |
| 35 | 1.5 | 14.2 |
| 36 | 2.7 | 45.9 |
| 37 | 1.5 | 12.9 |
| 38 | 2.9 | 53.1 |
| 39 | 2.7 | 7.6 |
| 40 | 2.6 | 4.8 |
| 41 | 3.3 | 20.7 |
| 42 | 10.2 | 199 |
| 43 | 4.1 | 443 |
| 44 | 2.7 | 12 |
| 45 | 7.5 | 19.9 |
| 46 | 3.2 | 25.1 |
| 47 | 2.2 | 10.3 |
| 48 | 5.9 | 53.6 |
| 49 | 1.1 | 2.9 |
| 50 | 3.3 | 11.1 |
| 51 | 2.7 | 3 |
| 52 | 1.9 | 2 |
| 53 | 5.4 | 6.5 |
| 54 | 4.8 | 4 |
| 55 | 5.4 | 15.8 |
| 56 | 4.5 | 29.3 |
| 57 | 45 | 8 |
| 58 | 45.6 | 15.1 |
| 59 | 7.9 | 6.8 |
| 60 | 38.4 | 19.3 |
| 61 | 5.3 | 16 |
| 62 | 3.9 | 10.6 |
| 63 | 4.9 | 8.4 |
| 64 | 3.1 | 6.9 |
| 65 | 5 | 5.6 |
| 66 | 8.4 | 113 |
| 67 | 15.7 | 3 |
| 68 | 7.9 | 5.7 |
| 69 | 44.8 | 52.4 |
| 70 | 6.5 | 40.9 |
| 71 | 20.5 | 5.6 |
| 72 | 25.9 | 386 |
| 73 | 4.1 | 1.7 |
| 74 | 4.2 | 1.3 |
| 75 | 11.1 | 12.5 |
| 76 | 44.9 | 162 |
| 77 | 4.3 | 11.9 |
| 78 | 17.8 | 1.6 |
| 79 | 23.3 | 7.5 |
| 80 | 5.8 | 1 |
| 81 | 48 | 7.1 |
| 82 | 11.7 | 4.7 |
| 83 | 53.9 | 41.3 |
| 84 | 8.1 | 4.3 |
| 85 | 8.1 | 10.4 |
| 86 | 4.9 | 3.5 |
| 87 | 3 | 1.3 |
| 88 | 2.4 | 1.6 |
| 89 | 35.6 | 13.7 |
| 90 | 8.8 | 3.7 |
| 91 | 15.1 | 8.9 |
| 92 | 26 | 1 |
| 93 | 10.7 | 2.6 |
| 94 | 5.2 | 2.1 |
| 95 | 20.6 | 9.2 |
| 96 | 74.3 | 3.4 |
| 97 | 3.5 | 1 |
| 98 | 9.6 | 1.4 |
| 99 | 15.9 | 2.6 |
| 100 | 13.5 | 2 |
| 101 | 9.8 | 1.7 |
| 102 | 7.2 | 1.1 |
| 103 | 10.1 | 1.7 |
| 104 | 6.5 | 1.1 |
| 105 | 7.9 | 1 |
| 106 | 210 | 10.5 |
| 107 | 188 | 37.8 |
| 108 | 197 | 9 |
| 109 | 430 | 28.6 |
| 110 | 213 | 7.2 |
| 111 | 8.1 | 2.5 |
| 112 | 33.6 | 21.1 |

TABLE 5-continued

EC50 values of exendin-4 derivatives at GLP-1
and Glucagon receptors (indicated in pM)

| SEQ ID NO | EC50 hGLP-1R | EC50 hGlucagon-R |
|---|---|---|
| 113 | 11.4 | 5.4 |
| 114 | 62.3 | 31.1 |
| 115 | 2.4 | 1.9 |
| 116 | 6 | 3.6 |
| 117 | 3.8 | 16.5 |
| 118 | 15.3 | 4.3 |
| 119 | 30.8 | 41.2 |
| 121 | 6.1 | 23.7 |
| 122 | 24.9 | 156 |
| 123 | 2.6 | 9.7 |
| 124 | 3 | 8.4 |
| 125 | 31.4 | 6.9 |
| 126 | 6.6 | 6.8 |
| 127 | 14.7 | 9.4 |
| 128 | 6.2 | 1.6 |
| 129 | 14.8 | 4.1 |
| 131 | 9.1 | 24.9 |
| 138 | 5.5 | 9.2 |
| 140 | 1.3 | 1.5 |
| 142 | 4.1 | 2.1 |
| 150 | 6 | 35.5 |
| 152 | 3.2 | 2.3 |
| 155 | 2.5 | 25.1 |
| 156 | 2.9 | 12.5 |
| 161 | 5 | 2.4 |
| 162 | 3.1 | 2.4 |
| 173 | 5.7 | 5.9 |
| 174 | 2.6 | 1.9 |
| 175 | 2.5 | 3.1 |
| 196 | 7.8 | 1.8 |
| 197 | 6.8 | 5.8 |
| 198 | 8.2 | 2.4 |
| 199 | 10.1 | 7.2 |
| 200 | 4.6 | 4.4 |
| 201 | 22.7 | 29.6 |
| 202 | 26.2 | 6.9 |
| 203 | 34.9 | 13.1 |
| 204 | 34.1 | 12.5 |
| 205 | 12.3 | 5.2 |
| 206 | 3.2 | 12.5 |
| 207 | 1.1 | 1.2 |
| 208 | 2.0 | 1.3 |
| 209 | 5.4 | 1.9 |
| 210 | 6.7 | 3.0 |
| 211 | 15.5 | 26.4 |
| 212 | 14.1 | 6.6 |
| 213 | 2.7 | 59.1 |
| 214 | 4.2 | 16.0 |
| 215 | 5.3 | 42.6 |
| 216 | 4.7 | 19.5 |
| 217 | 4.3 | 2.1 |
| 219 | 2.1 | 3.7 |
| 220 | 2.0 | 2.3 |
| 221 | 1.5 | 9.2 |
| 222 | 1.8 | 2.9 |
| 226 | 1.4 | 19.1 |
| 227 | 1.4 | 1.1 |

Example 10: Pharmacokinetic Testing

Pharmacokinetic profiles were determined as described in Methods. Calculated $T_{1/2}$ and $c_{max}$ values are shown in Table 6.

TABLE 6

Pharmacokinetic profiles of exendin-4 derivatives.

| SEQ ID NO | $T_{1/2}$ [h] | Cmax [ng/ml] |
|---|---|---|
| 35 | 3.6 | 4910 |
| 36 | 3.8 | 5260 |
| 44 | 3.4 | 2450 |
| 24 | 3.7 | 6560 |
| 8 | 3.3 | 2680 |
| 126 | 1.5 | 3160 |
| 97 | 3.2 | 2000 |
| 4 | 2.8 | 3590 |
| 117 | 2.7 | 5000 |
| 5 | 1.7 | 3180 |

Example 11: Effect of SEQ ID NO: 97 on Gastric Emptying and Intestinal Passage in Female NMRI-Mice Female NMRI-mice, weighing on average 25-30 g, received 0.02 mg/kg of SEQ ID NO: 97, Liraglutide (SEQ ID NO: 195) as reference compound, or phosphate buffered saline (vehicle control) subcutaneously, 30 min prior to the administration of the coloured bolus. 30 min later, the assessment of stomach contents and intestinal passage was done (FIG. 1a, b).

In another study, female NMRI-mice, weighing on average 25-30 g, were administered subcutaneously 0.02 and 0.002 mg/kg of SEQ ID NO: 97 or phosphate buffered saline (vehicle control), 30 min prior to the administration of the coloured bolus. 30 min later, the assessment of stomach contents and intestinal passage was done (FIG. 1c, d).

In the study with reference compound Liraglutide, SEQ ID NO: 97 reduced intestinal passage by 67% (versus 44% and 34%, respectively) and increased gastric content by 90% (versus 19% and 21%, respectively) (p<0.0001 versus vehicle control and versus comparators, 1-W-ANOVA, followed by Newman-Keul's post-hoc test) (FIG. 1a, b).

When SEQ ID NO: 97 was tested at 0.02 and 0.002 mg/kg, s.c. versus PBS-control, intestinal passage was reduced by 43% and 63%, respectively, and gastric content was increased by 37% and 47%, respectively (p<0.0001 versus vehicle control, 1-W-ANOVA, followed by Dunnett's post-hoc test) (FIG. 1c, d).

Example 12: Effect of SEQ ID NO: 97 on 22-Hours Food Intake in Female NMRI-Mice

Fed female NMRI-mice, weighing on average 25-30 g, were administered 0.01 or 0.1 mg/kg of SEQ ID NO: 97 or phosphate buffered saline (vehicle control) subcutaneously, directly prior to start of feeding monitoring (time=0 h). Lights-off phase (dark phase) started 4 hours later.

At the tested doses, SEQ ID NO: 97 demonstrated a dose-dependent reduction of feed intake, reaching 23% (p<0.0001) and 66% (p<0.0001, 2-W-ANOVA-RM, post hoc Dunnett's Test) at the end of the study, respectively (FIG. 2).

Example 13: Acute and Subchronic Effects of SEQ ID NO: 97 after Subcutaneous Treatment on Blood Glucose and Body Weight in Female Diet-Induced Obese (DIO) C57BL/6NCrl Mice (10 Months on High Fat Diet)

1) Glucose Profile

After blood sampling to determine the blood glucose baseline level, fed diet-induced obese female C57BL/6NCrl mice were administered 3, 10 or 100 µg/kg of SEQ ID NO: 97 or phosphate buffered solution (vehicle control on standard or high-fat diet) subcutaneously. At predefined time points, more blood samples were taken to measure blood glucose and generate the blood glucose profile over 24 h.

At the tested doses, SEQ ID NO: 97 demonstrated a significant dose-dependent decrease in blood glucose compared to DIO control mice, lasting at least 8 h in the low and medium dose group and >24 h in the high dose group (p<0.0001, 2-W-ANOVA-RM, post hoc Dunnett's Test; FIG. 3, mean±SEM).

2) Body Weight

Female obese C57BL/6NCrl mice were treated for 4 weeks once daily subcutaneously in the morning, at the beginning of the light phase (12 h lights on) with 3, 10 or 100 µg/kg SEQ ID NO: 97 or vehicle. Body weight was recorded daily, and body fat content was determined before the start of treatment and after 4 weeks of treatment.

Treatment with SEQ ID NO: 97 reduced body weight, whereas in the high-fat diet control group an increase in body weight could be observed. These changes resulted from a decrease (or increase in the HFD control group) in body fat, as shown by the absolute changes in body fat content. These changes reached statistical significance in the medium and high dose group (*: p<0.05, 1-W-ANOVA, post hoc Dunnett's Test, Table 7).

TABLE 7

Weight change in DIO mice over a 4-week treatment period (mean ± SEM)

| Example (Dose) | Overall weight change (g) | Body fat change (g) |
| --- | --- | --- |
| Control standard diet | −0.7 ± 0.5 | −1.1 ± 0.5 |
| Control high-fat diet | 1.3 ± 0.5 | 1.0 ± 0.4 |
| SEQ ID NO: 97 (3 µg/kg) | −0.9 ± 1.0 | −0.5 ± 0.8 |
| SEQ ID NO: 97 (10 µg/kg) | −3.0 ± 1.4* | −2.5 ± 1.0* |
| SEQ ID NO: 97 (100 µg/kg) | −2.3 ± 0.9* | −2.4 ± 0.8* |

Example 14: Acute and Subchronic Effects of SEQ ID NO: 97 after Subcutaneous Treatment on Blood Glucose and HbA1c in Female Leptin-Receptor Deficient Diabetic db/db Mice 1. Glucose Profile After blood sampling to determine the blood glucose baseline level, fed diabetic female db/db mice were administered 3, 10 or 100 µg/kg of SEQ ID NO: 97 or phosphate buffered solution (vehicle-treated db/db control) subcutaneously. At predefined time points, more blood samples were taken to measure blood glucose and generate the blood glucose profile over 24 h.

At the tested doses, SEQ ID NO: 97 demonstrated a significant decrease in blood glucose compared to db/db control mice, lasting up to 8 h in the low and medium dose group and >24 h in the high dose group (p<0.0001 for lean control mice; p<0.01 1-8 h after treatment for low and medium dose, p≤0.0002 4-24 h for high dose; 2-W-ANOVA-RM, post hoc Dunnett's Test; FIG. 4, mean±SEM).

2. Blood Glucose & HbA1c

Female diabetic mice were treated for 4 weeks once daily subcutaneously with 3, 10 or 100 µg/kg SEQ ID NO: 97 or vehicle. Blood glucose and HbA1c were determined before start of treatment and at the end of the study after 4 weeks of treatment.

Before treatment started, no significant differences in blood glucose levels could be detected between db/db groups, only the lean control animals had significant lower glucose levels. During the 4 weeks of treatment, glucose levels increased in the vehicle-treated db/db control group, indicating a worsening of the diabetic situation. All SEQ ID NO: 97-treated animals displayed a significant lower blood glucose level than the db control mice at the end of the study (p<0.0001 for lean control mice; p<0.01 in SEQ ID NO: 97 groups; 2-W-ANOVA-RM, post hoc Dunnett's Test; FIG. 5, mean±SEM).

Corresponding to blood glucose, at the beginning of the study, no significant differences in HbA1c levels could be detected between db/db groups, only the lean control animals had significant lower levels. During the 4 weeks of treatment, HbA1c increased in the vehicle-treated db/db control group, corresponding to the increasing blood glucose levels. Animals treated with high dose SEQ ID NO: 97 displayed a significant lower HbA1c level than the db control mice at the end of the study (p<0.0001, 2-W-ANOVA-RM, post hoc Dunnett's Test; FIG. 6, mean±SEM).

Example 15: Comparison Testing

A selection of inventive exendin-4 derivatives comprising a functionalized amino acid in position 14 has been tested versus corresponding compounds having in this position 14 a 'non-functionalized' amino acid. The reference pair compounds and the corresponding EC50 values at GLP-1 and Glucagon receptors (indicated in pM) are given in Table 8. As shown, the inventive exendin-4 derivatives show a superior activity in comparison to the compounds with a 'non-functionalized' amino acid in position 14.

TABLE 8

Comparison of exendin-4 derivatives comprising a non-functionalized amino acid in position 14 vs. exendin-4 derivatives comprising a functionalized amino acid in position 14. EC50 values at GLP-1 and Glucagon receptors are indicated in pM.

| SEQ ID NO | EC50 hGLP-1R | EC50 hGlucagon-R | residue in position 14 |
| --- | --- | --- | --- |
| 182 | 5.8 | 419.0 | M |
| 115 | 2.4 | 1.9 | K(γE-x53) |
| 183 | 1020.0 | 916.0 | K |
| 97 | 6.8 | 1.2 | K(γE-x53) |
| 194 | 159.0 | 1290.0 | K(Ac) |
| 184 | 85.7 | 991.0 | M |
| 4 | 5.0 | 4.0 | K(γE-x53) |
| 185 | 75.7 | 262.0 | M |
| 125 | 31.4 | 6.9 | K(γE-x53) |
| 186 | 102.0 | 590.0 | M |
| 84 | 8.1 | 4.3 | K(γE-x53) |
| 187 | 152.0 | 195.0 | M |
| 78 | 17.8 | 1.6 | K(γE-x53) |
| 188 | 89.6 | 186.0 | M |
| 74 | 4.2 | 1.3 | K(γE-x53) |
| 189 | 5.6 | 1680.0 | M |
| 24 | 2.0 | 9.8 | K(γE-x53) |
| 190 | 21.3 | 1560.0 | M |
| 75 | 11.1 | 12.5 | K(γE-x53) |
| 192 | 6.8 | 478 | Nle |
| 30 | 3.2 | 7.0 | K(γE-x53) |
| 224 | 1.3 | 2930 | L |
| 216 | 4.7 | 19.5 | K(γE-x70) |
| 225 | 0.7 | 2870 | L |
| 215 | 5.3 | 42.6 | K(γE-x70) |

(M = methionine, K = lysine, Nle = norleucine, γE-x53 = (S)-4-Carboxy-4-hexadecanoylamino-butyryl-, Ac = acetate)

Example 16: Acute and Chronic Effects of SEQ ID NO: 24 after Subcutaneous Treatment on Body Weight in Male Diet-Induced Obese (DIO) C57BL/6NCrl Mice Body Weight Male obese C57BL/6NCrl mice were treated for 3 weeks twice daily subcutaneously with 0.5, 1.5, 5 or 15 µg/kg SEQ ID NO: 24 or vehicle. Body weight was recorded daily, and body fat content was determined before the start and after 3 weeks of treatment.

Treatment with SEQ ID NO: 24 reduced body weight significantly at dosages of 1.5, 5 and 15 µg/kg (*: p<0.05, 1-W-ANOVA, post hoc Dunnett's Test, Table 9, FIGS. 7 and 8). These changes resulted from a decrease in body fat, as shown by the absolute changes in body fat content (Table 9, FIG. 9).

TABLE 9

Weight change in DIO mice over a 3-week treatment period (mean ± SEM)

| Example (Dose) | Overall weight change (g) | Body fat change (g) |
|---|---|---|
| Control standard diet | 0.02 ± 0.2 | −0.02 ± 0.22 |
| Control high-fat diet | −0.5 ± 0.3 | −0.8 ± 0.3 |
| SEQ ID NO: 24 (0.5 µg/kg bid) | −0.9 ± 0.4 | −0.09 ± 0.3 |
| SEQ ID NO: 24 (1.5 µg/kg bid) | −6.9 ± 0.7 | −3.9 ± 0.5 |
| SEQ ID NO: 24 (5 µg/kg bid) | −7.4 ± 0.8 | −4.4 ± 0.7 |
| SEQ ID NO: 24 (15 µg/kg bid) | −9.1 ± 0.7 | −6.7 ± 0.4 |

Example 17: Acute and Chronic Effects of SEQ ID NO: 24 after Subcutaneous Treatment on Blood Glucose and HbA1c in Female Leptin-Receptor Deficient Diabetic db/db Mice 1. Glucose Profile After blood sampling to determine the blood glucose baseline level, fed diabetic female db/db mice were administered 50 µg/kg of SEQ ID NO: 24 or phosphate buffered solution (vehicle-treated db/db control) twice daily subcutaneously. At predefined time points, more blood samples were taken to measure blood glucose and generate the blood glucose profile over 24 h.

At the tested dose, SEQ ID NO: 24 demonstrated a significant decrease in blood glucose compared to db/db control mice, lasting >24 h (p<0.001; 2-W-ANOVA-RM, post hoc Dunnett's Test; FIG. 10, mean±SEM).

2. Blood Glucose & HbA1c

Female diabetic mice were treated for 4 weeks subcutaneously with 50 µg/kg SEQ ID NO: 24 or vehicle twice daily. Blood glucose and HbA1c were determined before start of treatment and at the end of the study after 4 weeks of treatment.

Before treatment started, no significant differences in blood glucose levels could be detected between db/db groups, only the lean control animals had significant lower glucose levels. During the 4 weeks of treatment, glucose levels increased in the vehicle-treated db/db control group, indicating a worsening of the diabetic situation. The SEQ ID NO: 24-treated animals displayed a significant lower blood glucose level than the db control mice at the end of the study (p<0.01 in SEQ ID NO: 24 group; 2-W-ANOVA-RM, post hoc Dunnett's Test; FIG. 11, mean±SEM).

Corresponding to blood glucose, at the beginning of the study, no significant differences in HbA1c levels could be detected between db/db groups, only the lean control animals had significant lower levels. During the 4 weeks of treatment, HbA1c increased in the vehicle-treated db/db control group, corresponding to the increasing blood glucose levels. Animals treated with SEQ ID NO: 24 displayed a significantly lower HbA1c level than the db control mice at the end of the study (p<0.001, 2-W-ANOVA-RM, post hoc Dunnett's Test; FIG. 12, mean±SEM).

TABLE 10

Sequences

| SEQ. ID | sequence |
|---|---|
| 1 | H-G-E-G-T-F-T-S-D-L-S-K-Q-M-E-E-E-A-V-R-L-F-I-E-W-L-K-N-G-G-P-S-S-G-A-P-P-P-S-NH2 |
| 2 | H-A-E-G-T-F-T-S-D-V-S-S-Y-L-E-G-Q-A-A-K-E-I-A-W-L-V-K-G-R-NH2 |
| 3 | H-S-Q-G-T-F-T-S-D-Y-S-K-Y-L-D-S-R-R-A-Q-D-V-Q-W-L-M-N-T-OH |
| 4 | H-dSer-Q-G-T-F-T-S-D-L-S-K-Q-K(γE-x53)-E-S-R-R-A-Q-D-F-I-E-W-L-K-A-G-G-P-S-S-G-A-P-P-P-S-NH2 |
| 5 | H-Aib-Q-G-T-F-T-S-D-L-S-K-Q-K(x53)-E-S-R-R-A-Q-D-F-I-E-W-L-K-A-G-P-S-S-G-A-P-P-P-S-NH2 |
| 6 | H-dSer-Q-G-T-F-T-S-D-L-S-K-Q-K(γE-x53)-E-S-R-R-A-Q-L-F-I-E-W-L-K-A-G-G-P-S-S-G-A-P-P-P-S-K(γE-x53)-NH2 |
| 7 | H-dSer-Q-G-T-F-T-S-D-L-S-K-Q-K(GABA-x53)-E-S-K-A-A-Q-D-F-I-E-W-L-K-A-G-G-P-S-S-G-A-P-P-P-S-NH2 |
| 8 | H-dSer-Q-G-T-F-T-S-D-L-S-K-Q-K(γE-x70)-D-S-R-R-A-Q-D-F-I-E-W-L-K-N-G-G-P-S-S-G-A-P-P-P-S-NH2 |
| 9 | H-dSer-Q-G-T-F-T-S-D-L-S-K-Q-K(γE-x75)-E-S-R-A-A-Q-D-F-I-E-W-L-K-A-G-G-P-S-S-G-A-P-P-P-S-NH2 |

TABLE 10-continued

Sequences

| SEQ. ID | sequence |
|---|---|
| 10 | H-dSer-Q-G-T-F-T-S-D-L-S-K-Q-K(γE-x53)-D-S-R-R-A-Q-D-F-I-E-W-L-K-N-G-G-P-S-S-G-A-P-P-P-S-NH(n-Propyl) |
| 11 | H-dSer-Q-G-T-F-T-S-D-L-S-K-Q-K(γE-x70)-E-S-Aib-A-A-Q-D-F-I-E-W-L-K-A-G-G-P-S-S-G-A-P-P-P-S-NH2 |
| 12 | H-dSer-Q-G-T-F-T-S-D-L-S-K-Q-K(γE-x53)-E-S-Aib-A-A-Aib-L-F-I-E-W-L-K-A-G-G-P-S-S-G-A-P-P-P-S-NH2 |
| 13 | H-Aib-Q-G-T-F-T-S-D-L-S-K-Q-K(γE-x53)-E-S-Aib-A-A-Q-D-F-I-E-W-L-K-A-G-G-P-S-S-G-A-P-P-P-S-NH2 |
| 14 | H-dSer-Q-G-T-F-T-S-D-L-S-K-Q-K(γE-x53)-E-S-Aib-A-A-Q-D-F-I-E-W-L-K-A-G-G-P-S-S-G-A-P-P-P-S-NH2 |
| 15 | H-dSer-Q-G-T-F-T-S-D-L-S-K-Q-K(γE-x53)-E-S-Aib-A-A-Q-L-F-I-E-W-L-K-A-G-G-P-S-S-G-A-P-P-P-S-NH2 |
| 16 | H-dSer-Q-G-T-F-T-S-D-L-S-K-Q-K(γE-x53)-E-E-E-A-A-Q-D-F-I-E-W-L-K-A-G-G-P-S-S-G-A-P-P-P-S-NH2 |
| 17 | H-dSer-Q-G-T-F-T-S-D-L-S-K-Q-K(γE-x53)-E-E-E-A-A-K-D-F-I-E-W-L-K-A-G-G-P-S-S-G-A-P-P-P-S-NH2 |
| 18 | H-dSer-Q-G-T-F-T-S-D-L-S-K-Q-K(γE-x53)-E-E-E-A-A-Aib-D-F-I-E-W-L-K-A-G-G-P-S-S-G-A-P-P-P-S-NH2 |
| 19 | H-dSer-Q-G-T-F-T-S-D-L-S-K-Q-K(γE-x53)-E-E-E-A-A-K-L-F-I-E-W-L-K-A-G-G-P-S-S-G-A-P-P-P-S-NH2 |
| 20 | H-dSer-Q-G-T-F-T-S-D-L-S-K-Q-K(γE-x53)-E-S-E-A-A-Q-D-F-I-E-W-L-K-A-G-G-P-S-S-G-A-P-P-P-S-NH2 |
| 21 | H-dSer-Q-G-T-F-T-S-D-L-S-K-Q-K(γE-x53)-E-S-E-A-A-Q-L-F-I-E-W-L-K-A-G-G-P-S-S-G-A-P-P-P-S-NH2 |
| 22 | H-dSer-Q-G-T-F-T-S-D-L-S-K-Q-K(γE-x53)-D-E-K-A-A-Q-D-F-I-E-W-L-K-A-G-G-P-S-S-G-A-P-P-P-S-NH2 |
| 23 | H-dSer-Q-G-T-F-T-S-D-L-S-K-Q-K(γE-x53)-E-E-K-K-A-K-L-F-I-E-W-L-K-A-G-G-P-S-S-G-A-P-P-P-S-NH2 |
| 24 | H-dSer-Q-G-T-F-T-S-D-L-S-K-Q-K(γE-x53)-E-S-K-A-A-Q-D-F-I-E-W-L-K-A-G-G-P-S-S-G-A-P-P-P-S-NH2 |
| 25 | H-Aib-Q-G-T-F-T-S-D-L-S-K-Q-K(γE-x53)-E-S-K-A-A-Q-D-F-I-E-W-L-K-A-G-G-P-S-S-G-A-P-P-P-S-NH2 |
| 26 | H-dSer-Q-G-T-F-T-S-D-L-S-K-Q-K(γE-x70)-E-S-K-A-A-Q-D-F-I-E-W-L-K-A-G-G-P-S-S-G-A-P-P-P-S-NH2 |
| 27 | H-dSer-Q-G-T-F-T-S-D-L-S-K-Q-K(γE-x70)-E-S-K-A-A-Q-L-F-I-E-W-L-K-A-G-G-P-S-S-G-A-P-P-P-S-NH2 |
| 28 | H-dSer-Q-G-T-F-T-S-D-L-S-K-Q-K(γE-x53)-E-S-K-A-A-Q-E-F-I-E-W-L-K-A-G-G-P-S-S-G-A-P-P-P-S-NH2 |
| 29 | H-dSer-Q-G-T-F-T-S-D-L-S-K-Q-K(γE-x53)-E-S-K-A-A-Q-L-F-I-E-W-L-K-A-G-G-P-S-S-G-A-P-P-P-S-NH2 |
| 30 | H-dSer-Q-G-T-F-T-S-D-L-S-K-Q-K(γE-x53)-D-S-K-A-A-Q-D-F-I-E-W-L-K-A-G-G-P-S-S-G-A-P-P-P-S-NH2 |
| 31 | H-Aib-Q-G-T-F-T-S-D-L-S-K-Q-K(γE-x53)-D-S-K-A-A-Q-D-F-I-E-W-L-K-A-G-G-P-S-S-G-A-P-P-P-S-NH2 |
| 32 | H-dSer-Q-G-T-F-T-S-D-L-S-K-Q-K(x53)-E-S-K-A-A-Q-D-F-I-E-W-L-K-A-G-G-P-S-S-G-A-P-P-P-S-NH2 |
| 33 | H-Aib-Q-G-T-F-T-S-D-L-S-K-Q-K(x53)-E-S-K-A-A-Q-D-F-I-E-W-L-K-A-G-G-P-S-S-G-A-P-P-P-S-NH2 |
| 34 | H-dSer-Q-G-T-F-T-S-D-L-S-K-Q-K(γE-x53)-D-E-Q-A-A-Q-D-F-I-E-W-L-K-A-G-G-P-S-S-G-A-P-P-P-S-NH2 |

TABLE 10-continued

Sequences

| SEQ. ID | sequence |
|---|---|
| 35 | H-dSer-Q-G-T-F-T-S-D-L-S-K-Q-K(γE-x53)-E-S-Q-A-A-Q-D-F-I-E-W-L-K-A-G-G-P-S-S-G-A-P-P-P-S-NH2 |
| 36 | H-Aib-Q-G-T-F-T-S-D-L-S-K-Q-K(γE-x53)-E-S-Q-A-A-Q-D-F-I-E-W-L-K-A-G-G-P-S-S-G-A-P-P-P-S-NH2 |
| 37 | H-dSer-Q-G-T-F-T-S-D-L-S-K-Q-K(γE-x53)-E-S-Q-A-A-Q-E-F-I-E-W-L-K-A-G-G-P-S-S-G-A-P-P-P-S-NH2 |
| 38 | H-Aib-Q-G-T-F-T-S-D-L-S-K-Q-K(γE-x53)-E-S-Q-A-A-Q-E-F-I-E-W-L-K-A-G-G-P-S-S-G-A-P-P-P-S-NH2 |
| 39 | H-dSer-Q-G-T-F-T-S-D-L-S-K-Q-K(γE-x53)-D-S-Q-A-A-Q-D-F-I-E-W-L-K-A-G-G-P-S-S-G-A-P-P-P-S-NH2 |
| 40 | H-dSer-Q-G-T-F-T-S-D-L-S-K-Q-K(γE-x70)-E-S-Q-A-A-Q-D-F-I-E-W-L-K-A-G-G-P-S-S-G-A-P-P-P-S-NH2 |
| 41 | H-Aib-Q-G-T-F-T-S-D-L-S-K-Q-K(γE-x70)-E-S-Q-A-A-Q-D-F-I-E-W-L-K-A-G-G-P-S-S-G-A-P-P-P-S-NH2 |
| 42 | H-dSer-Q-G-T-F-T-S-D-L-S-K-Q-K(x53)-E-S-Q-A-A-Q-D-F-I-E-W-L-K-A-G-G-P-S-S-G-A-P-P-P-S-NH2 |
| 43 | H-Aib-Q-G-T-F-T-S-D-L-S-K-Q-K(x53)-E-S-Q-A-A-Q-D-F-I-E-W-L-K-A-G-G-P-S-S-G-A-P-P-P-S-NH2 |
| 44 | H-dSer-Q-G-T-F-T-S-D-L-S-K-Q-K(γE-x53)-E-S-R-A-A-Q-D-F-I-E-W-L-K-A-G-G-P-S-S-G-A-P-P-P-S-NH2 |
| 45 | H-dSer-Q-G-T-F-T-S-D-L-S-K-Q-K(γE-x70)-E-S-R-A-A-Q-L-F-I-E-W-L-K-A-G-G-P-S-S-G-A-P-P-P-S-NH2 |
| 46 | H-dSer-Q-G-T-F-T-S-D-L-S-K-Q-K(γE-x53)-E-S-R-A-A-Aib-L-F-I-E-W-L-K-A-G-G-P-S-S-G-A-P-P-P-S-NH2 |
| 47 | H-dSer-Q-G-T-F-T-S-D-L-S-K-Q-K(γE-x53)-E-S-R-A-A-Q-E-F-I-E-W-L-K-A-G-G-P-S-S-G-A-P-P-P-S-NH2 |
| 48 | H-dSer-Q-G-T-F-T-S-D-L-S-K-Q-K(γE-x53)-E-S-R-A-A-Q-L-F-I-E-W-L-K-A-G-G-P-S-S-G-A-P-P-P-S-NH2 |
| 49 | H-dSer-Q-G-T-F-T-S-D-L-S-K-Q-K(γE-γE-x53)-E-S-R-A-A-Q-D-F-I-E-W-L-K-A-G-G-P-S-S-G-A-P-P-P-S-NH2 |
| 50 | H-dSer-Q-G-T-F-T-S-D-L-S-K-Q-K(GABA-x53)-E-S-R-A-A-Q-D-F-I-E-W-L-K-A-G-G-P-S-S-G-A-P-P-P-S-NH2 |
| 51 | H-dSer-Q-G-T-F-T-S-D-L-S-K-Q-K(γE-x70)-E-S-R-A-A-Q-D-F-I-E-W-L-K-A-G-G-P-S-S-G-A-P-P-P-S-NH2 |
| 52 | H-dSer-Q-G-T-F-T-S-D-L-S-K-Q-K(γE-γE-x70)-E-S-R-A-A-Q-D-F-I-E-W-L-K-A-G-G-P-S-S-G-A-P-P-P-S-NH2 |
| 53 | H-dSer-Q-G-T-F-T-S-D-L-S-K-Q-K(GABA-x70)-E-S-R-A-A-Q-D-F-I-E-W-L-K-A-G-G-P-S-S-G-A-P-P-P-S-NH2 |
| 54 | H-dSer-Q-G-T-F-T-S-D-L-S-K-Q-K(βA-βA-x70)-E-S-R-A-A-Q-D-F-I-E-W-L-K-A-G-G-P-S-S-G-A-P-P-P-S-NH2 |
| 55 | H-dSer-Q-G-T-F-T-S-D-L-S-K-Q-K(γE-x74)-E-S-R-A-A-Q-D-F-I-E-W-L-K-A-G-G-P-S-S-G-A-P-P-P-S-NH2 |
| 56 | H-dSer-Q-G-T-F-T-S-D-L-S-K-Q-K(GABA-x74)-E-S-R-A-A-Q-D-F-1-E-W-L-K-A-G-G-P-S-S-G-A-P-P-P-S-NH2 |
| 57 | H-dSer-Q-G-T-F-T-S-D-L-S-K-Q-K(γE-x60)-E-S-R-A-A-Q-D-F-I-E-W-L-K-A-G-G-P-S-S-G-A-P-P-P-S-NH2 |
| 58 | H-dSer-Q-G-T-F-T-S-D-L-S-K-Q-K(GABA-x60)-E-S-R-A-A-Q-D-F-I-E-W-L-K-A-G-G-P-S-S-G-A-P-P-P-S-NH2 |
| 59 | H-dSer-Q-G-T-F-T-S-D-L-S-K-Q-K(γE-x76)-E-S-R-A-A-Q-D-F-I-E-W-L-K-A-G-G-P-S-S-G-A-P-P-P-S-NH2 |

TABLE 10-continued

Sequences

| SEQ. ID | sequence |
|---|---|
| 60 | H-dSer-Q-G-T-F-T-S-D-L-S-K-Q-K(γE-x77)-E-S-R-A-A-Q-D-F-I-E-W-L-K-A-G-G-P-S-S-G-A-P-P-P-S-NH2 |
| 61 | H-dSer-Q-G-T-F-T-S-D-L-S-K-Q-K(γE-x79)-E-S-R-A-A-Q-D-F-I-E-W-L-K-A-G-G-P-S-S-G-A-P-P-P-S-NH2 |
| 62 | H-dSer-Q-G-T-F-T-S-D-L-S-K-Q-K(γE-x80)-E-S-R-A-A-Q-D-F-I-E-W-L-K-A-G-G-P-S-S-G-A-P-P-P-S-NH2 |
| 63 | H-dSer-Q-G-T-F-T-S-D-L-S-K-Q-K(γE-x81)-E-S-R-A-A-Q-D-F-I-E-W-L-K-A-G-G-P-S-S-G-A-P-P-P-S-NH2 |
| 64 | H-dSer-Q-G-T-F-T-S-D-L-S-K-Q-K(γE-x82)-E-S-R-A-A-Q-D-F-I-E-W-L-K-A-G-G-P-S-S-G-A-P-P-P-S-NH2 |
| 65 | H-dSer-Q-G-T-F-T-S-D-L-S-K-Q-K(γE-x70)-E-S-R-A-A-Q-D-F-I-E-W-L-K-A-G-G-P-S-S-G-A-P-P-P-S-NH2 |
| 66 | H-dSer-Q-G-T-F-T-S-D-L-S-K-Q-K(x53)-E-S-R-A-A-Q-D-F-I-E-W-L-K-A-G-G-P-S-S-G-A-P-P-P-S-NH2 |
| 67 | H-dSer-Q-G-T-F-T-S-D-L-S-K-Q-K(γE-x53)-D-S-R-R-A-Aib-D-F-I-E-W-L-K-A-G-G-P-S-S-G-A-P-P-P-S-NH2 |
| 68 | H-dSer-Q-G-T-F-T-S-D-L-S-K-Q-K(γE-x53)-E-S-R-R-A-Q-L-F-I-E-W-L-K-A-G-G-P-S-S-G-A-P-P-P-S-NH2 |
| 69 | H-dSer-Q-G-T-F-T-S-D-L-S-K-Q-K(x53)-E-S-R-R-A-Q-L-F-I-E-W-L-K-A-G-G-P-S-S-G-A-P-P-P-S-NH2 |
| 70 | H-dSer-Q-G-T-F-T-S-D-L-S-K-Q-K(γE-x53)-E-S-R-A-A-Q-L-F-I-E-W-L-K-A-G-G-P-S-S-G-A-P-P-P-S-NH2 |
| 71 | H-dSer-Q-G-T-F-T-S-D-L-S-K-Q-Orn(γE-x53)-E-S-R-R-A-Q-D-F-I-E-W-L-K-A-G-G-P-S-S-G-A-P-P-P-S-NH2 |
| 72 | H-dSer-Q-G-T-F-T-S-D-L-S-K-Q-Dab(γE-x53)-E-S-R-R-A-Q-D-F-I-E-W-L-K-A-G-G-P-S-S-G-A-P-P-P-S-NH2 |
| 73 | H-dSer-H-G-T-F-T-S-D-L-S-K-Q-K(γE-x53)-E-S-R-R-A-Q-D-F-I-E-W-L-K-A-G-G-P-S-S-G-A-P-P-P-S-NH2 |
| 74 | H-dSer-Q-G-T-F-T-S-D-L-S-K-Q-K(γE-x53)-D-S-R-R-A-Q-D-F-I-E-W-L-K-A-G-G-P-S-S-G-A-P-P-P-S-NH2 |
| 75 | H-dSer-Q-G-T-F-T-S-D-L-S-K-Q-K(γE-x53)-E-S-R-R-A-Aib-D-F-I-E-W-L-K-A-G-G-P-S-S-G-A-P-P-P-S-NH2 |
| 76 | H-dSer-Q-G-T-F-T-S-D-L-S-K-Q-K(x53)-E-S-R-R-A-Aib-D-F-I-E-W-L-K-A-G-G-P-S-S-G-A-P-P-P-S-NH2 |
| 77 | H-Aib-Q-G-T-F-T-S-D-L-S-K-Q-K(γE-x53)-E-S-R-A-A-Q-D-F-I-E-W-L-K-A-G-G-P-S-S-G-A-P-P-P-S-NH2 |
| 78 | H-dSer-Q-G-T-F-T-S-D-L-S-K-Q-K(γE-x53)-D-S-R-R-A-Q-D-F-I-E-W-L-K-Aib-G-G-P-S-S-G-A-P-P-P-S-NH2 |
| 79 | H-dSer-Q-G-T-F-T-S-D-L-S-K-Q-K(γE-x53)-E-S-R-R-A-Q-D-F-I-E-W-L-K-Aib-G-G-P-S-S-G-A-P-P-P-S-NH2 |
| 80 | H-dSer-Q-G-T-F-T-S-D-L-S-K-Q-K(γE-x53)-D-S-R-R-A-Q-D-F-I-E-W-L-K-D-G-G-P-S-S-G-A-P-P-P-S-NH2 |
| 81 | H-dSer-Q-G-T-F-T-S-D-L-S-K-Q-K(x53)-D-S-R-R-A-Q-D-F-I-E-W-L-K-D-G-G-P-S-S-G-A-P-P-P-S-NH2 |
| 82 | H-dSer-Q-G-T-F-T-S-D-L-S-K-Q-K(γE-x53)-E-S-R-R-A-Q-D-F-I-E-W-L-K-E-G-G-P-S-S-G-R-P-P-P-S-NH2 |
| 83 | H-dSer-Q-G-T-F-T-S-D-L-S-K-Q-K(x53)-E-S-R-R-A-Q-D-F-I-E-W-L-K-E-G-G-P-S-S-G-R-P-P-P-S-NH2 |
| 84 | H-dSer-Q-G-T-F-T-S-D-L-S-K-Q-K(γE-x53)-D-S-R-R-A-Q-D-F-I-E-W-L-K-K-G-G-P-S-S-G-A-P-P-P-S-NH2 |

TABLE 10-continued

Sequences

| SEQ. ID | sequence |
|---|---|
| 85 | H-dSer-Q-G-T-F-T-S-D-L-S-K-Q-K(γE-x53)-E-S-R-R-A-Q-D-F-I-E-W-L-K-K-G-G-P-S-S-G-A-P-P-P-S-NH2 |
| 86 | H-dSer-Q-G-T-F-T-S-D-L-S-K-Q-K(γE-x53)-D-S-Q-A-A-Q-D-F-I-E-W-L-K-N-T-G-P-S-S-G-A-P-P-P-S-NH2 |
| 87 | H-dSer-Q-G-T-F-T-S-D-L-S-K-Q-K(γE-x53)-D-E-R-R-A-K-D-F-I-E-W-L-K-N-G-G-P-S-S-G-A-P-P-P-S-NH2 |
| 88 | H-dSer-Q-G-T-F-T-S-D-L-S-K-Q-K(γE-x53)-E-K-R-R-A-Q-D-F-I-E-W-L-K-N-G-G-P-S-S-G-A-P-P-P-S-NH2 |
| 89 | H-dSer-Q-G-T-F-T-S-D-L-S-K-Q-K(γE-x60)-D-S-R-R-A-Q-D-F-I-E-W-L-K-N-G-G-P-S-S-G-A-P-P-P-S-NH2 |
| 90 | H-dSer-Q-G-T-F-T-S-D-L-S-K-Q-K(γE-x69)-D-S-R-R-A-Q-D-F-I-E-W-L-K-N-G-G-P-S-S-G-A-P-P-P-S-NH2 |
| 91 | H-dSer-Q-G-T-F-T-S-D-L-S-K-Q-K(γE-x72)-D-S-R-R-A-Q-D-F-I-E-W-L-K-N-G-G-P-S-S-G-A-P-P-P-S-NH2 |
| 92 | H-dSer-Q-G-T-F-T-S-D-L-S-K-Q-K(γE-x53)-D-S-R-R-A-Q-D-F-I-E-W-L-K-N-T-G-P-S-S-G-A-P-P-P-S-NH2 |
| 93 | H-dSer-Q-G-T-F-T-S-D-L-S-K-Q-K(γE-x53)-D-S-R-R-A-Q-D-F-I-E-W-L-K-N-A-G-P-S-S-G-A-P-P-P-S-NH2 |
| 94 | H-dSer-Q-G-T-F-T-S-D-L-S-K-Q-K(γE-x53)-D-S-R-R-A-Q-D-F-I-E-W-L-K-N-dAla-G-P-S-S-G-A-P-P-P-S-NH2 |
| 95 | H-dSer-Q-G-T-F-T-S-D-L-S-K-Q-K(γE-x53)-E-S-R-R-A-Q-D-F-I-E-W-L-K-N-A-G-P-S-S-G-A-P-P-P-S-NH2 |
| 96 | H-dSer-Q-G-T-F-T-S-D-L-S-K-Q-K(γE-x53)-E-S-R-R-A-Q-D-F-I-E-W-L-K-N-T-G-P-S-S-G-A-P-P-P-S-NH2 |
| 97 | H-dSer-Q-G-T-F-T-S-D-L-S-K-Q-K(γE-x53)-D-S-R-R-A-Q-D-F-I-E-W-L-K-N-G-G-P-S-S-G-A-P-P-P-S-NH2 |
| 98 | H-dSer-Q-G-T-F-T-S-D-L-S-K-Q-K(γE-x53)-D-S-R-R-A-Q-D-F-I-E-W-L-K-N-G-G-P-S-S-G-A-P-P-P-S-NH(pyrrolidin) |
| 99 | H-dSer-Q-G-T-F-T-S-D-L-S-K-Q-K(γE-x53)-D-S-R-R-A-Q-D-F-I-E-W-L-K-N-G-G-P-S-S-G-A-P-P-P-S-NH(benzyl) |
| 100 | H-dSer-Q-G-T-F-T-S-D-L-S-K-Q-K(γE-x53)-D-S-R-R-A-Q-D-F-I-E-W-L-K-N-G-G-P-S-S-G-A-P-P-P-S-NH(tert.butyl) |
| 101 | H-dSer-Q-G-T-F-T-S-D-L-S-K-Q-K(γE-x53)-D-S-R-R-A-Q-D-F-I-E-W-L-K-N-G-G-P-S-S-G-A-P-P-P-S-N(diethyl) |
| 102 | H-dSer-Q-G-T-F-T-S-D-L-S-K-Q-K(γE-x53)-D-S-R-R-A-Q-D-F-I-E-W-L-K-N-G-G-P-S-S-G-A-P-P-P-S-N(morpholin) |
| 103 | H-dSer-Q-G-T-F-T-S-D-L-S-K-Q-K(γE-x53)-D-S-R-R-A-Q-D-F-I-E-W-L-K-N-G-G-P-S-S-G-A-P-P-P-S-NH(CH2—CF3) |
| 104 | H-dSer-Q-G-T-F-T-S-D-L-S-K-Q-K(γE-x53)-D-S-R-R-A-Q-D-F-I-E-W-L-K-N-G-G-P-S-S-G-A-P-P-P-S-NH[(CH2—CH2—O)4-CH2—CH2—COOH] |
| 105 | H-dSer-Q-G-T-F-T-S-D-L-S-K-Q-K(γE-x53)-D-S-R-R-A-Q-D-F-I-E-W-L-K-N-G-G-P-S-S-G-A-P-P-P-S-NH[(CH2—CH2—O)24-CH2—CH2—COOH] |
| 106 | H-dSer-Q-G-T-F-T-S-D-L-S-K-Q-K(γE-x53)-D-S-R-R-A-Q-D-F-I-E-W-L-K-N-G-G-P-S-S-G-A-P-P-P-S-NH[(CH2)15-CH3] |
| 107 | H-dSer-Q-G-T-F-T-S-D-L-S-K-Q-K(γE-x53)-D-S-R-R-A-Q-D-F-I-E-W-L-K-N-G-G-P-S-S-G-A-P-P-P-S-NH[(CH2)12-OH] |
| 108 | H-dSer-Q-G-T-F-T-S-D-L-S-K-Q-K(γE-x53)-D-S-R-R-A-Q-D-F-I-E-W-L-K-N-G-G-P-S-S-G-A-P-P-P-S-NH[(CH2)14-CH3] |
| 109 | H-dSer-Q-G-T-F-T-S-D-L-S-K-Q-K(γE-x53)-D-S-R-R-A-Q-D-F-I-E-W-L-K-N-G-G-P-S-S-G-A-P-P-P-S-NH[(CH2)17-CH3] |

TABLE 10-continued

Sequences

| SEQ. ID | sequence |
|---|---|
| 110 | H-dSer-Q-G-T-F-T-S-D-L-S-K-Q-K(γE-x53)-D-S-R-R-A-Q-D-F-I-E-W-L-K-N-G-G-P-S-S-G-A-P-P-P-S-NH[(CH2)13-CH3] |
| 111 | H-dSer-Q-G-T-F-T-S-D-L-S-K-Q-K(γE-x53)-E-S-R-R-A-Q-D-F-I-E-W-L-K-N-G-G-P-S-S-G-A-P-P-P-S-K-NH2 |
| 112 | H-dSer-Q-G-T-F-T-S-D-L-S-K-Q-K(x53)-E-S-R-R-A-Q-D-F-I-E-W-L-K-N-G-G-P-S-S-G-A-P-P-P-S-K-NH2 |
| 113 | H-dSer-Q-G-T-F-T-S-D-L-S-K-Q-K(γE-x53)-E-S-R-R-A-Q-D-F-I-E-W-L-K-N-G-G-P-S-S-G-A-P-P-P-K-NH2 |
| 114 | H-dSer-Q-G-T-F-T-S-D-L-S-K-Q-K(x53)-E-S-R-R-A-Q-D-F-I-E-W-L-K-N-G-G-P-S-S-G-A-P-P-P-K-NH2 |
| 115 | H-Aib-Q-G-T-F-T-S-D-L-S-K-Q-K(γE-x53)-D-S-R-R-A-Q-D-F-I-E-W-L-K-N-G-G-P-S-S-G-A-P-P-P-S-NH2 |
| 116 | H-dSer-Q-G-T-F-T-S-D-L-S-K-Q-K(γE-x53)-E-S-R-R-A-Q-D-F-I-E-W-L-K-N-G-G-P-S-S-G-A-P-P-P-S-NH2 |
| 117 | H-Aib-Q-G-T-F-T-S-D-L-S-K-Q-K(γE-x53)-E-S-R-R-A-Q-D-F-I-E-W-L-K-N-G-G-P-S-S-G-A-P-P-P-S-NH2 |
| 118 | H-dSer-Q-G-T-F-T-S-D-L-S-K-Q-K(γE-x53)-D-S-R-R-A-Aib-D-F-I-E-W-L-K-N-G-G-P-S-S-G-A-P-P-P-S-NH2 |
| 119 | H-dSer-Q-G-T-F-T-S-D-L-S-K-Q-K(x53)-E-S-R-R-A-Aib-D-F-I-E-W-L-K-N-G-G-P-S-S-G-A-P-P-P-S-NH2 |
| 120 | H-dSer-Q-G-T-F-T-S-D-L-S-K-Q-K(γE-x53)-E-S-R-R-A-Aib-D-F-I-E-W-L-K-N-G-G-P-S-S-G-A-P-P-P-S-NH2 |
| 121 | H-dSer-Q-G-T-F-T-S-D-L-S-K-Q-K(γE-x53)-E-S-R-A-A-Aib-L-F-I-E-W-L-K-N-G-G-P-S-S-G-A-P-P-P-S-NH2 |
| 122 | H-dSer-Q-G-T-F-T-S-D-L-S-K-Q-K(x53)-E-S-R-A-A-Aib-L-F-I-E-W-L-K-N-G-G-P-S-S-G-A-P-P-P-S-NH2 |
| 123 | H-dSer-Q-G-T-F-T-S-D-L-S-K-Q-K(γE-x53)-D-S-Q-A-A-Q-D-F-I-E-W-L-K-R-G-G-P-S-S-G-A-P-P-P-S-NH2 |
| 124 | H-dSer-Q-G-T-F-T-S-D-L-S-K-Q-K(γE-x53)-D-S-Q-A-A-Q-D-F-I-E-W-L-K-R-A-G-P-S-S-G-A-P-P-P-S-NH2 |
| 125 | H-dSer-Q-G-T-F-T-S-D-L-S-K-Q-K(γE-x53)-D-S-R-R-A-Q-D-F-I-E-W-L-K-R-G-G-P-S-S-G-A-P-P-P-S-NH2 |
| 126 | H-dSer-Q-G-T-F-T-S-D-L-S-K-Q-K(γE-x53)-E-S-R-R-A-Q-D-F-I-E-W-L-K-R-dAla-G-P-S-S-G-A-P-P-P-S-NH2 |
| 127 | H-dSer-Q-G-T-F-T-S-D-L-S-K-Q-K(γE-x53)-E-S-R-R-A-Q-D-F-I-E-W-L-K-R-G-G-P-S-S-G-A-P-P-P-S-NH2 |
| 128 | H-dSer-Q-G-T-F-T-S-D-L-S-K-Q-K(γE-x53)-D-S-R-R-A-Q-D-F-I-E-W-L-K-S-G-G-P-S-S-G-A-P-P-P-S-NH2 |
| 129 | H-dSer-Q-G-T-F-T-S-D-L-S-K-Q-K(γE-x53)-E-S-R-R-A-Q-D-F-I-E-W-L-K-S-G-G-P-S-S-G-A-P-P-P-S-NH2 |
| 130 | H-dSer-Q-G-T-F-T-S-D-L-S-K-Q-K(γE-x70)-E-S-Aib-A-A-Q-L-F-I-E-W-L-K-A-G-G-P-S-S-G-A-P-P-P-S-NH2 |
| 131 | H-dSer-Q-G-T-F-T-S-D-L-S-K-Q-K(GABA-x70)-E-S-Aib-A-A-Q-L-F-I-E-W-L-K-A-G-G-P-S-S-G-A-P-P-P-S-NH2 |
| 132 | H-Aib-Q-G-T-F-T-S-D-L-S-K-Q-K(γE-x53)-E-S-Aib-A-A-Q-L-F-I-E-W-L-K-A-G-G-P-S-S-G-A-P-P-P-S-NH2 |
| 133 | H-Aib-Q-G-T-F-T-S-D-L-S-K-Q-K(γE-x70)-D-E-K-A-A-K-L-F-I-E-W-L-K-A-dAla-G-P-S-S-G-A-P-P-P-S-NH2 |
| 134 | H-dSer-Q-G-T-F-T-S-D-L-S-K-Q-K(x52)-E-S-K-A-A-Q-D-F-I-E-W-L-K-A-G-G-P-S-S-G-A-P-P-P-S-NH2 |

TABLE 10-continued

Sequences

| SEQ. ID | sequence |
|---|---|
| 135 | H-dSer-Q-G-T-F-T-S-D-L-S-K-Q-K(x52)-E-S-K-A-A-Q-E-F-I-E-W-L-K-A-G-G-P-S-S-G-A-P-P-P-S-NH2 |
| 136 | H-dSer-Q-G-T-F-T-S-D-L-S-K-Q-K(x52)-E-S-K-A-A-Q-L-F-I-E-W-L-K-A-G-G-P-S-S-G-A-P-P-P-S-NH2 |
| 137 | H-dSer-H-G-T-F-T-S-D-L-S-K-Q-K(γE-X70)-D-S-K-A-A-Q-D-F-I-E-W-L-K-A-G-G-P-S-S-G-A-P-P-P-S-NH2 |
| 138 | H-dSer-H-G-T-F-T-S-D-L-S-K-Q-K(γE-X70)-D-S-K-A-A-Q-L-F-I-E-W-L-K-A-dAla-G-P-S-S-G-A-P-P-P-S-NH2 |
| 139 | H-dSer-Q-G-T-F-T-S-D-L-S-K-Q-K(γE-x76)-D-S-K-A-A-Q-D-F-I-E-W-L-K-A-G-G-P-S-S-G-A-P-P-P-S-NH2 |
| 140 | H-dSer-Q-G-T-F-T-S-D-L-S-K-Q-K(γE-γE-x53)-D-S-K-A-A-Q-D-F-I-E-W-L-K-A-G-G-P-S-S-G-A-P-P-P-S-NH2 |
| 141 | H-dSer-Q-G-T-F-T-S-D-L-S-K-Q-K(Phospho1)-D-S-K-A-A-Q-D-F-I-E-W-L-K-A-G-G-P-S-S-G-A-P-P-P-S-NH2 |
| 142 | H-dSer-Q-G-T-F-T-S-D-L-S-K-Q-K(γE-X95)-D-S-K-A-A-Q-D-F-I-E-W-L-K-A-G-G-P-S-S-G-A-P-P-P-S-NH2 |
| 143 | H-dSer-Q-G-T-F-T-S-D-L-S-K-Q-K(γE-X70)-D-S-K-A-A-Q-D-F-I-E-W-L-K-A-dAla-G-P-S-S-G-A-P-P-P-S-NH2 |
| 144 | H-dSer-Q-G-T-F-T-S-D-L-S-K-Q-K(γE-x53)-D-S-K-A-Aib-Q-D-F-I-E-W-L-K-A-G-G-P-S-S-G-A-P-P-P-S-NH2 |
| 145 | H-dSer-Q-G-T-F-T-S-D-L-S-K-Q-K(γE-x53)-D-S-K-A-S-Q-D-F-I-E-W-L-K-A-G-G-P-S-S-G-A-P-P-P-S-NH2 |
| 146 | H-dSer-Q-G-T-F-T-S-D-L-S-K-Q-K(γE-x53)-D-S-K-A-L-Q-D-F-I-E-W-L-K-A-G-G-P-S-S-G-A-P-P-P-S-NH2 |
| 147 | H-dSer-Q-G-T-F-T-S-D-L-S-K-Q-K(γE-x53)-D-S-K-A-A-Q-D-F-I-E-W-K-K-A-G-G-P-S-S-G-A-P-P-P-S-NH2 |
| 148 | H-Aib-Q-G-T-F-T-S-D-L-S-K-Q-K(γE-x70)-D-S-K-A-A-Q-L-F-I-E-W-L-K-A-dAla-G-P-S-S-G-A-P-P-P-S-NH2 |
| 149 | H-Aib-Q-G-T-F-T-S-D-L-S-K-Q-K(γE-x76)-D-S-K-A-A-Q-L-F-I-E-W-L-K-A-dAla-G-P-S-S-G-A-P-P-P-S-NH2 |
| 150 | H-dSer-Q-G-T-F-T-S-D-L-S-K-Q-K(γE-x53)-E-S-L-A-A-Q-D-F-I-E-W-L-K-A-G-G-P-S-S-G-A-P-P-P-S-NH2 |
| 151 | H-dSer-Q-G-T-F-T-S-D-L-S-K-Q-K(γE-x53)-D-E-Q-A-A-K-D-F-I-E-W-L-K-A-G-G-P-S-S-G-A-P-P-P-S-NH2 |
| 152 | H-Aib-Q-G-T-F-T-S-D-L-S-K-Q-K(γE-X70)-D-E-Q-R-A-K-E-F-I-E-W-L-K-A-G-G-P-S-S-G-A-P-P-P-S-NH2 |
| 153 | H-Aib-Q-G-T-F-T-S-D-L-S-K-Q-K(γE-x70)-D-E-Q-A-A-K-L-F-I-E-W-L-K-A-dAla-G-P-S-S-G-A-P-P-P-S-NH2 |
| 154 | H-Aib-Q-G-T-F-T-S-D-L-S-K-Q-K(γE-x70)-E-S-Q-A-A-Q-D-F-I-E-W-L-K-A-G-G-P-S-S-G-A-P-P-P-S-NH2 |
| 155 | H-Aib-Q-G-T-F-T-S-D-L-S-K-Q-K(γE-x53)-D-S-Q-A-A-Q-D-F-I-E-W-L-K-A-G-G-P-S-S-G-A-P-P-P-S-NH2 |
| 156 | H-Aib-Q-G-T-F-T-S-D-L-S-K-Q-K(γE-X70)-D-S-Q-A-A-Q-D-F-I-E-W-L-K-A-G-G-P-S-S-G-A-P-P-P-S-NH2 |
| 157 | H-dSer-Q-G-T-F-T-S-D-L-S-K-Q-K(γE-X70)-D-S-Q-A-A-Q-D-F-I-E-W-L-K-A-G-G-P-S-S-G-A-P-P-P-S-NH2 |
| 158 | H-Aib-Q-G-T-F-T-S-D-L-S-K-Q-K(γE-x70)-D-S-Q-A-A-Q-L-F-I-E-W-L-K-A-dAla-G-P-S-S-G-A-P-P-P-S-NH2 |
| 159 | H-Aib-Q-G-T-F-T-S-D-L-S-K-Q-K(γE-x76)-D-S-Q-A-A-Q-L-F-I-E-W-L-K-A-dAla-G-P-S-S-G-A-P-P-P-S-NH2 |

TABLE 10-continued

Sequences

| SEQ. ID | sequence |
|---|---|
| 160 | H-dSer-Q-G-T-F-T-S-D-L-S-K-Q-K(γE-x61)-E-S-R-A-A-Q-D-F-I-E-W-L-K-A-G-G-P-S-S-G-A-P-P-P-S-NH2 |
| 161 | H-dSer-Q-G-T-F-T-S-D-L-S-K-Q-K(γE-X70)-D-S-R-R-A-Q-D-F-I-E-W-L-K-A-dAla-G-P-S-S-G-A-P-P-P-S-NH2 |
| 162 | H-Aib-Q-G-T-F-T-S-D-L-S-K-Q-K(γE-X70)-D-S-R-R-A-Q-D-F-I-E-W-L-K-A-G-G-P-S-S-G-A-P-P-P-S-NH2 |
| 163 | H-dSer-Q-G-T-F-T-S-D-L-S-K-Q-K(γE-X70)-D-S-R-R-A-Q-D-F-I-E-W-L-K-A-G-G-P-S-S-G-A-P-P-P-S-NH2 |
| 164 | H-dSer-Q-G-T-F-T-S-D-L-S-K-Q-K(γE-X70)-D-S-K-A-A-Q-D-F-I-E-W-L-K-Aib-G-G-P-S-S-G-A-P-P-P-S-NH2 |
| 165 | H-dSer-Q-G-T-F-T-S-D-L-S-K-Q-K(γE-x53)-E-S-R-R-A-Q-D-F-I-E-W-L-K-E-G-G-P-S-S-G-K-P-P-P-S-NH2 |
| 166 | H-dSer-Q-G-T-F-T-S-D-L-S-K-Q-K(γE-X70)-D-S-Q-A-A-Q-D-F-I-E-W-L-K-N-T-G-P-S-S-G-A-P-P-P-S-NH2 |
| 167 | H-dSer-Q-G-T-F-T-S-D-L-S-K-Q-K(γE-x59)-D-S-R-R-A-Q-D-F-I-E-W-L-K-N-G-G-P-S-S-G-A-P-P-P-S-NH2 |
| 168 | H-dSer-Q-G-T-F-T-S-D-L-S-K-Q-K(γE-x61)-D-S-R-R-A-Q-D-F-I-E-W-L-K-N-G-G-P-S-S-G-A-P-P-P-S-NH2 |
| 169 | H-dSer-Q-G-T-F-T-S-D-L-S-K-Q-K(γE-x64)-D-S-R-R-A-Q-D-F-I-E-W-L-K-N-G-G-P-S-S-G-A-P-P-P-S-NH2 |
| 170 | H-dSer-Q-G-T-F-T-S-D-L-S-K-Q-K(γE-x65)-D-S-R-R-A-Q-D-F-I-E-W-L-K-N-G-G-P-S-S-G-A-P-P-P-S-NH2 |
| 171 | H-dSer-Q-G-T-F-T-S-D-L-S-K-Q-K(γE-x73)-D-S-R-R-A-Q-D-F-I-E-W-L-K-N-G-G-P-S-S-G-A-P-P-P-S-NH2 |
| 172 | H-dSer-Q-G-T-F-T-S-D-L-S-K-Q-K(γE-x53)-E-S-R-R-A-Q-D-F-I-E-W-L-K-R-G-G-P-S-S-G-E-P-P-P-S-NH2 |
| 173 | H-dSer-Q-G-T-F-T-S-D-L-S-K-Q-K(γE-x53)-D-S-K-A-A-Q-D-F-I-E-W-L-K-S-G-G-P-S-S-G-A-P-P-P-S-NH2 |
| 174 | H-Aib-Q-G-T-F-T-S-D-L-S-K-Q-K(γE-X70)-D-E-Q-R-A-K-E-F-I-E-W-L-K-S-G-G-P-S-S-G-A-P-P-P-S-NH2 |
| 175 | H-Aib-Q-G-T-F-T-S-D-L-S-K-Q-K(γE-X70)-D-E-Q-R-A-K-D-F-I-E-W-L-K-S-G-G-P-S-S-G-A-P-P-P-S-NH2 |
| 176 | H-Aib-Q-G-T-F-T-S-D-L-S-K-Q-K(γE-X70)-D-E-Q-R-A-K-E-F-I-E-W-L-K-S-G-G-P-S-S-G-A-P-P-P-S-NH2 |
| 177 | H-dSer-Q-G-T-F-T-S-D-L-S-K-Q-K(γE-x53)-E-S-K-A-A-Q-D-F-I-E-W-L-K-A-G-G-P-S-S-G-A-P-P-P-S-NH[(CH2—CH2—O)24-CH2—CH2—COOH] |
| 178 | H-dSer-Q-G-T-F-T-S-D-L-S-K-Q-K(γE-x53)-E-S-K-A-A-Q-D-F-I-E-W-L-K-A-G-G-P-S-S-G-A-P-P-P-S-NH[(CH2—CH2—P)4-CH2—CH2—COOH] |
| 179 | H-S-MeQ-G-T-F-T-S-D-L-S-K-Q-K(γE-x53)-E-S-R-R-A-Q-D-F-I-E-W-L-K-N-G-G-P-S-S-G-A-P-P-P-S-NH2 |
| 180 | H-S-MeQ-G-T-F-T-S-D-L-S-K-Q-K(γE-x53)-E-S-R-R-A-Q-D-F-I-E-W-L-K-A-G-G-P-S-S-G-A-P-P-P-S-NH2 |
| 181 | H-Aib-Q-G-T-F-T-S-D-L-S-K-Q-K(γE-x53)-D-S-R-R-A-Q-D-F-I-E-W-L-K-A-G-G-P-S-S-G-A-P-P-P-S-NH2 |
| 182 | H-Aib-Q-G-T-F-T-S-D-L-S-K-Q-M-D-S-R-R-A-Q-D-F-I-E-W-L-K-N-G-G-P-S-S-G-A-P-P-P-S-NH2 |
| 183 | H-dSer-Q-G-T-F-T-S-D-L-S-K-Q-K-D-S-R-R-A-Q-D-F-I-E-W-L-K-N-G-G-P-S-S-G-A-P-P-P-S-NH2 |
| 184 | H-dSer-Q-G-T-F-T-S-D-L-S-K-Q-M-E-S-R-R-A-Q-D-F-I-E-W-L-K-A-G-G-P-S-S-G-A-P-P-P-S-NH2 |

TABLE 10-continued

Sequences

| SEQ. ID | sequence |
|---|---|
| 185 | H-dSer-Q-G-T-F-T-S-D-L-S-K-Q-M-D-S-R-R-A-Q-D-F-I-E-W-L-K-R-G-G-P-S-S-G-A-P-P-P-S-NH2 |
| 186 | H-dSer-Q-G-T-F-T-S-D-L-S-K-Q-M-D-S-R-R-A-Q-D-F-I-E-W-L-K-K-G-G-P-S-S-G-A-P-P-P-S-NH2 |
| 187 | H-dSer-Q-G-T-F-T-S-D-L-S-K-Q-M-D-S-R-R-A-Q-D-F-I-E-W-L-K-Aib-G-G-P-S-S-G-A-P-P-P-S-NH2 |
| 188 | H-dSer-Q-G-T-F-T-S-D-L-S-K-Q-M-D-S-R-R-A-Q-D-F-I-E-W-L-K-A-G-G-P-S-S-G-A-P-P-P-S-NH2 |
| 189 | H-dSer-Q-G-T-F-T-S-D-L-S-K-Q-M-E-S-K-A-A-Q-D-F-I-E-W-L-K-A-G-G-P-S-S-G-A-P-P-P-S-NH2 |
| 190 | H-dSer-Q-G-T-F-T-S-D-L-S-K-Q-M-E-S-R-R-A-Aib-D-F-I-E-W-L-K-A-G-G-P-S-S-G-A-P-P-P-S-NH2 |
| 191 | H-dSer-Q-G-T-F-T-S-D-L-S-K-Q-Nle-E-S-Q-A-A-Q-D-F-I-E-W-L-K-A-G-G-P-S-S-G-A-P-P-P-S-NH2 |
| 192 | H-dSer-Q-G-T-F-T-S-D-L-S-K-Q-Nle-D-S-K-A-A-Q-D-F-I-E-W-L-K-A-G-G-P-S-S-G-A-P-P-P-S-NH2 |
| 193 | H-dSer-Q-G-T-F-T-S-D-L-S-K-Q-Nle-D-S-Q-A-A-Q-D-F-I-E-W-L-K-A-G-G-P-S-S-G-A-P-P-P-S-NH2 |
| 194 | H-dSer-Q-G-T-F-T-S-D-L-S-K-Q-K(Ac)-E-S-R-R-A-Q-D-F-I-E-W-L-K-A-G-G-P-S-S-G-A-P-P-P-S-NH2 |
| 195 | H-A-E-G-T-F-T-S-D-V-S-S-Y-L-E-G-Q-A-A-K(γE-x53)-E-I-A-W-L-V-R-G-R-G-OH |
| 196 | H-dSer-Q-G-T-F-T-S-D-L-S-K-Q-K(γE-x70)-D-S-K-R-A-Aib-D-F-I-E-W-L-K-A-G-G-P-S-S-G-A-P-P-P-S-NH2 |
| 197 | H-Aib-Q-G-T-F-T-S-D-L-S-K-Q-K(γE-x70)-D-E-Q-R-A-K-L-F-I-E-W-L-K-A-G-G-P-S-S-G-A-P-P-P-S-NH2 |
| 198 | H-Aib-Q-G-T-F-T-S-D-L-S-K-Q-K(γE-x70)-D-S-R-R-A-Q-L-F-I-E-W-L-K-A-G-G-P-S-S-G-A-P-P-P-S-NH2 |
| 199 | H-Aib-Q-G-T-F-T-S-D-L-S-K-Q-K(γE-x70)-D-E-Q-R-A-K-D-F-I-E-W-L-K-A-dAla-G-P-S-S-G-A-P-P-P-S-NH2 |
| 200 | H-Aib-Q-G-T-F-T-S-D-L-S-K-Q-K(γE-x70)-D-E-Q-R-A-K-L-F-I-E-W-L-K-A-dAla-G-P-S-S-G-A-P-P-P-S-NH2 |
| 201 | H-Aib-Q-G-T-F-T-S-D-L-S-K-Q-K(γE-x76)-D-E-Q-A-A-K-L-F-I-E-W-L-K-A-dAla-G-P-S-S-G-A-P-P-P-S-NH2 |
| 202 | H-Aib-Q-G-T-F-T-S-D-L-S-K-Q-K(γE-x76)-E-S-R-A-A-Q-D-F-I-E-W-L-K-A-G-G-P-S-S-G-A-P-P-P-S-NH2 |
| 203 | H-Aib-Q-G-T-F-T-S-D-L-S-K-Q-K(γE-x76)-E-S-R-A-A-Q-L-F-I-E-W-L-K-A-G-G-P-S-S-G-A-P-P-P-S-NH2 |
| 204 | H-Aib-Q-G-T-F-T-S-D-L-S-K-Q-K(γE-x76)-E-S-R-A-A-Q-L-F-I-E-W-L-K-A-dAla-G-P-S-S-G-A-P-P-P-S-NH2 |
| 205 | H-Aib-Q-G-T-F-T-S-D-L-S-K-Q-K(γE-x70)-E-S-R-A-A-Q-L-F-I-E-W-L-K-A-dAla-G-P-S-S-G-A-P-P-P-S-NH2 |
| 206 | H-Aib-Q-G-T-F-T-S-D-L-S-K-Q-K(γE-x70)-D-E-Q-K-A-K-L-F-I-E-W-L-K-S-G-G-P-S-S-G-A-P-P-P-S-NH2 |
| 207 | H-Aib-Q-G-T-F-T-S-D-L-S-K-Q-K(γE-γE-x53)-D-E-Q-R-A-K-E-F-I-E-W-L-K-S-G-G-P-S-S-G-A-P-P-P-S-NH2 |
| 208 | H-S-H-G-T-F-T-S-D-L-S-K-Q-K(γE-x53)-E-S-R-R-A-Q-D-F-I-E-W-L-K-A-G-G-P-S-S-G-A-P-P-P-S-NH2 |
| 209 | H-Aib-Q-G-T-F-T-S-D-L-S-K-Q-K(γE-x70)-D-K-R-R-A-Q-D-F-I-E-W-L-K-A-dAla-G-P-S-S-G-A-P-P-P-S-NH2 |

TABLE 10-continued

Sequences

| SEQ. ID | sequence |
|---|---|
| 210 | H-Aib-Q-G-T-F-T-S-D-L-S-K-Q-K(γE-x70)-D-K-R-R-A-Q-L-F-I-E-W-L-K-A-dAla-G-P-S-S-G-A-P-P-P-S-NH2 |
| 211 | H-Aib-Q-G-T-F-T-S-D-L-S-K-Q-K(γE-x70)-D-K-R-A-A-Q-L-F-I-E-W-L-K-A-dAla-G-P-S-S-G-A-P-P-P-S-NH2 |
| 212 | H-Aib-Q-G-T-F-T-S-D-L-S-K-Q-K(γE-x76)-D-K-R-A-A-Q-L-F-I-E-W-L-K-A-dAla-G-P-S-S-G-A-P-P-P-S-NH2 |
| 213 | H-Aib-Q-G-T-F-T-S-D-L-S-K-Q-K(γE-x70)-D-E-A-A-K-L-F-I-E-W-L-K-A-G-G-P-S-S-G-A-P-P-P-S-NH2 |
| 214 | H-Aib-Q-G-T-F-T-S-D-L-S-K-Q-K(γE-x70)-D-E-E-A-A-R-L-F-I-E-W-L-K-A-G-G-P-S-S-G-A-P-P-P-S-NH2 |
| 215 | H-Aib-Q-G-T-F-T-S-D-L-S-K-Q-K(γE-X70)-E-E-E-A-A-R-L-F-I-E-W-L-K-A-G-G-P-S-S-G-A-P-P-P-S-NH2 |
| 216 | H-Aib-Q-G-T-F-T-S-D-L-S-K-Q-K(γE-X70)-D-E-E-A-A-R-L-F-I-E-W-L-K-A-G-G-P-S-S-G-A-P-P-P-S-NH2 |
| 217 | H-Aib-H-G-T-F-T-S-D-L-S-K-Q-K(γE-X70)-E-E-E-A-A-R-L-F-I-E-W-L-K-A-G-G-P-S-S-G-A-P-P-P-S-NH2 |
| 218 | H-Aib-H-G-T-F-T-S-D-L-S-K-Q-K(γE-X70)-D-E-E-A-A-R-L-F-I-E-W-L-K-A-G-G-P-S-S-G-A-P-P-P-S-NH2 |
| 219 | H-dSer-H-G-T-F-T-S-D-L-S-K-Q-K(γE-X70)-E-E-E-A-A-R-L-F-I-E-W-L-K-A-G-G-P-S-S-G-A-P-P-P-S-NH2 |
| 220 | H-dSer-H-G-T-F-T-S-D-L-S-K-Q-K(γE-X70)-D-E-E-A-A-R-L-F-I-E-W-L-K-A-G-G-P-S-S-G-A-P-P-P-S-NH2 |
| 221 | H-dSer-Q-G-T-F-T-S-D-L-S-K-Q-K(γE-x53)-D-E-E-A-A-R-L-F-I-E-W-L-K-A-G-G-P-S-S-G-A-P-P-P-S-NH2 |
| 222 | H-dSer-Q-G-T-F-T-S-D-L-S-K-Q-K(γE-X70)-D-E-E-A-A-R-L-F-I-E-W-L-K-A-G-G-P-S-S-G-A-P-P-P-S-NH2 |
| 223 | H-dSer-Q-G-T-F-T-S-D-L-S-K-Q-K(γE-x70)-E-E-E-A-A-R-L-F-I-E-W-L-K-A-G-G-P-S-S-G-A-P-P-P-S-NH2 |
| 224 | H-Aib-Q-G-T-F-T-S-D-L-S-K-Q-L-D-E-E-A-A-R-L-F-I-E-W-L-K-A-G-G-P-S-S-G-A-P-P-P-S-NH2 |
| 225 | H-Aib-Q-G-T-F-T-S-D-L-S-K-Q-L-E-E-E-A-A-R-L-F-I-E-W-L-K-A-G-G-P-S-S-G-A-P-P-P-S-NH2 |
| 226 | H-Aib-Q-G-T-F-T-S-D-L-S-K-Q-K(γE-γE-x53)-D-E-E-A-A-R-L-F-I-E-W-L-K-A-G-G-P-S-S-G-A-P-P-P-S-NH2 |
| 227 | H-Aib-H-G-T-F-T-S-D-L-S-K-Q-K(γE-γE-x53)-D-E-E-A-A-R-L-F-I-E-W-L-K-A-G-G-P-S-S-G-A-P-P-P-S-NH2 |
| 228 | H-Aib-Q-G-T-F-T-S-D-L-S-K-Q-K(γE-γE-x53)-E-E-E-A-A-R-L-F-I-E-W-L-K-A-G-G-P-S-S-G-A-P-P-P-S-NH2 |
| 229 | H-Aib-H-G-T-F-T-S-D-L-S-K-Q-K(γE-γE-x53)-E-E-E-A-A-R-L-F-I-E-W-L-K-A-G-G-P-S-S-G-A-P-P-P-S-NH2 |

The invention claimed is:

1. A method for treating type 1 diabetes in a patient in need thereof, the method comprising administering to said patient a therapeutically effective amount of the peptidic compound of formula (I):

$$R^1-Z-R^2 \quad (I)$$

or a salt, or solvate thereof, or a pharmaceutical composition comprising a compound of formula (I) or a salt or solvate thereof as an active agent together with at least one pharmaceutically acceptable carrier, wherein Z is a peptide moiety having formula (II):

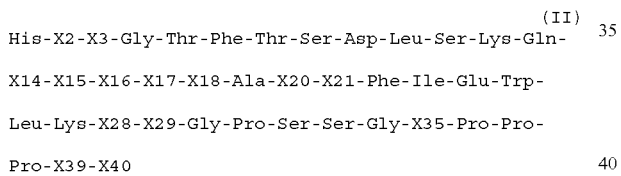

wherein:

X2 is an amino acid residue selected from Ser, D-Ser, and Aib,

X3 is an amino acid residue selected from Gln, His, and α-amino-functionalized Gln, wherein Gln is optionally functionalized in that an H of the α-$NH_2$ group is substituted by ($C_1$-$C_4$)-alkyl, X14 is an amino acid residue having a side chain with a functionalized —$NH_2$ group, wherein the functionalized —$NH_2$ side chain group is functionalized by —C(O)—$R^5$, —C(O)O—$R^5$, —C(O)NH—$R^5$, —S(O)$_2$—$R^5$ or $R^5$, wherein $R^5$ is a moiety comprising up to 100 carbon atoms and optionally heteroatoms independently selected from halogen, N, O, S, P, and combinations thereof, X15 is an amino acid residue selected from Glu and Asp, X16 is an amino acid residue selected from Ser, Glu, and Lys, X17 is an amino acid residue selected from Arg, Glu, Gln, Leu, Aib, and Lys, X18 is an amino acid residue selected from Arg, Ala, and Lys, X20 is an amino acid residue selected from Gln, Arg, Lys, His, Glu, and Aib, X21 is an amino acid residue selected from Asp, Leu, and Glu, X28 is an amino acid residue selected from Asn, Arg, Lys, Aib, Ser, Glu, Ala, and Asp, X29 is an amino acid residue selected from Gly, Ala, D-Ala, and Thr, X35 is an amino acid residue selected from Ala, Glu, Arg, and Lys, X39 is Ser or is absent, and X40 is absent or is an amino acid residue having a side chain with an —$NH_2$ group, wherein the —$NH_2$ side chain group is optionally functionalized by —C(O)—$R^5$, —C(O)O—$R^5$, —C(O)NH—$R^5$, —S(O)$_2$—$R^5$ or $R^5$, wherein $R^5$ is a moiety comprising up to 100 carbon atoms and optionally heteroatoms selected from halogen, N, O, S, P, and combinations thereof, $R^1$ is the N-terminal group of the peptidic compound and is selected from —$NH_2$ and mono- or bisfunctionalized —$NH_2$, wherein the mono- or bisfunctionalized —$NH_2$ is selected from the group consisting of —NH[($C_1$-$C_5$)alkyl], —N[($C_1$-$C_5$)alkyl]$_2$, —NH[($C_0$-$C_4$)alkylene-($C_3$-$C_8$)cycloalkyl], —NH—C(O)—H, —NH—C(O)—($C_1$-$C_5$)-alkyl, and —NH—C(O)—($C_0$-$C_3$)alkylene-($C_3$-$C_8$)cycloalkyl, in which alkyl or cycloalkyl is unsubstituted or up to 5-fold substituted by —OH or halogen selected from F, Cl, Br, and I, $R^2$ is the C-terminal group of the peptidic compound and is selected from (i) —OH and functionalized —OH, wherein the functionalized —OH is selected from —O—($C_1$-$C_{20}$)alkyl and —O($C_0$-$C_8$)alkylene-($C_3$-$C_8$)cycloalkyl, and (ii) —$NH_2$ and mono- or bisfunctionalized —$NH_2$, wherein the mono- or bisfunctionalized —$NH_2$ is selected from the group consisting of —NH[($C_1$-$C_{30}$)alkyl], —N[($C_1$-$C_{30}$)alkyl]$_2$, —NH[($C_0$-$C_8$)alkylene-($C_3$-$C_8$)cycloalkyl], —N[$C_0$-$C_8$)alkylene-($C_3$-$C_8$)cycloalkyl]$_2$, —NH[($CH_2$—$CH_2$—O)$_{1-40}$—($C_1$-$C_4$)alkyl], —NH—($C_3$-$C_8$)heterocyclyl or —NH—($C_0$-$C_8$)alkylene-aryl, wherein aryl is selected from phenyl or naphthyl, the ($C_3$-$C_8$)-heterocyclyl contains one N-atom and optionally two additional heteroatoms selected from O, N and S, and alkyl or cycloalkyl is unsubstituted or up to 5-fold substituted by —OH or a halogen selected from F, Cl, Br, and I.

2. The method according to claim 1, wherein said peptidic compound of formula (I) is any one of SEQ ID NOs: 4-181, 196-223, 226-229, or a salt or solvate thereof.

3. A method for treating type 2 diabetes in a patient in need thereof, the method comprising administering to said patient a therapeutically effective amount of the peptidic compound of formula (I):

$$R^1-Z-R^2 \qquad (I)$$

or a salt, or solvate thereof, or a pharmaceutical composition comprising a compound of formula (I) or a salt or solvate thereof as an active agent together with at least one pharmaceutically acceptable carrier,
wherein Z is a peptide moiety having formula (II):

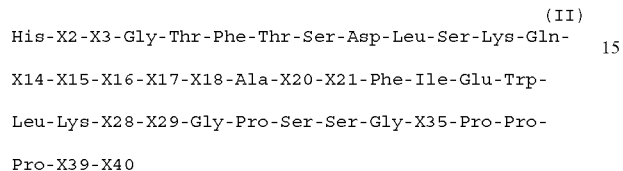

wherein:
X2 is an amino acid residue selected from Ser, D-Ser, and Aib,
X3 is an amino acid residue selected from Gln, His, and α-amino-functionalized Gln, wherein Gln is optionally functionalized in that an H of the α-$NH_2$ group is substituted by ($C_1$-$C_4$)-alkyl,
X14 is an amino acid residue having a side chain with a functionalized —$NH_2$ group, wherein the functionalized —$NH_2$ side chain group is functionalized by —C(O)—$R^5$, —C(O)O—$R^5$, —C(O)NH—$R^5$, —S(O)$_2$—$R^5$ or $R^5$, wherein $R^5$ is a moiety comprising up to 100 carbon atoms and optionally heteroatoms independently selected from halogen, N, O, S, P, and combinations thereof,
X15 is an amino acid residue selected from Glu and Asp,
X16 is an amino acid residue selected from Ser, Glu, and Lys,
X17 is an amino acid residue selected from Arg, Glu, Gln, Leu, Aib, and Lys,
X18 is an amino acid residue selected from Arg, Ala, and Lys,
X20 is an amino acid residue selected from Gln, Arg, Lys, His, Glu, and Aib,
X21 is an amino acid residue selected from Asp, Leu, and Glu,
X28 is an amino acid residue selected from Asn, Arg, Lys, Aib, Ser, Glu, Ala, and Asp,
X29 is an amino acid residue selected from Gly, Ala, D-Ala, and Thr,
X35 is an amino acid residue selected from Ala, Glu, Arg, and Lys,
X39 is Ser or is absent, and
X40 is absent or is an amino acid residue having a side chain with an —$NH_2$ group, wherein the —$NH_2$ side chain group is optionally functionalized by —C(O)—$R^5$, —C(O)O—$R^5$, —C(O)NH—$R^5$, —S(O)$_2$—$R^5$ or $R^5$, wherein $R^5$ is a moiety comprising up to 100 carbon atoms and optionally heteroatoms selected from halogen, N, O, S, P, and combinations thereof,
$R^1$ is the N-terminal group of the peptidic compound and is selected from —$NH_2$ and mono- or bisfunctionalized —$NH_2$, wherein the mono- or bisfunctionalized —$NH_2$ is selected from the group consisting of —NH[($C_1$-$C_5$)alkyl], —N[($C_1$-$C_5$)alkyl]$_2$, —NH[($C_0$-$C_4$)alkylene-($C_3$-$C_8$)cycloalkyl], —NH—C(O)—H, —NH—C(O)—($C_1$-$C_5$)-alkyl, and —NH—C(O)—($C_0$-$C_3$) alkylene-($C_3$-$C_8$)cycloalkyl, in which alkyl or cycloalkyl is unsubstituted or up to 5-fold substituted by —OH or halogen selected from F, Cl, Br, and I,
$R^2$ is the C-terminal group of the peptidic compound and is selected from
(i) —OH and functionalized —OH, wherein the functionalized —OH is selected from —O—($C_1$-$C_{20}$) alkyl and —O($C_0$-$C_8$)alkylene-($C_3$-$C_8$)cycloalkyl, and
(ii) —$NH_2$ and mono- or bisfunctionalized —$NH_2$, wherein the mono- or bisfunctionalized —$NH_2$ is selected from the group consisting of —NH[($C_1$-$C_{30}$)alkyl], —N[($C_1$-$C_{30}$)alkyl]$_2$, —NH[($C_0$-$C_8$) alkylene-($C_3$-$C_8$)cycloalkyl], —N[$C_0$-$C_8$)alkylene-($C_3$-$C_8$)cycloalkyl]$_2$, —NH[($CH_2$—$CH_2$—O)$_{1-40}$—($C_1$-$C_4$)alkyl], —NH—($C_3$-$C_8$)heterocyclyl or —NH—($C_0$-$C_8$)alkylene-aryl, wherein aryl is selected from phenyl or naphthyl, the ($C_3$-$C_8$)-heterocyclyl contains one N-atom and optionally two additional heteroatoms selected from O, N and S, and alkyl or cycloalkyl is unsubstituted or up to 5-fold substituted by —OH or a halogen selected from F, Cl, Br, and I.

4. The method according to claim 3, wherein said peptidic compound of formula (I) is any one of SEQ ID NOs: 4-181, 196-223, 226-229, or a salt or solvate thereof.

5. The method according to claim 3, wherein said method further comprises treating one or more vascular disease conditions in the patient, wherein the one or more vascular disease conditions are selected from the group consisting of ischemic heart disease, myocardial infarction, stroke, peripheral vascular disease, diabetic retinopathy, diabetic nephropathy, and diabetic neuropathy.

6. A method for delaying disease progression of type 2 diabetes in a patient in need thereof, the method comprising administering to said patient a therapeutically effective amount of the peptidic compound of formula (I):

$$R^1-Z-R^2 \qquad (I)$$

or a salt, or solvate thereof, or a pharmaceutical composition comprising a compound of formula (I) or a salt or solvate thereof as an active agent together with at least one pharmaceutically acceptable carrier,
wherein Z is a peptide moiety having formula (II):

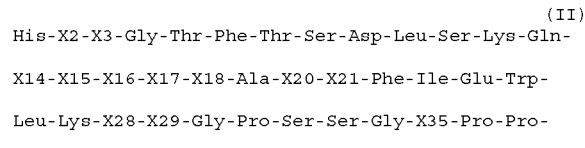

wherein:
X2 is an amino acid residue selected from Ser, D-Ser, and Aib,
X3 is an amino acid residue selected from Gln, His, and α-amino-functionalized Gln, wherein Gln is optionally functionalized in that an H of the α-$NH_2$ group is substituted by ($C_1$-$C_4$)-alkyl,
X14 is an amino acid residue having a side chain with a functionalized —$NH_2$ group, wherein the functionalized —$NH_2$ side chain group is functionalized by —C(O)—$R^5$, —C(O)O—$R^5$, —C(O)NH—$R^5$, —S(O)$_2$—$R^5$ or $R^5$, wherein $R^5$ is a moiety comprising up to 100 carbon atoms and optionally heteroatoms independently selected from halogen, N, O, S, P, and combinations thereof, X15 is an amino acid residue selected from Glu and Asp, X16 is an amino acid residue selected from Ser, Glu, and Lys, X17 is an amino acid residue selected from Arg, Glu, Gln, Leu, Aib, and Lys, X18 is an amino acid residue selected from Arg, Ala, and Lys, X20 is an amino acid residue selected from Gln, Arg, Lys, His, Glu, and Aib, X21 is an amino acid residue selected from Asp, Leu, and Glu, X28 is an amino acid residue selected from Asn, Arg, Lys, Aib, Ser, Glu, Ala, and Asp, X29 is an amino acid residue selected from Gly, Ala, D-Ala, and Thr, X35 is an amino acid residue selected from Ala, Glu, Arg, and Lys, X39 is Ser or is absent, and X40 is absent or is an amino acid residue having a side chain with an —NH$_2$ group, wherein the —NH$_2$ side chain group is optionally functionalized by —C(O)—R$^5$, —C(O)O—R$^5$, —C(O)NH—R$^5$, —S(O)$_2$—R$^5$ or R$^5$, wherein R$^5$ is a moiety comprising up to 100 carbon atoms and optionally heteroatoms selected from halogen, N, O, S, P, and combinations thereof, R$^1$ is the N-terminal group of the peptidic compound and is selected from —NH$_2$ and mono- or bisfunctionalized —NH$_2$, wherein the mono- or bisfunctionalized —NH$_2$ is selected from the group consisting of —NH[(C$_1$-C$_5$)alkyl], —N[(C$_1$-C$_5$)alkyl]2, —NH[(C$_0$-C$_4$)alkylene-(C$_3$-C$_8$)cycloalkyl], —NH—C(O)—H, —NH—C(O)—(C$_1$-C$_5$)-alkyl, and —NH—C(O)—(C$_0$-C$_3$)alkylene-(C$_3$-C$_8$)cycloalkyl, in which alkyl or cycloalkyl is unsubstituted or up to 5-fold substituted by —OH or halogen selected from F, Cl, Br, and I, R$^2$ is the C-terminal group of the peptidic compound and is selected from
(i) —OH and functionalized —OH, wherein the functionalized —OH is selected from —O—(C$_1$-C$_{20}$)alkyl and —O(C$_0$-C$_8$)alkylene-(C$_3$-C$_8$)cycloalkyl, and
(ii) —NH$_2$ and mono- or bisfunctionalized —NH$_2$, wherein the mono- or bisfunctionalized —NH$_2$ is selected from the group consisting of —NH[(C$_1$-C$_{30}$)alkyl], —N[(C$_1$-C$_{30}$)alkyl]$_2$, —NH[(C$_0$-C$_8$)alkylene-(C$_3$-C$_8$)cycloalkyl], —N[C$_0$-C$_8$)alkylene-(C$_3$-C$_8$)cycloalkyl]$_2$, —NH[(CH$_2$—CH$_2$—O)$_{1-40}$—(C$_1$-C$_4$)alkyl], —NH—(C$_3$-C$_8$)heterocyclyl or —NH—(C$_0$-C$_8$)alkylene-aryl, wherein aryl is selected from phenyl or naphthyl, the (C$_3$-C$_8$)-heterocyclyl contains one N-atom and optionally two additional heteroatoms selected from O, N and S, and alkyl or cycloalkyl is unsubstituted or up to 5-fold substituted by —OH or a halogen selected from F, Cl, Br, and I.

7. The method according to claim 6, wherein said peptidic compound of formula (I) is any one of SEQ ID NOs: 4-181, 196-223, 226-229, or a salt or solvate thereof.

8. The method of claim 6, wherein said method comprises delaying the progression from type 2 diabetes to insulin-requiring diabetes.

9. A method for treating impaired glucose tolerance in a patient in need thereof, the method comprising administering to said patient a therapeutically effective amount of the peptidic compound of formula (I):

or a salt, or solvate thereof, or a pharmaceutical composition comprising a compound of formula (I) or a salt or solvate thereof as an active agent together with at least one pharmaceutically acceptable carrier, wherein Z is a peptide moiety having formula (II):

wherein:

X2 is an amino acid residue selected from Ser, D-Ser, and Aib,

X3 is an amino acid residue selected from Gln, His, and α-amino-functionalized Gln, wherein Gln is optionally functionalized in that an H of the α-NH$_2$ group is substituted by (C$_1$-C$_4$)-alkyl, X14 is an amino acid residue having a side chain with a functionalized —NH$_2$ group, wherein the functionalized —NH$_2$ side chain group is functionalized by —C(O)—R$^5$, —C(O)O—R$^5$, —C(O)NH—R$^5$, —S(O)$_2$—R$^5$ or R$^5$, wherein R$^5$ is a moiety comprising up to 100 carbon atoms and optionally heteroatoms independently selected from halogen, N, O, S, P, and combinations thereof, X15 is an amino acid residue selected from Glu and Asp, X16 is an amino acid residue selected from Ser, Glu, and Lys, X17 is an amino acid residue selected from Arg, Glu, Gln, Leu, Aib, and Lys, X18 is an amino acid residue selected from Arg, Ala, and Lys, X20 is an amino acid residue selected from Gln, Arg, Lys, His, Glu, and Aib, X21 is an amino acid residue selected from Asp, Leu, and Glu, X28 is an amino acid residue selected from Asn, Arg, Lys, Aib, Ser, Glu, Ala, and Asp, X29 is an amino acid residue selected from Gly, Ala, D-Ala, and Thr, X35 is an amino acid residue selected from Ala, Glu, Arg, and Lys, X39 is Ser or is absent, and X40 is absent or is an amino acid residue having a side chain with an —NH$_2$ group, wherein the —NH$_2$ side chain group is optionally functionalized by —C(O)—R$^5$, —C(O)O—R$^5$, —C(O)NH—R$^5$, —S(O)$_2$—R$^5$ or R$^5$, wherein R$^5$ is a moiety comprising up to 100 carbon atoms and optionally heteroatoms selected from halogen, N, O, S, P, and combinations thereof, R$^1$ is the N-terminal group of the peptidic compound and is selected from —NH$_2$ and mono- or bisfunctionalized —NH$_2$, wherein the mono- or bisfunctionalized —NH$_2$ is selected from the group consisting of —NH[(C$_1$-C$_5$)alkyl], —N[(C$_1$-C$_5$)alkyl]$_2$, —NH[(C$_0$-C$_4$)alkylene-(C$_3$-C$_8$)cycloalkyl], —NH—C(O)—H, —NH—C(O)—(C$_1$-C$_5$)-alkyl, and —NH—C(O)—(C$_0$-C$_3$)alkylene-(C$_3$-C$_8$)cycloalkyl, in which alkyl or cycloalkyl is unsubstituted or up to 5-fold substituted by —OH or halogen selected from F, Cl, Br, and I, $R^2$ is the C-terminal group of the peptidic compound and is selected from
(i) —OH and functionalized —OH, wherein the functionalized —OH is selected from —O—$(C_1-C_{20})$alkyl and —O$(C_0-C_8)$alkylene-$(C_3-C_8)$cycloalkyl, and
(ii) —$NH_2$ and mono- or bisfunctionalized —$NH_2$, wherein the mono- or bisfunctionalized —$NH_2$ is selected from the group consisting of —NH[$(C_1-C_{30})$alkyl], —N[$(C_1-C_{30})$alkyl]$_2$, —NH[$(C_0-C_8)$alkylene-$(C_3-C_8)$cycloalkyl], —N[$C_0-C_8$)alkylene-$(C_3-C_8)$cycloalkyl]$_2$, —NH[$(CH_2—CH_2—O)_{1-40}$—$(C_1-C_4)$alkyl], —NH—$(C_3-C_8)$heterocyclyl or —NH—$(C_0-C_8)$alkylene-aryl, wherein aryl is selected from phenyl or naphthyl, the $(C_3-C_8)$-heterocyclyl contains one N-atom and optionally two additional heteroatoms selected from O, N and S, and alkyl or cycloalkyl is unsubstituted or up to 5-fold substituted by —OH or a halogen selected from F, Cl, Br, and I.

10. The method according to claim 9, wherein said peptidic compound of formula (I) is any one of SEQ ID NOs: 4-181, 196-223, 226-229, or a salt or solvate thereof.

11. A method for reducing a blood glucose level in a patient in need thereof, the method comprising administering to said patient a therapeutically effective amount of the peptidic compound of formula (I):

$$R^1—Z—R^2 \qquad (I)$$

or a salt, or solvate thereof, or a pharmaceutical composition comprising a compound of formula (I) or a salt or solvate thereof as an active agent together with at least one pharmaceutically acceptable carrier, wherein Z is a peptide moiety having formula (II):

(II)
His-X2-X3-Gly-Thr-Phe-Thr-Ser-Asp-Leu-Ser-Lys-Gln-
X14-X15-X16-X17-X18-Ala-X20-X21-Phe-Ile-Glu-Trp-
Leu-Lys-X28-X29-Gly-Pro-Ser-Ser-Gly-X35-Pro-Pro-
Pro-X39-X40 wherein:
X2 is an amino acid residue selected from Ser, D-Ser, and Aib,
X3 is an amino acid residue selected from Gln, His, and α-amino-functionalized Gln, wherein Gln is optionally functionalized in that an H of the α-$NH_2$ group is substituted by $(C_1-C_4)$-alkyl,
X14 is an amino acid residue having a side chain with a functionalized —$NH_2$ group, wherein the functionalized —$NH_2$ side chain group is functionalized by —C(O)—$R^5$, —C(O)O—$R^5$, —C(O)NH—$R^5$, —S(O)$_2$—$R^5$ or $R^5$, wherein $R^5$ is a moiety comprising up to 100 carbon atoms and optionally heteroatoms independently selected from halogen, N, O, S, P, and combinations thereof,
X15 is an amino acid residue selected from Glu and Asp,
X16 is an amino acid residue selected from Ser, Glu, and Lys,
X17 is an amino acid residue selected from Arg, Glu, Gln, Leu, Aib, and Lys,
X18 is an amino acid residue selected from Arg, Ala, and Lys,
X20 is an amino acid residue selected from Gln, Arg, Lys, His, Glu, and Aib,
X21 is an amino acid residue selected from Asp, Leu, and Glu,
X28 is an amino acid residue selected from Asn, Arg, Lys, Aib, Ser, Glu, Ala, and Asp,
X29 is an amino acid residue selected from Gly, Ala, D-Ala, and Thr,
X35 is an amino acid residue selected from Ala, Glu, Arg, and Lys,
X39 is Ser or is absent, and
X40 is absent or is an amino acid residue having a side chain with an —$NH_2$ group, wherein the —$NH_2$ side chain group is optionally functionalized by —C(O)—$R^5$, —C(O)O—$R^5$, —C(O)NH—$R^5$, —S(O)$_2$—$R^5$ or $R^5$, wherein $R^5$ is a moiety comprising up to 100 carbon atoms and optionally heteroatoms selected from halogen, N, O, S, P, and combinations thereof,
$R^1$ is the N-terminal group of the peptidic compound and is selected from —$NH_2$ and mono- or bisfunctionalized —$NH_2$, wherein the mono- or bisfunctionalized —$NH_2$ is selected from the group consisting of —NH[$(C_1-C_5)$alkyl], —N[$(C_1-C_5)$alkyl]$_2$, —NH[$(C_0-C_4)$alkylene-$(C_3-C_8)$cycloalkyl], —NH—C(O)—H, —NH—C(O)—$(C_1-C_5)$-alkyl, and —NH—C(O)—$(C_0-C_3)$alkylene-$(C_3-C_8)$cycloalkyl, in which alkyl or cycloalkyl is unsubstituted or up to 5-fold substituted by —OH or halogen selected from F, Cl, Br, and I,
$R^2$ is the C-terminal group of the peptidic compound and is selected from
(i) —OH and functionalized —OH, wherein the functionalized —OH is selected from —O—$(C_1-C_{20})$alkyl and —O$(C_0-C_8)$alkylene-$(C_3-C_8)$cycloalkyl, and
(ii) —$NH_2$ and mono- or bisfunctionalized —$NH_2$, wherein the mono- or bisfunctionalized —$NH_2$ is selected from the group consisting of —NH[$(C_1-C_{30})$alkyl], —N[$(C_1-C_{30})$alkyl]$_2$, —NH[$(C_0-C_8)$alkylene-$(C_3-C_8)$cycloalkyl], —N[$C_0-C_8$)alkylene-$(C_3-C_8)$cycloalkyl]$_2$, —NH[$(CH_2—CH_2—O)_{1-40}$—$(C_1-C_4)$alkyl], —NH—$(C_3-C_8)$heterocyclyl or —NH—$(C_0-C_8)$alkylene-aryl, wherein aryl is selected from phenyl or naphthyl, the $(C_3-C_8)$-heterocyclyl contains one N-atom and optionally two additional heteroatoms selected from O, N and S, and alkyl or cycloalkyl is unsubstituted or up to 5-fold substituted by —OH or a halogen selected from F, Cl, Br, and I.

12. The method according to claim 11, wherein said peptidic compound of formula (I) is any one of SEQ ID NOs: 4-181, 196-223, 226-229, or a salt or solvate thereof.

13. A method for reducing an HbA1c level in a patient in need thereof, the method comprising administering to said patient a therapeutically effective amount of the peptidic compound of formula (I):

$$R^1—Z—R^2 \qquad (I)$$

or a salt, or solvate thereof, or a pharmaceutical composition comprising a compound of formula (I) or a salt or solvate thereof as an active agent together with at least one pharmaceutically acceptable carrier, wherein Z is a peptide moiety having formula (II):

(II)
His-X2-X3-Gly-Thr-Phe-Thr-Ser-Asp-Leu-Ser-Lys-Gln-
X14-X15-X16-X17-X18-Ala-X20-X21-Phe-Ile-Glu-Trp-
Leu-Lys-X28-X29-Gly-Pro-Ser-Ser-Gly-X35-Pro-Pro-
Pro-X39-X40 wherein:

X2 is an amino acid residue selected from Ser, D-Ser, and Aib,

X3 is an amino acid residue selected from Gln, His, and α-amino-functionalized Gln, wherein Gln is optionally functionalized in that an H of the α-NH$_2$ group is substituted by (C$_1$-C$_4$)-alkyl, X14 is an amino acid residue having a side chain with a functionalized —NH$_2$ group, wherein the functionalized —NH$_2$ side chain group is functionalized by —C(O)—R$^5$, —C(O)O—R$^5$, —C(O)NH—R$^5$, —S(O)$_2$—R$^5$ or R$^5$, wherein R$^5$ is a moiety comprising up to 100 carbon atoms and optionally heteroatoms independently selected from halogen, N, O, S, P, and combinations thereof, X15 is an amino acid residue selected from Glu and Asp, X16 is an amino acid residue selected from Ser, Glu, and Lys, X17 is an amino acid residue selected from Arg, Glu, Gln, Leu, Aib, and Lys, X18 is an amino acid residue selected from Arg, Ala, and Lys, X20 is an amino acid residue selected from Gln, Arg, Lys, His, Glu, and Aib, X21 is an amino acid residue selected from Asp, Leu, and Glu, X28 is an amino acid residue selected from Asn, Arg, Lys, Aib, Ser, Glu, Ala, and Asp, X29 is an amino acid residue selected from Gly, Ala, D-Ala, and Thr, X35 is an amino acid residue selected from Ala, Glu, Arg, and Lys, X39 is Ser or is absent, and X40 is absent or is an amino acid residue having a side chain with an —NH$_2$ group, wherein the —NH$_2$ side chain group is optionally functionalized by —C(O)—R$^5$, —C(O)O—R$^5$, —C(O)NH—R$^5$, —S(O)$_2$—R$^5$ or R$^5$, wherein R$^5$ is a moiety comprising up to 100 carbon atoms and optionally heteroatoms selected from halogen, N, O, S, P, and combinations thereof, R$^1$ is the N-terminal group of the peptidic compound and is selected from —NH$_2$ and mono- or bisfunctionalized —NH$_2$, wherein the mono- or bisfunctionalized —NH$_2$ is selected from the group consisting of —NH[(C$_1$-C$_5$)alkyl], —N[(C$_1$-C$_5$)alkyl]$_2$, —NH[(C$_0$-C$_4$)alkylene-(C$_3$-C$_8$)cycloalkyl], —NH—C(O)—H, —NH—C(O)—(C$_1$-C$_5$)-alkyl, and —NH—C(O)—(C$_0$-C$_3$)alkylene-(C$_3$-C$_8$)cycloalkyl, in which alkyl or cycloalkyl is unsubstituted or up to 5-fold substituted by —OH or halogen selected from F, Cl, Br, and I, R$^2$ is the C-terminal group of the peptidic compound and is selected from
(i) —OH and functionalized —OH, wherein the functionalized —OH is selected from —O—(C$_1$-C$_{20}$)alkyl and —O(C$_0$-C$_8$)alkylene-(C$_3$-C$_8$)cycloalkyl, and
(ii) —NH$_2$ and mono- or bisfunctionalized —NH$_2$, wherein the mono- or bisfunctionalized —NH$_2$ is selected from the group consisting of —NH[(C$_1$-C$_{30}$)alkyl], —N[(C$_1$-C$_{30}$)alkyl]$_2$, —NH[(C$_0$-C$_8$)alkylene-(C$_3$-C$_8$)cycloalkyl], —N[C$_0$-C$_8$)alkylene-(C$_3$-C$_8$)cycloalkyl]$_2$, —NH[(CH$_2$—CH$_2$—O)$_{1-40}$—(C$_1$-C$_4$)alkyl], —NH—(C$_3$-C$_8$)heterocyclyl or —NH—(C$_0$-C$_8$)alkylene-aryl, wherein aryl is selected from phenyl or naphthyl, the (C$_3$-C$_8$)-heterocyclyl contains one N-atom and optionally two additional heteroatoms selected from O, N and S, and alkyl or cycloalkyl is unsubstituted or up to 5-fold substituted by —OH or a halogen selected from F, Cl, Br, and I.

14. The method according to claim 13, wherein said peptidic compound of formula (I) is any one of SEQ ID NOs: 4-181, 196-223, 226-229, or a salt or solvate thereof.

15. A method for delaying disease progression from impaired glucose tolerance (IGT) to type 2 diabetes in a patient in need thereof, the method comprising administering to said patient a therapeutically effective amount of the peptidic compound of formula (I):

$$R^1-Z-R^2 \qquad (I)$$

or a salt, or solvate thereof, or a pharmaceutical composition comprising a compound of formula (I) or a salt or solvate thereof as an active agent together with at least one pharmaceutically acceptable carrier,
wherein Z is a peptide moiety having formula (II):

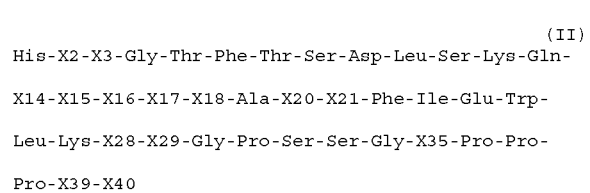

```
                                                    (II)
His-X2-X3-Gly-Thr-Phe-Thr-Ser-Asp-Leu-Ser-Lys-Gln-

X14-X15-X16-X17-X18-Ala-X20-X21-Phe-Ile-Glu-Trp-

Leu-Lys-X28-X29-Gly-Pro-Ser-Ser-Gly-X35-Pro-Pro-

Pro-X39-X40
``` wherein:

X2 is an amino acid residue selected from Ser, D-Ser, and Aib,

X3 is an amino acid residue selected from Gln, His, and α-amino-functionalized Gln, wherein Gln is optionally functionalized in that an H of the α-NH$_2$ group is substituted by (C$_1$-C$_4$)-alkyl, X14 is an amino acid residue having a side chain with a functionalized —NH$_2$ group, wherein the functionalized —NH$_2$ side chain group is functionalized by —C(O)—R$^5$, —C(O)O—R$^5$, —C(O)NH—R$^5$, —S(O)$_2$—R$^5$ or R$^5$, wherein R$^5$ is a moiety comprising up to 100 carbon atoms and optionally heteroatoms independently selected from halogen, N, O, S, P, and combinations thereof, X15 is an amino acid residue selected from Glu and Asp, X16 is an amino acid residue selected from Ser, Glu, and Lys, X17 is an amino acid residue selected from Arg, Glu, Gln, Leu, Aib, and Lys, X18 is an amino acid residue selected from Arg, Ala, and Lys, X20 is an amino acid residue selected from Gln, Arg, Lys, His, Glu, and Aib, X21 is an amino acid residue selected from Asp, Leu, and Glu, X28 is an amino acid residue selected from Asn, Arg, Lys, Aib, Ser, Glu, Ala, and Asp, X29 is an amino acid residue selected from Gly, Ala, D-Ala, and Thr, X35 is an amino acid residue selected from Ala, Glu, Arg, and Lys, X39 is Ser or is absent, and X40 is absent or is an amino acid residue having a side chain with an —NH$_2$ group, wherein the —NH$_2$ side chain group is optionally functionalized by —C(O)—R$^5$, —C(O)O—R$^5$, —C(O)NH—R$^5$, —S(O)$_2$—R$^5$ or R$^5$, wherein R$^5$ is a moiety comprising up to 100 carbon atoms and optionally heteroatoms selected from halogen, N, O, S, P, and combinations thereof, R¹ is the N-terminal group of the peptidic compound and is selected from —NH₂ and mono- or bisfunctionalized —NH₂, wherein the mono- or bisfunctionalized —NH₂ is selected from the group consisting of —NH[(C₁-C₅)alkyl], —N[(C₁-C₅)alkyl]₂, —NH[(C₀-C₄)alkylene-(C₃-C₈)cycloalkyl], —NH—C(O)—H, —NH—C(O)—(C₁-C₅)-alkyl, and —NH—C(O)—(C₀-C₃)alkylene-(C₃-C₈)cycloalkyl, in which alkyl or cycloalkyl is unsubstituted or up to 5-fold substituted by —OH or halogen selected from F, Cl, Br, and I, R² is the C-terminal group of the peptidic compound and is selected from
(i) —OH and functionalized —OH, wherein the functionalized —OH is selected from —O—(C₁-C₂₀)alkyl and —O(C₀-C₈)alkylene-(C₃-C₈)cycloalkyl, and
(ii) —NH₂ and mono- or bisfunctionalized —NH₂, wherein the mono- or bisfunctionalized —NH₂ is selected from the group consisting of —NH[(C₁-C₃₀)alkyl], —N[(C₁-C₃₀)alkyl]₂, —NH[(C₀-C₈)alkylene-(C₃-C₈)cycloalkyl], —N[C₀-C₈)alkylene-(C₃-C₈)cycloalkyl]₂, —NH[(CH₂—CH₂—O)₁₋₄₀—(C₁-C₄)alkyl], —NH—(C₃-C₈)heterocyclyl or —NH—(C₀-C₈)alkylene-aryl, wherein aryl is selected from phenyl or naphthyl, the (C₃-C₈)-heterocyclyl contains one N-atom and optionally two additional heteroatoms selected from O, N and S, and alkyl or cycloalkyl is unsubstituted or up to 5-fold substituted by —OH or a halogen selected from F, Cl, Br, and I.

16. The method according to claim 15, wherein said peptidic compound of formula (I) is any one of SEQ ID NOs: 4-181, 196-223, 226-229, or a salt or solvate thereof.

17. A method for treating hyperglycemia in a patient in need thereof, the method comprising administering to said patient a therapeutically effective amount of the peptidic compound of formula (I):

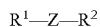

or a salt, or solvate thereof, or a pharmaceutical composition comprising a compound of formula (I) or a salt or solvate thereof as an active agent together with at least one pharmaceutically acceptable carrier,
wherein Z is a peptide moiety having formula (II):

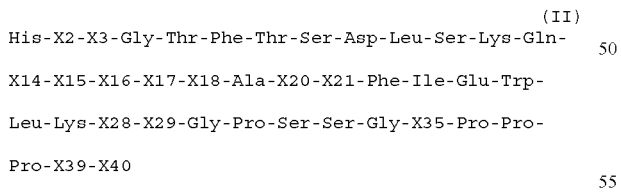

wherein:
X2 is an amino acid residue selected from Ser, D-Ser, and Aib,
X3 is an amino acid residue selected from Gln, His, and α-amino-functionalized Gln, wherein Gln is optionally functionalized in that an H of the α-NH₂ group is substituted by (C₁-C₄)-alkyl,
X14 is an amino acid residue having a side chain with a functionalized —NH₂ group, wherein the functionalized —NH₂ side chain group is functionalized by —C(O)—R⁵, —C(O)O—R⁵, —C(O)NH—R⁵, —S(O)₂—R⁵ or R⁵, wherein R⁵ is a moiety comprising up to 100 carbon atoms and optionally heteroatoms independently selected from halogen, N, O, S, P, and combinations thereof, X15 is an amino acid residue selected from Glu and Asp,
X16 is an amino acid residue selected from Ser, Glu, and Lys,
X17 is an amino acid residue selected from Arg, Glu, Gln, Leu, Aib, and Lys,
X18 is an amino acid residue selected from Arg, Ala, and Lys,
X20 is an amino acid residue selected from Gln, Arg, Lys, His, Glu, and Aib,
X21 is an amino acid residue selected from Asp, Leu, and Glu,
X28 is an amino acid residue selected from Asn, Arg, Lys, Aib, Ser, Glu, Ala, and Asp,
X29 is an amino acid residue selected from Gly, Ala, D-Ala, and Thr,
X35 is an amino acid residue selected from Ala, Glu, Arg, and Lys,
X39 is Ser or is absent, and
X40 is absent or is an amino acid residue having a side chain with an —NH₂ group, wherein the —NH₂ side chain group is optionally functionalized by —C(O)—R⁵, —C(O)O—R⁵, —C(O)NH—R⁵, —S(O)₂—R⁵ or R⁵, wherein R⁵ is a moiety comprising up to 100 carbon atoms and optionally heteroatoms selected from halogen, N, O, S, P, and combinations thereof, R¹ is the N-terminal group of the peptidic compound and is selected from —NH₂ and mono- or bisfunctionalized —NH₂, wherein the mono- or bisfunctionalized —NH₂ is selected from the group consisting of —NH[(C₁-C₅)alkyl], —N[(C₁-C₅)alkyl]₂, —NH[(C₀-C₄)alkylene-(C₃-C₈)cycloalkyl], —NH—C(O)—H, —NH—C(O)—(C₁-C₅)-alkyl, and —NH—C(O)—(C₀-C₃)alkylene-(C₃-C₈)cycloalkyl, in which alkyl or cycloalkyl is unsubstituted or up to 5-fold substituted by —OH or halogen selected from F, Cl, Br, and I, R² is the C-terminal group of the peptidic compound and is selected from
(i) —OH and functionalized —OH, wherein the functionalized —OH is selected from —O—(C₁-C₂₀)alkyl and —O(C₀-C₈)alkylene-(C₃-C₈)cycloalkyl, and
(ii) —NH₂ and mono- or bisfunctionalized —NH₂, wherein the mono- or bisfunctionalized —NH₂ is selected from the group consisting of —NH[(C₁-C₃₀)alkyl], —N[(C₁-C₃₀)alkyl]₂, —NH[(C₀-C₈)alkylene-(C₃-C₈)cycloalkyl], —N[C₀-C₈)alkylene-(C₃-C₈)cycloalkyl]₂, —NH[(CH₂—CH₂—O)₁₋₄₀—(C₁-C₄)alkyl], —NH—(C₃-C₈)heterocyclyl or —NH—(C₀-C₈)alkylene-aryl, wherein aryl is selected from phenyl or naphthyl, the (C₃-C₈)-heterocyclyl contains one N-atom and optionally two additional heteroatoms selected from O, N and S, and alkyl or cycloalkyl is unsubstituted or up to 5-fold substituted by —OH or a halogen selected from F, Cl, Br, and I.

18. The method according to claim 17, wherein said peptidic compound of formula (I) is any one of SEQ ID NOs: 4-181, 196-223, 226-229, or a salt or solvate thereof.

19. A method for treating obesity in a patient in need thereof, the method comprising administering to said patient a therapeutically effective amount of the peptidic compound of formula (I):

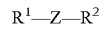

or a salt, or solvate thereof, or a pharmaceutical composition comprising a compound of formula (I) or a salt or solvate thereof as an active agent together with at least one pharmaceutically acceptable carrier, wherein Z is a peptide moiety having formula (II):

$$\text{His-X2-X3-Gly-Thr-Phe-Thr-Ser-Asp-Leu-Ser-Lys-Gln-} \\ \text{X14-X15-X16-X17-X18-Ala-X20-X21-Phe-Ile-Glu-Trp-} \\ \text{Leu-Lys-X28-X29-Gly-Pro-Ser-Ser-Gly-X35-Pro-Pro-} \\ \text{Pro-X39-X40} \quad (II)$$

wherein:

X2 is an amino acid residue selected from Ser, D-Ser, and Aib,

X3 is an amino acid residue selected from Gln, His, and α-amino-functionalized Gln, wherein Gln is optionally functionalized in that an H of the α-$NH_2$ group is substituted by ($C_1$-$C_4$)-alkyl, X14 is an amino acid residue having a side chain with a functionalized —$NH_2$ group, wherein the functionalized —$NH_2$ side chain group is functionalized by —C(O)—$R^5$, —C(O)O—$R^5$, —C(O)NH—$R^5$, —S(O)$_2$—$R^5$ or $R^5$, wherein $R^5$ is a moiety comprising up to 100 carbon atoms and optionally heteroatoms independently selected from halogen, N, O, S, P, and combinations thereof, X15 is an amino acid residue selected from Glu and Asp, X16 is an amino acid residue selected from Ser, Glu, and Lys, X17 is an amino acid residue selected from Arg, Glu, Gln, Leu, Aib, and Lys, X18 is an amino acid residue selected from Arg, Ala, and Lys, X20 is an amino acid residue selected from Gln, Arg, Lys, His, Glu, and Aib, X21 is an amino acid residue selected from Asp, Leu, and Glu, X28 is an amino acid residue selected from Asn, Arg, Lys, Aib, Ser, Glu, Ala, and Asp, X29 is an amino acid residue selected from Gly, Ala, D-Ala, and Thr, X35 is an amino acid residue selected from Ala, Glu, Arg, and Lys, X39 is Ser or is absent, and X40 is absent or is an amino acid residue having a side chain with an —$NH_2$ group, wherein the —$NH_2$ side chain group is optionally functionalized by —C(O)—$R^5$, —C(O)O—$R^5$, —C(O)NH—$R^5$, —S(O)$_2$—$R^5$ or $R^5$, wherein $R^5$ is a moiety comprising up to 100 carbon atoms and optionally heteroatoms selected from halogen, N, O, S, P, and combinations thereof, $R^1$ is the N-terminal group of the peptidic compound and is selected from —$NH_2$ and mono- or bisfunctionalized —$NH_2$, wherein the mono- or bisfunctionalized —$NH_2$ is selected from the group consisting of —NH[($C_1$-$C_5$)alkyl], —N[($C_1$-$C_5$)alkyl]$_2$, —NH[($C_0$-$C_4$)alkylene-($C_3$-$C_8$)cycloalkyl], —NH—C(O)—H, —NH—C(O)—($C_1$-$C_5$)-alkyl, and —NH—C(O)—($C_0$-$C_3$)alkylene-($C_3$-$C_8$)cycloalkyl, in which alkyl or cycloalkyl is unsubstituted or up to 5-fold substituted by —OH or halogen selected from F, Cl, Br, and I, $R^2$ is the C-terminal group of the peptidic compound and is selected from (i) —OH and functionalized —OH, wherein the functionalized —OH is selected from —O—($C_1$-$C_{20}$)alkyl and —O($C_0$-$C_8$)alkylene-($C_3$-$C_8$)cycloalkyl, and (ii) —$NH_2$ and mono- or bisfunctionalized —$NH_2$, wherein the mono- or bisfunctionalized —$NH_2$ is selected from the group consisting of —NH[($C_1$-$C_{30}$)alkyl], —N[($C_1$-$C_{30}$)alkyl]$_2$, —NH[($C_0$-$C_8$)alkylene-($C_3$-$C_8$)cycloalkyl], —N[$C_0$-$C_8$)alkylene-($C_3$-$C_8$)cycloalkyl]$_2$, —NH[(CH$_2$—CH$_2$—O)$_{1-40}$—($C_1$-$C_4$)alkyl], —NH—($C_3$-$C_8$)heterocyclyl or —NH—($C_0$-$C_8$)alkylene-aryl, wherein aryl is selected from phenyl or naphthyl, the ($C_3$-$C_8$)-heterocyclyl contains one N-atom and optionally two additional heteroatoms selected from O, N and S, and alkyl or cycloalkyl is unsubstituted or up to 5-fold substituted by —OH or a halogen selected from F, Cl, Br, and I.

20. The method according to claim 19, wherein said peptidic compound of formula (I) is any one of SEQ ID NOs: 4-181, 196-223, 226-229, or a salt or solvate thereof.

21. The method according to claim 19, further comprising treating obesity-linked inflammation, obesity-linked gallbladder disease, and/or obesity induced sleep apnea in the patient.

22. A method for decreasing food intake, reducing body weight, regulating appetite, or inducing satiety in a patient in need thereof, the method comprising administering to said patient a therapeutically effective amount of the peptidic compound of formula (I):

$$R^1\text{—}Z\text{—}R^2 \quad (I)$$

or a salt, or solvate thereof, or a pharmaceutical composition comprising a compound of formula (I) or a salt or solvate thereof as an active agent together with at least one pharmaceutically acceptable carrier, wherein Z is a peptide moiety having formula (II):

$$\text{His-X2-X3-Gly-Thr-Phe-Thr-Ser-Asp-Leu-Ser-Lys-Gln-} \\ \text{X14-X15-X16-X17-X18-Ala-X20-X21-Phe-Ile-Glu-Trp-} \\ \text{Leu-Lys-X28-X29-Gly-Pro-Ser-Ser-Gly-X35-Pro-Pro-} \\ \text{Pro-X39-X40} \quad (II)$$

wherein:

X2 is an amino acid residue selected from Ser, D-Ser, and Aib,

X3 is an amino acid residue selected from Gln, His, and α-amino-functionalized Gln, wherein Gln is optionally functionalized in that an H of the α-$NH_2$ group is substituted by ($C_1$-$C_4$)-alkyl, X14 is an amino acid residue having a side chain with a functionalized —$NH_2$ group, wherein the functionalized —$NH_2$ side chain group is functionalized by —C(O)—$R^5$, —C(O)O—$R^5$, —C(O)NH—$R^5$, —S(O)$_2$—$R^5$ or $R^5$, wherein $R^5$ is a moiety comprising up to 100 carbon atoms and optionally heteroatoms independently selected from halogen, N, O, S, P, and combinations thereof, X15 is an amino acid residue selected from Glu and Asp, X16 is an amino acid residue selected from Ser, Glu, and Lys, X17 is an amino acid residue selected from Arg, Glu, Gln, Leu, Aib, and Lys, X18 is an amino acid residue selected from Arg, Ala, and Lys, X20 is an amino acid residue selected from Gln, Arg, Lys, His, Glu, and Aib, X21 is an amino acid residue selected from Asp, Leu, and Glu, X28 is an amino acid residue selected from Asn, Arg, Lys, Aib, Ser, Glu, Ala, and Asp, X29 is an amino acid residue selected from Gly, Ala, D-Ala, and Thr, X35 is an amino acid residue selected from Ala, Glu, Arg, and Lys, X39 is Ser or is absent, and X40 is absent or is an amino acid residue having a side chain with an —$NH_2$ group, wherein the —$NH_2$ side chain group is optionally functionalized by —C(O)—$R^5$, —C(O)O—$R^5$, —C(O)NH—$R^5$, —S(O)$_2$—$R^5$ or $R^5$, wherein $R^5$ is a moiety comprising up to 100 carbon atoms and optionally heteroatoms selected from halogen, N, O, S, P, and combinations thereof, $R^1$ is the N-terminal group of the peptidic compound and is selected from —$NH_2$ and mono- or bisfunctionalized —$NH_2$, wherein the mono- or bisfunctionalized —$NH_2$ is selected from the group consisting of —NH[($C_1$-$C_5$)alkyl], —N[($C_1$-$C_5$)alkyl]$_2$, —NH[($C_0$-$C_4$)alkylene-($C_3$-$C_8$)cycloalkyl], —NH—C(O)—H, —NH—C(O)—($C_1$-$C_5$)-alkyl, and —NH—C(O)—($C_0$-$C_3$)alkylene-($C_3$-$C_8$)cycloalkyl, in which alkyl or cycloalkyl is unsubstituted or up to 5-fold substituted by —OH or halogen selected from F, Cl, Br, and I, $R^2$ is the C-terminal group of the peptidic compound and is selected from
(i) —OH and functionalized —OH, wherein the functionalized —OH is selected from —O—($C_1$-$C_{20}$)alkyl and —O($C_0$-$C_8$)alkylene-($C_3$-$C_8$)cycloalkyl, and
(ii) —$NH_2$ and mono- or bisfunctionalized —$NH_2$, wherein the mono- or bisfunctionalized —$NH_2$ is selected from the group consisting of —NH[($C_1$-$C_{30}$)alkyl], —N[($C_1$-$C_{30}$)alkyl]$_2$, —NH[($C_0$-$C_8$)alkylene-($C_3$-$C_8$)cycloalkyl], —N[$C_0$-$C_8$)alkylene-($C_3$-$C_8$)cycloalkyl]$_2$, —NH[($CH_2$—$CH_2$—O)$_{1\text{-}40}$—($C_1$-$C_4$)alkyl], —NH—($C_3$-$C_8$)heterocyclyl or —NH—($C_0$-$C_8$)alkylene-aryl, wherein aryl is selected from phenyl or naphthyl, the ($C_3$-$C_8$)-heterocyclyl contains one N-atom and optionally two additional heteroatoms selected from O, N and S, and alkyl or cycloalkyl is unsubstituted or up to 5-fold substituted by —OH or a halogen selected from F, Cl, Br, and I.

23. The method according to claim 22, wherein said peptidic compound of formula (I) is any one of SEQ ID NOs: 4-181, 196-223, 226-229, or a salt or solvate thereof.

* * * * *